(12) United States Patent
Zhuo et al.

(10) Patent No.: US 11,622,970 B2
(45) Date of Patent: Apr. 11, 2023

(54) BCL-2 INHIBITORS AND THEIR USE AS PHARMACEUTICALS

(71) Applicant: PRELUDE THERAPEUTICS INCORPORATED, Wilmington, DE (US)

(72) Inventors: Jincong Zhuo, Wimington, DE (US); Andrew Paul Combs, Wilmington, DE (US); Peng Wei, Wilmington, DE (US); Jialiang Wang, Wilmington, DE (US)

(73) Assignee: Prelude Therapeutics Incorporation, Wilmington, DE (US)

( * ) Notice: Subject to any disclaimer, the term of this patent is extended or adjusted under 35 U.S.C. 154(b) by 23 days.

(21) Appl. No.: 17/241,390

(22) Filed: Apr. 27, 2021

(65) Prior Publication Data

US 2021/0346405 A1    Nov. 11, 2021

Related U.S. Application Data

(60) Provisional application No. 63/016,643, filed on Apr. 28, 2020.

(51) Int. Cl.
| | | |
|---|---|---|
| *A61K 31/635* | (2006.01) |
| *A61K 45/06* | (2006.01) |
| *C07D 213/81* | (2006.01) |
| *C07D 333/54* | (2006.01) |
| *C07D 249/04* | (2006.01) |
| *C07D 215/48* | (2006.01) |
| *C07D 241/24* | (2006.01) |
| *C07D 239/69* | (2006.01) |
| *C07D 295/096* | (2006.01) |
| *C07D 261/18* | (2006.01) |
| *C07D 231/14* | (2006.01) |
| *C07D 495/04* | (2006.01) |
| *C07D 309/04* | (2006.01) |
| *C07D 401/04* | (2006.01) |
| *C07D 471/04* | (2006.01) |
| *C07D 519/00* | (2006.01) |
| *C07D 401/12* | (2006.01) |
| *A61P 35/00* | (2006.01) |

(52) U.S. Cl.
CPC ............ *A61K 31/635* (2013.01); *A61K 45/06* (2013.01); *A61P 35/00* (2018.01); *C07D 213/81* (2013.01); *C07D 215/48* (2013.01); *C07D 231/14* (2013.01); *C07D 239/69* (2013.01); *C07D 241/24* (2013.01); *C07D 249/04* (2013.01); *C07D 261/18* (2013.01); *C07D 295/096* (2013.01); *C07D 309/04* (2013.01); *C07D 333/54* (2013.01); *C07D 401/04* (2013.01); *C07D 401/12* (2013.01); *C07D 471/04* (2013.01); *C07D 495/04* (2013.01); *C07D 519/00* (2013.01)

(58) Field of Classification Search
None
See application file for complete search history.

(56) References Cited

U.S. PATENT DOCUMENTS

| | | |
|---|---|---|
| 2014/0057890 A1 | 2/2014 | Bruncko et al. |
| 2017/0281649 A1 | 10/2017 | David |
| 2019/0151287 A1 | 5/2019 | Friedhoff et al. |

OTHER PUBLICATIONS

International Search Report and Written Opinion issued for International Application No. PCT/US2021/029298, dated Aug. 13, 2021.

*Primary Examiner* — Samantha L Shterengarts
(74) *Attorney, Agent, or Firm* — BakerHostetler

(57) ABSTRACT

The disclosure is directed to, in part, to BCL-2 inhibitors, pharmaceutical compositions comprising the same, as well as methods of their use and preparation.

20 Claims, No Drawings

BCL-2 INHIBITORS AND THEIR USE AS PHARMACEUTICALS

CROSS-REFERENCE TO RELATED APPLICATIONS

This application claims priority to U.S. Provisional Application No. 63/016,643, filed Apr. 28, 2020, which is hereby incorporated by reference in its entirety.

TECHNICAL FIELD

The disclosure is directed to BCL-2 inhibitors and methods of their use.

BACKGROUND

B-cell lymphoma 2 ("BCL-2"), encoded in humans by the BCL-2 gene, is the founding member of the BCL-2 family of regulator proteins that regulate cell death (apoptosis) by either inhibiting (anti-apoptotic) or inducing (pro-apoptotic) apoptosis. (Tsujimoto et al. (November 1984). "Cloning of the chromosome breakpoint of neoplastic B cells with the t(14;18) chromosome translocation". Science. 226 (4678): 1097-9; Cleary et al. (October 1986). "Cloning and structural analysis of cDNAs for BCL-2 and a hybrid BCL-2/immunoglobulin transcript resulting from the t(14;18) translocation". Cell. 47 (1): 19-28. The BCL-2 family proteins are the key regulators of mitochondria-dependent apoptosis in nucleated cells and consist of both anti-apoptotic (BCL-xL, BCL-2, BCL-w, A1, Mcl-1) and pro-apoptotic (Bak, Bax, Bid, Bim, Bad, Bik, Bmf, Noxa, Puma) members.

Anti-apoptotic BCL-2 proteins are associated with various medical conditions such as disorders and diseases. In general, the expression of BCL-2 protein is associated with many physiologic functions, including the inhibition of apoptosis in the body, for example resulting in the proliferation of cells affected by the BCL-2 inhibition. Thus, inhibition of BCL-2 protein may reduce cell proliferation, which in return leads to improved outcomes related to the treatment and prevention of medical conditions, disorders, and diseases such as cancer. Therefore, there is an existing need in the therapeutic fields for compounds that inhibit the activity of anti-apoptotic BCL-2 proteins.

SUMMARY OF EMBODIMENTS

In some embodiments, compounds, or pharmaceutically acceptable salts thereof, are provided that, in part, modulate the activity of the BCL-2 protein such as inhibition of BCL-2 protein. The compounds can have, for example, a formula as described herein. In some embodiments, the compound is selected from a compound described herein. In some embodiments, methods of inhibiting the activity of BCL-2 protein described herein are provided. In some embodiments, methods of treating or preventing a disease or disorder condition associated with BCL-2 protein described herein are provided.

In some embodiments, the compound is a compound having a formula of

Formula (I)

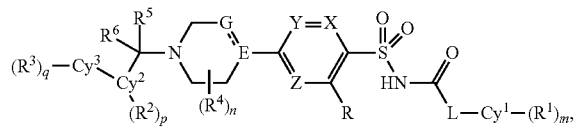

or a pharmaceutically acceptable salt thereof, wherein E, G, L, X, Y, Z, R, $R^1$, $R^2$, $R^3$, $R^4$, $R^5$, $R^6$, $Cy^1$, $Cy^2$, $Cy^3$, m, n, p, and q are as provided for herein and, for example, can be selected from the respective groups of chemical moieties described herein. In some embodiments, isotopic variants, tautomers, and stereoisomers of the compounds of the various formula provided herein and pharmaceutical salts and solvates thereof are also contemplated, described, and encompassed herein. Also provided are processes for preparing these compounds.

In some embodiments, also provided are pharmaceutical compositions comprising one or more compounds as described herein, which can also comprise a pharmaceutically acceptable carrier. In some embodiments, the compounds described herein can be provided in any form, such as a solid or solution (e.g., aqueous solution), as described herein. The compounds described herein, for example, can be obtained and employed in lyophilized form alone or with suitable additives.

Also provided are methods for treating a disease or disorder condition associated with BCL-2 and the like as described herein. In some embodiments, the diseases or disorder conditions are cancers, hyperproliferative diseases, autoimmune diseases, psychiatric disorders, or senescence-associated diseases and disorders, neoplastic diseases, neurodegenerative diseases, and the like. In some embodiments, the methods comprise administering one or more compounds described herein to a subject or a subject in need thereof.

DETAILED DESCRIPTION OF ILLUSTRATIVE EMBODIMENTS

The disclosure may be more fully appreciated by reference to the following description, including the following definitions and examples. Certain features of the disclosed compositions and methods that are described herein in the context of separate aspects may also be provided in combination in a single aspect. Alternatively, various features of the disclosed compositions and methods that are, for brevity, described in the context of a single aspect, may also be provided separately or in any subcombination.

Unless defined otherwise, all technical and scientific terms have the same meaning as is commonly understood by one of ordinary skill in the art to which the embodiments disclosed belongs.

At various places in the present specification, substituents of compounds are disclosed in groups or in ranges. It is specifically intended that the embodiments include each and every individual subcombination of the members of such groups and ranges. For example, the term "$C_{1-6}$ alkyl" or "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain embodiments, which are, for clarity, described in the context of separate embodiments, can also be provided in combination in a single embodiment. Conversely, various features of the embodiments, which are, for brevity, described in the context of a single embodiment, can also be provided separately or in any suitable subcombination.

All percentages and ratios used herein, unless otherwise indicated, are by weight.

As used herein, the terms "a" or "an" mean that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "alkyl," when used alone or as part of a substituent group, refers to a straight- or branched-chain hydrocarbon group, a spirocyclic group, or a fused or bridged bicyclic group, each of which has from 1 to 12 carbon atoms ("$C_{1-12}$"), preferably 1 to 6 carbons atoms ("$C_{1-6}$"), in the group. Examples of alkyl groups include methyl (Me, $C_1$ alkyl), ethyl (Et, $C_2$ alkyl), n-propyl ($C_3$ alkyl), isopropyl ($C_3$ alkyl), butyl ($C_4$ alkyl), isobutyl ($C_4$ alkyl), sec-butyl ($C_4$ alkyl), tert-butyl ($C_4$ alkyl), pentyl ($C_5$ alkyl), isopentyl ($C_5$ alkyl), tert-pentyl ($C_5$ alkyl), hexyl ($C_6$ alkyl), isohexyl ($C_6$ alkyl), and the like. The term "spirocyclic group" refers to spirocyclic compounds in which the two rings share only one single atom, the spiro atom, which is usually a quaternary carbon. Examples of spirocyclic compounds are spiro[2,3]undecane, spiro[3,3]heptane, and spiro[5,5]undecane. The term "fused bicyclic group" refers to fused bicyclic compounds, in which two rings share two adjacent atoms. Examples of fused bicyclic compounds include bicyclo[4.4.0]decane, α-thujene and decalin, and the like. The term "bridged bicyclic group" refers to bridged bicyclic compounds, in which the two rings share three or more atoms, separating the two bridgehead atoms by a bridge containing at least one atom. Examples of bridged bicyclic compounds include bicyclo[2.2.1]heptane, bicyclo [1,1,1] pentane, bicyclo[2.2.1]heptane, bicyclo[2.2.2]octane, bicyclo-[3.3.1]nonane, bicyclo[3.3.3]undecane, and the like.

As used herein, the term "heteroalkyl" refers to an alkyl group in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy," which, as used herein, refers to alkyl-O (e.g., methoxy and ethoxy).

As used herein, the term "aryl" when used alone or as part of a substituent group refers to a monocyclic, bicyclic, or polycyclic (e.g., having 2, 3, or 4 fused rings) aromatic hydrocarbons. In some embodiments, aryl groups have from 6 to 20 carbon atoms or from 6 to 10 carbon atoms. Examples of aryl groups include, but are not limited to, phenyl, naphthyl, anthracenyl, phenanthrenyl, indanyl, indenyl, tetrahydronaphthyl, and the like. Examples of aryl and heteroaryl groups include, but are not limited to:

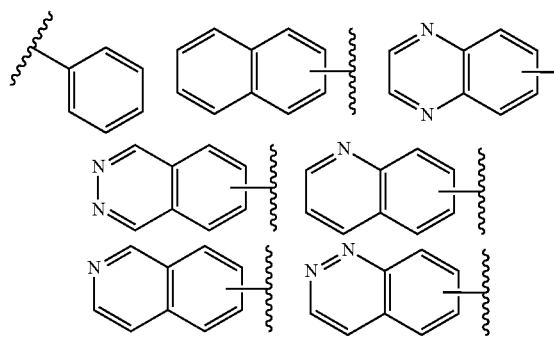

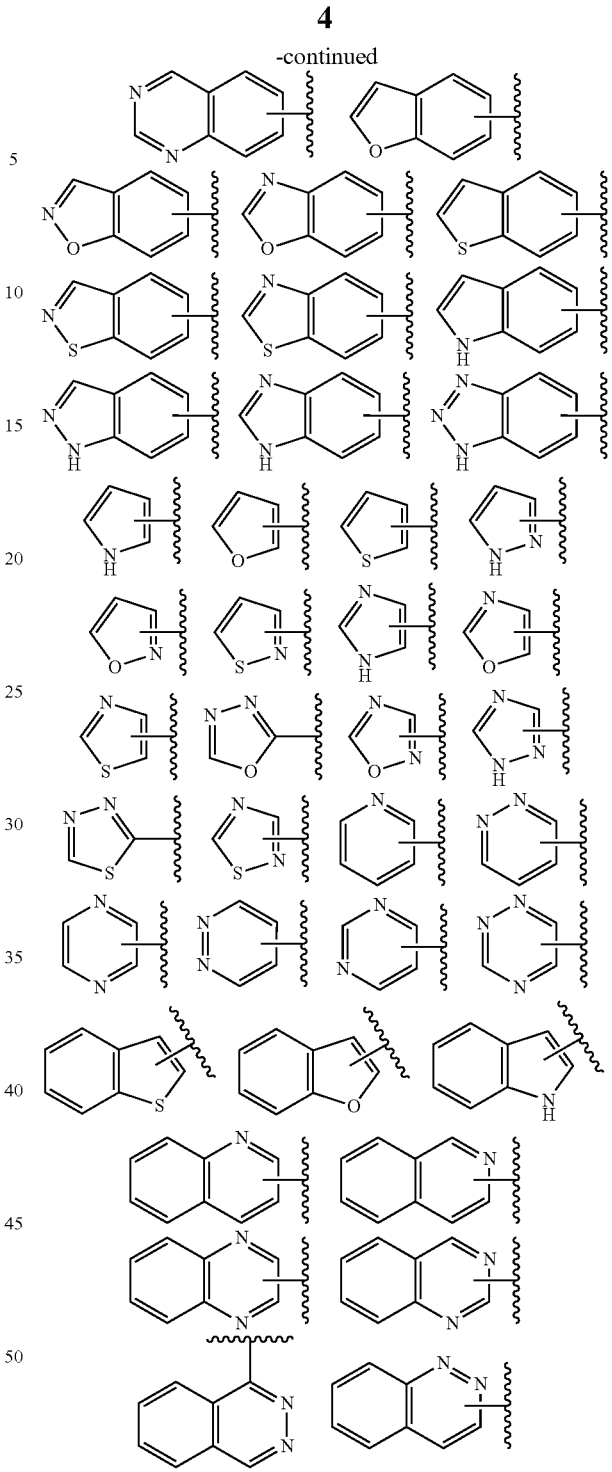

As used herein, the term "alkoxy" refers to an O-alkyl group. Examples of alkoxy groups include methoxy, ethoxy, propoxy (e.g., n-propoxy and isopropoxy), t-butoxy, and the like.

As used herein, the term "alkenyl" when used alone or as part of a substituent group refers to a straight- or branched-chain group having from 2 to 12 carbon atoms ("$C_{2-12}$"), preferably 2 to 6 carbons atoms ("$C_{2-6}$"), in the group, wherein the group includes at least one carbon-carbon double bond of alkenyl groups include vinyl (CH=$CH_2$; $C_2$ alkenyl), allyl ($CH_2$—CH=$CH_2$; $C_3$ alkenyl), propenyl (CH=$CHCH_3$; $C_3$ alkenyl); isopropenyl (C($CH_3$)=$CH_2$;

$C_3$ alkenyl), butenyl (CH=CHCH$_2$CH$_3$; $C_4$ alkenyl), sec-butenyl (—C(CH$_3$)=CHCH$_3$; $C_4$ alkenyl), iso-butenyl (CH=C(CH$_3$)$_2$; $C_4$ alkenyl), 2-butenyl (CH$_2$CH=CHCH$_3$; $C_4$ alkenyl), pentenyl (CH=CHCH$_2$CH$_2$CH$_3$ or CH2=CHCH$_2$CH$_2$CH$_2$; $C_5$alkenyl), and the like.

As used herein, the terms "alkoxy," "phenyloxy," "benzoxy," and "pyrimidinyloxy" refer to an alkyl group, phenyl group, benzyl group, or pyrimidinyl group, respectively, each of which is optionally substituted and bonded through an oxygen atom. For example, the term "alkoxy" means a straight or branched O-alkyl group of 1 to 20 carbon atoms, including, but not limited to, methoxy, ethoxy, n-propoxy, isopropoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length.

As used herein, the term "alkynyl" means a straight or branched alkyl group having one or more triple carbon-carbon bonds and 2-20 carbon atoms, including, but not limited to, acetylene, 1-propylene, 2-propylene, and the like. In some embodiments, the alkynyl chain is 2 to 10 carbon atoms in length, from 2 to 8 carbon atoms in length, from 2 to 6 carbon atoms in length, or from 2 to 4 carbon atoms in length.

As used herein, the terms "comprising" (and any form of comprising, such as "comprise," "comprises," and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional unrecited elements or method steps.

As used herein, the term "cyano" means CN.

As used herein, the term "cycloalkyl" means non-aromatic cyclic hydrocarbons, including cyclized alkyl, alkenyl, and alkynyl groups that contain up to 20 ring-forming carbon atoms. In some embodiments, cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfido. In some embodiments, the term "cycloalkyl" when used alone or as part of a substituent group refers to monocyclic, bicyclic, tricyclic, or non-aromatic hydrocarbon groups having from 3 to 10 carbon atoms ("$C_{3-10}$"), preferably from 3 to 6 carbon atoms ("$C_{3-6}$"), or from 3 to 7 carbon atoms ("$C_{3-7}$"). Examples of cycloalkyl groups include, for example, cyclopropyl (C3), cyclobutyl (C4), cyclopropylmethyl (C4), cyclopentyl (C5), cyclohexyl (C6), 1-methylcyclopropyl (C4), 2-methylcyclopentyl (C4), adamantanyl (C10), and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-indene-1-yl or 1H-inden-2(3H)-one-1-yl).

As used herein, the term "cycloalkenyl" refers to a cycloalkyl with one or more sites of unsaturation, e.g., one or more double bonds on one or more cyclic rings of the cycloalkyl. For example, $C_{4-8}$ cycloalkenyl refers to cyclobutenyl, cyclopentyl, cyclohexenyl, cycloheptenyl, and cyclooctenyl rings having one or more sites of unsaturation, e.g., one or more double bonds.

As used herein, the term "cycloalkylalkyl" means a $C_{1-6}$ alkyl substituted by cycloalkyl.

As used herein, the term "halo" means halogen groups including, but not limited to, fluoro, chloro, bromo, and iodo.

As used herein, the term "haloalkoxy" means an O-haloalkyl group. An example of a haloalkoxy group is $OCF_3$.

As used herein, the term "haloalkyl," when used alone or as part of a substituent group, refers to a straight- or branched-chain hydrocarbon group having from 1 to 12 carbon atoms ("$C_{1-12}$"), preferably 1 to 6 carbons atoms ("$C_{1-6}$"), in the group, wherein one or more of the hydrogen atoms in the group have been replaced by a halogen atom. Examples of haloalkyl groups include trifluoromethyl ($CF_3$, $C_1$haloalkyl), trifluoroethyl ($CH_2CF_3$, $C_2$haloalkyl), $CF_3$, $C_2F_5$, $CH_2F$, $CHF_2$, $CCl_3$, $CHCl_2$, $CH_2CF_3$, and the like.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatoms (ring-forming atoms), each of which is, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3, or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyranyl, oxadiazolyl, isoxazolyl, triazolyl, thianthrenyl, pyrazolyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furanyl, phenoxazinyl groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

As used herein, the term "heteroarylalkyl" means a $C_{1-6}$ alkyl group substituted by a heteroaryl group.

As used herein, the term "heterocycle" or "heterocyclic ring" means a 5- to 7-membered mono- or bicyclic or 7- to 10-membered bicyclic heterocyclic ring system, each of which may be saturated or unsaturated and consists of carbon atoms and from one to three heteroatoms chosen from N, O and S, wherein the N and S heteroatoms may optionally be oxidized, and the N heteroatom may optionally be quaternized, and including any bicyclic group in which any of the above-defined heterocyclic rings is fused to a benzene ring. Particularly useful are rings containing one oxygen or sulfur, one to three nitrogen atoms, or one oxygen or sulfur combined with one or two nitrogen atoms. The heterocyclic ring may be attached to any heteroatom or carbon atom, which results in the creation of a stable structure. Examples of heterocyclic groups include, but are not limited to, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

As used herein, the term "heterocycloalkyl" refers to non-aromatic heterocycles having up to 20 ring-forming atoms, including cyclized alkyl, alkenyl, and alkynyl groups, where one or more of the ring-forming carbon atoms is replaced by a heteroatom such as an O, N, or S atom. Hetercycloalkyl groups can be mono- or polycyclic (e.g., fused, bridged, or spiro systems). In some embodiments, the heterocycloalkyl group has from 1 to 20 carbon atoms or from 3 to 20 carbon atoms. In some embodiments, the heterocycloalkyl group contains 3 to 14 ring-forming atoms, 3 to 7 ring-forming atoms, or 5 or 6 ring-forming atoms. In some embodiments, the heterocycloalkyl group has 1 to 4 heteroatoms, 1 to 3 heteroatoms, or 1 or 2 heteroatoms. In some embodiments, the heterocycloalkyl group contains 0 to 3 double bonds. In some embodiments, the heterocycloalkyl group contains 0 to 2 triple bonds. Examples of heterocycloalkyl groups include, but are not limited to morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, oxazolidinyl, isothiazolidinyl, pyrazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form an S(O) or S(O)$_2$). For another example, a ring-forming C atom can be substituted by oxo (form carbonyl). Also included in the definition of heterocycloalkyl are moieties that have one or more aromatic rings fused (having a bond in common with) to the nonaromatic heterocyclic ring, including, but not limited to, pyridinyl, thiophenyl, phthalimidyl, naphthalimidyl, and benzo derivatives of heterocycles such as indolene, isoindolene, 4,5,6,7-tetrahydrothieno[2,3-c]pyridine-5-yl, 5,6-dihydrothieno[2,3-c]pyridin-7(4H)-one-5-yl, isoindolin-1-one-3-yl, and 3,4-dihydroisoquinolin-1(2H)-one-3yl groups. Ring-forming carbon atoms and heteroatoms of the heterocycloalkyl group can be optionally substituted by oxo or sulfido.

As used herein, the term "heterocycloalkylalkyl" refers to a $C_{1-6}$ alkyl substituted by heterocycloalkyl.

As used herein, the term "hydroxy" or "hydroxyl" means an OH group.

As used herein, the term "hydroxyalkyl" or "hydroxylalkyl" means an alkyl group substituted by a hydroxyl group. Examples of a hydroxyalkyl include, but are not limited to, $CH_2OH$ and $CH_2CH_2OH$.

As used herein, the phrase "in need thereof" means that the animal or mammal (subject) has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent. In some embodiments, the subject in need thereof is suspected of having the condition that needs to be treated.

As used herein, the phrase "integer from X to Y" means any integer that includes the endpoints. For example, the phrase "integer from X to Y" means 1, 2, 3, 4, or 5.

As used herein, the term "isolated" means that the compounds described herein are separated from other components of either (a) a natural source, such as a plant or cell, or (b) a synthetic organic chemical reaction mixture by conventional techniques.

As used herein, the term "isotopic variant" refers to a compound that contains proportions of isotopes at one or more of the atoms that constitute such a compound that is greater than natural abundance. For example, an "isotopic variant" of a compound can be radiolabeled, that is, contain one or more radioactive isotopes, or can be labeled with non-radioactive isotopes such as, for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H/D$, any carbon may be $^{13}C$, or any nitrogen may be $^{15}N$, and that the presence and placement of such atoms may be determined within the skill of the art.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "neoplastic disease" refers to a condition that causes tumor growth—both benign and malignant. Benign tumors are noncancerous growths. They usually grow slowly and cannot spread to other tissues. Malignant tumors are cancerous and can grow slowly or quickly. Malignant tumors carry the risk of metastasis or spreading to multiple tissues and organs.

As used herein, the term "N-alkyl" refers to an alkyl chain that is substituted with an amine group. Non-limiting examples include, but are not limited to

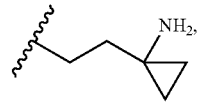 [SMILES: *CCC1(N)CC1]

and the like. The alkyl chain can be linear, branched, cyclic, or any combination thereof. In some embodiments, the alkyl comprises 1-10, 1-9, 1-8, 1-7, 1-6, 1-5, 1-4, 1-3, or 1-2 carbons.

As used herein, the term "nitro" means $NO_2$.

As used herein, the term "n-membered," where n is an integer, typically describes the number of ring-forming atoms in a moiety, where the number of ring-forming atoms is n. For example, pyridine is an example of a 6-membered heteroaryl ring, and thiophene is an example of a 5-membered heteroaryl ring.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded and that the substitution results in a stable compound. For example, if a methyl group is optionally substituted, then 3 hydrogen atoms on the carbon atom can be replaced with substituent groups. Also for example, a $C_{1-6}$ alkyl, $C_{2-6}$ alkenyl, $C_{1-10}$ alkyl, $C_{2-10}$ alkenyl, $C_{2-10}$ alkynyl, cycloalkyl, cycloalkenyl, heterocycloalkyl, aryl, or heteroaryl group is "optional substituted" by 1, 2, or 3 substituents, wherein each said substituent is independently H, D, halo, oxo, CN, $NO_2$, $N_3$, $OR^{a1}$, $SR^{a1}$, $C(O)R^{b1}$, $C(O)NR^{c1}R^{d1}$, $CH_2C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $C(=NR^{g1})R^{b1}$, $NR^{c1}S(O)R^{b1}$, $NR^{c1}S(O)_2NR^{d1}$, $NR^{c1}C(=NOR^{a1})NR^{c1}R^{d1}$, $NR^{c1}C(=NCN)NR^{c1}R^{d1}$, $S(O)(=NR^{g1})R^{b1}$, $S(O)(=NR^{g1})NR^{c1}R^{d1}$, $SF_5$, $B(OR^{a1})_2$, $NR^{c1}C(O)OR^{a1}$, $C(=NR^{g1})NR^{c1}R^{d1}$, $NR^{c1}C(=NR^{g1})NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)(=NR^{b1})$; $S(O)NR^{c1}R^{d1}$, $S(O)_2R^{b1}$, $NR^{c1}S(O)_2R^{b1}$, $S(O)_2NR^{c1}R^{d1}$, $C_{1-6}$ alkyl, $C_{1-6}$ heteroalkyl, $C_{2-6}$ alkenyl, $C_{2-6}$ alkynyl, $C_{1-6}$haloalkyl, $C_{1-6}$ alkyl-$NR^{c1}R^{d1}$, $(CH_2CH_2O)_{1-10}C_{1-6}$ alkyl, $C_{2-6}$ alkenyl-$NR^{c1}R^{d1}$, $C_{2-6}$ alkynyl-$NR^{c1}R^{d1}$, $OC_{2-6}$ alkyl-$NR^{c1}R^{d1}$, aryl, heteroaryl, spirocycloalkyl, spiroheterocycloalkyl, cycloalkyl, or heterocycloalkyl, wherein said $C_{1-6}$ alkyl, $C_{1-6}$ heteroalkyl, $C_{2-6}$ alkenyl, $C_{2-6}$ alkynyl, $C_{1-6}$ haloalkyl, $C_{1-6}$alkyl-$NR^{c1}R^{d1}$, $(CH_2CH_2O)_{1-10}C_{1-6}$ alkyl, $C_{2-6}$ alkenyl-$NR^{c1}R^{d1}$, $C_{2-6}$ alkynyl-$NR^{c1}R^{d1}$, $OC_{2-6}$ alkyl-$NR^{c1}R^{d1}$, aryl, heteroaryl, spirocycloalkyl, spiroheterocycloalkyl, cycloalkyl, and heterocycloalkyl are optionally substituted with 1, 2, or 3 substituents, wherein each substituent is independently H, D, halo, oxo, $C_{1-6}$ alkyl, $C_{1-6}$ heteroalkyl, $C_{2-6}$ alkenyl, $C_{2-6}$ alkynyl, $C_{1-6}$haloalkyl, cycloalkyl, heterocycloalkyl, aryl, heteroaryl, $C_{1-6}$ alkyl-$NR^{c1}R^{d1}$, $C_{2-6}$ alkenyl-$NR^{c1}R^{d1}$, $C_{2-6}$ alkynyl-$NR^{c1}R^{d1}$, $OC_{2-6}$ alkyl-$NR^{c1}R^{d1}$, CN, $NO_2$, $N_3$, $OR^{a1}$, $SR^{a1}$, $C(O)R^{b1}$, $C(O)NR^{c1}R^{d1}$, $CH_2C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $C(=NR^{g1})R^{b1}$, $NR^{c1}S(O)R^{b1}$, $NR^{c1}S(O)_2NR^{c1}R^{d1}$, $NR^{c1}C(=NOR^{a1})NR^{c1}R^{d1}$, $NR^{c1}C(=NCN)NR^{c1}R^{d1}$, $S(O)(=NR^{g1})R^{b1}$, $S(O)(=NR^{g1})NR^{c1}R^{d1}$, $SF_5$, $B(OR^{a1})_2$, $NR^{c1}C(O)OR^{a1}$, $C(=NR^{g1})NR^{c1}R^{d1}$, $NR^{c1}C(=NR^{g1})NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein:

each $R^{a1}$ is independently H, D, $C_{1-6}$ alkyl, $C_{1-6}$haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, wherein said $C_{1-6}$ alkyl, $C_{1-6}$haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl are optionally substituted with 1, 2, or 3 substituents, wherein each substituent is independently OH, CN, amino, halo, $C_{1-6}$ alkyl, $C_{1-6}$ alkoxy, $C_{1-6}$haloalkyl, and $C_{1-6}$haloalkoxy, $C_{3-10}$ cycloalkyl, $C_{1-6}$heteroalkyl, 3- to 12-membered heterocyclyl, $C_{6-10}$ aryl, 5- to 10-membered heteroaryl, C(O)H, $C(O)NH_2$, C(O)NH($C_{1-6}$ alkyl), $C(O)N(C_{1-6}$ alkyl$)_2$, COOH, $C(O)C_{1-6}$ alkyl, or $C(O)OC_{1-6}$ alkyl;

each $R^{b1}$ is independently H, D, $C_{1-6}$ alkyl, $C_{1-6}$haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, wherein said $C_{1-6}$ alkyl, $C_{1-6}$haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl are optionally substituted with 1, 2, or 3 substituents, wherein each said substituent is independently OH, CN, amino, halo, $C_{1-6}$ alkyl, $C_{1-6}$ alkoxy, $C_{1-6}$haloalkyl, and $C_{1-6}$ haloalkoxy, $C_{3-10}$ cycloalkyl, $C_{1-6}$heteroalkyl, 3- to 12-membered heterocyclyl, $C_{6-10}$ aryl, 5- to 10-membered heteroaryl, C(O)H, $C(O)NH_2$, C(O)NH ($C_{1-6}$ alkyl), $C(O)N(C_{1-6}$ alkyl$)_2$, COOH, $C(O)C_{1-6}$ alkyl, or $C(O)OC_{1-6}$ alkyl;

each $R^{c1}$ and each $R^{d1}$ is independently H, D, $C_{1-10}$ alkyl, $C_{1-6}$haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl are optionally substituted with 1, 2, or 3 substituents, wherein each said substituent is independently OH, CN, amino, halo, $C_{1-6}$ alkyl, $C_{1-6}$ alkoxy, $C_{1-6}$ haloalkyl, $C_{1-6}$ haloalkoxy, hydroxyalkyl, cyanoalkyl, aryl, heteroaryl, $C(O)OR^{a1}$, $C(O)R^{b1}$, $S(O)_2R^{b1}$, alkoxyalkyl, alkoxyalkoxy; $C_{3-10}$ cycloalkyl, $C_{1-6}$ heteroalkyl, 3- to 12-membered heterocyclyl, $C_6$-$C_{10}$ aryl, 5- to 10-membered heteroaryl, $C(O)NH_2$, C(O)NH($C_{1-6}$ alkyl), or $C(O)N(C_{1-6}$alkyl$)_2$;

or $R^{c1}$ and $R^{d1}$ together with the N atom to which they are attached form a 4-, 5-, 6- or 7-membered heterocycloalkyl group or heteroaryl group, each of which is optionally substituted with 1, 2, or 3 substituents, wherein each said substituent is independently OH, CN, amino, halo, $C_1$-$C_6$ alkyl, $C_1$-$C_6$ alkoxy, $C_1$-$C_6$ haloalkyl, $C_1$-$C_6$ haloalkoxy, hydroxyalkyl, cyanoalkyl, aryl, heteroaryl, $C(O)OR^{a1}$, $C(O)R^{b1}$, $S(O)_2R^{b1}$, alkoxyalkyl, or alkoxyalkoxy;

each $R^{e1}$ is independently H, $C_{1-6}$ alkyl, $C_{1-6}$ haloalkyl, $C_{2-6}$ alkenyl, ($C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl, or heterocycloalkylalkyl;

each $R^{f1}$ is independently H, $C_{1-6}$ alkyl, $C_{1-6}$ haloalkyl, $C_{2-6}$ alkenyl, $C_{2-6}$ alkynyl, aryl, cycloalkyl, heteroaryl, or heterocycloalkyl; and each $R^{g1}$ is independently H, CN, or $NO_2$.

As used herein, the term "oxo" refers to an oxygen atom (i.e., =O) as a divalent substituent, forming a carbonyl group when attached to a carbon (e.g., C=O), or attached to a nitrogen or sulfur heteroatom forming a nitroso, sulfinyl, or sulfonyl.

Compounds described herein can be asymmetric (e.g., having one or more stereocenters). All stereoisomers, such as enantiomers and diastereomers, are intended unless otherwise indicated.

Compounds provided herein that contain asymmetrically substituted carbon atoms can be isolated in optically active or racemic forms. Methods on how to prepare optically active forms from optically active starting materials are known in the art, such as by resolution of racemic mixtures or by stereoselective synthesis, or by separation the racemic mixture or diastereomeric mixture with chiral chromatography. Geometric isomers of olefins, C=N double bonds, and the like can also be present in the compounds described herein, and all such stable isomers are contemplated in the present embodiments. Geometric isomers of the compounds of the present embodiments are described and may be isolated as a mixture of isomers or as separated isomeric forms.

Compounds provided herein may also include tautomeric forms. All tautomeric forms are encompassed. In some embodiments, the compounds may exist as rotational isomers. In some embodiments, the compounds exist as mixtures of rotational isomers in any proportion. In other embodiments, the compounds exist as particular rotational isomers, substantially free of other rotational isomers.

Compounds provided herein can also include all isotopes of atoms occurring in the intermediates or final compounds. Isotopes include those atoms having the same atomic number but different mass numbers. For example, isotopes of hydrogen include tritium and deuterium ("D").

Also provided herein are pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include, but are not limited to, the conventional non-toxic salts of the parent compound formed, for example, from non-toxic inorganic or organic acids. The pharmaceutically acceptable salts can be synthesized from the parent compound, which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

As used herein, the term "phenyl" means $C_6H_5$. A phenyl group can be unsubstituted or substituted with one, two, or three suitable substituents as defined in the present disclosure.

As used herein, the term "prodrug" means a derivative of a known direct-acting drug, which derivative has enhanced delivery characteristics and therapeutic value as compared to the drug, and is transformed into the active drug by an enzymatic or chemical process. In some embodiments, a prodrug is inactive when administered to a subject but is converted in vivo to an active compound, for example, by hydrolysis. The prodrug compound often offers advantages of solubility, tissue compatibility, or delayed release in a mammalian organism (see, e.g., Bundgard, H., Design of Prodrugs (1985), pp. 7-9, 21-24 (Elsevier, Amsterdam).

As used herein, the term "purified" means that when isolated, the isolate contains at least at least 80%, least 85%, at least 90%, at least 95%, at least 98%, or at least 99% of a compound described herein by weight of the isolate.

As used herein, the phrase "quaternary ammonium salts" means derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as $Cl^-$, $CH_3COO^-$, and $CF_3COO^-$), for example, methylation or ethylation.

As used herein, the term "solvate" refers to a physical association of a compound provided herein with one or more solvent molecules.

As used herein, the term "subject" includes humans. The terms "human," "patient," and "subject" are used interchangeably herein.

As used herein, the phrase "solubilizing agent" means agents that result in the formation of a micellar solution or a true solution of the drug or compounds of the present disclosure.

As used herein, the term "solution/suspension" means a liquid composition wherein a first portion of the active agent is present in solution and a second portion of the active agent is present in particulate form, in suspension in a liquid matrix.

As used herein, the phrase "substantially isolated" means a compound that is at least partially or substantially separated from the environment in which it is formed or detected. In some embodiments, the compounds and salts thereof, as described herein, are substantially isolated. By "substantially isolated" is meant that the compound is at least partially or substantially separated from the environment in which is formed or detected. Partial separation can include, for example, a composition enriched in the compound. Substantial separation can include compositions containing at least about 50%, at least about 60%, at least about 70%, at least about 80%, at least about 90%, at least about 95%, at least about 97%, or at least about 99% by weight of the compound, or salt thereof. Methods for isolating compounds and their salts are routine in the art.

As used herein, the phrase "suitable substituent" or "substituent" means a group that does not nullify the synthetic or pharmaceutical utility of the compounds described herein or the intermediates useful for preparing them. Examples of suitable substituents include, but are not limited to: $C_{1-6}$ alkyl, $C_{1-6}$ alkenyl, $C_{1-6}$ alkynyl, $C_{5-6}$ aryl, $C_{1-6}$ alkoxy, $C_{3-5}$ heteroaryl, $C_{3-6}$ cycloalkyl, $C_{5-6}$ aryloxy, CN, OH, oxo, halo, haloalkyl, $NO_2$, $CO_2H$, $NH_2$, $NH(C_{1-8}$ alkyl), $N(C_{1-8}$ alkyl)$_2$, $NH(C_6$ aryl), $N(C_{5-6}$ aryl)$_2$, CHO, $CO(C_{1-6}$ alkyl), $CO((C_{5-6})$ aryl), $CO_2((C_{1-6})$alkyl), and $CO_2((C_{5-6})$ aryl). One of skill in the art can readily choose a suitable substituent based on the stability and pharmacological and synthetic activity of the compounds described herein.

As used herein, the phrase "therapeutically effective amount" means the amount of active compound or pharmaceutical agent that elicits the biological or medicinal response that is being sought in a tissue, system, animal, individual, or human by a researcher, a veterinarian, a medical doctor, or another clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side effects. The amount needed to elicit the therapeutic response can be determined based on the age, health, size and sex of the subject. Optimal amounts can also be determined based on monitoring of the subject's response to treatment.

As used herein, the terms "treat," "treated," and "treating" mean both therapeutic treatment and prophylactic measures wherein the object is to slow down (lessen) an undesired physiological condition, disorder, or disease, or obtain beneficial or desired clinical results. Beneficial or desired clinical results include, but are not limited to, alleviation of symptoms; diminishment of the extent of the condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of the condition, disorder or disease. Treatment includes eliciting a clinically significant response without excessive levels of side effects. Treatment also includes prolonging survival as compared to expected survival if not receiving treatment. Thus, "treatment of pain" or "treating pain" means an activity that alleviates or ameliorates any of the primary phenomena or secondary symptoms associated with the pain or other condition described herein.

"Compounds of the present disclosure" and equivalent expressions are meant to embrace compounds of any formula or structural representation as described herein, as well as their subgenera, which expression includes the stereoisomers (e.g., enantiomers, diastereomers) and constitutional isomers (e.g., tautomers) of the various compounds and formula provided for herein as well as pharmaceutically acceptable salts thereof, where the context so permits.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers at each asymmetric center or as any combination thereof. Unless indicated otherwise, the description or naming of a particular compound in the specification and claims is intended to include all stereoisomers and mixtures, racemic or otherwise, thereof. Where one chiral center exists in a structure, but no specific stereochemistry is shown for that center, both enantiomers, individually or as a mixture of enantiomers, are encompassed by that structure. Where more than one chiral center exists in a structure, but no specific stereochemistry is shown for the centers, all enantiomers and diastereomers, individually or as a mixture, are encompassed by that structure. The methods for the determination of stereochemistry and the separation of stereoisomers are well known in the art.

It will be apparent that the compounds provided herein, including all subgenera described herein, may have multiple stereogenic centers. As a result, there exist multiple stereoisomers (enantiomers and diastereomers) of the compounds of the various formula provided herein (and subgenera provided herein). The present disclosure contemplates and encompasses each stereoisomer of any compound of any formula provided herein (and subgenera provided herein), as well as mixtures of said stereoisomers.

All enantiomers, diastereomers, and any combination thereof, are included within the scope of compounds described herein.

Throughout the description, where compositions are described as having, including, or comprising specific components, or where processes are described as having, including, or comprising specific process steps, it is contemplated that compositions described herein also consist essentially of, or consist of, the recited components, and that the processes described herein also consist essentially of, or consist of, the recited processing steps. Further, it should be understood that the order of steps or order for performing certain actions is immaterial so long as the process remains operable. Moreover, two or more steps or actions can be conducted simultaneously.

Pharmaceutically acceptable salts and solvates of the compounds of any formula provided herein (including all subgenera provided herein) are also within the scope of the present disclosure.

Isotopic variants of the compounds of any formula provided herein (including all subgenera provided herein) are also contemplated by the present disclosure.

Pharmaceutical Compositions and Methods of Administration

The subject pharmaceutical compositions are typically formulated to provide a therapeutically effective amount of a compound of the present disclosure as the active ingredient, or a pharmaceutically acceptable salt, ester, prodrug, solvate, hydrate, or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers, and adjuvants.

The subject pharmaceutical compositions can be administered alone or in combination with one or more other agents, which are also typically administered in the form of pharmaceutical compositions. Where desired, one or more compounds and other agent(s) may be mixed into a preparation, or both components may be formulated into separate preparations to use them in combination separately or at the same time.

In some embodiments, the concentration of one or more compounds provided in the pharmaceutical compositions is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g 0.15 g, 0.2 g 0.25 g, 0.3 g 0.35 g, 0.4 g 0.45 g, 0.5 g, 0.55 g, 0.6 g 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds is in the range of 0.0001-10 g, 0.0005-9 g, 0.001-8 g, 0.005-7 g, 0.01-6 g, 0.05-5 g, 0.1-4 g, 0.5-4 g, or 1-3 g.

In some embodiments, a pharmaceutical composition comprising the R enantiomer is free or substantially free of the S enantiomer.

In some embodiments, a pharmaceutical composition comprising the S enantiomer is free or substantially free of the R enantiomer.

In some embodiments, a pharmaceutical composition comprises an enantiomeric excess of at least or about 80, 85, 90, 91, 92, 93, 94, 95, 96, 97, 98, or 99% of a specific enantiomer of a compound of the present disclosure as the active ingredient, or a pharmaceutically acceptable salt, ester, prodrug, solvate, hydrate or derivative thereof, such as the R or the S enantiomer. In some embodiments, the enantiomeric excess is at least or about 90%. In some embodiments, the enantiomeric excess is at least or about 95%. In some embodiments, the enantiomeric excess is at least or about 98%. In some embodiments, the enantiomeric excess is at least or about 99%.

The compounds compound of the present disclosure can be effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition can contain an active ingredient (i.e., a compound of the present disclosure) provided for herein or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers, and adjuvants.

Described below are non-limiting exemplary pharmaceutical compositions and methods for preparing the same.

Pharmaceutical Compositions for Oral Administration.

In some embodiments, pharmaceutical compositions for oral administration are provided that contain a compound of the present disclosure or a pharmaceutically acceptable salt, ester, prodrug, solvate, hydrate, or derivative thereof, and a pharmaceutical excipient suitable for oral administration.

In some embodiments, embodiments provide a solid pharmaceutical composition for oral administration containing: (i) an amount (e.g., effective amount) of a compound; (ii) optionally an amount of a second agent; and (iii) a pharmaceutical excipient suitable for oral administration. In some embodiments, the composition further contains: (iv) an amount of a third agent.

In some embodiments, the pharmaceutical composition may be a liquid pharmaceutical composition suitable for oral consumption. Pharmaceutical compositions suitable for oral administration can be presented as discrete dosage forms, such as capsules, cachets, or tablets, or liquids or aerosol sprays, each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface-active or dispersing agent. Molded tablets can be made by molding in a suitable machine a mixture of the powdered compound moistened with an inert liquid diluent.

Embodiments provided for herein further encompass anhydrous pharmaceutical compositions and dosage forms comprising an active ingredient since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture-containing ingredients and low moisture or low humidity conditions. Pharmaceutical compositions and dosage forms that contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and any combination thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and any combination thereof.

Disintegrants may be used in the compositions provided for herein to provide tablets that disintegrate when exposed to an aqueous environment. Too much of a disintegrant may produce tablets, which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or any mixture thereof.

Lubricants that can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or any combination thereof. Additional lubricants include, for example, a solid silica gel, a coagulated aerosol of synthetic silica, or any combination thereof. A lubricant can optionally be added in an amount of less than about 1 weight percent of the pharmaceutical composition.

When aqueous suspensions and/or elixirs are desired for oral administration, the active ingredient therein may be combined with various sweetening or flavoring agents, coloring matter or dyes, and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example, peanut oil, liquid paraffin or olive oil.

Surfactants that can be used to form pharmaceutical compositions and dosage forms include, but are not limited to, hydrophilic surfactants, lipophilic surfactants, and any combination thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB"

value). Surfactants with lower HLB values are more lipophilic or hydrophobic and have greater solubility in oils, while surfactants with higher HLB values are more hydrophilic and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, the HLB value of a surfactant is merely a rough guide generally used to enable the formulation of industrial, pharmaceutical and cosmetic emulsions.

Hydrophilic surfactants may be either ionic or non-ionic. Suitable ionic surfactants include, but are not limited to, alkylammonium salts, fusidic acid salts, fatty acid derivatives of amino acids, oligopeptides, polypeptides, glyceride derivatives of amino acids, oligopeptides, polypeptides, lecithins and hydrogenated lecithins, lysolecithins and hydrogenated lysolecithins, phospholipids and derivatives thereof, lysophospholipids and derivatives thereof, carnitine fatty acid ester salts, salts of alkylsulfates, fatty acid salts, sodium docusate, acyl lactylates, mono- and di-acetylated tartaric acid esters of mono- and di-glycerides, succinylated mono- and di-glycerides, citric acid esters of mono- and di-glycerides, and any combination thereof.

Within the aforementioned group, ionic surfactants include, by way of example: lecithins, lysolecithin, phospholipids, lysophospholipids and derivatives thereof, carnitine fatty acid ester salts, salts of alkylsulfates, fatty acid salts, sodium docusate, acylactylates, mono- and di-acetylated tartaric acid esters of mono- and di-glycerides, succinylated mono- and di-glycerides, citric acid esters of mono- and di-glycerides, and any combination thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and any combination thereof.

Hydrophilic non-ionic surfactants may include, but are not limited to, alkylglucosides, alkylmaltosides, alkylthioglucosides, lauryl macrogolglycerides, polyoxyalkylene alkyl ethers such as polyethylene glycol alkyl ethers, polyoxyalkylene alkylphenols such as polyethylene glycol alkyl phenols, polyoxyalkylene alkyl phenol fatty acid esters such as polyethylene glycol fatty acids monoesters and polyethylene glycol fatty acids diesters, polyethylene glycol glycerol fatty acid esters, polyglycerol fatty acid esters, polyoxyalkylene sorbitan fatty acid esters such as polyethylene glycol sorbitan fatty acid esters, hydrophilic transesterification products of a polyol with at least one member of the group consisting of glycerides, vegetable oils, hydrogenated vegetable oils, fatty acids, sterols, polyoxyethylene sterols and derivatives and analogues thereof, polyoxyethylated vitamins and derivatives thereof, polyoxyethylene-polyoxypropylene block copolymers, polyethylene glycol sorbitan fatty acid esters, hydrophilic transesterification products of a polyol with at least one member of the group consisting of triglycerides, vegetable oils and hydrogenated vegetable oils, and any combination thereof. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-1Ooleate, Tween 40, Tween 60, sucrose monostearate, sucrose mono laurate, sucrose monopalmitate, PEG 10-100 nonyl phenol series, PEG 14-100 octyl phenol series, poloxamers, and any combination thereof.

Suitable lipophilic surfactants include, by way of example only: fatty alcohols, glycerol fatty acid esters, acetylated glycerol fatty acid esters, lower alcohol fatty acids esters, propylene glycol fatty acid esters, sorbitan fatty acid esters, polyethylene glycol sorbitan fatty acid esters, sterols and sterol derivatives, polyoxyethylated sterols and sterol derivatives, polyethylene glycol alkyl ethers, sugar esters, sugar ethers, lactic acid derivatives of mono- and di-glycerides, hydrophobic transesterification products of a polyol with at least one member of the group consisting of glycerides, vegetable oils, hydrogenated vegetable oils, fatty acids and sterols, oil-soluble vitamins/vitamin derivatives; and any combination thereof. Within this group, preferred lipophilic surfactants include glycerol fatty acid esters, propylene glycol fatty acid esters, and any combination thereof, or are hydrophobic transesterification products of a polyol with at least one member of the group consisting of vegetable oils, hydrogenated vegetable oils, triglycerides, and any combination thereof.

In some embodiments, the composition may include a solubilizer to ensure good solubilization and/or dissolution of the compound(s) and to minimize precipitation of the compound(s). This can be used, for example, for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, and cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide, and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, a mixture of triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide in any combination thereof. Particularly preferred solubilizers include sorbitol, glycerol, triacetin, ethyl alcohol, PEG-400, glycofurol, and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example, to maximize the concentration of the drug, with excess solubilizer removed prior to providing the composition to a subject or a subject in need thereof using conventional techniques, such as distillation or evaporation. Thus, if present, the solubilizer can be in a weight ratio of 10%, 25% o, 50%), 100% o, or up to about 200%> by weight, based on the combined weight of the drug and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and any combination thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS), and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate, can also be used. When the base is a salt, the cation can be any convenient and pharmaceutically acceptable cation, such as ammonium, alkali metals, alkaline earth metals, and the like. Examples may include but are not limited to sodium, potassium, lithium, magnesium, calcium, and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, pharmaceutical compositions for injection are provided containing a compound of the present disclosure, or a pharmaceutically acceptable salt, ester, prodrug, solvate, hydrate, or derivative thereof, and a pharmaceutical excipient suitable for injection. Components and amounts of agents in the compositions are as described herein.

The forms in which the compositions may be incorporated for administration by injection include aqueous, oil suspensions, emulsions with sesame oil, corn oil, cottonseed oil, or peanut oil as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and any suitable combination thereof), cyclodextrin derivatives, and vegetable oils may also be employed. The proper fluidity can be maintained, for example, by the use of a coating, such as a lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound(s) as provided herein in an amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques, which yield a powder of the active ingredient plus any additional desired ingredient from a previously sterile-filtered solution thereof.

Pharmaceutical Compositions for Topical (e.g. Transdermal) Delivery.

In some embodiments, pharmaceutical compositions for transdermal delivery are provided containing a compound(s) and a pharmaceutical excipient suitable for transdermal delivery.

Compositions can be formulated into preparations in solid, semisolid, or liquid forms suitable for local or topical administration, such as gels, water-soluble jellies, creams, lotions, suspensions, foams, powders, slurries, ointments, solutions, oils, pastes, suppositories, sprays, emulsions, saline solutions, and dimethylsulfoxide (DMSO)-based solutions. In general, carriers with higher densities are capable of providing an area with prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods employs transdermal delivery devices ("patches"). Such transdermal patches may be used to provide a continuous or discontinuous infusion of a compound of the present disclosure or a pharmaceutically acceptable salt, ester, prodrug, solvate, hydrate, or derivative thereof, in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on-demand delivery of pharmaceutical agents.

Pharmaceutical Compositions for Inhalation.

Compositions for inhalation or insufflation include solutions and suspensions in pharmaceutically acceptable, aqueous or organic solvents, or any combination thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by the use of inert gases. Nebulized solutions may be inhaled directly from the nebulizing device, or the nebulizing device may be attached to a facemask tent or intermittent positive pressure-breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety.

Administration of the compounds or pharmaceutical compositions can be effected by any method that enables the delivery of the compounds to the site of action. These methods include oral routes, intraduodenal routes, parenteral injection (including intravenous, intraarterial, subcutaneous, intramuscular, intravascular, intraperitoneal, or infusion), topical (e.g., transdermal application), rectal administration, via local delivery by catheter or stent or through inhalation. Compounds can also be administered intraadiposally or intrathecally.

The amount of the compound of the present disclosure, or a pharmaceutically acceptable salt, ester, prodrug, solvate, hydrate, or derivative thereof, administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases, still larger doses may be employed without causing any harmful side effect, e.g., by dividing such larger doses into several small doses for administration throughout the day.

In some embodiments, a compound of the present disclosure, or a pharmaceutically acceptable salt, ester, prodrug, solvate, hydrate, or derivative thereof, is administered in a single dose.

Typically, such administration can be by injection, e.g., intravenous injection, in order to introduce the agent quickly. However, other routes, such as oral, may be used as appropriate. A single dose of a compound of the present disclosure, or a pharmaceutically acceptable salt, ester, prodrug, solvate, hydrate, or derivative thereof, may also be used for the treatment of an acute condition.

In some embodiments, a compound of the present disclosure, or a pharmaceutically acceptable salt, ester, prodrug, solvate, hydrate or derivative thereof, or a pharmaceutical composition of the present disclosure, is administered in multiple doses. Dosing may be about once, twice, three times, four times, five times, six times, or more than six times per day. Dosing may be about once a month, once every two weeks, once a week, or once every other day. In some embodiments, a compound and another agent are administered together about once per day to about 6 times per day. In some embodiments, the administration of a compound of the present disclosure, or a pharmaceutically acceptable salt, ester, prodrug, solvate, hydrate, or derivative thereof, and an agent continues for less than about 7 days. In yet another embodiment, the administration continues for more than about 6, 10, 14, 28 days, two months, six months, or one year. In some cases, continuous dosing is achieved and maintained as long as necessary.

Administration of the compounds of the present disclosure, or pharmaceutically acceptable salts, ester, prodrugs, solvates, hydrates, or derivatives thereof, may continue as long as necessary. In some embodiments, a compound is administered for more than 1, 2, 3, 4, 5, 6, 7, 14, or 28 days. In some embodiments, a compound is administered for less than 28, 14, 7, 6, 5, 4, 3, 2, or 1 day. In some embodiments, a compound is administered chronically on an ongoing basis, e.g., for the treatment of chronic effects.

A compound of the present disclosure, or a pharmaceutically acceptable salt, ester, prodrug, solvate, hydrate, or derivative thereof, may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

Compounds or pharmaceutically acceptable salts, esters, prodrugs, solvates, hydrates or derivatives thereof and pharmaceutical compositions of the present disclosure may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds may slow or inhibit the migration and proliferation of smooth muscle cells in the arterial wall, which contribute to restenosis. A compound of the present disclosure, or a pharmaceutically acceptable salt, ester, prodrug, solvate, hydrate, or derivative thereof, may be administered, for example, by local delivery from the struts of a stent, from a stent graft, from grafts, or from the cover or sheath of a stent. In some embodiments, a of the present disclosure, or a pharmaceutically acceptable salt, ester, prodrug, solvate, hydrate, or derivative thereof, is admixed with a matrix. Such a matrix may be a polymeric matrix and may serve to bond the compound to the stent. Polymeric matrices suitable for such use include, for example, lactone-based polyesters or copolyesters such as polylactide, polycaprolactonglycolide, polyorthoesters, polyanhydrides, polyaminoacids, polysaccharides, polyphosphazene, poly (ether-ester) copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be non-degrading or may degrade with time, releasing the compound or compounds. Compounds may be applied to the surface of the stent by various methods such as dip/spin coating, spray coating, dip-coating, and/or brush-coating. The compounds may be applied in a solvent and the solvent may be allowed to evaporate, thus forming a layer of the compound onto the stent. Alternatively, the compound may be located in the body of the stent or graft, for example, in microchannels or micropores. When implanted, the compound diffuses out of the body of the stent to contact the arterial wall. Such stents may be prepared by dipping a stent manufactured to contain such micropores or microchannels into a solution of the compound in a suitable solvent, followed by evaporation of the solvent. Excess drug on the surface of the stent may be removed via an additional brief solvent wash. In yet other embodiments, compounds may be covalently linked to a stent or graft. A covalent linker may be used, which degrades in vivo, leading to the release of the compound. Any bio-labile linkage may be used for such a purpose, such as an ester, amide, or anhydride linkages. Compounds may be additionally administered intravascularly from a balloon used during angioplasty. Extravascular administration of the compounds via the pericardial or adventitial application of formulations n may also be performed to decrease restenosis.

A variety of stent devices, which may be used as described, are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the present disclosure, or pharmaceutically acceptable salts, esters, prodrugs, solvates, hydrates, or derivatives thereof, may be administered in dosages. It is known in the art that due to intersubject variability in compound pharmacokinetics, individualization of the dosing regimen is necessary for optimal therapy. Dosing for a compound may be found by routine experimentation in light of the instant disclosure.

When a of the present disclosure, or a pharmaceutically acceptable salt, ester, prodrug, solvate, hydrate, or derivative thereof, is administered in a composition that comprises one or more agents, which has a shorter half-life than the compound unit dose forms of the agent and the compound may be adjusted accordingly.

The subject pharmaceutical composition may, for example, be in a form suitable for oral administration as a tablet, capsule, pill, powder, sustained-release formulations, solution, and suspension, for parenteral injection as a sterile solution, suspension or emulsion, for topical administration as an ointment or cream or for rectal administration as a suppository. The pharmaceutical composition may be in unit dosage forms suitable for the single administration of precise dosages. The pharmaceutical composition can include a conventional pharmaceutical carrier or excipient and a compound of the present disclosure, or a pharmaceutically acceptable salt, ester, prodrug, solvate, hydrate, or derivative thereof, as an active ingredient. In addition, it may include other medicinal or pharmaceutical agents, carriers, adjuvants, etc.

Exemplary parenteral administration forms include solutions or suspensions of active compounds of the present disclosure, in sterile aqueous solutions, for example, aqueous propylene glycol or dextrose solutions. Such dosage forms can be suitably buffered if desired.

Methods of Use

In some embodiments, the method comprises administering to a subject or a subject in need thereof an amount, such as a therapeutically effective amount, of a compound of the present disclosure, or a pharmaceutically acceptable salt or solvate thereof, or a pharmaceutical composition of the present disclosure. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "IC50" refers to the half-maximal inhibitory concentration of an inhibitor in inhibiting biological or biochemical function. This quantitative measure indicates how much of a particular inhibitor is needed to inhibit a given biological process (or component of a process, i.e., an enzyme, cell, cell receptor, or microorganism) by half. In other words, it is the half-maximal (50%) inhibitory concentration (IC) of a substance (50% IC, or IC50). EC50 refers to the plasma concentration required for obtaining 50% of a maximum effect in vivo.

In some embodiments, the subject methods utilize a BCL-2 inhibitor with an IC50 value of about or less than a predetermined value, as ascertained in an in vitro assay. In some embodiments, the BCL-2 inhibitor inhibits BCL-2 with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 µM or less, 1.1 µM or less, 1.2 µM or less, 1.3 µM or less, 1.4 µM or less, 1.5 µM or less, 1.6 µM or less, 1.7 µM or less, 1.8 µM or less, 1.9 µM or less, 2 µM or less, 5 µM or less, 10 µM or less, 15 µM or less, 20 µM or less, 25 µM or less, 30 µM or less, 40 µM or less, 50 µM, 60 µM, 70 µM, 80 µM, 90 µM, 100 µM, 200 µM, 300 µM, 400 µM, or 500 µM, or less, (or a number in the range defined by and including any two numbers above).

In some embodiments, the subject method of inhibiting the activity of BCL-2 protein comprises contacting the BCL-2 protein with an effective amount of a compound or a pharmaceutically acceptable salt thereof, as described herein.

In some embodiments, the BCL-2 inhibitor selectively inhibits BCL-2 with an IC50 value that is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two, or three other BCL-2 family proteins.

In some embodiments, the BCL-2 inhibitor selectively inhibits BCL-2 with an IC50 value that is less than about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, 1.1 µM, 1.2 µM, 1.3 µM, 1.4 µM, 1.5 µM, 1.6 µM, 1.7 µM, 1.8 µM, 1.9 µM, 2 µM, 5 µM, 10 µM, 15 µM, 20 µM, 25 µM, 30 µM, 40 µM, 50 µM, 60 µM, 70 µM, 80 µM, 90 µM, 100 µM, 200 µM, 300 µM, 400 µM, or 500 µM (or in the range defined by and including any two numbers above), and said IC50 value is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two or three other BCL-2 family proteins.

The subject methods are useful for treating a disease or disorder condition associated with BCL-2. Any disease or disorder condition that results directly or indirectly from an abnormal activity or expression level of BCL-2 can be an intended disease or disorder condition. In some embodiments, the said method for treating disease or disorder condition associated with BCL-2 in a subject or a subject in need thereof comprises administering to the subject, a compound of the present disclosure a pharmaceutically acceptable salt thereof, or a pharmaceutical composition thereof as described herein.

Different disease or disorder conditions associated with BCL-2 have been reported. BCL-2 has been implicated, for example, cancers, hyperproliferative diseases, autoimmune diseases, psychiatric disorders, or senescence-associated diseases and disorders, neoplastic diseases, and neurodegenerative diseases.

Non-limiting examples of such conditions include but are not limited to Acanthoma, Acinic cell carcinoma, Acoustic neuroma, Acral lentiginous melanoma, Acrospiroma, Acute eosinophilic leukemia, Acute lymphoblastic leukemia, Acute lymphocytic leukemia, Acute megakaryoblastic leukemia, Acute monocytic leukemia, Acute myeloblasts leukemia with maturation, Acute myeloid dendritic cell leukemia, Acute myeloid leukemia, Acute myelogenous leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastic Plasmacytoid Dendritic Cell Neoplasm, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epidermoid cancer, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Head and neck cancer, Heart cancer, Hemoglobinopathies such as b-thalassemia and sickle cell disease (SCD), Hemangioblastoma, Hemangiopericytoma, Hemangio sarcoma, Hematological malignancy, Hepatocellular carcinoma, Hepatosplenic T-cell lymphoma, Hereditary breast-ovarian cancer syndrome, Hodgkin Lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mastocytosis, Mediastinal germ cell tumor, Mediastinal tumor, Medullary thyroid cancer, Medulloblastoma, Medulloepithelioma, Melanoma, Meningioma, Merkel Cell Carcinoma, Mesothelioma Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Mycosis Fungoides, Myelodysplasia Disease, Myelodysplasia Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neurofibroma, Neuroma, Nodular melanoma, Non-Hodgkin Lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer Oropharyngeal Cancer, Osteosarcoma, Ovarian Cancer, Ovarian Epithelial Cancer, Ovarian Germ Cell Tumor, Ovarian Low Malignant Potential Tumor, Paget's disease of the breast, Pancoast tumor, Pancreatic Cancer Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene onChromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, and any combination thereof.

In some embodiments, said method is for treating a disease selected from the group consisting of tumor angiogenesis, chronic inflammatory diseases such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma cancer, ovarian cancer, breast cancer, lung cancer, pancreatic cancer, prostate cancer, colon cancer, and epidermoid cancer.

In other embodiments, said method is for treating a disease selected from the group consisting of breast cancer, lung cancer, pancreatic cancer, prostate cancer, colon cancer, ovarian cancer, uterine cancer, and cervical cancer. In some embodiments, the said method comprises administering to a subject or a subject in need thereof, a compound of the present disclosure or a pharmaceutically acceptable salt or pharmaceutical composition thereof as described herein.

In other embodiments, said method is for treating a disease selected from the group consisting of leukemia such as acute myeloid leukemia (AML), acute lymphocytic leukemia chronic myeloid leukemia, hairy cell leukemia, myelodysplasia, myeloproliferative disorders, acute myelogenous leukemia (AML), chronic myelogenous leukemia (CML), mastocytosis, and chronic lymphocytic leukemia (CLL), multiple myeloma (MM), myelodysplastic syndrome (MDS), and epidermoid cancer.

Compounds of the present disclosure, as well as pharmaceutical compositions comprising them, can be administered to treat any of the described diseases, alone or in combination with medical therapy. Medical therapies include, for example, surgery and radiotherapy (e.g., gamma-radiation, neutron beam radiotherapy, electron beam radiotherapy, proton therapy, brachytherapy, and systemic radioactive isotopes).

In other methods, compounds of the present disclosure, as well as pharmaceutical compositions comprising thereof, can be administered to treat any of the described diseases, alone or in combination with one or more other agents.

In other methods, the compounds of the present disclosure, as well as pharmaceutical compositions comprising thereof, can be administered in combination with agonists of nuclear receptor agents.

In other methods, the compounds of the present disclosure, as well as pharmaceutical compositions comprising thereof, can be administered in combination with nuclear receptor antagonist agents.

In other methods, the compounds of the present disclosure, as well as pharmaceutical compositions comprising thereof, can be administered in combination with an anti-proliferative agent.

Combination Therapies

For treating cancer and other proliferative diseases, the compounds of the present disclosure, as well as pharmaceutical compositions comprising thereof, can be used in combination with chemotherapeutic agents, agonists or antagonists of nuclear receptors, or other anti-proliferative agents. The compounds of the present disclosure, as well as pharmaceutical compositions comprising thereof, can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, all-trans retinoic acid, altretamine, anastrozole, arsenic trioxide, asparaginase, azacitidine, bendamustine, bevacizumab, bexarotene, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, diftitox, dexrazoxane, docetaxel, doxorubicin, dromostanolone propionate, eculizumab, epirubicin, erlotinib, estramustine, etoposide phosphate, etoposide, everolimus, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, midostaurin, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tagraxofusp-erzs, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinstat, zoledronate, and any combination thereof.

In some embodiments, the compounds of the present disclosure, or pharmaceutically acceptable salts, esters, prodrugs, solvates, hydrates, or derivatives thereof, as well as pharmaceutical compositions comprising thereof, can be used in combination with a therapeutic agent that targets an epigenetic regulator. Examples of epigenetic regulators include bromodomain inhibitors, histone lysine methyltransferase inhibitors, histone arginine methyl transferase inhibitors, histone demethylase inhibitors, histone deacetylase inhibitors, histone acetylase inhibitors, and DNA methyltransferase inhibitors. Histone deacetylase inhibitors include, e.g., vorinostat. Histone arginine methyl transferase inhibitors include inhibitors of protein arginine methyltransferases (PRMTs) such as PRMT5, PRMT1, and PRMT4. DNA methyltransferase inhibitors include inhibitors of DNMT1 and DNMT3.

In some embodiments, for treating cancer and other proliferative diseases, the compounds of the present disclosure, or pharmaceutically acceptable salts, esters, prodrugs, solvates, hydrates, or derivatives thereof, as well as pharmaceutical compositions comprising thereof, can be used in combination with targeted therapies, including JAK kinase inhibitors (e.g. Ruxolitinib, Fedratinib, Momelotinib), PI3 kinase inhibitors including PI3K-delta selective and broad spectrum PI3K inhibitors, MEK inhibitors, cyclin dependent kinase inhibitors including CDK-4/6 inhibitors and CDK-9 inhibitors, BRAF inhibitors, mTOR inhibitors, proteasome inhibitors (e.g. Bortezomib, Carfilzomib), HDAC inhibitors (e.g. panobinostat, vorinostat), DNA methyl transferase inhibitors, dexamethasone, bromo and extra terminal family member (BET) inhibitors, BTK inhibitors (e.g. ibrutinib, acalabrutinib), other BCL-2 inhibitors (e.g. venetoclax), dual BCL-2 family inhibitors (e.g. BCL-2/BCLxL), MCL1 inhibitors, PARP inhibitors, FLT3 inhibitors, IDH inhibitors (e.g. ivosidenib, enasidenib), IRAK inhibitors, MDM2 inhibitors (e.g. idasanutlin), Notch inhibitors, TRAIL receptor agonists, androgen receptor antagonists (e.g. flutamide, enzalutamide), endocrine therapy agents (also known as hormone therapy agents) including estrogen receptor (ER) modulators, aromatase inhibitors, and selective ER degraders, and LSD1 inhibitors.

In some embodiments, for treating cancer and other proliferative diseases, the compounds of the present disclosure, or pharmaceutically acceptable salts, esters, prodrugs, solvates, hydrates, or derivatives thereof, as well as pharmaceutical compositions comprising thereof, can be used in combination with at least one monoclonal antibody. In some embodiments, the monoclonal antibody is an anti-CD20 antibody, including ofatumumab and obinutuzumab, an anti-PD-1 antibody, or an anti-CTLA4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), or PDR001. In some embodiments, the anti-PD-1 monoclonal antibody is nivolumab or pembrolizumab. In some embodiments, the anti-PD1 antibody is pembrolizumab. In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, durvalumab, or BMS-935559. In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the chemotherapeutic agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

In some embodiments, for treating autoimmune or inflammatory conditions, the compound of the present disclosure, or a pharmaceutically acceptable salt, ester, prodrug, solvate, hydrate or derivative thereof, as well as a pharmaceutical composition comprising thereof, can be administered in combination with an immune suppressant such as fluocinolone acetonide (Retisert®), rimexolone (AL-2178, Vexol, Alcon), or cyclosporine (Restasis®).

In some embodiments, the compounds of the present disclosure, or pharmaceutically acceptable salts, esters, prodrugs, solvates, hydrates or derivatives thereof, as well as pharmaceutical compositions comprising thereof, are used in methods of prevention (prevent or preventing) or prophylaxis of the diseases, disorders, or conditions provided herein. In some embodiments, the compounds are used to prevent the recurrence of a condition or disease provided herein.

The present disclosure also provides the following non-limiting embodiments:

In order that the embodiments disclosed herein may be more efficiently understood, examples are provided below. It should be understood that these examples are for illustrative purposes only and are not to be construed as limiting the embodiments in any manner.

In some embodiments, the following embodiments are provided:
1. A compound having the formula of Formula (I) or a pharmaceutically acceptable salt or solvate thereof:

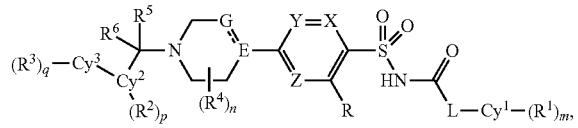

Formula (I)

wherein:
L is absent, $(CR^{29}R^{30})_k$, O, $NR^{15}$, optionally substituted cycloalkyl, optionally substituted heterocycloalkyl, optionally substituted aryl, or optionally substituted heteroaryl;
E is C, N, or $CR^{11}$, wherein when E is C, ==== is a double bond; when E is $CR^{11}$, ==== is a single bond; and when E is N, ==== is a single bond;
G is $CR^{16}$ or $CR^{16}R^{17}$, wherein when ==== is a double bond, G is $CR^{16}$;
X, Y, and Z are each, independently, N or $CR^{20}$;
$Cy^1$ and $Cy^2$ are each, independently, optionally substituted aryl, optionally substituted cycloalkyl, optionally substituted cycloalkenyl, optionally substituted heteroaryl, or optionally substituted heterocycloalkyl;
$Cy^3$ is optionally substituted aryl, optionally substituted cycloalkyl, or optionally substituted heteroaryl;
R is H, D, halo, optionally substituted $C_{1-6}$ alkyl, $OR^8$, $SR^8$, or $NR^9R^{10}$,

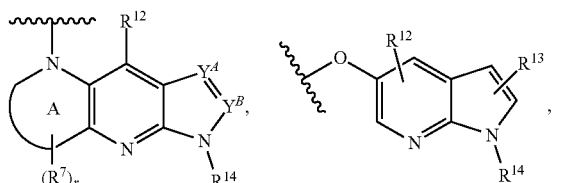

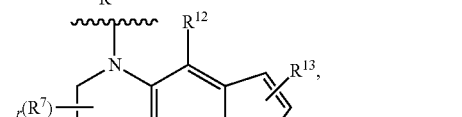

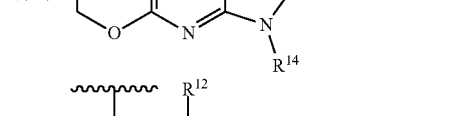

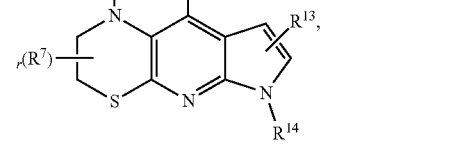

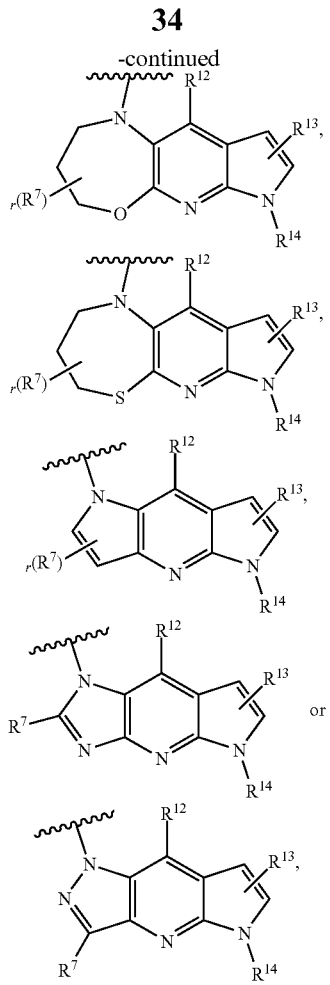

wherein ring A is a 4- to 14-membered heterocycle or heteroaryl containing at least one nitrogen;
$Y^A$ and $Y^B$ are each, independently, N, O, S, or $CR^{21}$;
$R^1$ is H, D, halo, oxo, $C_{1-6}$ alkyl, $C_{2-6}$ alkenyl, $C_{2-6}$ alkynyl, $C_{1-6}$ haloalkyl, CN, $NO_2$, $N_3$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^D$, $NR^CC(O)NR^CR^D$, $C(=NR^C)R^B$, $C(=NR^C)NR^CR^D$, $NR^CS(O)R^B$, $NR^CS(O)_2NR^CR^D$, $NR^CC(=NR^C)NR^CR^D$, $NR^CC(=NOR^A)NR^CR^D$, $NR^CC(=NCN)NR^CR^D$, $S(O)(=NR^C)R^B$, $S(O)(=NR^C)NR^CR^D$, $NR^CC(O)OR^A$, $P(O)R^ER^F$, $P(O)OR^EOR^F$, $OP(O)OR^EOR^F$, $SF_5$, $S(O)R^B$, $S(O)NR^CR^D$, $S(O)_2R^B$, $NR^CS(O)_2R^B$, $S(O)_2NR^CR^D$, $B(OR^A)_2$, $Cy^4$, $C_{1-6}$ alkyl-$Cy^4$, O—$C_{1-6}$ alkyl-$Cy^4$, or O—$C_{1-6}$ alkyl-$Cy^4$-$C_{0-6}$ alkyl-$Cy^5$, wherein said $C_{1-6}$ alkyl, $C_{2-6}$ alkenyl, $C_{2-6}$ alkynyl, $C_{1-6}$ haloalkyl, O—$C_{1-6}$ alkyl, $Cy^4$, and $Cy^5$ are each optionally substituted;
wherein two adjacent $R^1$, together with the atom or atoms to which they are attached, optionally form a fused 3- to 10-membered cycloalkyl ring or a fused 4- to 10-membered heterocycloalkyl ring, each of which is optionally substituted by 1, 2, 3, 4, 5, or 6 substituents, wherein each said substituent is independently D, halo, $C_{1-6}$ alkyl, $C_{2-6}$ alkenyl, $C_{2-6}$ alkynyl, $C_{1-6}$ haloalkyl, CN, $NO_2$, oxo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $C(=NR^c)NR^cR^d$, $NR^cS(O)R^b$, $NR^cS(O)_2NR^cR^d$, $NR^cC(=NR^c)NR^cR^d$, $NR^cC(=NOR^a)NR^cR^d$, $NR^cC(=NCN)NR^cR^d$, $S(O)(=NR^c)R^b$, $S(O)(=NR^c)NR^cR^d$, $NR^cC(O)OR^a$, $P(O)R^eR^f$, P(O)

$OR^eOR^f$, $OP(O)OR^eOR^f$, $S(O)R^b$, $S(O)NR^cR^d$, $S(O)_2R^b$, $NR^cS(O)_2R^b$, or $S(O)_2NR^cR^d$, $B(OR^a)_2$, aryl, cycloalkyl, heteroaryl, or heterocycloalkyl, wherein said $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl are each optionally substituted;

each $R^2$ is H, D, halo, oxo, $C_{1-6}$ alkyl, $C_{2-6}$ alkenyl, $C_{2-6}$ alkynyl, $C_{1-6}$ haloalkyl, $C_{1-6}$ haloalkoxy, cycloalkyl, heterocycloalkyl, CN, $NO_2$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^D$, $NR^CC(O)NR^CR^D$, $C(=NR^C)R^B$, $C(=NR^C)NR^CR^D$, $NR^CS(O)R^B$, $NR^CS(O)_2NR^CR^D$, $NR^CC(=NR^C)NR^CR^D$, $NR^CC(=NOR^A)NR^CR^D$, $NR^CC(=NCN)NR^CR^D$, $S(O)(=NR^C)R^B$, $S(O)(=NR^C)NR^CR^D$, $NR^CC(O)OR^A$, $P(O)R^ER^F$, $P(O)OR^EOR^F$, $OP(O)OR^EOR^F$, $SF_5$, $S(O)R^B$, $S(O)NR^CR^D$, $S(O)_2R^B$, $NR^CS(O)_2R^B$, $S(O)_2NR^CR^D$ or $B(OR^A)_2$;

wherein two $R^2$, together with the atom or atoms to which they are attached form a 3- to 7-membered cycloalkyl group or 4- to 7-membered heterocycloalkyl group, each of which is optionally substituted by 1, 2, or 3 substituents, wherein each said substituent is independently H, D, halo, $C_{1-6}$ alkyl, $C_{2-6}$ alkenyl, $C_{2-6}$ alkynyl, $C_{1-6}$ haloalkyl, $C_{1-6}$ alkyl $NR^cR^d$, CN, $NO_2$, oxo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $C(=NR^c)R^b$, $C(=NR^c)NR^cR^d$, $NR^cS(O)R^b$, $NR^cS(O)_2NR^cR^d$, $NR^cC(=NR^c)NR^cR^d$, $NR^cC(=NOR^a)NR^cR^d$, $NR^cC(=NCN)NR^cR^d$, $S(O)(=NR^c)R^b$, $S(O)(=NR^c)NR^cR^d$, $NR^cC(O)OR^a$, $P(O)R^eR^f$, $P(O)OR^e OR^f$, $S(O)R^b$, $S(O)NR^cR^d$, $S(O)_2R^b$, $NR^cS(O)_2R^b$, or $S(O)_2NR^cR^d$;

each $R^3$ is H, D, halo, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $Cy^4$, $C_{1-6}$ alkyl-$Cy^4$, CN, $NO_2$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^D$, $NR^CC(O)NR^CR^D$, $C(=NR^C)R^B$, $C(=NR^C)NR^CR^D$, $NR^CS(O)R^B$, $NR^CS(O)_2NR^CR^D$, $NR^CC(=NR^C)NR^CR^D$, $NR^CC(=NOR^A)NR^CR^D$, $NR^CC(=NCN)NR^CR^D$, $S(O)(=NR^C)R^B$, $S(O)(=NR^C)NR^CR^D$, $NR^CC(O)OR^A$, $P(O)R^ER^F$, $P(O)OR^EOR^F$, $OP(O)OR^EOR^F$, $SF_5$, $S(O)R^B$, $S(O)NR^CR^D$, $S(O)_2R^B$, $NR^CS(O)_2R^B$, $S(O)_2NR^CR^D$ or $B(OR^A)_2$;

wherein two $R^3$, together with the atom or atoms to which they are attached form a 3- to 7-membered cycloalkyl group or 4- to 7-membered heterocycloalkyl group, each of which is optionally substituted by 1, 2, or 3 substituents, wherein each said substituent is independently H, D, halo, $C_{1-6}$ alkyl, $C_{2-6}$ alkenyl, $C_{2-6}$ alkynyl, $C_{1-6}$ haloalkyl, $C_{1-6}$ alkyl $NR^cR^d$, CN, $NO_2$, oxo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $C(=NR^c)NR^cR^d$, $NR^cS(O)R^b$, $NR^cS(O)_2NR^cR^d$, $NR^cC(=NR^c)NR^cR^d$, $NR^cC(=NOR^a)NR^cR^d$, $NR^cC(=NCN)NR^cR^d$, $S(O)(=NR^c)R^b$, $S(O)(=NR^c)NR^cR^d$, $NR^cC(O)OR^a$, $P(O)R^eR^f$, $P(O)OR^eOR^f$, $S(O)R^b$, $S(O)NR^cR^d$, $S(O)_2R^b$, $NR^cS(O)_2R^b$, or $S(O)_2NR^cR^d$;

each $R^4$ is H, D, halo, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $Cy^4$, $C_{1-6}$ alkyl-$Cy^4$, CN, $NO_2$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^D$, $NR^CC(O)NR^CR^D$, $C(=NR^C)R^B$, $C(=NR^C)NR^CR^D$, $NR^CS(O)R^B$, $NR^CS(O)_2NR^CR^D$, $NR^CC(=NR^C)NR^CR^D$, $NR^CC(=NOR^A)NR^CR^D$, $NR^CC(=NCN)NR^CR^D$, $S(O)(=NR^C)R^B$, $S(O)(=NR^C)NR^CR^D$, $NR^CC(O)OR^A$, $P(O)R^ER^F$, $P(O)OR^EOR^F$, $OP(O)OR^EOR^F$, $SF_5$, $S(O)R^B$, $S(O)NR^CR^D$, $S(O)_2R^B$, $NR^CS(O)_2R^B$, $S(O)_2NR^CR^D$ or $B(OR^A)_2$;

wherein two $R^4$, together with the atom or atoms to which they are attached form a 3- to 7-membered cycloalkyl group or 4- to 7-membered heterocycloalkyl group, each of which is optionally substituted by 1, 2, or 3 substituents, wherein each said substituent is independently H, D, halo, $C_{1-6}$ alkyl, $C_{2-6}$ alkenyl, $C_{2-6}$ alkynyl, $C_{1-6}$ haloalkyl, $C_{1-6}$ alkyl $NR^cR^d$, CN, $NO_2$, oxo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $C(=NR^c)R^b$, $C(=NR^c)NR^cR^d$, $NR^cS(O)R^b$, $NR^cS(O)_2NR^cR^d$, $NR^cC(=NR^c)NR^cR^d$, $NR^cC(=NOR^a)NR^cR^d$, $NR^cC(=NCN)NR^cR^d$, $S(O)(=NR^c)R^b$, $S(O)(=NR^c)NR^cR^d$, $NR^cC(O)OR^a$, $P(O)R^eR^f$, $P(O)OR^e-OR^f$, $S(O)R^b$, $S(O)NR^cR^d$, $S(O)_2R^b$, $NR^cS(O)_2R^b$, or $S(O)_2NR^cR^d$;

$R^5$, $R^6$, $R^7$, $R^{11}$, $R^{12}$, $R^{13}$, $R^{14}$, $R^{15}$, $R^{16}$, $R^{17}$, $R^{29}$, and $R^{30}$ are each, independently, absent, H, D, halo, oxo, $C_{1-6}$ alkyl, $C_{2-6}$ alkenyl, $C_{2-6}$ alkynyl, $C_{1-6}$ haloalkyl, $C_{3-6}$ cycloalkyl, CN, $NO_2$, $C(O)NR^CR^D$, $C(O)OR^A$ or $B(OR^A)_2$;

wherein $R^5$ and $R^6$, together with the atom or atoms to which they are attached form a 3- to 7-membered cycloalkyl group or 4- to 7-membered heterocycloalkyl group, each of which is optionally substituted by 1, 2, or 3 substituents, wherein each said substituent is independently H, D, halo, $C_{1-6}$ alkyl, $C_{2-6}$ alkenyl, $C_{2-6}$ alkynyl, $C_{1-6}$ haloalkyl, $C_{1-6}$ alkyl $NR^cR^d$, CN, $NO_2$, oxo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $C(=NR^c)R^b$, $C(=NR^c)NR^cR^d$, $NR^cS(O)R^b$, $NR^cS(O)_2NR^cR^d$, $NR^cC(=NR^c)NR^cR^d$, $NR^cC(=NOR^a)NR^cR^d$, $NR^cC(=NCN)NR^cR^d$, $S(O)(=NR^c)R^b$, $S(O)(=NR^c)NR^cR^d$, $NR^cC(O)OR^a$, $P(O)R^eR^f$, $P(O)OR^eOR^f$, $S(O)R^b$, $S(O)NR^cR^d$, $S(O)_2R^b$, $NR^cS(O)_2R^b$, or $S(O)_2NR^cR^d$;

$R^8$, $R^9$, and $R^{10}$ are each, independently, H, D, $C_{1-6}$ alkyl, $C_{2-6}$ alkenyl, $C_{2-6}$ alkynyl, $C_{1-6}$ haloalkyl, $Cy^4$, $Cy^4$-$C_{1-4}$ alkyl, wherein said $C_{1-4}$ alkyl, $C_{1-6}$ alkyl, $C_{2-6}$ alkenyl, $C_{2-6}$ alkynyl, $C_{1-6}$ haloalkyl, and $Cy^4$ are each optionally substituted;

wherein $R^9$ and $R^{10}$ together with the N atom to which they are attached, optionally form a fused 4- to 14-membered heterocycloalkyl ring or 4- to 14-membered heteroaryl ring, each of which is optionally substituted by 1, 2, or 3 substituents, wherein each said substituent is independently H, D, halo, $C_{1-6}$ alkyl, $C_{2-6}$ alkenyl, $C_{2-6}$ alkynyl, $C_{1-6}$ haloalkyl, CN, $NO_2$, oxo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $C(=NR^c)R^b$, $C(=NR^c)NR^cR^d$, $NR^cS(O)R^b$, $NR^cS(O)_2NR^cR^d$, $NR^cC(=NR^c)NR^cR^d$, $NR^cC(=NOR^a)NR^cR^d$, $NR^cC(=NCN)NR^cR^d$, $S(O)(=NR^c)R^b$, $S(O)(=NR^c)NR^cR^d$, $NR^cC(O)OR^a$, $OP(O)OR^eOR^f$, $P(O)OR^eOR^f$, $S(O)R^b$, $S(O)NR^cR^d$, $S(O)_2R^b$, $NR^cS(O)_2R^b$, or $S(O)_2NR^cR^d$;

$R^{20}$ and $R^{21}$ are each, independently, H, D, halo, $C_{1-6}$ alkyl, $C_{2-6}$ alkenyl, $C_{2-6}$ alkynyl, $C_{1-6}$ haloalkyl, $C_{3-6}$ cycloalkyl, CN, $NO_2$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^D$, $NR^CC(O)NR^CR^D$, $C(=NR^C)R^B$, $C(=NR^C)NR^CR^D$, $NR^CS(O)R^B$, $NR^CS(O)_2NR^CR^D$, $NR^CC(=NR^C)NR^CR^D$, $NR^CC(=NOR^A)NR^CR^D$, $NR^CC(=NCN)NR^CR^D$, $S(O)(=NR^C)R^B$, $S(O)(=NR^C)NR^CR^D$, $NR^CC(O)OR^A$, $SF_5$, $S(O)R^B$, S(O)NR^C R^D, S(O)_2R^B, NR^C S(O)_2R^B, S(O)_2NR^C R^D, NR^C S(O)_2NR^C R^D or B(OR^A)_2;

Cy^4 and Cy^5 are each, independently, aryl, cycloalkyl, heterocycloalkyl, heteroaryl, or heterocycloalkyl;

each R^A is independently H, C_{1-6} alkyl, C_{2-4} alkenyl, C_{2-4} alkynyl, Cy^4, or C_{1-6} alkyl-Cy^4, wherein said C_{1-6} alkyl, C_{2-4} alkenyl, C_{2-4} alkynyl, C_{1-6} alkyl-Cy^4, and Cy^4 are optionally substituted with 1, 2, or 3 substituents, wherein each said substituent is independently OH, CN, halo, C_{1-4} alkyl; NO_2, oxo, OR^a, SR^a, C(O)R^b, C(O)NR^c R^d, C(O)OR^a, OC(O)R^b, OC(O)NR^c R^d, NR^c R^d, NR^c C(O)R^b, NR^c C(O)NR^c R^d, C(=NR^e)R^b, C(=NR^e)NR^c R^d, NR^c S(O)R^b, NR^c S(O)_2NR^c R^d, NR^c C(=NR^e)NR^c R^d, NR^c C(=NOR^a)NR^c R^d, NR^c C(=NCN)NR^c R^d, S(O)(=NR^e)R^b, S(O)(=NR^e)NR^c R^d, NR^c C(O)OR^a, OP(O)OR^e OR^f, P(O)OR^e OR^f, S(O)R^b, S(O)NR^c R^d, S(O)_2R^b, NR^c S(O)_2R^b, or S(O)_2NR^c R^d;

each R^B is independently H, C_1-C_6 alkyl, C_{2-4} alkenyl, C_{2-4} alkynyl, or Cy^4, wherein said C_1-C_6 alkyl, C_{2-4} alkenyl, C_{2-4} alkynyl, and Cy^4 are optionally substituted with 1, 2, or 3 substituents, wherein each said substituent is independently OH, CN, amino, alkylamino, dialkylamino, halo, or C_1-C_4 alkyl;

each R^C and each R^D are independently H, C_{1-6} alkyl, C_{2-4} alkenyl, or C_{2-4} alkynyl, wherein said C_{1-6} alkyl, C_{2-4} alkenyl, and C_{2-4} alkynyl are optionally substituted with 1, 2, or 3 substituents, wherein each said substituent is independently OH, CN, amino, alkylamino, dialkylamino, halo, or C_{1-4} alkyl;

or R^C and R^D together with the N atom to which they are attached form a 4-, 5-, 6- or 7-membered heterocycloalkyl group or heteroaryl group, each of which is optionally substituted with 1, 2, or 3 substituents, wherein each said substituent is independently OH, CN, amino, alkylamino, dialkylamino, halo, or C_{1-4} alkyl;

each R^E and each R^e are independently H, C_{1-4} alkyl, C_{1-4} haloalkyl, C_{2-4} alkenyl, (C_{1-4} alkoxy)-C_{1-4} alkyl, C_{2-4} alkynyl, aryl, cycloalkyl, heteroaryl, heterocycloalkyl, arylalkyl, cycloalkylalkyl, heteroarylalkyl, or heterocycloalkylalkyl;

each R^F and each R^f are independently H, C_{1-4} alkyl, C_{2-4} alkenyl, C_{2-4} alkynyl, aryl, cycloalkyl, heteroaryl, or heterocycloalkyl;

each R^a and each R^b are independently H, D, C_{1-4} alkyl, C_{1-4} haloalkyl, C_{2-4} alkenyl, C_{2-4} alkynyl, aryl, cycloalkyl, heteroaryl, heterocycloalkyl, arylalkyl, heteroarylalkyl, cycloalkylalkyl, or heterocycloalkylalkyl, wherein said C_{1-4} alkyl, C_{1-4} haloalkyl, C_{2-4} alkenyl, C_{2-4} alkynyl, aryl, cycloalkyl, heteroaryl, heterocycloalkyl, arylalkyl, heteroarylalkyl, cycloalkylalkyl, and heterocycloalkylalkyl are optionally substituted with 1, 2, or 3 substituents, wherein each said substituent is independently OH, CN, amino, alkylamino, dialkylamino, halo, C_{1-4} alkyl, C_{1-4} alkoxy, C_{1-4} haloalkyl, or C_{1-4} haloalkoxy;

each R^c and each R^d are independently H, C_{1-4} alkyl, C_{1-4} haloalkyl, C_{2-4} alkenyl, C_{2-4} alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, or biheteroaryl, wherein said C_{1-4} alkyl, C_{1-4} haloalkyl, C_{2-4} alkenyl, C_{2-4} alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl are optionally substituted with 1, 2, or 3 substituents, wherein each said substituent is independently OH, CN, amino, alkylamino, dialkylamino, halo, C_{1-4} alkyl, C_{1-4} alkoxy, C_{1-4} haloalkyl, C_{1-4} haloalkoxy, C_{1-4} hydroxyalkyl, C_{1-4} cyanoalkyl, aryl, heteroaryl, C(O)OR^{a2}, C(O)R^{b2}, S(O)_2R^{b2}, alkoxyalkyl, or alkoxyalkoxy;

or R^c and R^d together with the N atom to which they are attached form a 4-, 5-, 6- or 7-membered heterocycloalkyl group or heteroaryl group, each of which is optionally substituted with 1, 2, or 3 substituents, wherein each said substituent is independently OH, CN, amino, alkylamino, dialkylamino, halo, C_{1-4} alkyl, C_{1-4} alkoxy, C_{1-4} haloalkyl, C_{1-4} haloalkoxy, hydroxyalkyl, cyanoalkyl, aryl, heteroaryl, C(O)OR^{a2}, C(O)R^{b2}, S(O)_2R^{b2}, alkoxyalkyl, or alkoxyalkoxy;

each R^{a2} and each R^{b2} are independently H, D, C_{1-4} alkyl, C_{1-4} haloalkyl, C_{2-4} alkenyl, C_{2-4} alkynyl, aryl, cycloalkyl, heteroaryl, heterocycloalkyl, arylalkyl, heteroarylalkyl, cycloalkylalkyl, or heterocycloalkylalkyl, wherein said C_{1-4} alkyl, C_{1-4} haloalkyl, C_{2-4} alkenyl, C_{2-4} alkynyl, aryl, cycloalkyl, heteroaryl, heterocycloalkyl, arylalkyl, heteroarylalkyl, cycloalkylalkyl, and heterocycloalkylalkyl are optionally substituted with 1, 2, or 3 substituents, wherein each said substituent is independently OH, CN, amino, alkylamino, dialkylamino, halo, C_{1-4} alkyl, C_{1-4} alkoxy, C_{1-4} haloalkyl, or C_{1-4} haloalkoxy;

m is 0-5;

n is 0-8;

p, q, and r are each, independently, 0-6; and k is 0-3, wherein when k is 2 or 3, each R^{29} is independent from any other R^{29} and each R^{30} is independent from any other R^{30}.

2. The compound of embodiment 1, or a pharmaceutically acceptable salt or solvate thereof, wherein X is CH.

3. The compound of any one of embodiments 1-2 or a pharmaceutically acceptable salt or solvate thereof, wherein Y is CH.

4. The compound of any one of embodiments 1-3, or a pharmaceutically acceptable salt or solvate thereof, wherein Z is CH.

5. The compound of any one of embodiments 1-4, or a pharmaceutically acceptable salt or solvate thereof, wherein Cy^2 is optionally substituted cycloalkenyl or optionally substituted cycloalkyl;

6. The compound of any one of embodiments 1-5, or a pharmaceutically acceptable salt or solvate thereof, wherein Cy^3 is optionally substituted aryl or optionally substituted heteroaryl.

7. The compound of any one of embodiments 1-6, or a pharmaceutically acceptable salt or solvate thereof, wherein Cy^1 is optionally substituted

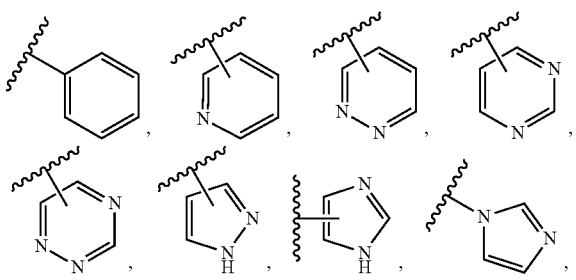

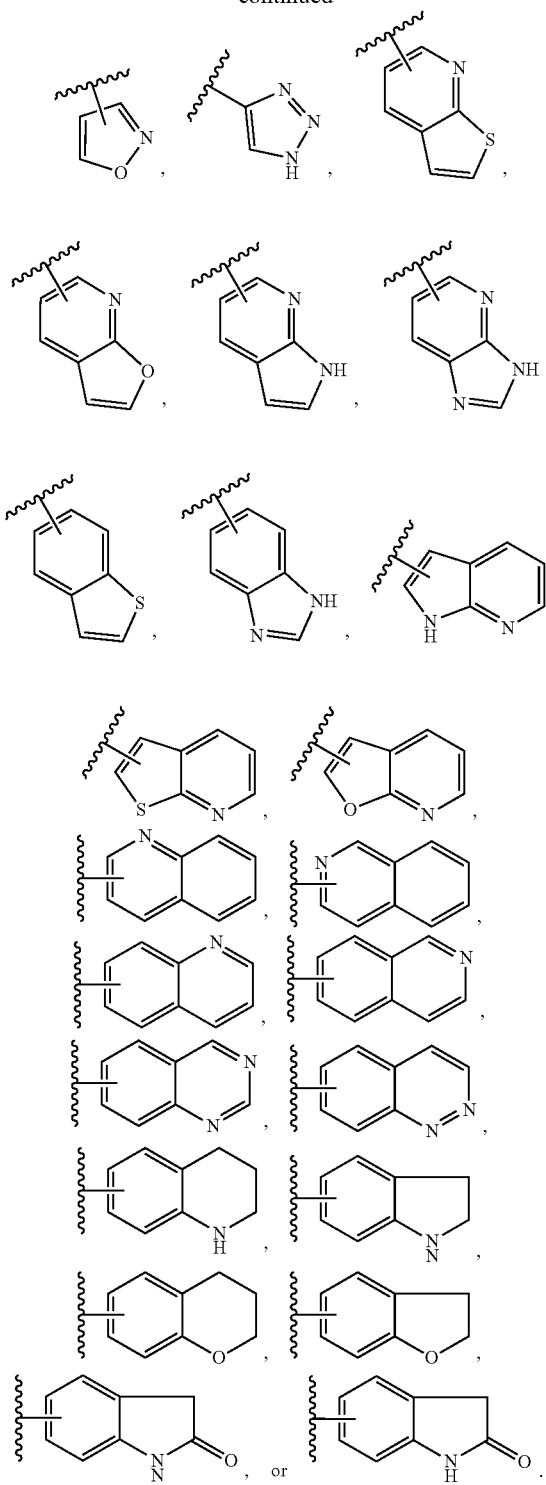

8. The compound of any one of embodiments 1-7, or a pharmaceutically acceptable salt or solvate thereof, wherein $R^1$ is U—$V^A$—$W^A$, where U is absent, $CR^{29}R^{30}$, $OCR^{29}R^{30}$, $(CR^{29}R^{30})_{nn}N$, or $N(CR^{29}R^{30})_{nn}$, wherein $R^{29}$ and $R^{30}$ are as defined in embodiment 1 and nn is 0-10; $V^A$ is absent, heterocycle, cycloalkyl, heterocycloalkyl, aryl, or heteroaryl; $W^A$ is H, D, F, Br, Cl, I, $NO_2$, optionally substituted $C_{1-6}$ alkyl, optionally substituted $C_{1-6}$ alkoxy wherein $R^{1C}$ is H, D, halo, CN, $NO_2$, $OR^{a3}$, $SR^{a3}$, $NHOR^{a3}$, $C(O)R^{a3}$, $C(O)NR^{a3}R^{b3}$, $C(O)OR^{a3}$, $OC(O)R^{a3}$, $OC(O)NR^{a3}R^{b3}$, $NHR^{a3}$, $NR^{a3}R^{b3}$, $NR^{a3}C(O)R^{a3}$, $NR^{a3}C(O)OR^{a3}$, $NR^{a3}C(O)NR^{a3}R^{b3}$, $C(=NR^{a3})R^{a3}$, $C(=NR^{a3})NR^{a3}R^{b3}$, $NR^{a3}C(=NR^{a3})NR^{a3}R^{b3}$, $NR^{a3}C(=NOH)NR^{a3}R^{b3}$, $NR^{a3}C(=NCN)NR^{a3}R^{b3}$, $NR^{a3}S(O)R^{a3}$, $NR^{a3}S(O)_2R^{a3}$, $NR^{a3}S(O)_2NR^{a3}R^{b3}$, $S(O)R^{a3}$, $S(O)NR^{a3}R^{b3}$ $S(O)_2R^{a3}$, $SF_5$, $P(O)R^{a3}R^{b3}$, $P(O)(OR^{a3})(OR^{b3})$, $B(OR^{a3})_2$, or $S(O)_2NR^{a3}R^{b3}$, or optionally substituted $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5- to 10-membered heteroaryl, 4- to 14-membered heterocycloalkyl, $C_{6-10}$ aryl- $C_{1-4}$ alkyl, $C_{3-10}$ cycloalkyl$C_{1-4}$ alkyl, (5- to 14-membered heteroaryl)-$C_{1-4}$ alkyl, or (4- to 14-membered heterocycloalkyl)-$C_{1-4}$ alkyl, wherein each $R^{a3}$ and each $R^{b3}$ are independently H, D, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl are optionally substituted with 1, 2, or 3 substituents, wherein each said substituent is independently OH, CN, amino, halo, $C_{1-6}$ alkyl, $C_{1-6}$ alkoxy, $C_{1-6}$ haloalkyl, and $C_{1-6}$ haloalkoxy, $C_{3-10}$ cycloalkyl, $C_{1-6}$ heteroalkyl, 3- to 12-membered heterocyclyl, $C_{6-10}$ aryl, 5- to 10-membered heteroaryl, C(O)H, C(O)NH$_2$, C(O)NH(C$_{1-6}$ alkyl), C(O)N(C$_{1-6}$ alkyl)$_2$, COOH, C(O)C$_{1-6}$ alkyl, or C(O)OC$_{1-6}$ alkyl and W is 0 to 6.

9. The compound any one of embodiment 1-8, or a pharmaceutically acceptable salt or solvate thereof, wherein E is N.

10. The compound any one of embodiment 1-8, or a pharmaceutically acceptable salt or solvate thereof, wherein E is CR$^{11}$.

11. The compound of any one of embodiment or a pharmaceutically acceptable salt or solvate thereof, wherein E is C and ≡≡≡ is a double bond.

12. The compound of embodiment 11, or a pharmaceutically acceptable salt or solvate thereof, wherein G is CH and ≡≡≡ is a double bond.

13. The compound of any one of embodiment 1-12, or a pharmaceutically acceptable salt or solvate thereof, wherein L is absent.

14. The compound of any one of embodiments 1-9, or a pharmaceutically acceptable salt or solvate thereof, wherein the compound has the formula of

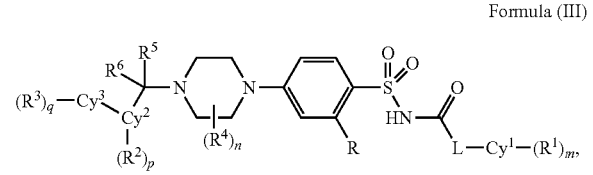

Formula (III)

wherein the variables are as defined in any one of embodiments 1-8.

15. The compound of embodiment 14, or a pharmaceutically acceptable salt or solvate thereof, wherein L is absent.

16. The compound of any one of embodiments 14-15, or a pharmaceutically acceptable salt or solvate thereof, wherein the compound has the formula of

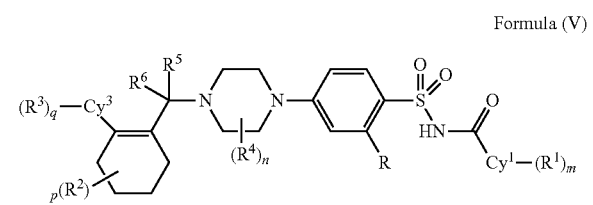

Formula (V)

wherein the variables are as defined in any one of embodiments 1-8.

17. The compound of embodiment 16, or a pharmaceutically acceptable salt or solvate thereof, wherein R$^5$ and R$^6$ are H.

18. The compound of any one of embodiments 1-9 and 14-17, or a pharmaceutically acceptable salt or solvate thereof, wherein the compound has the formula of

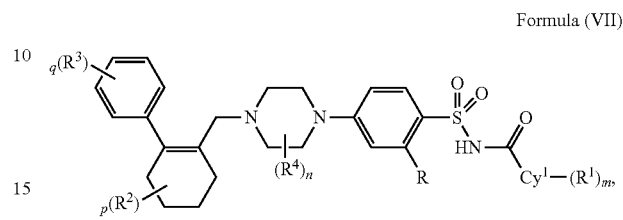

Formula (VII)

wherein the variables are as defined in any one of embodiments 1-8.

19. The compound of any one of embodiments 1-9 and 14-18, or a pharmaceutically acceptable salt or solvate thereof, wherein the compound has the formula of

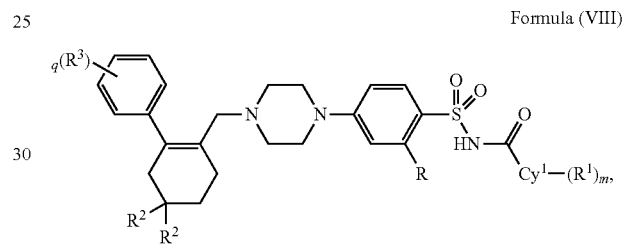

Formula (VIII)

wherein the variables are as defined in any one of embodiments 1-8.

20. The compound of any one of embodiments 1-9 and 14-19, or a pharmaceutically acceptable salt or solvate thereof, wherein the compound has the formula of

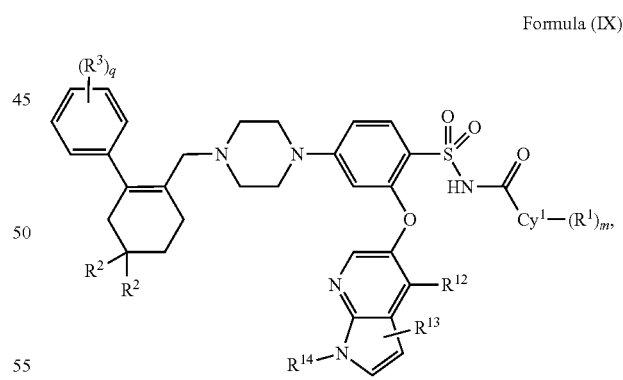

Formula (IX)

wherein the variables are as defined in any one of embodiments 1-8.

21. The compound of any one of embodiments 1-9 and 14-20, or a pharmaceutically acceptable salt or solvate thereof, wherein R$^3$ is halo.

22. The compound of any one of embodiments 1-9 and 14-21, or a pharmaceutically acceptable salt or solvate thereof, wherein q is 1.

23. The compound of any one of embodiments 1-9 and 14-22, or a pharmaceutically acceptable salt or solvate thereof, wherein R$^3$ is Cl.

24. The compound of embodiment 23, or a pharmaceutically acceptable salt or solvate thereof, wherein $R^{12}$ and $R^{13}$ are both H.

25. The compound of any one of embodiments 1-9 and 14-24, or a pharmaceutically acceptable salt or solvate thereof, wherein each $R^2$ is, independently, optionally substituted $C_{1-6}$ alkyl.

26. The compound of any one of embodiments 1-9 and 14-25, or a pharmaceutically acceptable salt or solvate thereof, wherein each $R^2$ is, independently, optionally substituted $C_{1-3}$ alkyl.

27. The compound of any one of embodiments 1-9 and 14-26, or a pharmaceutically acceptable salt or solvate thereof, wherein the compound has the formula of

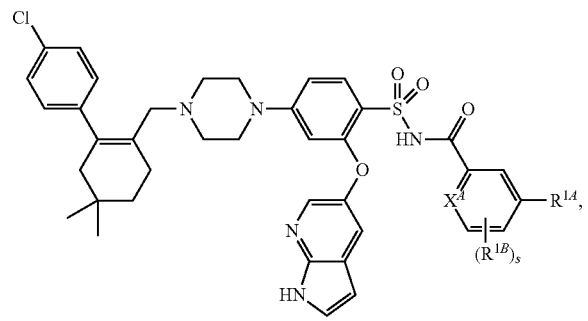

Formula (XII)

wherein:

$X^A$ is $CR^{1D}$ or N;

$R^{1A}$ is H, D, Me, $CF_3$, F, Cl, Br, OMe, $NO_2$, $SO_2Me$, or $SO_2CF_3$;

each $R^{1B}$ and $R^{1D}$ are each, independently, H, D, halo, oxo, $C_{1-6}$ alkyl, $C_{2-6}$ alkenyl, $C_{2-6}$ alkynyl, $C_{1-6}$ haloalkyl, CN, $NO_2$, $N_3$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^D$, $NR^CC(O)NR^CR^D$, $C(=NR^C)R^B$, $C(=NR^C)NR^CR^D$, $NR^CS(O)R^B$, $NR^CS(O)_2NR^CR^D$, $NR^CC(=NR^C)NR^CR^D$, $NR^CC(=NOR^A)NR^CR^D$, $NR^CC(=NCN)NR^CR^D$, $S(O)(=NR^C)R^B$, $S(O)(=NR^C)NR^CR^D$, $NR^CC(O)OR^A$, $P(O)R^ER^F$, $P(O)OR^EOR^F$, $OP(O)OR^EOR^F$, $SF_5$, $S(O)R^B$, $S(O)NR^CR^D$, $S(O)_2R^B$, $NR^CS(O)_2R^B$, $S(O)_2NR^CR^D$, $B(OR^A)_2$, $Cy^4$, $C_{1-6}$ alkyl-$Cy^4$, O—$C_{1-6}$ alkyl-$Cy^4$, or O—$C_{1-6}$ alkyl-$Cy^4$-$C_{0-6}$ alkyl-$Cy^5$, wherein said $Cy^4$, $C_{1-6}$ alkyl-$Cy^4$, O—$C_{1-6}$ alkyl-$Cy^4$, O—$C_{1-6}$ alkyl-$Cy^4$-$C_{0-6}$ alkyl-$Cy^5$, and $Cy^5$ are optionally substituted;

wherein two $R^{1B}$, one $R^{1B}$ and $R^{1A}$, or one $R^{1B}$ and one $R^{1D}$, together with the atom or atoms to which they are attached, optionally form a fused 4- to 10-membered cycloalkyl ring or a fused 4- to 10-membered heterocycloalkyl ring, each of which is optionally substituted by 1, 2, or 3 substituents, wherein each said substituent is independently halo, $C_{1-6}$ alkyl, $C_{2-6}$ alkenyl, $C_{2-6}$ alkynyl, $C_{1-6}$haloalkyl, CN, $NO_2$, oxo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $C(=NR^c)R^b$, $C(=NR^c)NR^cR^d$, $NR^cS(O)R^b$, $NR^cS(O)_2NR^cR^d$, $NR^cC(=NR^c)NR^cR^d$, $NR^cC(=NOR^a)NR^cR^d$, $NR^cC(=NCN)NR^cR^d$, $S(O)(=NR^c)R^b$, $S(O)(=NR^c)NR^cR^d$, $NR^cC(O)OR^a$, $P(O)R^eR^f$, $P(O)OR^eOR^f$, $OP(O)OR^eOR^f$, $S(O)R^b$, $S(O)NR^cR^d$, $S(O)_2R^b$, $NR^cS(O)_2R^b$, or $S(O)_2NR^cR^d$, $B(OR^a)_2$, aryl, cycloalkyl, heteroaryl, or heterocycloalkyl and s is 0-3; and $R^A$, $R^B$, $R^C$, $R^D$, $R^E$, $R^F$, $R^a$, $R^b$, $R^c$, $R^d$, $R^e$, $R^f$, $Cy^4$, and $Cy^5$ are as defined in any one of embodiments 1-8.

28. The compound of embodiment 27, or a pharmaceutically acceptable salt or solvate thereof, wherein $R^{1B}$ is H, D, F, Br, Cl, I, $NO_2$, $C_{1-6}$ alkyl, $C_{1-6}$ alkoxy, or O—$C_{1-6}$ alkyl-$Cy^4$, wherein said $C_{1-6}$ alkyl, $C_{1-6}$ alkoxy, or O—$C_{1-6}$ alkyl-$Cy^4$ is optionally substituted by 1, 2, or 3 substituents, wherein each said substituent is independently is H, D, halo, CN, $NO_2$, $OR^a$, $SR^a$, $NHOR^a$, $C(O)R^b$, $C(O)NR^cR^d$, $C(O)OR^a$, $OC(O)R^a$, $OC(O)NR^cR^d$, $NHR^c$, $NR^cR^d$, $NR^c(O)R^b$, $NR^c(O)OR^a$, $NR^cC(O)NR^cR^d$, $C(=NR^c)R^b$, $C(=NR^c)NR^cR^d$, $NR^cS(O)R^b$, $NR^cS(O)_2NR^cR^d$, $NR^cC(=NR^c)NR^cR^d$, $NR^cC(=NOR^a)$ $NR^cR^d$, $NR^cC(=NCN)NR^cR^d$, $S(O)(=NR^c)R^b$, $S(O)$ $(=NR^c)NR^cR^d$, $C(=NR^c)R^d$, $C(=NR^c)NR^cR^d$, $NR^cC(=NR^d)NR^cR^d$, $NR^cC(=NOH)NR^cR^d$, $NR^dC(=NCN)NR^cR^d$, $NR^cS(O)R^b$, $NR^cS(O)_2R^a$, $NR^cS(O)_2NR^cR^d$, $S(O)R^b$, $S(O)NR^cR^{da}S(O)_2R^b$, $SF_5$, $P(O)R^eR^f$, $P(O)(OR^e)$ $(OR^f)$, $B(OR^a)_2$ and $S(O)_2NR^cR^d$ or optionally substituted $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5- to 10-membered heteroaryl, 4- to R714-membered heterocycloalkyl, $C_{6-10}$ aryl-$C_{1-4}$ alkyl, $C_{3-10}$ cycloalkyl$C_{1-4}$alkyl, (5- to 14-membered heteroaryl)-$C_{1-4}$ alkyl, or (4- to 14-membered heterocycloalkyl)-$C_{14}$ alkyl; and $R^a$, $R^b$, $R^c$, $R^d$, $R^e$, and $R^f$ are as defined in any one of embodiments 1-8.

29. The compound of any one of embodiments 27-28, or a pharmaceutically acceptable salt or solvate thereof, wherein $X^A$ is N.

30. The compound of any one of embodiments 27-28, or a pharmaceutically acceptable salt or solvate thereof, wherein $X^A$ is CH.

31. The compound of embodiment 19, or a pharmaceutically acceptable salt or solvate thereof, wherein R is H.

32. The compound of embodiment 31, or a pharmaceutically acceptable salt or solvate thereof, wherein $R^3$ is halo.

33. The compound of any one of embodiments 31-32, or a pharmaceutically acceptable salt or solvate thereof, wherein q is 1.

34. The compound of any one of embodiments 31-33, or a pharmaceutically acceptable salt or solvate thereof, wherein $R^3$ is Cl.

35. The compound of any one of embodiments 31-34, or a pharmaceutically acceptable salt or solvate thereof, wherein each $R^2$ is, independently, optionally substituted $C_{1-6}$ alkyl.

36. The compound of any one of embodiments 31-35, or a pharmaceutically acceptable salt or solvate thereof, wherein each $R^2$ is, independently, optionally substituted $C_{1-3}$ alkyl.

37. The compound of any one of embodiments 1-9 and 14-19, or a pharmaceutically acceptable salt or solvate thereof, wherein the compound has the formula of

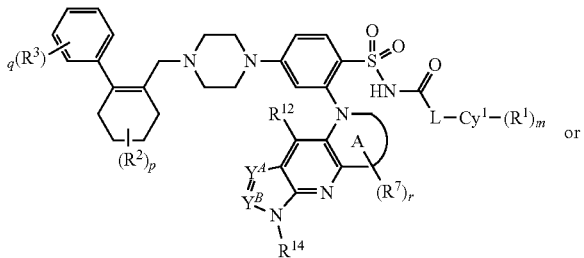

Formula (XX)

or

-continued

Formula (XX-I)

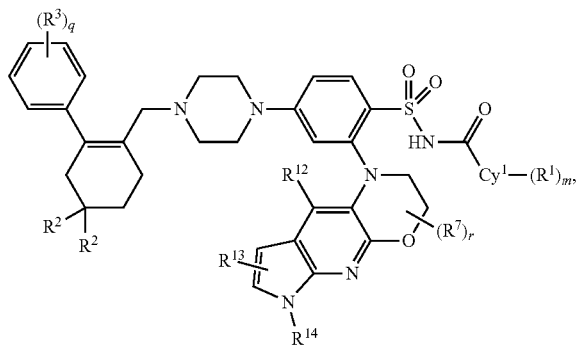

wherein the variables are as defined in any one of embodiments 1-8.

38. The compound of embodiment 37, or a pharmaceutically acceptable salt or solvate thereof, wherein $R^3$ is halo.

39. The compound of any one of embodiments 37-38, or a pharmaceutically acceptable salt or solvate thereof, wherein q is 1.

40. The compound of any one of embodiments 37-38, or a pharmaceutically acceptable salt or solvate thereof, wherein the compound has the formula of Formula (XXI)

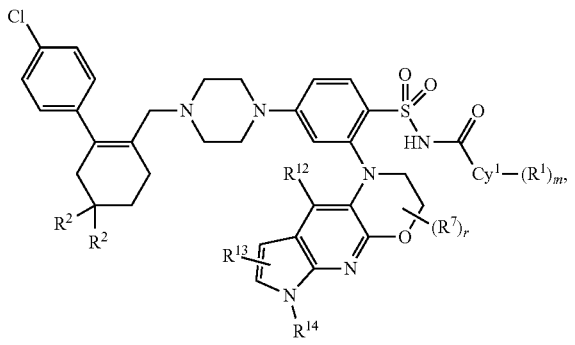

wherein the variables are as defined in any one of embodiments 1-8.

41. The compound of any one of embodiments 37-40, or a pharmaceutically acceptable salt or solvate thereof, wherein the compound has the formula of Formula (XXII)

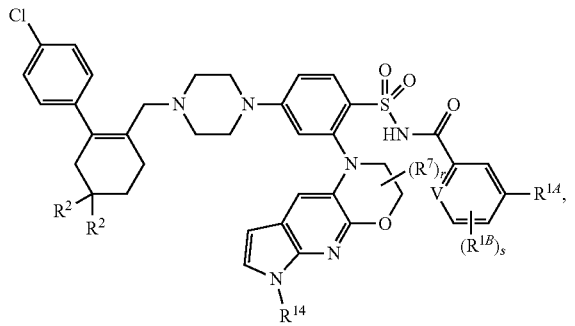

wherein:
V is $CR^{1D}$ or N;
$R^{14}$ is H, D, Me, $CF_3$, F, Cl, Br, OMe, $NO_2$, $SO_2Me$, or $SO_2CF_3$;
$R^{1B}$ and $R^{1D}$ are each, independently, H, D, halo, oxo, $C_{1-6}$ alkyl, $C_{2-6}$ alkenyl, $C_{2-6}$ alkynyl, $C_{1-6}$ haloalkyl, CN, $NO_2$, $N_3$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^D$, $NR^CC(O)NR^CR^D$, $C(=NR^C)R^B$, $C(=NR^C)NR^CR^D$, $NR^CS(O)R^B$, $NR^CS(O)_2NR^CR^D$, $NR^CC(=NR^C)NR^CR^D$, $NR^CC(=NOR^A)NR^CR^D$, $NR^CC(=NCN)NR^CR^D$, $S(O)(=NR^C)R^B$, $S(O)(=NR^C)NR^CR^D$, $NR^CC(O)OR^A$, $P(O)R^ER^F$, $P(O)OR^EOR^F$, $OP(O)OR^EOR^F$, $SF_5$, $S(O)R^B$, $S(O)NR^CR^D$, $S(O)_2R^B$, $NR^CS(O)_2R^B$, $S(O)_2NR^CR^D$, $B(OR^A)_2$, $Cy^4$, $C_{1-6}$ alkyl-$Cy^4$, O—$C_{1-6}$ alkyl-$Cy^4$, or O—$C_{1-6}$ alkyl-$Cy^4$-$C_{0-6}$ alkyl-$Cy^5$, wherein said $Cy^4$, $C_{1-6}$ alkyl-$Cy^4$, O—$C_{1-6}$ alkyl-$Cy^4$, O—$C_{1-6}$ alkyl-$Cy^4$-$C_{0-6}$ alkyl-$Cy^5$, and $Cy^5$ are optionally substituted;
wherein two $R^{1B}$, one $R^{1B}$ and $R^{1A}$, or one $R^{1B}$ and $R^{1D}$, together with the atom or atoms to which they are attached, optionally form a fused 4-10 membered cycloalkyl ring or a fused 4-10 membered heterocycloalkyl ring, each optionally substituted by 1, 2, or 3 substituents, wherein each said substituent is independently halo, $C_{1-6}$ alkyl, $C_{2-6}$ alkenyl, $C_{2-6}$ alkynyl, $C_{1-6}$ haloalkyl, CN, $NO_2$, oxo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $C(=NR^c)NR^cR^d$, $NR^cS(O)R^b$, $NR^cS(O)_2NR^cR^d$, $NR^cC(=NR^c)NR^cR^d$, $NR^cC(=NOR^a)NR^cR^d$, $NR^cC(=NCN)NR^cR^d$, $S(O)(=NR^c)R^b$, $S(O)(=NR^c)NR^cR^d$, $NR^cC(O)OR^a$, $P(O)R^eR^f$, $P(O)OR^eOR^f$, $OP(O)OR^eOR^f$, $S(O)R^b$, $S(O)NR^cR^d$, $S(O)_2R^b$, $NR^cS(O)_2R^b$, or $S(O)_2NR^cR^d$, $B(OR^a)_2$, aryl, cycloalkyl, heteroaryl, and heterocycloalkyl; and s is 0-3; and
$R^2$, $R^7$, $R^{14}$, and r are as defined in any one of embodiments 1-8.

42. The compound of embodiment 41, or a pharmaceutically acceptable salt or solvate thereof, wherein V is N.

43. The compound of embodiment 41, or a pharmaceutically acceptable salt or solvate thereof, wherein V is CH.

44. The compound of embodiment 43, or a pharmaceutically acceptable salt or solvate thereof, wherein each $R^2$ is independently optionally substituted $C_{1-6}$ alkyl.

45. The compound of embodiment 43, or a pharmaceutically acceptable salt or solvate thereof, wherein each $R^2$ is independently optionally substituted $C_{1-3}$ alkyl.

46. The compound of any one of embodiments 43-45, or a pharmaceutically acceptable salt or solvate thereof, wherein the compound has the formula of Formula (XXV)

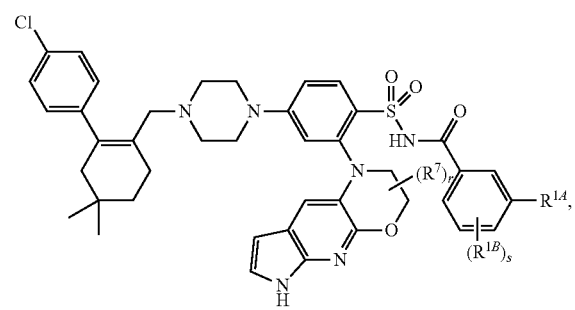

wherein the variables are as defined in embodiment 41.

47. The compound of embodiment 46, or a pharmaceutically acceptable salt or solvate thereof, wherein $R^{14}$ is H, D, $NO_2$, $SO_2Me$, or $SO_2CF_3$.

48. The compound of any one of embodiments 40-47, or a pharmaceutically acceptable salt or solvate thereof, wherein r is 1.

49. The compound of any one of embodiments 37-48, or a pharmaceutically acceptable salt or solvate thereof, wherein $R^7$ is absent.

50. The compound of embodiment 1, or a pharmaceutically acceptable salt or solvate thereof, wherein the compound is selected from the group consisting of 6-chloro-N-[4-[4-[[2-(4-chlorophenyl)-4,4-dimethylcyclohexen-1-yl]methyl]piperazin-1-yl]phenyl]sulfonyl-5-nitropyridine-2-carboxamide;

N-[4-[4-[[2-(4-chlorophenyl)-4,4-dimethylcyclohexen-1-yl]methyl]piperazin-1-yl]phenyl]sulfonylbenzo[b]thiophene-5-carboxamide;

1-benzyl-N-[4-[4-[[2-(4-chlorophenyl)-4,4-dimethylcyclohexen-1-yl]methyl]piperazin-1-yl]phenyl]sulfonyl-5-methyl-1H-1,2,3-triazole-4-carboxamide;

N-([4-[4-[[2-(4-chlorophenyl)-4,4-dimethylcyclohexen-1-yl]methyl]piperazin-1-yl]phenyl]sulfonyl)quinoline-6-carboxamide;

N-([4-[4-[[2-(4-chlorophenyl)-4,4-dimethylcyclohexen-1-yl]methyl]piperazin-1-yl]phenyl]sulfonyl)pyrazine-2-carboxamide;

N-([4-[4-[[2-(4-chlorophenyl)-4,4-dimethylcyclohexen-1-yl]methyl]piperazin-1-yl]phenyl]sulfonyl)bicyclo[1.1.1]pentane-1-carboxamide;

N-([4-[4-[[2-(4-chlorophenyl)-4,4-dimethylcyclohexen-1-yl]methyl]piperazin-1-yl]phenyl]sulfonyl)-2-methylpyrimidine-5-carboxamide;

N-((4-(4-((4'-chloro-5,5-dimethyl-3,4,5,6-tetrahydro-[1,1'-biphenyl]-2-yl)methyl)piperazin-1-yl)phenyl)sulfonyl)quinoline-3-carboxamide;

N-([4-[4-[[2-(4-chlorophenyl)-4,4-dimethylcyclohexen-1-yl]methyl]piperazin-1-yl]phenyl]sulfonyl)-1-methyl-2-oxo-1,2,3,4-tetrahydroquinoline-6-carboxamide;

N-([4-[4-[[2-(4-chlorophenyl)-4,4-dimethylcyclohexen-1-yl]methyl]piperazin-1-yl]phenyl]sulfonyl)-2-methoxybenzamide;

N-([4-[4-[[2-(4-chlorophenyl)-4,4-dimethylcyclohexen-1-yl]methyl]piperazin-1-yl]phenyl]sulfonyl)-5-cyclopropylisoxazole-3-carboxamide;

5-bromo-N-([4-[4-[[2-(4-chlorophenyl)-4,4-dimethylcyclohexen-1-yl]methyl]piperazin-1-yl]phenyl]sulfonyl)pyridine-2-carboxamide;

N-([4-[4-[[2-(4-chlorophenyl)-4,4-dimethylcyclohexen-1-yl]methyl]piperazin-1-yl]phenyl]sulfonyl)-3-methyl-1H-pyrazole-5-carboxamide;

3-chloro-N-([4-[4-[[2-(4-chlorophenyl)-4,4-dimethylcyclohexen-1-yl]methyl]piperazin-1-yl]phenyl]sulfonyl)benzamide;

N-([4-[4-[[2-(4-chlorophenyl)-4,4-dimethylcyclohexen-1-yl]methyl]piperazin-1-yl]phenyl]sulfonyl)-5-fluoro-6-methyl pyridine-2-carboxamide;

N-([4-[4-[[2-(4-chlorophenyl)-4,4-dimethylcyclohexen-1-yl]methyl]piperazin-1-yl]phenyl]sulfonyl)-4,5-dimethylisoxazole-3-carboxamide;

N-([4-[4-[[2-(4-chlorophenyl)-4,4-dimethylcyclohexen-1-yl]methyl]piperazin-1-yl]phenyl]sulfonyl)-3-(methoxymethyl)benzamide;

N-([4-[4-[[2-(4-chlorophenyl)-4,4-dimethylcyclohexen-1-yl]methyl]piperazin-1-yl]phenyl]sulfonyl)-4-(methoxymethyl)benzamide;

5,6-dichloro-N-([4-[4-[[2-(4-chlorophenyl)-4,4-dimethylcyclohexen-1-yl]methyl]piperazin-1-yl]phenyl]sulfonyl)pyridine-2-carboxamide;

N-([4-[4-[[2-(4-chlorophenyl)-4,4-dimethylcyclohexen-1-yl]methyl]piperazin-1-yl]phenyl]sulfonyl)-6-(trifluoromethyl)pyridine-2-carboxamide;

N-([4-[4-[[2-(4-chlorophenyl)-4,4-dimethylcyclohexen-1-yl]methyl]piperazin-1-yl]phenyl]sulfonyl)-3-(trifluoromethyl)pyridine-4-carboxamide;

N-([4-[4-[[2-(4-chlorophenyl)-4,4-dimethylcyclohexen-1-yl]methyl]piperazin-1-yl]phenyl]sulfonyl)-5-nitropyridine-3-carboxamide;

N-([4-[4-[[2-(4-chlorophenyl)-4,4-dimethylcyclohexen-1-yl]methyl]piperazin-1-yl]phenyl]sulfonyl) pyridine-2-carboxamide;

N-([4-[4-[[2-(4-chlorophenyl)-4,4-dimethylcyclohexen-1-yl]methyl]piperazin-1-yl]phenyl]sulfonyl)-3-(4-fluorophenyl)isoxazole-5-carboxamide;

N-([4-[4-[[2-(4-chlorophenyl)-4,4-dimethylcyclohexen-1-yl]methyl]piperazin-1-yl]phenyl]sulfonyl)-2-(6-methylpyridin-3-yl)acetamide;

N-([4-[4-[[2-(4-chlorophenyl)-4,4-dimethylcyclohexen-1-yl]methyl]piperazin-1-yl]phenyl]sulfonyl)thieno[2,3-b]pyridine-6-carboxamide;

N-([4-[4-[[2-(4-chlorophenyl)-4,4-dimethylcyclohexen-1-yl]methyl]piperazin-1-yl]phenyl]sulfonyl)cyclohex-3-ene-1-carboxamide;

N-([4-[4-[[2-(4-chlorophenyl)-4,4-dimethylcyclohexen-1-yl]methyl]piperazin-1-yl]phenyl]sulfonyl)-1-(4-nitrophenyl)cyclopropane-1-carboxamide;

N-([4-[4-[[2-(4-chlorophenyl)-4,4-dimethylcyclohexen-1-yl]methyl]piperazin-1-yl]phenyl]sulfonyl)-2-(2-fluorophenyl)acetamide;

N-([4-[4-[[2-(4-chlorophenyl)-4,4-dimethylcyclohexen-1-yl]methyl]piperazin-1-yl]phenyl]sulfonyl)-3-(pyridin-3-yl)propanamide;

N-([4-[4-[[2-(4-chlorophenyl)-4,4-dimethylcyclohexen-1-yl]methyl]piperazin-1-yl]phenyl]sulfonyl)-3-nitrobenzamide;

6-bromo-N-([4-[4-[[2-(4-chlorophenyl)-4,4-dimethylcyclohexen-1-yl]methyl]piperazin-1-yl]phenyl]sulfonyl)-5-fluoropyridine-2-carboxamide;

N-([4-[4-[[2-(4-chlorophenyl)-4,4-dimethylcyclohexen-1-yl]methyl]piperazin-1-yl]phenyl]sulfonyl)-3-((3-methylbenzyl)oxy)benzamide;

N-([4-[4-[[2-(4-chlorophenyl)-4,4-dimethylcyclohexen-1-yl]methyl]piperazin-1-yl]phenyl]sulfonyl)-4-((2,5-dichlorophenoxy)methyl)benzamide;

4-(benzyloxy)-N-([4-[4-[[2-(4-chlorophenyl)-4,4-dimethylcyclohexen-1-yl]methyl]piperazin-1-yl]phenyl]sulfonyl)-3-nitrobenzamide;

N-([4-[4-[[2-(4-chlorophenyl)-4,4-dimethylcyclohexen-1-yl]methyl]piperazin-1-yl]phenyl]sulfonyl)-3((4-chlorophenoxy)methyl)-4-fluorobenzamide;

N-([4-[4-[[2-(4-chlorophenyl)-4,4-dimethylcyclohexen-1-yl]methyl]piperazin-1-yl]phenyl]sulfonyl)-3((4-chlorophenoxy)methyl)-4-nitrobenzamide;

N-([4-[4-[[2-(4-chlorophenyl)-4,4-dimethylcyclohexen-1-yl]methyl]piperazin-1-yl]phenyl]sulfonyl)-4((4-chlorophenoxy)methyl)-3-nitrobenzamide;

3-(benzyloxy)-N-([4-[4-[[2-(4-chlorophenyl)-4,4-dimethylcyclohexen-1-yl]methyl]piperazin-1-yl]phenyl]sulfonyl)-4-nitrobenzamide;

2-Chloro-N-[4-[4-[[2-(4-chlorophenyl)-4,4-dimethylcyclohexen-1-yl]methyl]piperazin-1-yl]phenyl]sulfonyl-5-nitro-4-(tetrahydropyran-4-ylmethylamino)benzamide;

2-Chloro-N-([4-[4-[[2-(4-chlorophenyl)-4,4-dimethylcyclohexen-1-yl]methyl]piperazin-1-yl]phenyl]sulfonyl)-3-methyl-5-nitro-4-(tetrahydropyran-4-ylmethylamino)benzamide;

2-chloro-N-[4-[4-[[2-(4-chlorophenyl)-4,4-dimethylcyclohexen-1-yl]methyl]piperazin-1-yl]phenyl]sulfonyl-4-(ethylamino)-3-methyl-5-nitrobenzamide;

N-[4-[4-[[2-(4-chlorophenyl)-4,4-dimethylcyclohexen-1-yl]methyl]piperazin-1-yl]phenyl]sulfonyl-5-fluoro-6-(1,3,5-trimethylpyrazol-4-yl)pyridine-2-carboxamide;

N-[4-[4-[[2-(4-chlorophenyl)-4,4-dimethylcyclohexen-1-yl]methyl]piperazin-1-yl]phenyl]sulfonyl-5-fluoro-6-(1-methyl-1H-pyrazol-4-yl) pyridine-2-carboxamide;

N-[4-[4-[[2-(4-chlorophenyl)-4,4-dimethylcyclohexen-1-yl]methyl]piperazin-1-yl]phenyl]sulfonyl-5-fluoro-6-(1H-imidazol-1-yl)pyridine-2-carboxamide;

N-[4-[4-[[2-(4-chlorophenyl)-4,4-dimethylcyclohexen-1-yl]methyl]piperazin-1-yl]phenyl]sulfonyl-5-fluoro-6-(2-oxo-2,3-dihydro-1H-pyrrolo[2,3-b]pyridin-5-yl)pyridine-2-carboxamide;

N-[4-[4-[[2-(4-chlorophenyl)-4,4-dimethylcyclohexen-1-yl]methyl]piperazin-1-yl]phenyl]sulfonyl-5-fluoro-6-(1H-indazol-5-yl)pyridine-2-carboxamide;

6-(1H-benzo[d][1,2,3]triazol-5-yl)-N-[4-[4-[[2-(4-chlorophenyl)-4,4-dimethylcyclohexen-1-yl]methyl]piperazin-1-yl]phenyl]sulfonyl-5-fluoro pyridine-2-carboxamide;

N-[4-[4-[[2-(4-chlorophenyl)-4,4-dimethylcyclohexen-1-yl]methyl]piperazin-1-yl]phenyl]sulfonyl-5-fluoro-6-(1-methyl-1H-indazol-5-yl) pyridine-2-carboxamide;

6-(benzyloxy)-N-[4-[4-[[2-(4-chlorophenyl)-4,4-dimethylcyclohexen-1-yl]methyl]piperazin-1-yl]phenyl]sulfonyl-5-nitropyridine-2-carboxamide;

N-[4-[4-[[2-(4-chlorophenyl)-4,4-dimethylcyclohexen-1-yl]methyl]piperazin-1-yl]phenyl]sulfonyl-3-nitro-4-(phenoxymethyl)benzamide;

3-(benzyloxy)-N-[4-[4-[[2-(4-chlorophenyl)-4,4-dimethylcyclohexen-1-yl]methyl]piperazin-1-yl]phenyl]sulfonyl-4-fluorobenzamide;

2-chloro-N-[4-[4-[[2-(4-chlorophenyl)-4,4-dimethylcyclohexen-1-yl]methyl]piperazin-1-yl]phenyl]sulfonyl-4-(methylamino)-3-methyl-5-nitrobenzamide;

N-[4-[4-[[2-(4-Chlorophenyl)-4,4-dimethylcyclohexen-1-yl]methyl]piperazin-1-yl]phenyl]sulfonyl-3-fluoro-1'-methyl-2'-oxo-1',2'-dihydro-[2,4'-bipyridine]-6-carboxamide;

N-[4-[4-[[2-(4-Chlorophenyl)-4,4-dimethylcyclohexen-1-yl]methyl]piperazin-1-yl]phenyl]sulfonyl-5-fluoro-6-(2-methoxypyrimidin-5-yl)pyridine-2-carboxamide;

N-[4-[4-[[2-(4-Chlorophenyl)-4,4-dimethylcyclohexen-1-yl]methyl]piperazin-1-yl]phenyl]sulfonyl-3-fluoro-1'-methyl-6'-oxo-1',6'-dihydro-[2,3'-bipyridine]-6-carboxamide;

N-[4-[4-[[2-(4-Chlorophenyl)-4,4-dimethylcyclohexen-1-yl]methyl]piperazin-1-yl]phenyl]sulfonyl-5-fluoro-6-(1H-pyrazol-4-yl)pyridine-2-carboxamide;

N-[4-[4-[[2-(4-Chlorophenyl)-4,4-dimethylcyclohexen-1-yl]methyl]piperazin-1-yl]phenyl]sulfonyl-5-fluoro-6-(1-methyl-1H-indazol-6-yl)pyridine-2-carboxamide;

N-[4-[4-[[2-(4-chlorophenyl)-4,4-dimethyl-cyclohexen-1-yl]methyl]piperazin-1-yl]phenyl]sulfonyl-5-fluoro-6-(4-pyridyl)pyridine-2-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-6-bromo-5-fluoropyridine-2-carboxamide;

5,6-Dichloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonylpyridine-2-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-fluoro-6-methylpyridine-2-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-6-methyl-5-nitropyridine-2-carboxamide;

5-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-6-(trifluoromethyl)pyridine-2-carboxamide;

6-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-nitropyridine-2-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-chloro-6-methylpyridine-2-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3,4-dihydro-2H-chromene-6-carboxamide;

N-((2-((1H-pyrrolo[2,3-b]pyridin-5-yl)oxy)-4-(4-[[2-(4-Chlorophenyl)-4,4-dimethylcyclohexen-1-yl]methyl]piperazin-1-yl]phenyl)sulfonyl)thieno[2,3-b]pyridine-5-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-1,4-dimethylpyrazole-3-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-1,5-dimethylpyrazole-3-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-2,4,5-trimethylpyrazole-3-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitrobenzamide;

2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxan-4-ylmethylamino)benzamide;

2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxan-4-ylmethoxy)benzamide;

N-((2-((1H-pyrrolo[2,3-b]pyridin-5-yl)methyl)-4-(4-[[2-(4-Chlorophenyl)-4,4-dimethylcyclohexen-1-yl]methyl]piperazin-1-yl]phenyl)sulfonyl)-4-((4-chlorophenoxy)methyl)-3-nitrobenzamide;

4-[(4-Chlorophenoxy)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-fluorobenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-(cyclopropyloxymethyl)-4-fluorobenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-(methoxymethyl)-5-nitrobenzamide;

3-[(4-Chlorophenoxy)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-nitrobenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(methoxymethyl)-3-nitrobenzamide;

2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-[(4-chlorophenyl)methoxy]-3-methyl-5-nitrobenzamide;

4-[(4-chlorophenoxy)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methylsulfonylbenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(morpholin-4-ylmethyl)-3-nitrobenzamide;

4-[(4-chloroanilino)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-nitrobenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonylthieno[2,3-b]pyridine-6-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonylthieno[2,3-b]pyridine-4-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-6-methyl-5-nitropyridine-2-carboxamide;

3-[(4-Chlorophenoxy)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-nitrobenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-nitro-4-[(oxan-4-ylamino)methyl]benzamide;

N-[4-[4-[[2-(4-Chlorophenyl)-4,4-dimethylcyclohexen-1-yl]methyl]piperazin-1-yl]-2-(1H-pyrrolo[2,3-b]pyridin-5-yloxy)phenyl]sulfonyl-6-methyl-4-methylsulfonylpyridine-2-carboxamide;

2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-4-(methylamino)-5-nitrobenzamide;

2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(ethylamino)-3-methyl-5-nitrobenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-nitro-4-(oxan-4-ylmethylamino)benzamide;

2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-methoxy-3-methyl-5-nitrobenzamide;

2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-ethoxy-3-methyl-5-nitrobenzamide;

2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxetan-3-ylmethoxy)benzamide and;

2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(1,4-dioxan-2-ylmethylamino)-3-methyl-5-nitrobenzamide;

2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(1,4-dioxan-2-ylmethoxy)-3-methyl-5-nitrobenzamide;

2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxolan-3-ylmethoxy)benzamide; and 2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxolan-2-ylmethoxy)benzamide.

51. A pharmaceutical composition comprising a compound according to any one of embodiments 1-50, or a pharmaceutically acceptable salt or solvate thereof.

52. The pharmaceutical composition of embodiment 51, wherein the composition further comprises a pharmaceutically acceptable excipient.

53. The pharmaceutical composition any one of embodiments 51-52, the pharmaceutical composition further comprises a pharmaceutically acceptable carrier.

54. The pharmaceutical composition of any one of embodiments 51-53, wherein the pharmaceutical composition comprises an enantiomeric excess of at least 90%, 95%, 98%, or 99% of one enantiomer of the compound, or a pharmaceutically acceptable salt or solvate thereof.

55. The pharmaceutical composition of any one of embodiments 51-54, wherein the pharmaceutical composition further comprises at least one chemotherapeutic agent.

56. The pharmaceutical composition of embodiment 55, wherein the chemotherapeutic agent is a hypomethylating agent, an alkylating agent, a proteasome inhibitor, a topoisomerase inhibitor, or a DNA polymerase inhibitor.

57. The pharmaceutical composition of any one of embodiments 51-56, wherein the pharmaceutical composition further comprises at least one epigenetic regulator.

58. The pharmaceutical composition of embodiment 57, wherein the epigenetic regulator is a bromodomain inhibitor, a histone lysine methyltransferase inhibitor, a histone arginine methyl transferase inhibitor, a histone demethylase inhibitor, a histone deacetylase inhibitor, histone acetylase inhibitor, or a DNA methyltransferase inhibitor.

59. The pharmaceutical composition of any one of embodiments 51-58, wherein the pharmaceutical composition further comprises at least one kinase inhibitor.

60. The pharmaceutical composition of embodiment 59, wherein the kinase inhibitor is a JAK kinase, a PI3 kinase inhibitor such as PI3K-delta selective and broad-spectrum PI3K inhibitor, a MEK inhibitor, a cyclin-dependent kinase inhibitor such as CDK4/6 inhibitor and CDK9 inhibitor, a BRAF inhibitor, a BTK inhibitor, an FLT3 inhibitor, an EGFR inhibitor, or an mTOR inhibitor.
61. The pharmaceutical composition of any one of embodiments 51-60, wherein the pharmaceutical composition further comprises at least one more BCL-2 inhibitor.
62. The pharmaceutical composition of embodiment 61, wherein the BCL-2 family inhibitor is a dual BCL-2/BCL-XL inhibitor or an MCL1 inhibitor
63. The pharmaceutical composition of any one of embodiments 51-62, wherein the pharmaceutical composition further comprises at least one hormone therapy agent.
64. The pharmaceutical composition of embodiment 63, wherein the hormone therapy agent is an anti-androgen therapy agent, an estrogen receptor modulator, an aromatase inhibitor, or a selective ER degrader.
65. The pharmaceutical composition of any one of embodiments 51-64, wherein the pharmaceutical composition further comprises at least one monoclonal antibody.
66. The pharmaceutical composition of embodiment 65, wherein the monoclonal antibody is an anti-CD20 antibody, an anti-PD-1 antibody, or an anti-CTLA4 antibody.
67. The pharmaceutical composition of any one of embodiments 51-66, wherein the pharmaceutical composition further comprises at least one immunomodulatory agent.
68. The pharmaceutical composition of embodiment 67, wherein the immunomodulatory agent is lenalidomide (LEN) or pomalidomide (POM).
69. A method of inhibiting the activity of BCL-2 protein comprising contacting the BCL protein with a compound of any one of embodiments 1-50, or a pharmaceutically acceptable salt, a solvate, or a prodrug thereof, or a pharmaceutical composition of any one of embodiments 51-68.
70. A method of treating, ameliorating, or preventing a disease or disorder condition responsive to inhibition of BCL-2 in a subject comprising administering to the subject, a compound of any one of embodiments 1-50, or a pharmaceutically acceptable salt, a solvate, or a prodrug thereof, or a pharmaceutical composition of any one of embodiments 51-68 and optionally in combination with a second therapeutic agent.
71. The method of embodiment 70, wherein the disease or disorder condition is a cancer, a hyperproliferative disease, an autoimmune disease, a psychiatric disorder, a senescence-associated disease or disorder, a neoplastic disease, or a neurodegenerative disease.
72. The method of embodiment 71, wherein the cancer is mesothelioma, bladder cancer, pancreatic cancer, skin cancer, cancer of the head or neck, cutaneous or intraocular melanoma, breast cancer, uterine cancer, carcinoma of the fallopian tubes, carcinoma of the endometrium, carcinoma of the cervix, carcinoma of the vagina, carcinoma of the vulva, bone cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and biliary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, myeloproliferative neoplasms, blastic plasmacytoid dendritic cell neoplasms, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non-Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma, glioblastoma, or a combination thereof.
73. The method of embodiment 71, wherein the autoimmune disease is systemic lupus erythematosus (SLE), lupus nephritis, or Sjogren's syndrome.
74. The method of embodiment 71, wherein the psychiatric disorder is schizophrenia.
75. The method of embodiment 71, wherein the senescence-associated disease or disorder is atherosclerosis, idiopathic pulmonary fibrosis, senescence-associated pulmonary disease, osteoarthritis, senescence-associated ophthalmic diseases and disorders, or senescence-associated dermatological diseases and disorders.
76. The method of embodiment 75, wherein the senescence-associated pulmonary disease is pulmonary fibrosis, chronic obstructive pulmonary disease, asthma, cystic fibrosis, emphysema, bronchiectasis, or age-related loss of pulmonary function.
77. The method of any one of embodiments 56-76, wherein the subject is a subject in need thereof.
78. The method of any of embodiments 56-76, wherein the disease or disorder condition is prevented.
79. The method of embodiment 78, wherein the therapeutic for the disease or disorder condition is selected from those described herein.
80. The method of any one of embodiments 56-79, wherein the compound, or a pharmaceutically acceptable salt, a solvate, or a prodrug thereof, or the pharmaceutical composition is administered in a therapeutically effective amount.
81. Use of a compound of any one of embodiments 1-50, or a pharmaceutically acceptable salt, a solvate, or a prodrug thereof, for inhibiting the activity of BCL-2 protein comprising contacting the BCL protein with the compound of any one of embodiments 1-50, or a pharmaceutically acceptable salt, a solvate, or a prodrug thereof.
82. A compound of any one of embodiments 1-50, or a pharmaceutically acceptable salt, a solvate, or a prodrug thereof, in use for inhibiting the activity of BCL-2 protein comprising contacting the BCL protein with the compound of any one of embodiments 1-50, or a pharmaceutically acceptable salt, a solvate, or a prodrug thereof.
83. Use of a compound of any one of embodiments 1-50, or a pharmaceutically acceptable salt, a solvate, or a prodrug thereof, in the manufacture of a formulation for inhibiting the activity of BCL-2 protein comprising contacting the BCL protein with the compound of any one of embodiments 1-50, or a pharmaceutically acceptable salt, a solvate, or a prodrug thereof.
84. Use of a pharmaceutical composition of any one of embodiments 51-68 for inhibiting the activity of BCL-2 protein comprising contacting the BCL protein with the pharmaceutical composition of any one of embodiments 51-68.
85. A pharmaceutical composition of any one of embodiments 51-68 in use for inhibiting the activity of BCL-2 protein comprising contacting the BCL protein with the pharmaceutical composition of any one of embodiments 51-68.
86. Use of a pharmaceutical composition of any one of embodiments 51-68 in the manufacture of a formulation for inhibiting the activity of BCL-2 protein comprising contacting the BCL protein with the pharmaceutical composition of any one of embodiments 51-68.
87. Use of a compound of any one of embodiments 1-50, or a pharmaceutically acceptable salt, a solvate, or a prodrug thereof, for treating, ameliorating, or preventing a disease or disorder condition responsive to inhibition of BCL-2 in a subject comprising administering to the subject the compound of any one of embodiments 1-50, or a pharmaceutically acceptable salt, a solvate, or a prodrug thereof.
88. A compound of any one of embodiments 1-50, or a pharmaceutically acceptable salt, a solvate, or a prodrug thereof, in use for treating, ameliorating, or preventing a disease or disorder condition responsive to inhibition of BCL-2 in a subject comprising administering to the subject the compound of any one of embodiments 1-50, or a pharmaceutically acceptable salt, a solvate, or a prodrug thereof.
89. Use of a compound of any one of embodiments 1-50, or a pharmaceutically acceptable salt, a solvate, or a prodrug thereof, in the manufacture of a medicament for treating, ameliorating, or preventing a disease or disorder condition responsive to inhibition of BCL-2 in a subject comprising administering to the subject the compound of any one of embodiments 1-50, or a pharmaceutically acceptable salt, a solvate, or a prodrug thereof.
90. Use of a pharmaceutical composition of any one of embodiments 51-68 for treating, ameliorating, or preventing a disease or disorder condition responsive to inhibition of BCL-2 in a subject comprising administering to the subject the pharmaceutical composition of any one of embodiments 51-68.
91. A pharmaceutical composition of any one of embodiments 51-68 in use for treating, ameliorating, or preventing a disease or disorder condition responsive to inhibition of BCL-2 in a subject comprising administering to the subject the pharmaceutical composition of any one of embodiments 51-68.
92. Use of a pharmaceutical composition of any one of embodiments 51-68 in the manufacture of a medicament for treating, ameliorating, or preventing a disease or disorder condition responsive to inhibition of BCL-2 in a subject comprising administering to the subject the pharmaceutical composition of any one of embodiments 51-68.
93. The use of any one of embodiments 87-92, wherein the disease or disorder condition is a cancer, a hyperproliferative disease, an autoimmune disease, a psychiatric disorder, a senescence-associated disease or disorder, a neoplastic disease, or a neurodegenerative disease.
94. The use of embodiment 93, wherein the cancer is mesothelioma, bladder cancer, pancreatic cancer, skin cancer, cancer of the head or neck, cutaneous or intraocular melanoma, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and biliary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non-Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma, glioblastoma, or a combination thereof.
95. The use of embodiment 94, wherein the autoimmune disease is systemic lupus erythematosus (SLE), lupus nephritis, or Sjogren's syndrome.
96. The use of embodiment 94, wherein the psychiatric disorder is schizophrenia.
97. The use of embodiment 94, wherein the senescence-associated disease or disorder is atherosclerosis, idiopathic pulmonary fibrosis, senescence-associated pulmonary disease, osteoarthritis, senescence-associated ophthalmic diseases and disorders, or senescence-associated dermatological diseases and disorders.
98. The use of embodiment 97, wherein the senescence-associated pulmonary disease is pulmonary fibrosis, chronic obstructive pulmonary disease, asthma, cystic fibrosis, emphysema, bronchiectasis, or age-related loss of pulmonary function.
99. The use of any one of embodiments 87-98, wherein the subject is a subject in need thereof.
100. The use of any of embodiments 87-98, wherein the disease or disorder condition is prevented.
101. The use of embodiment 100, wherein the therapeutic for the disease or disorder condition is selected from those described herein.
102. The use of any one of embodiments 87-101, wherein the compound, or a pharmaceutically acceptable salt, a solvate, or a prodrug thereof, or the pharmaceutical composition is administered in a therapeutically effective amount.

Synthesis

Compounds of the present disclosure, including salts thereof, can be prepared using known organic synthesis techniques and can be synthesized according to any of numerous possible synthetic routes.

The reactions for preparing compounds of the present disclosure can be carried out in suitable solvents, which can be readily selected by one of skill in the art of organic synthesis. Suitable solvents can be substantially nonreactive with the starting materials (reactants), the intermediates, or products at the temperatures at which the reactions are carried out, e.g., temperatures, which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H NMR or $^{13}$C NMR), infrared spectroscopy, spectrophotometry (e.g., UV-visible), or mass spectrometry, or by chromatography such as high-performance liquid chromatography ("HPLC") or thin-layer chromatography, or liquid chromatography-mass spectrometry ("LC-MS").

The expressions, "ambient temperature," "room temperature," and "r.t." as used herein, are understood in the art and generally refer to a temperature, e.g., a reaction temperature, that is about the temperature of the room in which the reaction is carried out, for example, a temperature from about 20° C. to about 30° C.

Compounds of the present disclosure can be prepared using numerous preparatory reactions known in the literature. The Schemes below provide general guidance in connection with preparing the compounds provided herein. One skilled in the art would understand that the preparations shown in the Schemes can be modified or optimized using general knowledge of organic chemistry to prepare various compounds. Example synthetic methods for preparing compounds are provided in the schemes below.

General Schemes:
Synthesis

Some compounds of Formula (I) can be prepared as shown by the methods outlined in Scheme 1. Amide coupling of a sulfonamide 1-1 with the suitable acid 1-2 using a coupling agent (e.g., EDC, DCC, BOP, PyBOP, HATU, or HBTU) in the presence of a suitable base (e.g., pyridine, TEA, or DIEA) can yield the sulfonamides 1-3 having the Formula (I). The variables in Scheme 1 are as defined in the embodiments as described herein.

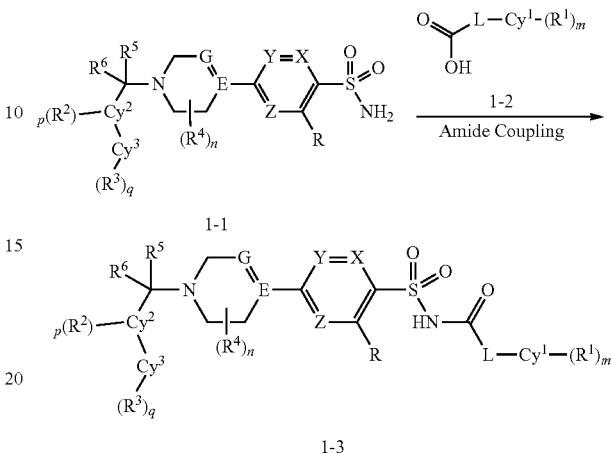

Scheme 1

Some sulfonamide intermediates for making compounds of Formula (I) can be prepared by the methods outlined in Scheme 2. $S_N2$ reaction of amine derivative 2-1 with a suitable substance 2-2 (LG=leaving groups such as I, Br, Cl, OMs, and OTf) can yield the sulfonamide intermediates 2-4a. As used herein and throughout the embodiments, "LG" refers to a leaving group, which is commonly known to one of skill in the art of synthetic organic chemistry. Alternatively, the sulfonamide intermediates 2-4b can be prepared by reductive amination of the sulfonamide 2-1 with an appropriate aldehyde or ketone 2-3 under suitable conditions (e.g., imine formation followed by treatment with a suitable reducing agent, such as $NaBH_3(CN)$ or $NaBH(OAc)_3$. The variables in Scheme 2 are as defined in the embodiments as described herein.

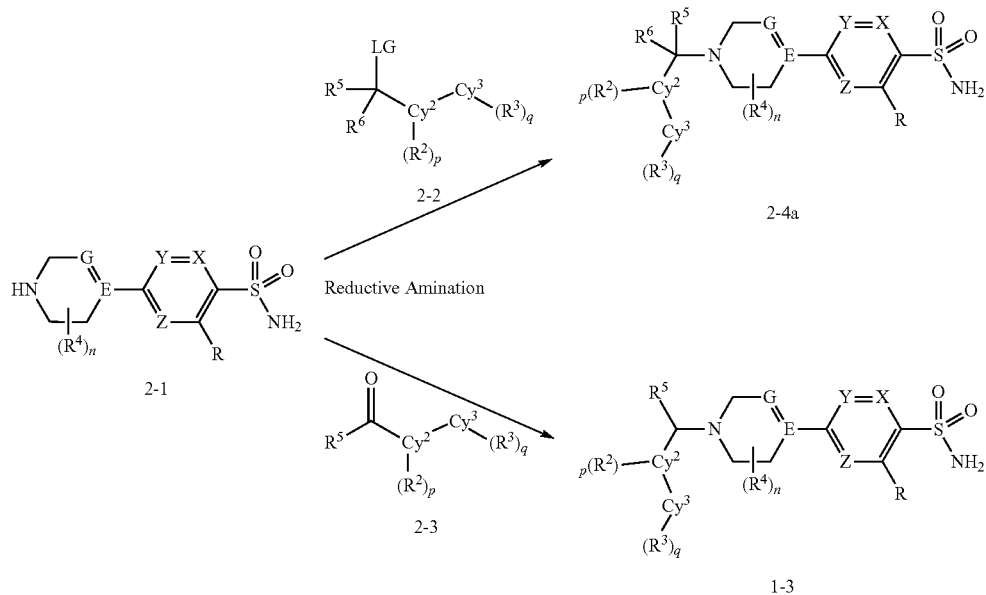

Scheme 2

Some sulfonamide intermediates for making compounds of Formula (I) can be prepared by the methods outlined in Scheme 3. Suzuki coupling reaction of sulfonamide derivative 3-1 (LG is a leaving group such as I, Br, Cl, OMs, and OTf) with a suitable boronic acid or ester 3-2 (OR' is OH, OMe, or OEt, or two OR' together are pinacol) can yield the sulfonamide 3-3 by using a coupling catalyst (e.g., Pd(PPh$_3$)$_4$, Pd(OAc)$_2$, and Pd(dppf)Cl$_2$) with or without additional ligand (e.g., SPhos or Xphos) in the presence of a suitable base (e.g., TEA, Na$_2$CO$_3$, K$_2$CO$_3$, Cs$_2$CO$_3$, K$_3$PO$_4$, NaHCO$_3$, K$_2$HPO$_4$, and KH$_2$PO$_4$). Reduction of the sulfonamide intermediates 3-3 can produce the corresponding sulfonamide intermediates 3-4 under suitable conditions (e.g., Pd/C catalyzed hydrogenation using H$_2$ or transfer hydrogenation using HCO$_2$NH$_4$). As used herein and throughout the embodiments, "PG" refers to a protecting group, which is commonly known to one of skill in the art of synthetic organic chemistry. The variables in Scheme 3 are as defined in the embodiments as described herein.

Scheme 3

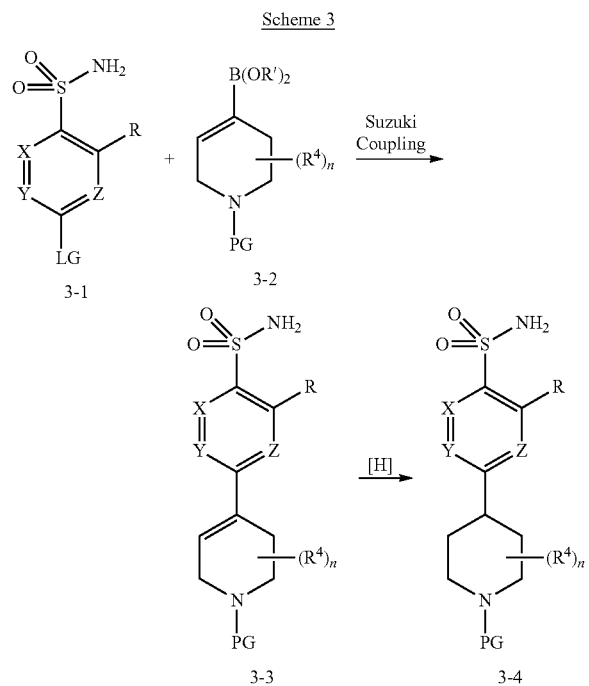

Some sulfonamide intermediates for making compounds of Formula (I) can be prepared by the methods outlined in Scheme 4. Buchwald coupling reaction of sulfonamide derivative 4-1 (LG is a leaving group such as F, NO$_2$, I, Br, Cl, OMs, or OTf) with suitable piperazine 4-2 can yield the sulfonamide intermediates 4-3 in the presence of a coupling catalyst (e.g., Pd$_2$(dba)$_3$ or Pd(OAc)$_2$) and a ligand (e.g., SPhos, Xphos, or Xantphos), or a precatalyst (e.g., Xphos Pd GIII, Brettphos or Pd GIII) and a suitable base (e.g., K$_2$CO$_3$, Cs$_2$CO$_3$, K$_3$PO$_4$, t-BuOK, t-BuONa). Alternatively, nucleophilic aromatic substitution reaction of the sulfonamide derivative 4-1 with the piperazine 4-2 can yield the sulfonamide intermediates 4-3 with or without the presence a suitable base (e.g., pyridine, TEA, or DIEA). The variables in Scheme 4 are as defined in the embodiments as described herein.

Scheme 4

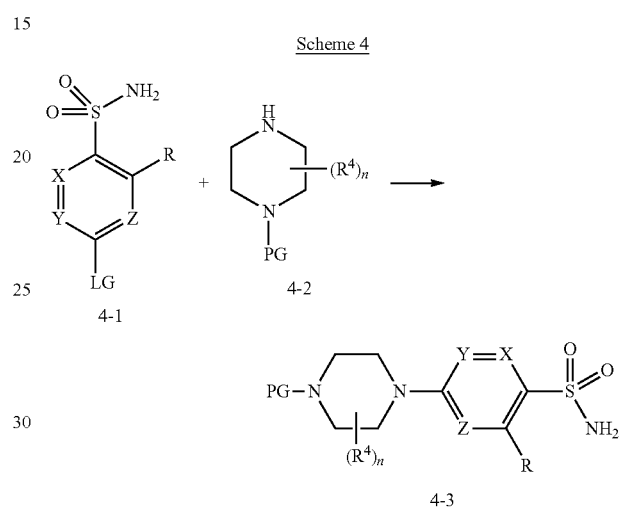

Some compounds for Formula (I) can be prepared by the methods outlined in Scheme 5. The appropriate ketone 5-1 can be transformed into aldehyde 5-2 by reacting with trihalophosphine (X is Br or Cl) in DMF. Suzuki coupling reaction of the aldehyde 5-2 with a boronic acid or ester 5-3 (OR' is OH, OMe, OEt, or pinacol) can yield the corresponding aldehyde 5-4, which can be reduced to alcohol 5-5 by using a suitable reductant (e.g., BH$_3$, NaBH$_4$, or LiAlH$_4$). Sulfonamide intermediates 5-8 can be obtained by reacting the sulfonamide 5-7 with compound 5-6 (LG is I, Br, Cl, OMs, or OTf) that can be obtained from the reaction of the alcohol 5-5 with halogenation reagent (e.g., I$_2$/imidazole, PBr$_3$, SOCl$_2$, mesyl chloride, or triflic anhydride). The sulfonamide intermediates 5-8 can couple with acid 5-9 to yield the desired sulfonamide 5-10 with the method as described in Scheme 1. The variables in Scheme 5 are as defined in the embodiments as described herein.

Scheme 5

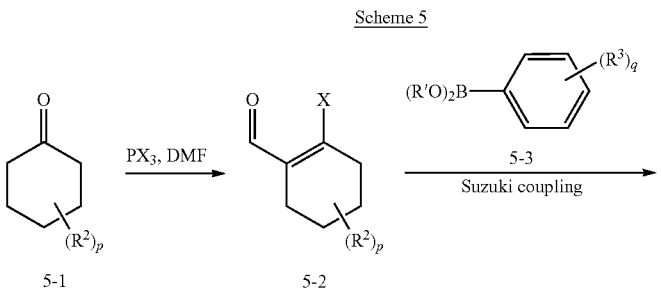

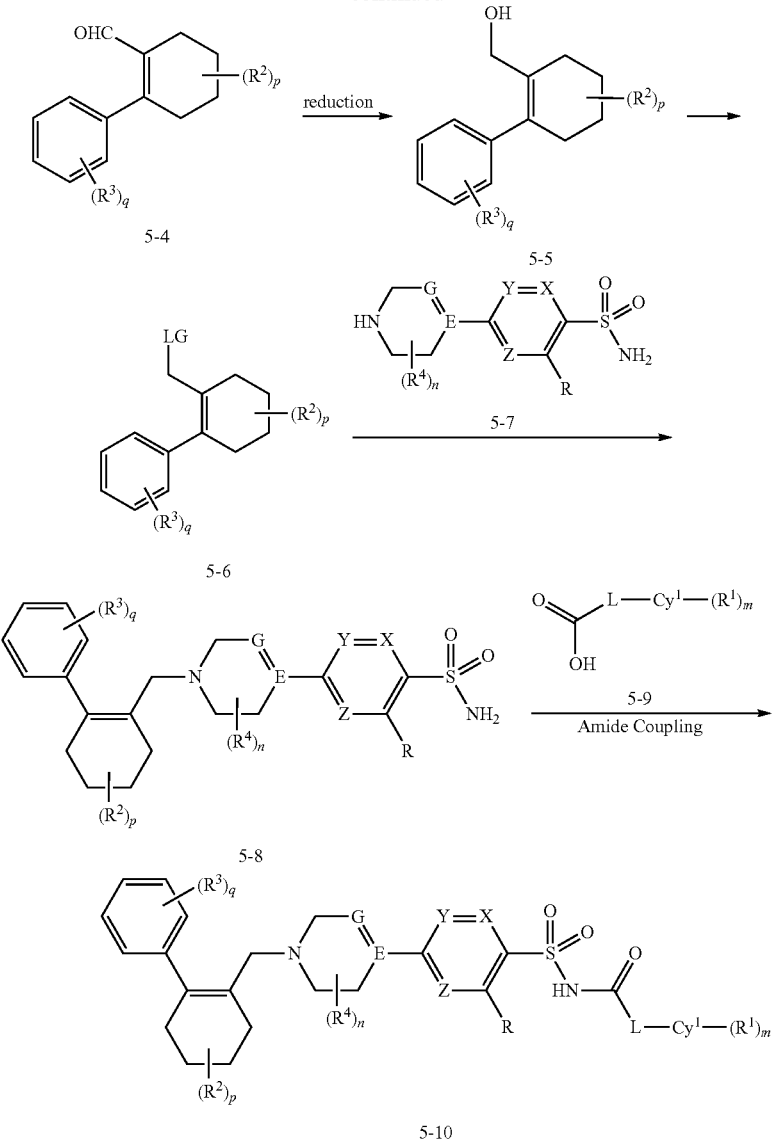

Some compounds for Formula (XX) can be prepared by the methods outlined in Scheme 6. Replacement reaction of compound 6-1 with mono-protected piperazine can produce the corresponding piperazine 6-2. Removal of the PG group of the piperazine 6-2 to afford the piperazine 6-3 can be achieved either under acidic conditions (e.g., TFA in dichloromethane ("DCM"), HBr or HCl in an organic solvent, or $H_3PO_4$) when the PG is a Boc-group or TBS group, or hydrogenation conditions (e.g., Pd/C catalyzed hydrogenation using $H_2$, or transfer hydrogenation using $HCO_2NH_4$) when PG is a Cbz-group or Cbz-like group. Sulfonamide 6-7 can be obtained by a nucleophilic aromatic substitution reaction of sulfonamide 6-4 with the piperazine 6-3 followed by Buchwald coupling reaction with a suitable heterocycle 6-6 in the presence of a coupling catalyst (e.g., $Pd_2(dba)_3$ or $Pd(OAc)_2$) and a ligand (e.g., SPhos, Xphos, or Xantphos), or a precatalyst (e.g., Xphos Pd GIII, Brettphos or Pd GIII) and a suitable base (e.g., $K_2CO_3$, $Cs_2CO_3$, $K_3PO_4$, t-BuOK or t-BuONa). The sulfonamide 6-7 can then couple with an appropriate acid 6-8 by using the methods as described in Scheme 1 to yield the desired sulfonamide 6-9. The variables in Scheme 6 are as defined in the embodiments as described herein.

Scheme 6

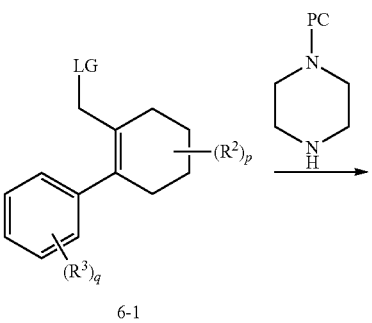

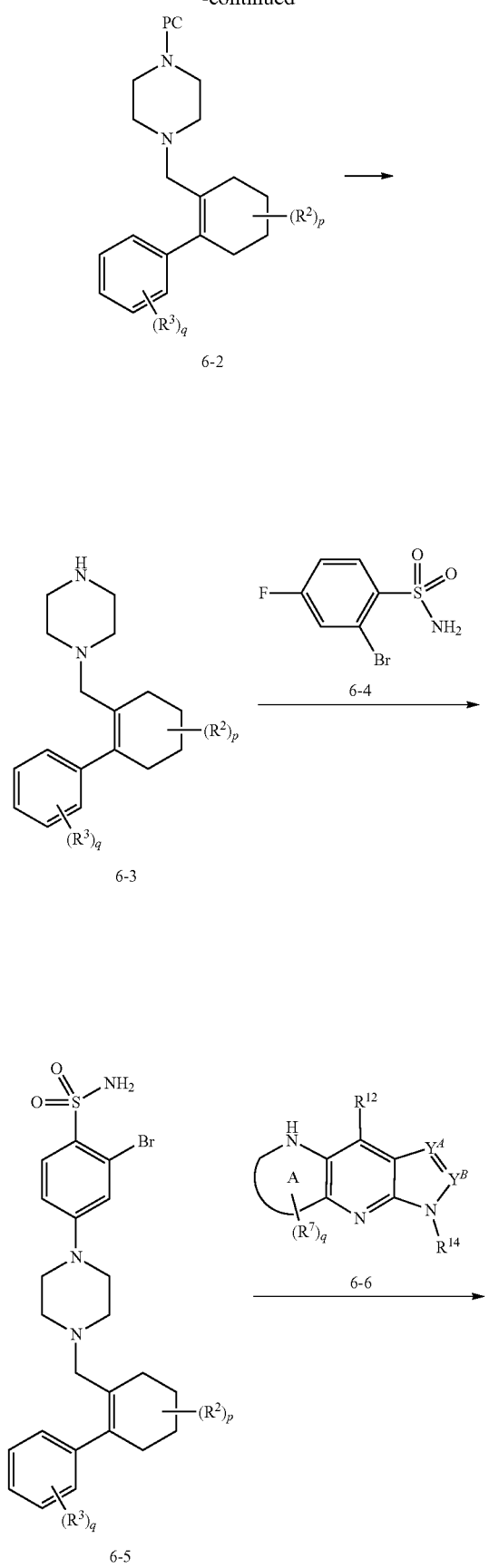
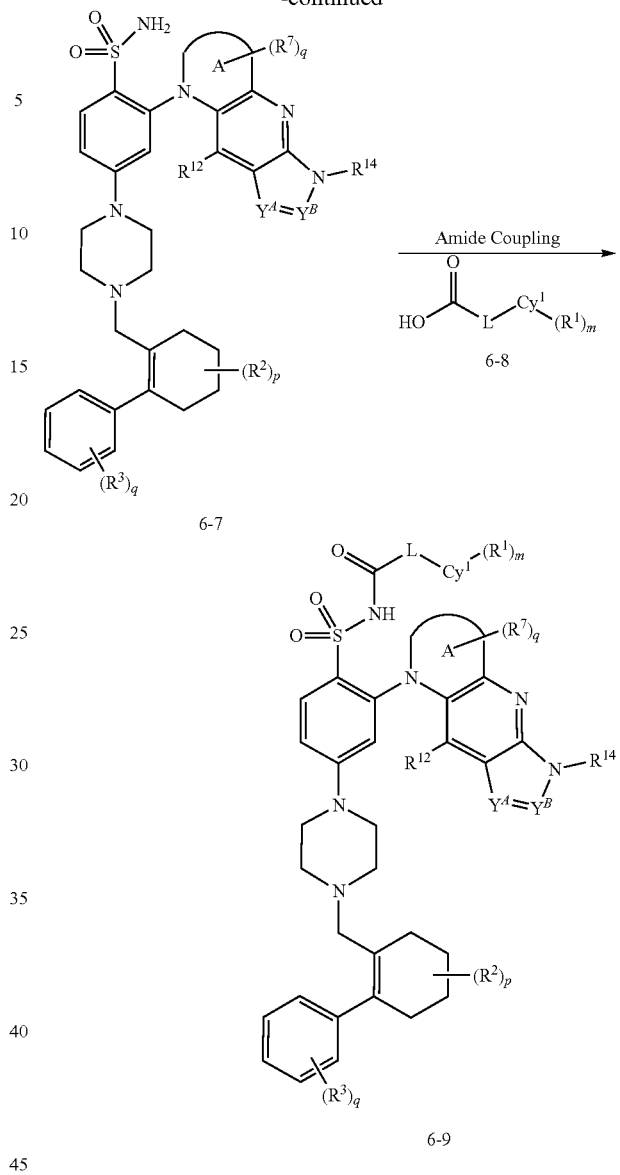

Some intermediates for making compounds of Formula (XX) can be prepared by the methods outlined in Scheme 8. Intermediates 7-6 (U is N, V is C—$R^5$; or U is N, V is N; or U is C—$R^5$, V is N) can be prepared by the methods outlined in Scheme 7. Buchwald coupling of an appropriate bicycloheterocycle 7-1 (LG is I, Br, Cl, OTf, OMs) with an amine PG-$NH_2$ or imine PG=NH can afford the corresponding bicycloheterocycle 7-2. Removal of the PG group of the bicycloheterocycle 7-2 to yield the amino bicycloheterocycle 7-3 can be achieved either under acidic conditions (e.g., TFA in DCM, HBr or HCl in an organic solvent, or $H_3PO_4$) when the PG is a Boc-group, TBS group, or benzophenone imine group, or hydrogenation conditions (e.g., Pd/C catalyzed hydrogenation using $H_2$, or transfer hydrogenation using $HCO_2NH_4$) when the PG is a Cbz-group or Cbz-like group. The amino bicycloheterocycle 7-3 can be transformed into the desired pyrazole derivative 7-6 via the sequential protection with an acetyl group, Jacobson modification of indazole synthesis by treatment with RONO and deprotection of the acetyl group. The variables in Scheme 7 are as defined in the embodiments as described herein.

Scheme 7

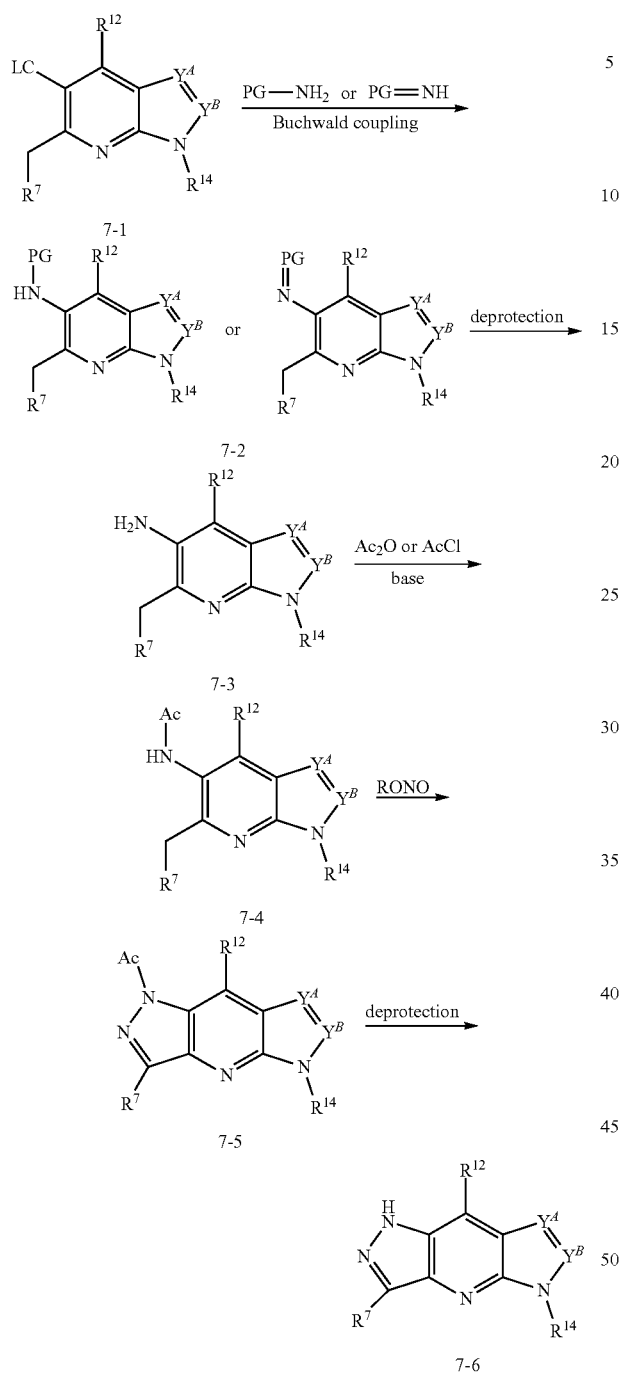

OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, C(=NR$^{g1}$)R$^{b1}$, NR$^{c1}$S(O)R$^{b1}$, NR$^{c1}$S(O)$_2$NR$^{c1}$R$^{d1}$, NR$^{c1}$C(=NOR$^{a1}$)NR$^{c1}$R$^{d1}$, NR$^{c1}$C(=NCN)NR$^{c1}$R$^{d1}$, S(O)(=NR$^{g1}$)R$^{b1}$, S(O)(=NR$^{g1}$)NR$^{c1}$R$^{d1}$, SF$_5$, B(OR$^A$)$_2$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, P(R$^{f1}$)$_2$, P(OR$^{e1}$)$_2$, P(O)R$^{e1}$R$^{f1}$, P(O)OR$^{e1}$OR$^{f1}$, S(O)R$^{b1}$, S(O)(=NR$^{b1}$); S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, C$_{1-6}$ alkyl, C$_{1-6}$ heteroalkyl, C$_{2-6}$ alkenyl, C$_{2-6}$ alkynyl, C$_{1-6}$ haloalkyl, C$_{1-6}$ alkyl-NR$^{c1}$R$^{d1}$, (CH$_2$CH$_2$O)$_{1-10}$C$_{1-6}$alkyl, C$_{2-6}$ alkenyl-NR$^{c1}$R$^{d1}$, C$_{2-6}$ alkynyl-NR$^{c1}$R$^{d1}$, OC$_{2-6}$ alkyl-NR$^{c1}$R$^{d1}$, aryl, heteroaryl, spirocycloalkyl, spiroheterocycloalkyl, cycloalkyl, or heterocycloalkyl, wherein R$^{a1}$, R$^{b1}$, R$^{c1}$, R$^{d1}$, R$^{e1}$, R$^{f1}$, and R$^{g1}$ are as defined in the embodiments as described herein.

Scheme 8

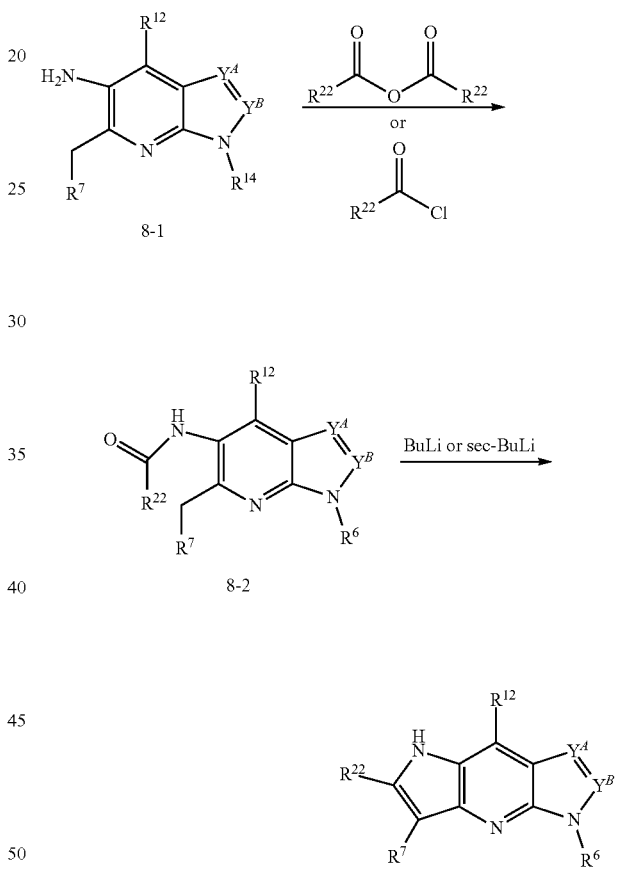

Some intermediates for making compounds of Formula (XX) can be prepared by the methods outlined in Scheme 8. Acyl amide 8-2 can be obtained by acylation of the amino derivative 8-1 with acyl chloride or anhydride under basic conditions (e.g., TEA, DIEA, and pyridine) with or without DMAP as a catalyst. The amide 8-2 can be transformed into the indole intermediates 8-3 by Madelung indole synthesis using a strong base (e.g., BuLi or sec-BuLi). The variables in Scheme 8 are as defined in the embodiments as described herein, wherein R$^{22}$ is H, D, halo, oxo, CN, NO$_2$, N$_3$, OR$^{a1}$, SR$^{a1}$, C(O)R$^{b1}$, C(O)NR$^{c1}$R$^{d1}$, CH$_2$C(O)NR$^{c1}$R$^{d1}$, C(O)

Some intermediates for making compounds of Formula (XX) can be prepared by the methods outlined in Scheme 9. Nucleophilic aromatic substitution reaction (S$_N$Ar) of aryl fluoride 9-1 with a suitable nucleophile 9-2 can yield aryl bromide 9-3, which can undergo Buchwald coupling reaction with a protected amine in the presence of a suitable Pd catalyst and base (as mentioned earlier in Scheme 6 for preparation of 6-7) to afford heterocycle 9-4. The tricycloheterocycle derivative 9-6 can be prepared by intramolecular reductive amination reaction of the amino-aldehyde 9-5, which can be obtained by removal of the protecting groups 9-4 under suitable conditions. The variables in Scheme 9 are as defined in the embodiments as described herein, wherein X$^c$ is S or O.

Scheme 9

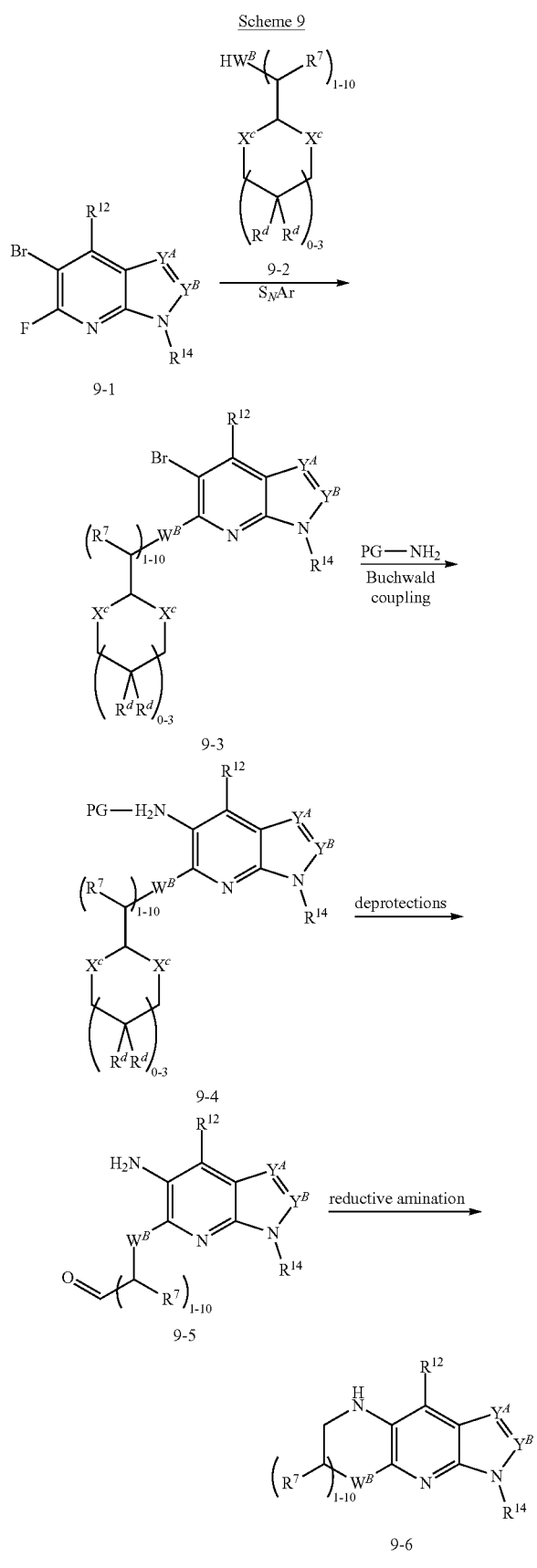

Some intermediates for making compounds of Formula (XX) can be prepared by the methods outlined in Scheme 10. Intermediates 10-4 can be prepared by the methods outlined in Scheme 10. $S_NAr$ of the aryl fluoride 10-1 with a suitable nucleophile 10-2 can provide heterocycle 10-3, which can be transformed into the tricycloheterocycle intermediates 10-4 by intramolecular Buchwald coupling and deprotection of the amino group. The variables in Scheme 10 are as defined in the embodiments as described herein, wherein $W^B$ is S or O.

Scheme 10

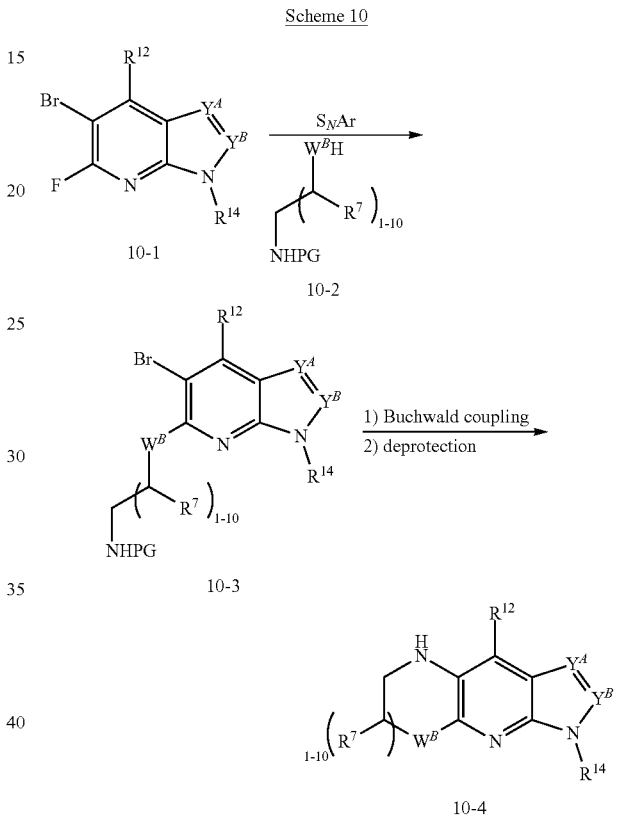

Some compounds of Formula (I) can be prepared by the methods outlined in Scheme 11. Double Michael's addition of an appropriate phosphine oxide 11-1 with a nucleophile amine 11-2 can yield the corresponding amine 11-3 after deprotection. Acid derivative 11-5 can be prepared either by $S_NAr$ of aryl ester 11-4 with the amine 11-3 or by Buchwald coupling reaction of aryl ester 11-4 with the amine 11-3 and following by saponification using basic conditions (e.g., LiOH, or tetrahydrofuran ("THF")/$H_2O$). The acid derivative 11-5 can be transformed into the sulfonamide derivative 11-7 by amide coupling reaction with sulfonamide 11-6 as described in Scheme 1. The variables in Scheme 11 are as defined in the embodiments as described herein, wherein $X^D$ is CH or N; LG is F, Cl, or $NO_2$; $L^1$ is absent, carbonyl, or alkyl; and ss is 0-3; and $R^{18}$, $R^{19}$, and $R^{31}$ are each, independently, H, D, halo, oxo, CN, $NO_2$, $N_3$, OR, $SR^{a1}$, $C(O)R^{b1}$, $C(O)NR^{c1}R^{d1}$, $CH_2C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $C(=NR^{g1})R^{b1}$, $NR^{c1}S(O)R^{b1}$, $NR^{c1}S(O)_2NR^{c1}R^{d1}$, $NR^{c1}C(=NOR^{a1})NR^{c1}R^{d1}$, $NR^{c1}C(=NCN)NR^{c1}R^{d1}$, $S(O)(=NR^{g1})R^{b1}$, $S(O)(=NR^{g1})NR^{c1}R^{d1}$, $SF_5$, $B(OR^{a1})_2$, $NR^{c1}C(O)OR^{a1}$, $C(=NR^{g1})NR^{c1}R^{d1}$, $NR^{c1}C$ (=NR$^{g1}$)NR$^{c1}$R$^{d1}$, P(R$^{f1}$)$_2$, P(OR$^{e1}$)$_2$, P(O)R$^{e1}$R$^{f1}$, P(O)OR$^{e1}$OR$^{f1}$, S(O)R$^{b1}$, S(O)(=NR$^{b1}$); S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, C$_{1-6}$ alkyl, C$_{1-6}$ heteroalkyl, C$_{2-6}$ alkenyl, C$_{2-6}$ alkynyl, C$_{1-6}$ haloalkyl, C$_{1-6}$alkyl-NR$^{c1}$R$^{d1}$, (CH$_2$CH$_2$O)$_{1-10}$C$_{1-6}$alkyl, C$_{2-6}$ alkenyl-NR$^{c1}$R$^{d1}$, C$_{2-6}$ alkynyl-NR$^{c1}$R$^{d1}$, OC$_{2-6}$ alkyl-NR$^{c1}$R$^{d1}$, aryl, heteroaryl, spirocycloalkyl, spiroheterocycloalkyl, cycloalkyl, or heterocycloalkyl, wherein R$^{a1}$, R$^{b1}$, R$^{c1}$, R$^{d1}$, R$^{e1}$, R$^{f1}$, and R$^{g1}$ are as defined in the embodiments as described herein.

or N; L$^1$ is absent, carbonyl, or alkyl; R$^{19}$, R$^{23}$, and R$^{24}$ are each, independently, H, D, halo, oxo, CN, NO$_2$, N$_3$, OR, SR$^{a1}$, C(O)R$^{b1}$, C(O)NR$^{c1}$R$^{d1}$, CH$_2$C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, C(=NR$^{g1}$)R$^{b1}$, NR$^{c1}$S(O)R$^{b1}$, NR$^{c1}$S(O)$_2$NR$^{c1}$R$^{d1}$, NR$^{c1}$C(=NOR$^{a1}$)NR$^{c1}$R$^{d1}$, NR$^{c1}$C(=NCN)NR$^{c1}$R$^{d1}$, S(O)(=NR$^{g1}$)R$^{b1}$, S(O)(=NR$^{g1}$)NR$^{c1}$R$^{d1}$, SF$_5$, B(OR$^{a1}$)$_2$, NR$^{c1}$C(O)OR$^{a1}$, C(=NR$^{g1}$)NR$^{c1}$R$^{d1}$, NR$^{c1}$C(=NR$^{g1}$)NR$^{c1}$R$^{d1}$, P(R$^{f1}$)$_2$, P(OR$^{e1}$)$_2$, P(O)R$^{e1}$R$^{f1}$, P(O)OR$^{e1}$OR$^{f1}$, S(O)R$^{b1}$, S(O)(=NR$^{b1}$); S(O)NR$^{c1}$R$^{d1}$,

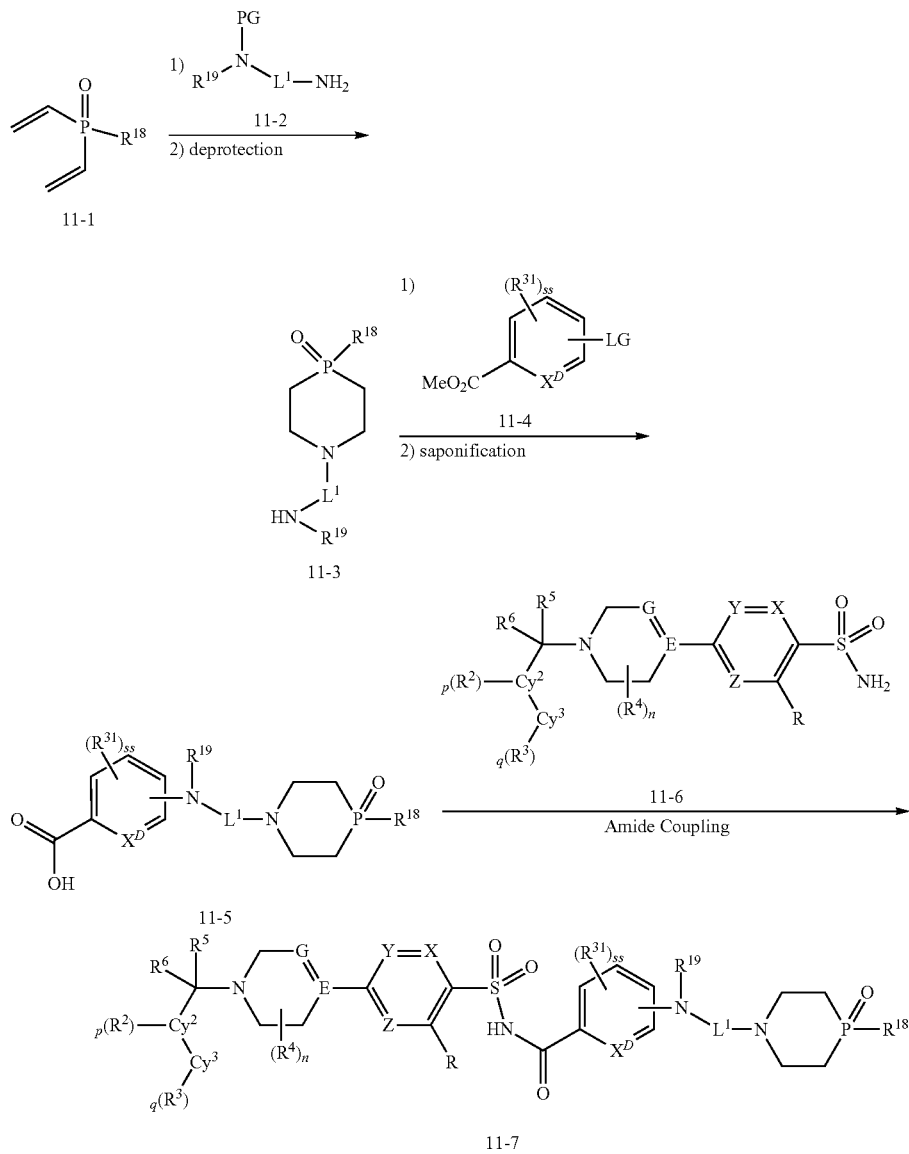

Scheme 11

Some intermediates for making compounds of Formula (I) can be prepared by the methods outlined in Scheme 12. Intermediates 12-5 can be prepared by a reductive amination reaction of an appropriate ketone 12-1 with sulfoximine 12-2 can yield the corresponding amine 12-3 upon deprotection. The reaction of the amine 12-3 with the aryl ester 12-4 to form the acid 12-5 can be obtained in a similar manner as described in Scheme 11. In Scheme 12, X$^D$ is CH or N; S(O)$_2$R$^{b1}$, NR$^{c1}$S(O)$_2$R$^{b1}$, S(O)$_2$NR$^{c1}$R$^{d1}$, C$_{1-6}$ alkyl, C$_{1-6}$ heteroalkyl, C$_{2-6}$ alkenyl, C$_{2-6}$ alkynyl, C$_{1-6}$ haloalkyl, C$_{1-6}$ alkyl-NR$^{c1}$R$^{d1}$, (CH$_2$CH$_2$O)$_{1-10}$C$_{1-6}$alkyl, C$_{2-6}$ alkenyl-NR$^{c1}$R$^{d1}$, C$_{2-6}$ alkynyl-NR$^{c1}$R$^{d1}$, OC$_{2-6}$ alkyl-NR$^{c1}$R$^{d1}$, aryl, heteroaryl, spirocycloalkyl, spiroheterocycloalkyl, cycloalkyl, or heterocycloalkyl, wherein R$^3$, R$^{a1}$, R$^{b1}$, R$^{c1}$, R$^{d1}$, R$^{e1}$, R$^{f1}$, R$^{g1}$ and q are as defined in the embodiments as described herein.

Scheme 12

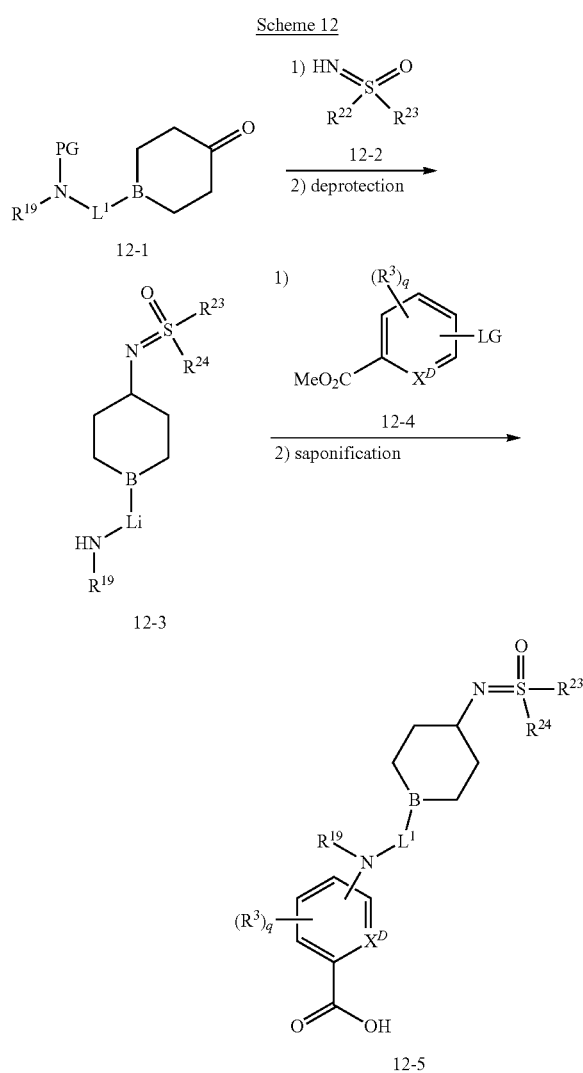

Scheme 13

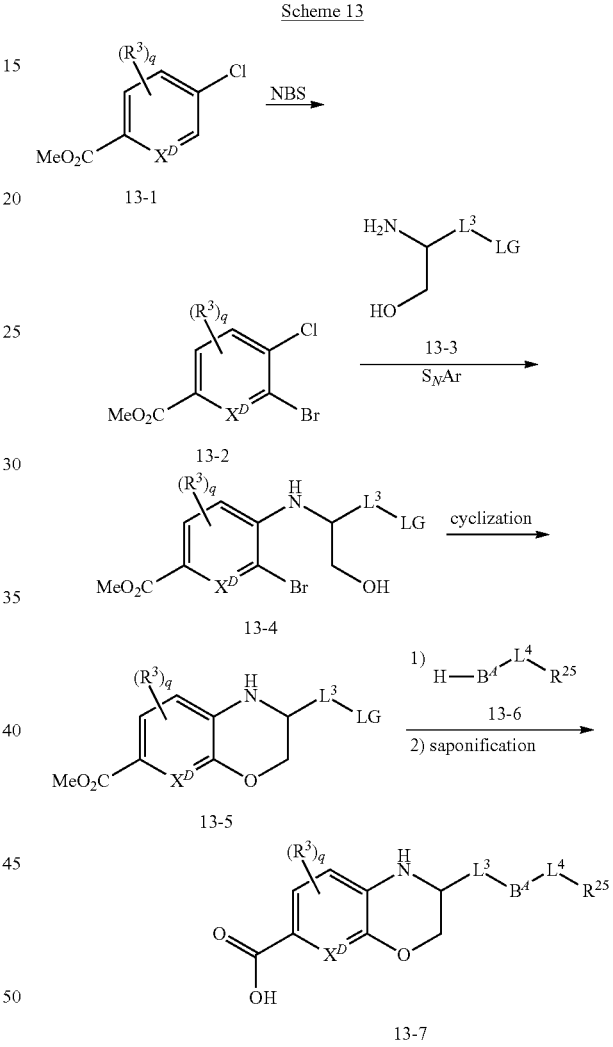

(=NR$^{g1}$)NR$^{c1}$R$^{d1}$, P(R$^{f1}$)$_2$, P(OR$^{e1}$)$_2$, P(O)OR$^{e1}$R$^{f1}$, P(O)OR$^{e1}$OR$^{f1}$, S(O)R$^{b1}$, S(O)(=NR$^{g1}$); S(O)NR$^{c1}$R$^{d1}$, S(O)$_2$R$^{b1}$, NR$^{c1}$S(O)$_2$R$^{b1}$, S(O)$_2$NR$^{c1}$R$^{d1}$, C$_{1-6}$ alkyl, C$_{1-6}$ heteroalkyl, C$_{2-6}$ alkenyl, C$_{2-6}$ alkynyl, C$_{1-6}$ haloalkyl, C$_{1-6}$ alkyl-NR$^{c1}$R$^{d1}$, (CH$_2$CH$_2$O)$_{1-10}$C$_{1-6}$alkyl, C$_{2-6}$ alkenyl-NR$^{c1}$R$^{d1}$, C$_{2-6}$ alkynyl-NR$^{c1}$R$^{d1}$, OC$_{2-6}$ alkyl-NR$^{c1}$R$^{d1}$, aryl, heteroaryl, spirocycloalkyl, spiroheterocycloalkyl, cycloalkyl, or heterocycloalkyl, wherein R$^3$, R$^{a1}$, R$^{b1}$, R$^{c1}$, R$^{d1}$, R$^{e1}$, R$^{f1}$, R$^{g1}$, LG and q are as defined in the embodiments as described herein.

Some intermediates for making compounds of Formula (I) can be prepared by the methods outlined in Scheme 12. Treatment of an appropriate ester 13-1 with NBS or NIS can afford the corresponding aryl bromide 13-2 or aryl iodide, which can be transformed into aryl amino derivative 13-4 by reacting with a suitable amine 13-3 either under directly replacement conditions (X$^D$ is N) or Buchwald reaction conditions (X$^D$ is CH). Intramolecular cyclization of the aryl amino derivative 13-4 to yield benzomorpholine 13-5 can be obtained by Buchwald coupling conditions in the presence of Pd catalyst or Modified Ullmann coupling conditions in the presence of Cu catalyst (e.g., CuI with suitable ligand: proline, glycine, N,N-dimethylethylenediamine, or phenanthroline). The S$_N$2 reaction of 13-5 with suitable nucleophile 13-6 can produce the corresponding acid 13-7 after saponification. In Scheme 13, X$^D$ is CH or N; B$^4$ is O, S, or NH; L$^3$ and L$^4$ are, independently, absent, carbonyl, or alkyl; R$^{25}$ is H, D, halo, oxo, CN, NO$_2$, N$_3$, OR$^{a1}$, SR$^{a1}$, C(O)R$^{b1}$, C(O)NR$^{c1}$R$^{d1}$, CH$_2$C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, C(=NR$^{g1}$)R$^{b1}$, NR$^{c1}$S(O)R$^{b1}$, NR$^{c1}$S (O)$_2$NR$^{c1}$R$^{d1}$, NR$^{c1}$C(=NOR$^{a1}$)NR$^{c1}$R$^{d1}$, NR$^{c1}$C(=NCN) NR$^{c1}$R$^{d1}$, S(O)(=NR$^{g1}$)R$^{b1}$, S(O)(=NR$^{g1}$)NR$^{c1}$R$^{d1}$, SF$_5$, B(OR$^{a1}$)$_2$, NR$^{c1}$C(O)OR$^{a1}$, C(=NR$^{g1}$)NR$^{c1}$R$^{d1}$, NR$^{c1}$C Some compounds of Formula (I) can be prepared by the methods outlined in Scheme 14. Amide coupling reaction of sulfonamide 14-1 with acid 14-2 bearing a leaving group can yield sulfonamide 14-3, which can react with an appropriate nucleophile through S$_N$Ar reaction, or Buchwald coupling reaction (when the nucleophile is an amine under the conditions as mentioned in Scheme 6 for preparation of 6-7, or react with a proper boronic acid or ester through Suzuki coupling to afford sulfonamide 14-4 under Suzuki coupling conditions (e.g., Pd(PPh$_3$)$_4$, Pd(OAc)$_2$, and Pd(dppf)Cl$_2$) with or without additional ligand (e.g., SPhos or Xphos) in the presence of a suitable base (e.g., TEA, Na$_2$CO$_3$, K$_2$CO$_3$, Cs$_2$CO$_3$, K$_3$PO$_4$, NaHCO$_3$, K$_2$HPO$_4$, and KH$_2$PO$_4$). In Scheme 14, X$^E$, X$^F$, and X$^G$ are each, independently, CR$^{26}$ or N; $B^A$ is O, S, or NH; $L^3$ and $L^4$ are, independently, absent, carbonyl, or alkyl and $R^{26}$ and $R^{27}$ is each, independently, H, D, halo, oxo, CN, $NO_2$, $N_3$, $OR^{a1}$, $SR^{a1}$, $C(O)R^{b1}$, $C(O)NR^{c1}R^{d1}$, $CH_2C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $C(=NR^{g1})R^{b1}$, $NR^{c1}S(O)R^{b1}$, $NR^{c1}S(O)_2NR^{c1}R^{d1}$, $NR^{c1}C(=NOR^{a1})NR^{c1}R^{d1}$, $NR^{c1}C(=NCN)NR^{c1}R^{d1}$, $S(O)(=NR^{g1})R^{b1}$, $S(O)(=NR^{g1})NR^{c1}R^{d1}$, $SF_5$, $B(OR^{a1})_2$, $NR^{c1}C(O)OR^{a1}$, $C(=NR^{g1})NR^{c1}R^{d1}$, $NR^{c1}C(=NR^{g1})NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)(=NR^{b1})$; $S(O)NR^{c1}R^{d1}$, $S(O)_2R^{b1}$, $NR^{c1}S(O)_2R^{b1}$, $S(O)_2NR^{c1}R^{d1}$, $C_{1-6}$ alkyl, $C_{1-6}$ heteroalkyl, $C_{2-6}$ alkenyl, $C_{2-6}$ alkynyl, $C_{1-6}$haloalkyl, $C_{1-4}$alkyl-$NR^{c1}R^{d1}$, $(CH_2CH_2O)_{1-10}C_{1-6}$alkyl, $C_{2-6}$ alkenyl-$NR^{c1}R^{d1}$, $C_{2-6}$ alkynyl-$NR^{c1}R^{d1}$, $OC_{2-6}$ alkyl-$NR^{c1}R^{d1}$, aryl, heteroaryl, spirocycloalkyl, spiroheterocycloalkyl, cycloalkyl, or heterocycloalkyl, wherein E, G, L, X, Y, Z, R, $R^2$, $R^3$, $R^4$, $R^5$, $R^6$, $Cy^2$, $Cy^3$, LG, n, p, q, $R^{a1}$, $R^{b1}$, $R^{c1}$, $R^{d1}$, $R^{e1}$, $R^{f1}$, and $R^{g1}$ are as defined in the embodiments as described herein.

Scheme 14

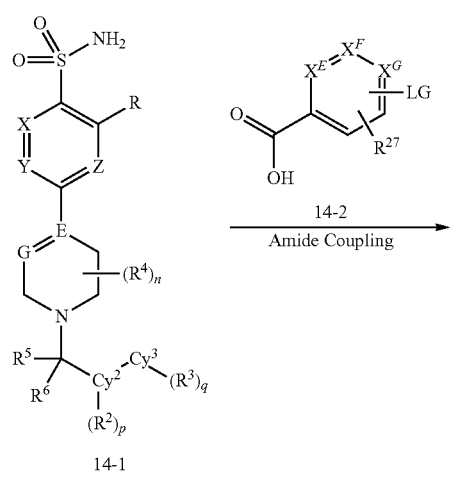

14-1

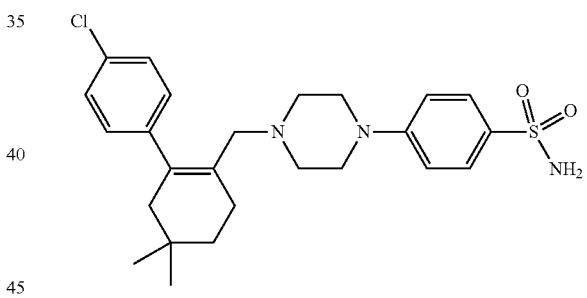

14-2
Amide Coupling

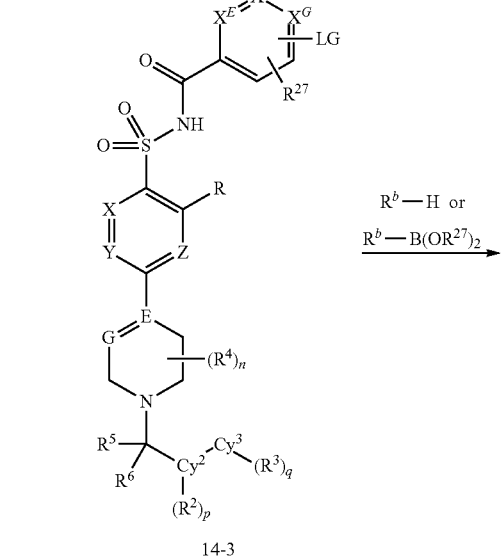

14-3

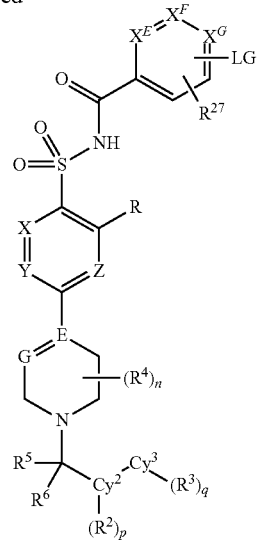

14-4

EXAMPLE INTERMEDIATES

Intermediate 1

4-[4-[[2-(4-chlorophenyl)-4,4-dimethylcyclohexen-1-yl]methyl]piperazin-1-yl]benzenesulfonamide

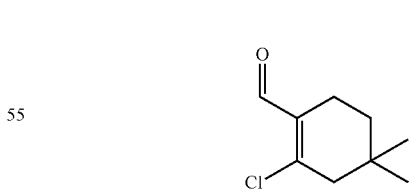

Step 1:
2-chloro-4,4-dimethylcyclohexene-1-carbaldehyde

Phosphorus oxychloride (20.5 g, 118.9 mmol) was slowly added to a mixture of DMF (9.8 mL, 126.8 mmol) and DCM (30 mL) at 0° C. The mixture was stirred at room temperature ("r.t.") for 1 h., then 3,3-dimethylcyclohexan-1-one (10.0 g, 79.2 mmol) was slowly added. The mixture was stirred at 40° C. overnight. The mixture was quenched with an ice-cooled mixture solution of NaOAc aqueous solution (20% w/w, 25 mL) and NaCl aqueous solution (14% w/w, 25 mL), and extracted with DCM (30 mL×3). The combined organic layers were washed with a mixture of $K_3PO_4$ aqueous solution (6% w/w, 25 mL) and NaCl aqueous solution (16% w/w, 25 mL). The organic layer was concentrated under reduced pressure to afford 2-chloro-4,4-dimethylcyclohexene-1-carbaldehyde (14.5 g), which was used in the next step without further purification.

Step 2: 2-(4-chlorophenyl)-4,4-dimethylcyclohexene-1-carbaldehyde

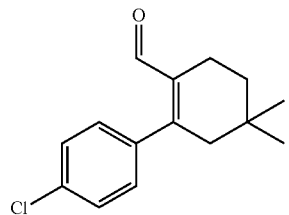 [SMILES: CC1(C)CCC(C=O)=C(c2ccc(Cl)cc2)C1]

A reaction flask was charged with 4-chlorophenylboronic acid (13.13 g, 83.98 mmol), tetrabutylammonium bromide (27.08 g, 83.98 mmol), potassium carbonate (28.0 g, 202.6 mmol) and 2-chloro-4,4-dimethylcyclohexene-1-carbaldehyde (14.5 g, 83.98 mmol) under $N_2$. Water (100 mL) was added and the mixture was bubbled with $N_2$ gas for 15 minutes ("min"). Palladium (II) acetate (942.73 mg, 4.2 mmol) was added and the mixture was stirred at 30° C. overnight. The mixture was filtered through a pad of Celite and rinsed with toluene (70 mL). The organic phase was washed with NaOH (aqueous ("aq")) (0.5 M, 40 mL) and then $NaHCO_3$ (aq) (5%, 40 mL). The organic layer was concentrated under reduced pressure to afford 2-(4-chlorophenyl)-4,4-dimethylcyclohexene-1-carbaldehyde (28.0 g) which was used in the next step without further purification. Proton nuclear magnetic resonance ("$^1$H NMR") (300 MHz, $CDCl_3$) δ 9.51 (s, 1H), 7.41-7.35 (m, 2H), 7.20-7.14 (m, 2H), 2.40 (td, J=6.6, 3.3 Hz, 2H), 2.31 (t, J=2.3 Hz, 2H), 1.52 (t, J=6.5 Hz, 2H), 1.03 (s, 6H).

Step 3: [2-(4-chlorophenyl)-4,4-dimethylcyclohexen-1-yl]methanol

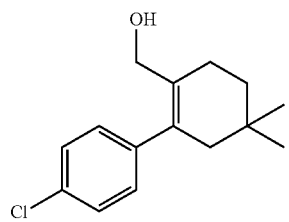 [SMILES: CC1(C)CCC(CO)=C(c2ccc(Cl)cc2)C1]

To a solution of 2-(4-chlorophenyl)-4,4-dimethylcyclohexene-1-carbaldehyde (28.0 g, 112.56 mmol) dissolved in THF (20 mL) and water (20 mL) was added sodium borohydride (8.52 g, 225.13 mmol). The mixture was stirred for 1 h. at r.t. and then quenched with $H_2O$ (40 mL). The mixture was extracted with ethyl acetate ("EtOAc") (40 mL×3). The organic layer was dried over $Na_2SO_4$, filtered, and concentrated under reduced pressure. The resulting residue was purified by flash column chromatography ("FCC") on a silica gel column eluting with ethyl acetate:heptane (0% to 30%) to afford[2-(4-chlorophenyl)-4,4-dimethylcyclohexen-1-yl]methanol (18.6 g, 66% yield).

Step 4: 1-[2-(bromomethyl)-5,5-dimethylcyclohexen-1-yl]-4-chlorobenzene

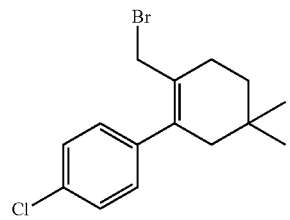 [SMILES: CC1(C)CCC(CBr)=C(c2ccc(Cl)cc2)C1]

A solution of [2-(4-chlorophenyl)-4,4-dimethylcyclohexen-1-yl]methanol (500.0 mg, 1.99 mmol) in DCM (10 mL) was cooled to −20° C. Phosphorus tribromide (0.13 mL, 1.4 mmol) was added and the mixture was slowly warmed to 0° C. The mixture was stirred for an additional 30 min. at 0° C. LC-MS showed the starting material converted into the desired product. The mixture was quenched with sat. $Na_2CO_3$ (aq) (20 mL) and extracted with DCM (10 mL×3). The organic layer was dried over $Na_2SO_4$, filtered, and concentrated under reduced pressure to afford 1-[2-(bromomethyl)-5,5-dimethylcyclohexen-1-yl]-4-chlorobenzene (550 mg, 88% yield), which was used in the next step without further purification. LC-MS calc. for $C_{15}H_{19}BrCl$ [M+H]$^+$: m/z=313.04/315.03. Found: 313.0/314.9.

Step 5: 4-piperazin-1-ylbenzenesulfonamide

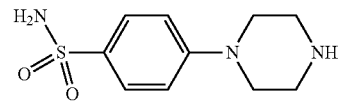

A mixture of 4-fluorobenzenesulfonamide (25.0 g, 142.71 mmol) and piperazine (49.17 g, 570.84 mmol) in water (300 mL) was heated at 100° C. for 24 h. The resulting precipitate was collected by filtration, washed with water and toluene, and dried under reduced pressure to give 4-piperazin-1-ylbenzenesulfonamide (32.3 g, 94% yield). $^1$H NMR (300 MHz, DMSO-$d_6$) δ 7.61 (d, J=9.0 Hz, 2H), 7.06 (s, 2H), 7.01 (d, J=9.0 Hz, 2H), 3.21-3.15 (m, 4H), 2.86-2.77 (m, 4H).

Step 6: 4-[4-[[2-(4-chlorophenyl)-4,4-dimethylcyclohexen-1-yl]methyl]piperazin-1-yl]benzenesulfonamide A mixture of 1-[2-(bromomethyl)-5,5-dimethylcyclohexen-1-yl]-4-chlorobenzene (5.0 g, 19.94 mmol) and potassium carbonate (11.0 g, 79.59 mmol) dissolved in dimethyl sulfoxide ("DMSO") (60 mL) was added 4-piperazin-1-ylbenzenesulfonamide (4.8 g, 19.89 mmol). The mixture was stirred at r.t. for 2 h. LC-MS showed the formation of the desired product. The mixture was quenched with HCl (aq) (0.5 M, 200 mL) and the precipitates formed was filtered and dried to afford 4-[4-[[2-(4-chlorophenyl)-4,4-dimethylcyclohexen-1-yl]methyl]piperazin-1-yl]benzenesulfonamide (8.3 g, 88% yield). LC-MS calc. for $C_{25}H_{33}ClN_3O_2S$ [M+H]$^+$: m/z=474.20/476.20. Found:

473.91/475.70. 1H NMR (300 MHz, DMSO-d6) δ 7.69-7.58 (m, 2H), 7.48-7.37 (m, 2H), 7.14 (m, 2H), 7.10 (br, 2H), 7.07-6.97 (m, 2H), 3.83 (d, J=13.7 Hz, 2H), 3.61 (s, 2H), 3.26 (m, 2H), 2.80 (s, 2H), 2.61-2.51 (m, 2H), 2.35 (d, J=6.5 Hz, 2H), 2.05 (s, 2H), 1.48 (t, J=6.4 Hz, 2H), 0.97 (s, 6H).

Intermediate 2

4-[4-[[2-(4-Chlorophenyl)-4,4-dimethylcyclohexen-1-yl]methyl]piperazin-1-yl]-2-(1H-pyrrolo[2,3-b]pyridin-5-yloxy)benzenesulfonamide

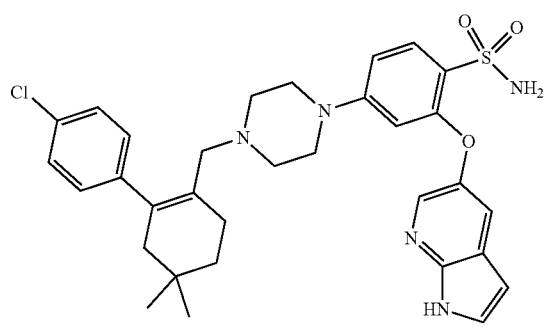 [SMILES: CC1(C)CCC(CN2CCN(c3ccc(S(N)(=O)=O)c(Oc4cnc5[nH]ccc5c4)c3)CC2)=C(c2ccc(Cl)cc2)C1]

Step 1: 4-fluoro-2-(1H-pyrrolo[2,3-b]pyridin-5-yloxy)benzenesulfonamide

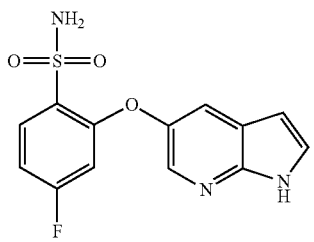 [SMILES: NS(=O)(=O)c1ccc(F)cc1Oc1cnc2[nH]ccc2c1]

A mixture of 1H-pyrrolo[2,3-b]pyridin-5-ol (6.31 g, 47.06 mmol) and 2,4-difluorobenzenesulfonamide (10.0 g, 51.77 mmol) was dissolved in dimethylformamide ("DMF") (80 mL). The mixture was stirred for 15 min. and cooled to 0° C. Sodium tert-butoxide (7.46 g, 77.65 mmol) was added in small portions. The mixture was stirred at r.t. for 1 h., and then 60° C. for 24 h. After cooling, the mixture was quenched with HCl(aq) (0.5 M, 100 mL) and extracted with ethyl acetate (50 mL×3). The organic layer was concentrated under reduced pressure. The resulting residue was purified by flash chromatography on a silica gel column eluting with ethyl acetate:heptane (10% to 60%) to afford 4-fluoro-2-(1H-pyrrolo[2,3-b]pyridin-5-yloxy)benzenesulfonamide (13.2 g, 83% yield) which contaminated with 2-fluoro-4-(1H-pyrrolo[2,3-b]pyridin-5-yloxy)benzenesulfonamide. LC-MS calc. for $C_{13}H_{11}FN_3O_3S$ [M+H]$^+$: m/z=308.05/309.05. Found: 307.8/309.2.

Step 2: 4-piperazin-1-yl-2-(1H-pyrrolo[2,3-b]pyridin-5-yloxy)benzenesulfonamide

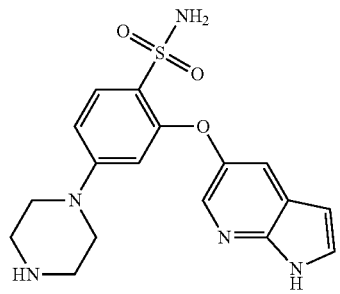 [SMILES: NS(=O)(=O)c1ccc(N2CCNCC2)cc1Oc1cnc2[nH]ccc2c1]

To a solution of 4-fluoro-2-(1H-pyrrolo[2,3-b]pyridin-5-yloxy) benzenesulfonamide (1.5 g, 4.88 mmol) in DMSO (10 mL) was added piperazine (3.36 g, 39.05 mmol). The mixture was stirred at 50° C. overnight. LC-MS showed the formation of the desired product. The mixture was poured into ice-cooled H$_2$O (60 mL) and extracted with ethyl acetate (50 mL×3). The organic layer was concentrated under reduced pressure and the resulting residue was purified by flash chromatography eluting with MeOH/ethyl acetate (0% to 30%) to afford 4-piperazin-1-yl-2-(1H-pyrrolo[2,3-b]pyridin-5-yloxy)benzenesulfonamide (450 mg, 25% yield). LC-MS calc. for $C_{17}H_{20}N_5O_3S$ [M+H]$^+$: m/z=374.13/375.13. Found: 373.9/375.2.

Step 3: 4-[4-[[2-(4-chlorophenyl)-4,4-dimethylcyclohexen-1-yl]methyl]piperazin-1-yl]-2-(1H-pyrrolo[2,3-b]pyridin-5-yloxy)benzenesulfonamide To a solution of 1-[2-(bromomethyl)-5,5-dimethylcyclohexen-1-yl]-4-chlorobenzene (378.0 mg, 1.21 mmol) and 4-piperazin-1-yl-2-(1H-pyrrolo[2,3-b]pyridin-5-yloxy)benzenesulfonamide (450.0 mg, 1.21 mmol) in DMSO (9 mL) was added potassium carbonate (666.17 mg, 4.82 mmol). The mixture was stirred at r.t. for 2 h. LC-MS showed the formation of the desired product. The mixture was filtered, concentrated under reduced pressure and purified by preparative High Performance Liquid Chromatography ("prep-HPLC") on a C18 column eluting with MeCN/H$_2$O (20% to 100%) to afford 4-[4-[[2-(4-chlorophenyl)-4,4-dimethylcyclohexen-1-yl]methyl]piperazin-1-yl]-2-(1H-pyrrolo[2,3-b]pyridin-5-yloxy)benzenesulfonamide (137 mg, 19% yield). LC-MS calc. for $C_{32}H_{37}ClN_5O_3S$ [M+H]$^+$: m/z=606.23/607.23. Found: 605.94/607.44. $^1$H NMR (300 MHz, CDCl$_3$) δ 11.88 (s, 1H), 8.04 (s, 1H), 7.97 (s, 1H), 7.83 (d, J=8.8 Hz, 1H), 7.52 (s, 1H), 7.34 (d, J=8.0 Hz, 2H), 6.94 (d, J=8.2 Hz, 2H), 6.59 (s, 2H), 6.20 (d, J=2.2 Hz, 1H), 3.59 (s, 2H), 2.65 (d, J=0.9 Hz, 1H), 2.28 (s, 2H), 2.07 (s, 2H), 1.54-1.20 (m, 9H), 0.97 (s, 6H).

Intermediate 3

5-Nitro-6-phenylmethoxypyridine-2-carboxylic acid

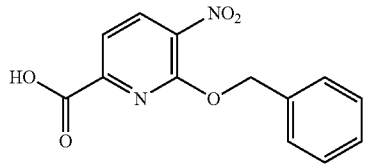 [SMILES: O=C(O)c1ccc([N+](=O)[O-])c(OCc2ccccc2)n1]

To a solution of benzyl alcohol (0.08 mL, 0.74 mmol) in THF (5 mL) was added sodium hydride (60%, dispersion in Paraffin Liquid) (0.09 mL, 1.97 mmol). The mixture was stirred for 5 min. and 6-chloro-5-nitropyridine-2-carboxylic acid (100.0 mg, 0.49 mmol) was added. The mixture was stirred at 40° C. overnight. The mixture was quenched with HCl(aq) (0.5 M, 5 mL) and extracted with ethyl acetate (3 mL×3). The organic layer was dried over $Na_2SO_4$, filtered, and concentrated under reduced pressure. The resulting residue was purified by flash chromatography on a silica gel column eluting with ethyl acetate/heptane (10% to 50%) to afford 5-nitro-6-phenylmethoxypyridine-2-carboxylic acid (19 mg, 14% yield). LC-MS calc. for $C_{13}H_9N_2O_5$ [M–H]$^+$: m/z=273.05/274.05. Found: 273.0/274.1.

Intermediate 4

3-Nitro-4-(phenoxymethyl)benzoic acid

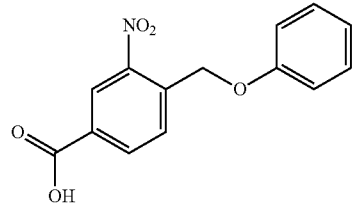 [SMILES: O=C(O)c1ccc(COc2ccccc2)c([N+](=O)[O-])c1]

To a solution of 4-(bromomethyl)-3-nitrobenzoic acid (100.0 mg, 0.38 mmol) and phenol (72.3 mg, 0.77 mmol) dissolved in acetone (3 mL) was added potassium carbonate (265.7 mg, 1.92 mmol). The mixture was stirred at 40° C. overnight, then quenched with HCl(aq) (0.5 M, 5 mL), and extracted with ethyl acetate (3 mL×3). The combined organic layers were concentrated under reduced pressure. The resulting residue was purified by flash chromatography on a silica gel column eluting with ethyl acetate/heptane (10% to 50%) to afford 3-nitro-4-(phenoxymethyl)benzoic acid (20 mg, 19% yield). LC-MS calc. for $C_{14}H_{10}NO_5$ [M–H]$^+$: m/z=272.06/273.06. Found: 272.0/273.1.

Intermediate 5

4-[(4-Chlorophenoxy)methyl]-3-nitrobenzoic acid

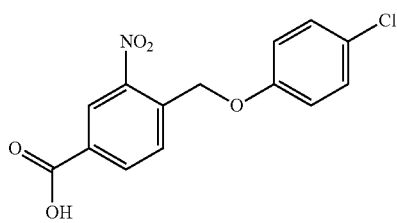 [SMILES: O=C(O)c1ccc(COc2ccc(Cl)cc2)c([N+](=O)[O-])c1]

This compound was prepared as yellow solid using procedures analogous to those described for preparing Intermediate 4 using 4-chlorophenol to replace phenol. LC-MS calc. for $C_{14}H_9ClNO_5$ [M–H]$^-$: m/z=306.02/308.01. Found: 305.9/307.8.

Intermediate 6

4-Fluoro-3-(4-chlorophenoxymethyl)benzoic acid

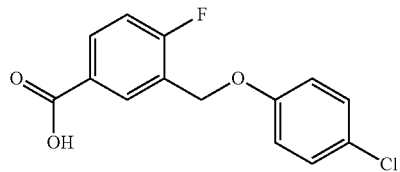 [SMILES: O=C(O)c1ccc(F)c(COc2ccc(Cl)cc2)c1]

Step 1: methyl 3-(bromomethyl)-4-fluorobenzoate

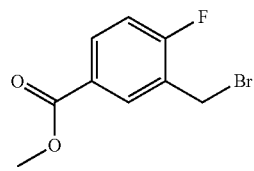

To a solution of methyl 4-fluoro-3-methylbenzoate (2.0 g, 11.89 mmol) in chlorobenzene (20 mL) was added 2,2'-azobisisobutyronitrile (195.3 mg, 1.19 mmol) and N-bromosuccinimide (2197.5 mg, 12.49 mmol). The mixture was stirred at 80° C. for 1 h. The crude was then cooled down to r.t. and added $H_2O$ (20 mL). The mixture was then extracted with ethyl acetate (10 mL×3). All combined organic layers were dried over $Na_2SO_4$, filtered, and concentrated under reduced pressure. The resulting residue was purified by flash chromatography on a silica gel column using EtOAc/Heptanes (5-30%) to afford methyl 3-(bromomethyl)-4-fluorobenzoate (1.5 g, 51% yield) as a white solid. TLC (Thin layer chromatography): $R_f$=0.58 (ethyl acetate/heptanes=1:1).

Step 2: Methyl 3-[(4-chlorophenoxy)methyl]-4-fluorobenzoate

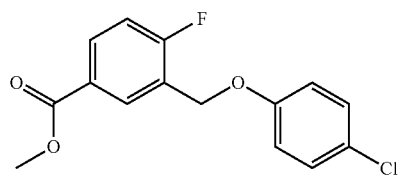 [SMILES: COC(=O)c1ccc(F)c(COc2ccc(Cl)cc2)c1]

A mixture of methyl 3-(bromomethyl)-4-fluorobenzoate (300.0 mg, 1.21 mmol), 4-chlorophenol (312.22 mg, 2.43 mmol) and $K_2CO_3$ (785 mg, 6.07 mmol) in acetone (5 mL) was stirred at 40° C. for 5 h. After cooling, the mixture was carefully quenched with 1N HCl (10 mL) and extracted with ethyl acetate (10 mL×3). The combined organic layers were dried over $Na_2SO_4$, filtered, and concentrated under reduced pressure. The resulting residue was purified by flash chromatography on a silica gel column using EtOAc/Heptanes (0-15%) to afford methyl 3-[(4-chlorophenoxy)methyl]-4-fluorobenzoate (355 mg, 99% yield). TLC: $R_f$=0.45 (ethyl acetate/heptanes=1:3).

Step 3: 3-[(4-chlorophenoxy)methyl]-4-fluorobenzoic acid

To a solution of methyl 3-[(4-chlorophenoxy)methyl]-4-fluorobenzoate (355.0 mg, 1.2 mmol) in THF (1 mL), methanol (1 mL), and water (1 mL) was added LiOH (253.14 mg, 6.02 mmol). The mixture was stirred at 40° C. for 30 min. The mixture was neutralized with 1N HCl (8 mL) and extracted with ethyl acetate (8 mL×3). The combined organic layers were dried over $Na_2SO_4$, filtered, and concentrated under reduced pressure to provide 3-[(4-chlorophenoxy)methyl]-4-fluorobenzoic acid (308 mg, 91% yield) as a white solid without further purification. LC-MS calc. for $C_{14}H_9ClFO_3$ [M−H]$^-$: m/z=279.0/281.0. Found 279.0/281.0.

Intermediate 7

3-(Cyclopropyloxymethyl)-4-fluorobenzoic acid

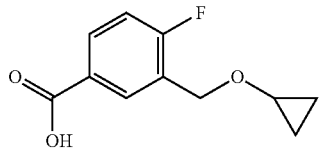 [SMILES: O=C(O)c1ccc(F)c(COC2CC2)c1]

Step 1: methyl 3-(cyclopropyloxymethyl)-4-fluorobenzoate

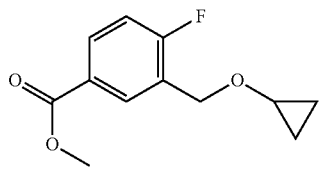 [SMILES: COC(=O)c1ccc(F)c(COC2CC2)c1]

To a solution of methyl 3-(bromomethyl)-4-fluorobenzoate (50.0 mg, 0.20 mmol) in DMF (3 mL) were added NaH (9.71 mg, 0.40 mmol) at 0° C. The mixture was stirred at 0° C. for 10 min, followed by the addition of cyclopropanol (23.51 mg, 0.40 mmol). The reaction was stirred at r.t. for overnight. The reaction was then quenched by 1N HCl (3 mL), and extracted with ethyl acetate (5 mL×3). The combined organic layers were dried over $Na_2SO_4$, filtered, and concentrated under reduced pressure. The resulting residue methyl 3-(cyclopropyloxymethyl)-4-fluorobenzoate (50 mg) was used in the next step without further purification. TLC: $R_f$=0.58 (ethyl acetate/heptanes=1:1).

Step 2: 3-(cyclopropyloxymethyl)-4-fluorobenzoic acid

This compound was prepared as a yellow solid using a procedure analogous to those described for Step 3 of preparing Intermediate 6 using methyl 3-(cyclopropyloxymethyl)-4-fluorobenzoate. LC-MS calc. for $C_{11}H_{10}FO_3$ [M−H]$^-$: m/z=209.1. Found 209.1.

Intermediate 8

3-[(4-Chlorophenoxy)methyl]-4-nitrobenzoic acid

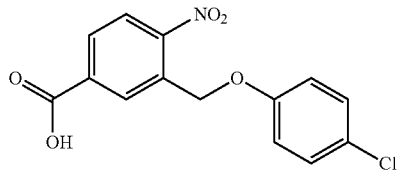 [SMILES: O=C(O)c1ccc([N+](=O)[O-])c(COc2ccc(Cl)cc2)c1]

This compound was prepared as yellow solid using procedures analogous to those described for preparing Intermediate 6 using methyl 3-methyl-4-nitrobenzoate to replace methyl 4-fluoro-3-methylbenzoate in Step 1. LC-MS calc. for $C_{14}H_9ClNO_5$ [M−H]$^-$: m/z=306.0/308.0. Found 306.0/307.9.

Intermediate 9

4-Nitro-3-(phenoxymethyl)benzoic acid

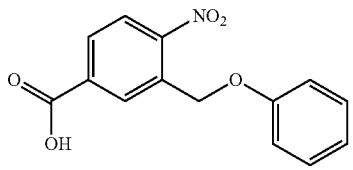 [SMILES: O=C(O)c1ccc([N+](=O)[O-])c(COc2ccccc2)c1]

This compound was prepared as yellow solid using procedures analogous to those described for preparing Intermediate 6 using methyl 3-methyl-4-nitrobenzoate to replace methyl 4-fluoro-3-methylbenzoate in Step 1, and using phenol to replace 4-chlorophenol in Step 2. LC-MS calc. for $C_{14}H_{10}NO_5$ [M−H]$^-$: m/z=272.1. Found 272.0.

Intermediate 10

4-Nitro-3-phenylmethoxybenzoic acid

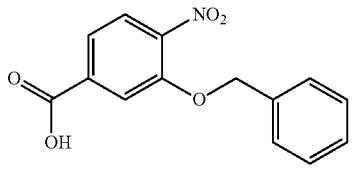 [SMILES: O=C(O)c1ccc([N+](=O)[O-])c(OCc2ccccc2)c1]

To a stirred solution of sodium hydride (60%, dispersion in Paraffin Liquid) (110.97 mg, 2.77 mmol) in THF (10 mL) was added benzyl alcohol (100.0 mg, 0.92 mmol). 3-Fluoro-4-nitrobenzoic acid (256.76 mg, 1.39 mmol) was then added to the reaction mixture. The resulting mixture was stirred at 60° C. for 6 h. The reaction was quenched with 1M HCl(aq) (10 mL), extracted with ethyl acetate (100 mL×3). The combined organic layers were concentrated under reduced pressure. The resulting residue was triturated in DCM to afford 4-nitro-3-phenylmethoxybenzoic acid (70 mg, 28% yield). LC-MS calc. for $C_{14}H_{10}NO_5$ [M−H]$^-$: m/z=272.1. Found 272.0.

Intermediate 11

3-Nitro-4-phenylmethoxybenzoic acid

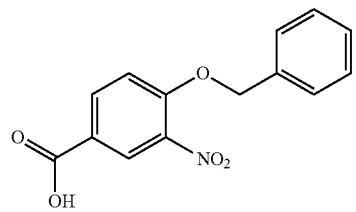 [SMILES: O=C(O)c1ccc(OCc2ccccc2)c([N+](=O)[O-])c1]

This compound was prepared as yellow solid using procedures analogous to those described for preparing Intermediate 10 using 4-fluoro-3-nitrobenzoic acid and benzyl alcohol. LC-MS calc. for $C_{14}H_{10}NO_5$ [M−H]⁻: m/z=272.1. Found 272.0.

Intermediate 12

4-Fluoro-3-phenylmethoxybenzoic acid

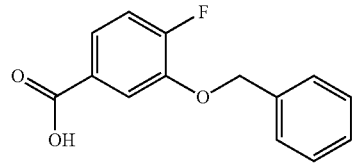 [SMILES: O=C(O)c1ccc(F)c(OCc2ccccc2)c1]

To a stirred solution of Sodium Hydride (60%, dispersion in Paraffin Liquid) (97.24 mg, 2.43 mmol) in THF (10 mL) was added 4-fluoro-3-hydroxybenzoic acid (126.5 mg, 0.81 mmol). Benzyl bromide (207.89 mg, 1.22 mmol) was then added to the reaction mixture at 60° C. and the resulting mixture was kept stirred overnight. LC-MS showed about 40% conversion of the starting material into the desired product. Reaction was quenched with 1M HCl(aq) (10 mL), extracted with ethyl acetate (100 mL×3). The organic layer was concentrated and the resulting residue was stirred in MeOH to afford 4-fluoro-3-phenylmethoxybenzoic acid (70 mg, 35% yield). LC-MS calc. for $C_{14}H_{10}FO_3$ [M−H]⁻: m/z=245.1. Found 245.0.

Intermediate 13

2-Chloro-3-methyl-5-nitro-4-(tetrahydropyran-4-ylmethylamino) benzoic acid

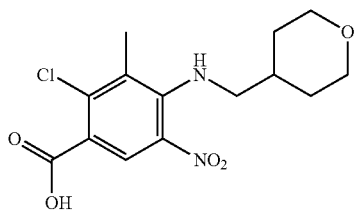 [SMILES: Cc1c(Cl)c(C(=O)O)cc([N+](=O)[O-])c1NCC1CCOCC1]

To a stirred solution of 2-chloro-4-fluoro-3-methyl-5-nitro-benzoic acid (50.0 mg, 0.21 mmol) in DMF (1.5 mL) was added tetrahydropyran-4-ylmethanamine (27.12 mg, 0.24 mmol) and the resulting solution was stirred at 20° C. for 4 h. The reaction was quenched by water (5 mL) and its pH was adjusted to 1-2 with 1M HCl aq. solution. The mixture was extracted with ethyl acetate (5 mL×2). The combined organic layers were dried over $Na_2SO_4$, filtered, and concentrated under reduced pressure to afford 2-chloro-3-methyl-5-nitro-4-(tetrahydropyran-4-ylmethylamino) benzoic acid (44 mg, 63% yield) which was directly used in next step without purification. LC-MS calc. for $C_{14}H_{18}ClN_2O_5$ [M+H]⁺: m/z=329.1. Found: 328.9.

Intermediate 14

2-Chloro-4-(ethylamino)-3-methyl-5-nitrobenzoic acid

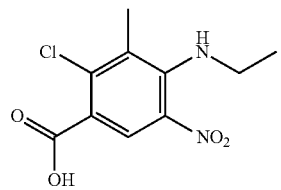 [SMILES: CCNc1c([N+](=O)[O-])cc(C(=O)O)c(Cl)c1C]

This compound was prepared using procedures analogous to those described for preparing Intermediate 13 using ethylamine solution (2.0M in THF) to replace tetrahydropyran-4-ylmethanamine.

Intermediate 15

2-Chloro-4-(methylamino)-3-methyl-5-nitrobenzoic acid

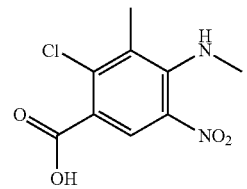 [SMILES: CNc1c([N+](=O)[O-])cc(C(=O)O)c(Cl)c1C]

This compound was prepared using procedures analogous to those described for preparing Intermediate 13 using methylamine solution (2.0M in THF) to replace tetrahydropyran-4-ylmethanamine.

Intermediate 16

2-Chloro-5-nitro-4-(tetrahydropyran-4-ylmethylamino)benzoic acid

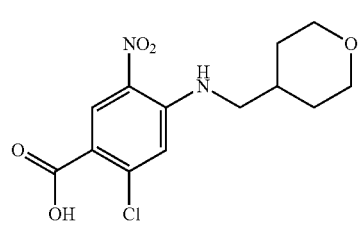 [SMILES: O=C(O)c1cc([N+](=O)[O-])c(NCC2CCOCC2)cc1Cl]

This compound was prepared using procedures analogous to those described for preparing Intermediate 13 using 2-chloro-4-fluoro-5-nitro-benzoic acid to replace 2-chloro- 4-fluoro-3-methyl-5-nitro-benzoic acid. LC-MS calc. for $C_{13}H_{14}ClN_2O_5$ [M–H]⁻: m/z=313.1. Found: 313.0.

Intermediate 17

3-(Methoxymethyl)-5-nitrobenzoic acid

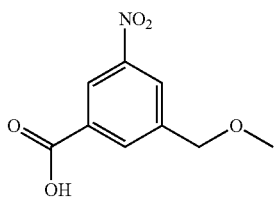

Step 1: methyl 3-methyl-5-nitrobenzoate

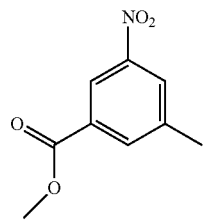

To a solution of 3-methyl-5-nitrobenzoic acid (0.2 g, 1.1 mmol) in methanol (10 mL) was added concentrated $H_2SO_4$ (0.2 mL). The mixture was stirred at 70° C. for 5 h. The solvent was removed under reduced pressure. The mixture was diluted with $H_2O$ (10 mL) and extracted with ethyl acetate (10 mL×3). The combined organic layers were dried over $Na_2SO_4$, filtered, and concentrated under reduced pressure to afford methyl 3-methyl-5-nitrobenzoate (220 mg), which was used in the next step without further purification. TLC: $R_f$=0.59 (ethyl acetate/heptanes=1:1).

Step 2: methyl 3-(bromomethyl)-5-nitrobenzoate

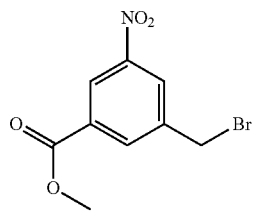

This compound was prepared using procedures analogous to those described for Step 1 of preparing Intermediate 6 using methyl 3-methyl-5-nitrobenzoate. TLC: $R_f$=0.55 (ethyl acetate/heptanes=1:1).

Step 3: 3-(methoxymethyl)-5-nitrobenzoic acid

To a solution of methyl 3-(bromomethyl)-5-nitrobenzoate (50.0 mg, 0.18 mmol) in methanol (1 mL), THF (1 mL), and water (1 mL) was added LiOH (30.67 mg, 0.73 mmol). The mixture was stirred at r.t. for 1 h. LC-MS showed that the starting material was consumed. The solvent was removed under reduced pressure. The mixture was then added 1N HCl (3 mL) and extracted with ethyl acetate (3 mL×3). The combined organic layers were dried over $Na_2SO_4$, filtered, and concentrated under reduced pressure. The resulting residue 3-(methoxymethyl)-5-nitrobenzoic acid (41 mg) was used in the next step without further purification. LC-MS calc. for $C_9H_8NO_5$ [M–H]⁻: m/z=210.0. Found 210.1.

Intermediate 18

3-[(4-Chlorophenoxy)methyl]-5-nitrobenzoic acid

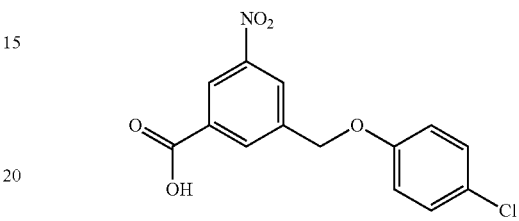

This compound was prepared using procedures analogous to those described for Steps 1-3 of preparing Intermediate 6 using methyl 3-methyl-5-nitrobenzoate to replace methyl 4-fluoro-3-methylbenzoate in Step 1. LC-MS calc. for $C_{14}H_9ClNO_5$ [M–H]⁻: m/z=306.0/380.0. Found 306.0/308.1.

Intermediate 19

4-(methoxymethyl)-3-nitrobenzoic acid

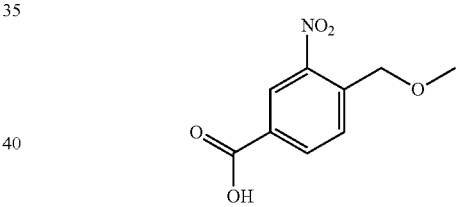

This compound was prepared using procedures analogous to those described for Step 3 of preparing Intermediate 17 using 4-(bromomethyl)-3-nitrobenzoic acid to replace methyl 3-(bromomethyl)-5-nitrobenzoate. LC-MS calc. for $C_9H_8NO_5$ [M–H]⁻: m/z=210.1. Found 210.1.

Intermediate 20

5-Fluoro-6-(1,3,5-trimethylpyrazol-4-yl)pyridine-2-carboxylic acid

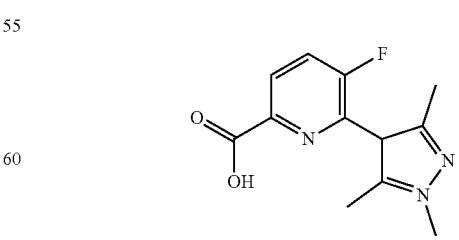

A mixture of 6-bromo-5-fluoropyridine-2-carboxylic acid (100.0 mg, 0.45 mmol), (1,3,5-trimethyl-1H-pyrazol-4-yl) boronic acid (69.99 mg, 0.45 mmol), Pd(dppf)Cl₂ (29.63 mg, 0.05 mmol) and potassium carbonate (188.46 mg, 1.36 mmol) in water (1 mL) and 1,4-dioxane (3 mL) were de-gassed and recharged with $N_2$ for 3 cycles. The mixture was stirred at 105° C. overnight. The reaction was quenched with 1N HCl (2 mL) and concentrated under reduced pressure. The resulting residue was purified by prep-HPLC on a C18 column (30×250 mm, 10 μm) using MeCN/H$_2$O (20 to 100%) to afford 5-fluoro-6-(1,3,5-trimethylpyrazol-4-yl)pyridine-2-carboxylic acid (8.8 mg, 8% yield). LC-MS calc. for $C_{12}H_1FN_3O_2$ [M+H]$^+$: m/z=250.1. Found: 250.0.

The following intermediates listed in Table 1 were prepared by using an appropriate boronic acid or ester as the methods substantially analogous to those disclosed for preparing Intermediate 20.

TABLE 1

| Preparation of Intermediates | | | |
|---|---|---|---|
| Intermediate # | Structure | Name | [M + H]$^-$ Calc./Found |
| 21 | | 5-Fluoro-6-(3-methoxyphenyl)pyridine-2-carboxylic acid | [M − H]$^-$ 246.1/245.9 |
| 22 | | 5-fluoro-6-(1-methylpyrazol-4-yl)pyridine-2-carboxylic acid | [M − H]$^-$ 220.1/219.9 |
| 23 | | 5-fluoro-6-(2-oxo-2,3-dihydro-1H-pyrrolo[2,3-b]pyridin-5-yl) pyridine-2-carboxylic acid | [M − H]$^-$ 272.1/272.1 |
| 24 | | 5-fluoro-6-(1H-indazol-5-yl) pyridine-2-carboxylic acid | [M − H]$^-$ 256.1/256.1 |
| 25 | | 5-fluoro-6-(1-methyl-1H-indazol-5-yl) pyridine-2-carboxylic acid | [M − H]$^-$ 270.1/270.1 |
| 26 | | 6-(1H-benzo[d][1,2,3]triazol-5-yl)-5-fluoro pyridine-2-carboxylic acid | [M − H]$^-$ 257.1/257.2 |

Intermediate 27

5-Fluoro-6-(1H-imidazol-1-yl)picolinic acid

A mixture of imidazole (202.0 mg, 2.97 mmol), copper(I) iodide (113.0 mg, 0.59 mmol), 6-bromo-5-fluoropyridine-2-carboxylic acid (783.3 mg, 3.56 mmol), and potassium carbonate (1230 mg, 8.9 mmol) in DMSO (5 mL) was stirred at 90° C. for 48 h. The reaction was diluted with H$_2$O (5 mL) and extracted with ethyl acetate (5 mL×3). The combined organic layers were washed, dried over Na$_2$SO$_4$, filtered, and concentrated under reduced pressure. The resulting residue was purified by prep-HPLC on C18 column (30×250 mm, 10 μm) with MeCN/H$_2$O (20 to 100%) to afford 5-fluoro-6-(1H-imidazole-1-yl)picolinic acid (158.2 mg, 22% yield). LC-MS calc. for C$_9$H$_5$FN$_3$O$_2$ [M−H]$^-$: m/z=206.0. Found 206.1.

Intermediate 28

2-Chloro-3-methyl-5-nitro-4-(oxan-4-ylmethoxy)benzoic acid

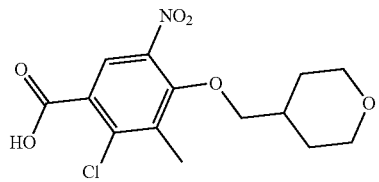 [SMILES: Cc1c(Cl)c(C(=O)O)cc([N+](=O)[O-])c1OCC1CCOCC1]

To a solution of 4-hydroxymethyltetrahydropyran (16.41 mg, 0.14 mmol) in DMF (1.5 mL) was added NaH (60% in mineral oil) (11.3 mg, 0.28 mmol) at 20° C. The mixture was stirred at 20° C. for 30 min., and 2-chloro-4-fluoro-3-methyl-5-nitro-benzoic acid (30.0 mg, 0.13 mmol) was added. After 2 h, the reaction was quenched by water (5 mL) and adjusted pH to about 3 with 1N HCl aq. solution. The mixture was extracted with ethyl acetate (5 mL×2). The combined organic layers were dried over Na$_2$SO$_4$, filtered, and concentrated under reduced pressure to afford 2-chloro-3-methyl-5-nitro-4-(oxan-4-ylmethoxy)benzoic acid (32 mg, 76% yield), which was directly used in the next step without purification. LC-MS calc. for C$_{14}$H$_{15}$ClNO$_6$ [M−H]$^-$: m/z=328.1/330.1. Found 327.9/330.0.

Intermediate 29

2-Chloro-4-[(4-chlorophenyl)methoxy]-3-methyl-5-nitrobenzoic acid

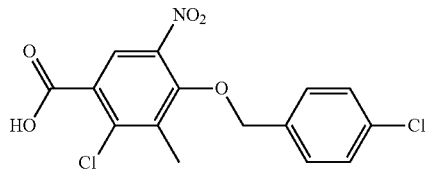 [SMILES: Cc1c(Cl)c(C(=O)O)cc([N+](=O)[O-])c1OCc1ccc(Cl)cc1]

This compound was prepared using procedures analogous to those described for preparing Intermediate 28 using (4-chlorophenyl)methanol to replace 4-hydroxymethyltetrahydropyran. LC-MS calc. for C$_{15}$H$_{10}$Cl$_2$NO$_5$ [M−H]$^-$: m/z=354.0/356.0. Found: 353.9/356.0.

Intermediate 30

3-Fluoro-4-(4-chlorophenoxymethyl)benzoic acid

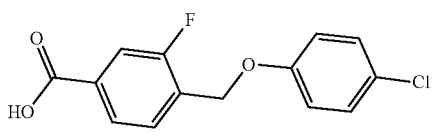 [SMILES: O=C(O)c1ccc(COc2ccc(Cl)cc2)c(F)c1]

This compound was prepared using procedures analogous to those described for Steps 2-3 preparing Intermediate 6 using methyl 4-(bromomethyl)-3-fluorobenzoate to replace methyl 3-(bromomethyl)-4-fluorobenzoate in Step 2. LC-MS calc. for C$_{14}$H$_9$ClFO$_3$ [M−H]$^-$: m/z=279.0/281.0. Found: 279.0/280.9.

Intermediate 31

4-[(4-Chlorophenoxy)methyl]-3-methylsulfonylbenzoic acid

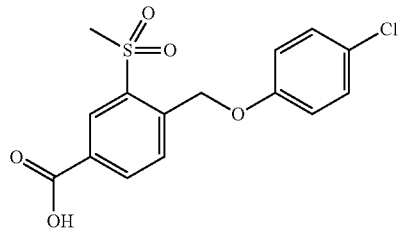 [SMILES: CS(=O)(=O)c1cc(C(=O)O)ccc1COc1ccc(Cl)cc1]

This compound was prepared using procedures analogous to those described for Steps 1-3 of preparing Intermediate 6 using methyl 4-methyl-3-methylsulfonyl benzoate to replace methyl 3-methyl-4-fluorobenzoate in Step 1. LC-MS calc. for C$_{15}$H$_{12}$ClO$_5$S [M−H]$^-$: m/z=339.0/341.0. Found: 338.9/340.9.

Intermediate 32

4-(Morpholin-4-ylmethyl)-3-nitrobenzoic acid

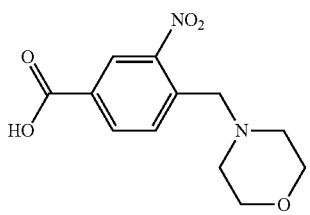 [SMILES: O=C(O)c1ccc(CN2CCOCC2)c([N+](=O)[O-])c1]

To a solution of 4-(bromomethyl)-3-nitrobenzoic acid (150.0 mg, 0.58 mmol) in MeCN (1 mL) was added morpholine (0.1 mL, 1.15 mmol). The mixture was stirred at r.t. for 2 h., quenched with H$_2$O (2 mL) and extracted with ethyl acetate (2 mL×3). The combined organic layers were concentrated under reduced pressure. The resulting residue was purified by prep-HPLC on a C18 column eluting with MeCN:H₂O (15% to 100%) to afford 4-(morpholin-4-ylmethyl)-3-nitrobenzoic acid (110 mg, 72% yield).

Intermediate 33

4-[(4-Chloroanilino)methyl]-3-nitrobenzoic acid

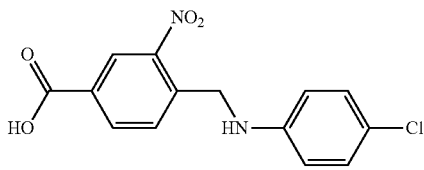 [SMILES: O=C(O)c1ccc(CNc2ccc(Cl)cc2)c([N+](=O)[O-])c1]

To a solution of 4-(bromomethyl)-3-nitrobenzoic acid (150.0 mg, 0.58 mmol) and 4-chloroaniline (367.93 mg, 2.88 mmol) dissolved in methanol (5 mL) was added DIPEA (372.06 mg, 2.88 mmol). The mixture was stirred at r.t. overnight. MeOH was partially removed under reduced pressure and the mixture was diluted with ethyl acetate, quenched with HCl (1M, 5 mL), and extracted with ethyl acetate (5 mL×3). The combined organic layers were dried over Na₂SO₄, filtered, and concentrated under reduced pressure. The resulting residue was purified on a silica gel column eluting with MeOH/ethyl acetate (0% to 30%) to afford 4-[(4-chloroanilino)methyl]-3-nitrobenzoic acid (170 mg, 96% yield).

Intermediate 34

3-Nitro-4-[(oxan-4-ylamino)methyl]benzoic acid

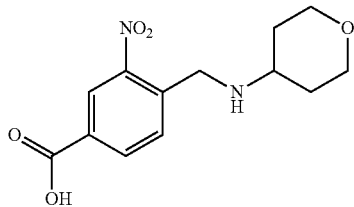 [SMILES: O=C(O)c1ccc(CNC2CCOCC2)c([N+](=O)[O-])c1]

This compound was prepared using procedures analogous to those described for preparing Intermediate 33 using 4-aminotetrahydropyran to replace 4-chloroaniline to afford 3-nitro-4-[(oxan-4-ylamino)methyl]benzoic acid.

Intermediate 35 and Intermediate 36

Thieno[2,3-b]pyridine-6-carboxylic acid and thieno[2,3-b]pyridine-4-carboxylic acid

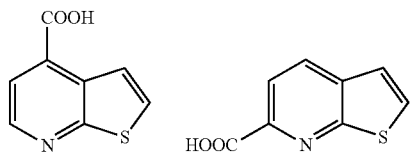 [SMILES: O=C(O)c1ccnc2sccc12 ; O=C(O)c1ccc2ccsc2n1]

Step 1: 7-oxidothieno[2,3-b]pyridin-7-ium

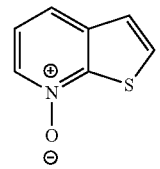

A mixture of thieno[2,3-b]pyridine (280.0 mg, 2.07 mmol), hydrogen peroxide-urea (389.7 mg, 4.14 mmol) and trifluoroacetic anhydride (913.5 mg, 4.35 mmol) in DCM (5 mL) was stirred from 0° C. to rt for 2 days. The reaction was diluted with DCM (10 mL) and washed with sat. Na₂CO₃ solution (10 mL) and brine (10 mL), dried over Na₂SO₄, filtered, and concentrated under reduced pressure to yield 7-oxidothieno[2,3-b]pyridin-7-ium (300 mg, 96% yield), which was directly used for the next step without further purification. LC-MS calc. for $C_7H_6NOS$ $[M+H]^+$: m/z=152.0. Found: 152.0.

Step 2: thieno[2,3-b]pyridine-6-carbonitrile and thieno[2,3-b]pyridine-4-carbonitrile

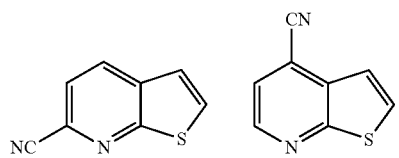

A mixture of 7-oxidothieno[2,3-b]pyridin-7-ium (300.0 mg, 1.98 mmol), N,N-dimethyl carbamoyl chloride (0.37 mL, 3.97 mmol) and trimethylsilyl cyanide (295.3 mg, 2.98 mmol) in MeCN (5 mL) was stirred at 100° C. for 4 h. After cooling, the reaction was quenched with Na₂CO₃ solution (5 mL) and extracted with EtOAc (5 mL×3). The combined organic layers were dried over Na₂SO₄, filtered, and concentrated under reduced pressure. The resulting residue was purified by flash chromatography on a silica gel column with EtOAc/Heptanes (5-50%) to afford a mixture of thieno[2,3-b]pyridine-6-carbonitrile and thieno[2,3-b]pyridine-4-carbonitrile (100.4 mg, 31% yield). TLC: $R_f$=0.3 (EtOAc:Heptane=1:3).

Step 3: thieno[2,3-b]pyridine-6-carboxylic acid and thieno[2,3-b]pyridine-4-carboxylic acid A mixture of thieno[2,3-b]pyridine-6-carbonitrile (100.0 mg, 0.62 mmol) and HCl solution (6N, 6.0 mL, 36 mmol) was stirred at 90° C. overnight. The solvent was removed under reduced pressure. The resulting residue was purified by prep-HPLC on a C18 column eluting with MeCN/H₂O (20%-100%) to yield thieno[2,3-b]pyridine-4-carboxylic acid (15.1 mg, 13% yield) (the first fraction) and thieno[2,3-b]pyridine-6-carboxylic acid (7.0 mg, 6% yield) (the second fraction). LC-MS calc. for $C_8H_4NO_2S$ $[M-H]^-$: m/z=178.0. Found: 177.8.

Intermediate 37

6-Methyl-4-methylsulfonylpyridine-2-carboxylic acid

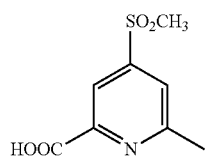

Step 1: 4-Chloro-2-methyl-1-oxidopyridin-1-ium

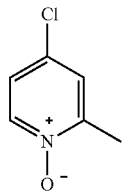

To a stirred solution of 4-chloro-2-methylpyridine (2.0 g, 15.68 mmol) in DCM (20 mL) was added m-CPBA (5.97 g, 26.65 mmol) in portions over 5 min. The resulting mixture was stirred at r.t. overnight. The reaction was quenched by adding 50 mL of saturated NaHCO$_3$ solution followed by 30 mL of DCM. The layers were separated, and the aqueous layer was extracted with DCM (50 mL×2). The combined organic layers were dried over sodium sulfate, filtered, and concentrated under reduced pressure. The resulting residue was purified by flash chromatography on a silica gel column with MeOH/EtOAc (0% to 20%) to afford 4-chloro-2-methyl-1-oxidopyridin-1-ium (1.68 g, 75% yield) as a yellow solid. LC-MS calc. for C$_6$H$_7$ClNO [M+H]$^+$: m/z=144.0/146.0. Found 143.9/146.0.

Step 2: 4-Chloro-6-methylpyridine-2-carbonitrile

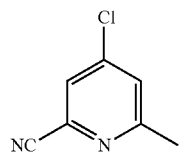

To a solution of 4-chloro-2-methyl-1-oxidopyridin-1-ium (1.8 g, 12.54 mmol) in MeCN (36 mL) was added N,N-dimethylcarbamoyl chloride (2.31 mL, 25.07 mmol) followed by trimethylsilyl cyanide ("TMSCN") (2.35 mL, 18.81 mmol) dropwise. The reaction was stirred at 80° C. in a sealed flask for 1 h. The reaction was cooled to r.t. and further stirred at r.t. overnight and quenched with saturated sodium bicarbonate solution (100 mL). The mixture was extracted with DCM (100 mL×3). The combined organic layers were dried over sodium sulfate, filtered, and concentrated under reduced pressure. The resulting residue was purified by flash chromatography on a silica gel column with EtOAc/heptane (2% to 35%) to afford 4-chloro-6-methylpyridine-2-carbonitrile (0.67 g, 35% yield) as a white solid. LC-MS calc. for C$_7$H$_6$ClN$_2$ [M+H]$^+$: m/z=153.0/155.0. Found 152.9/154.9.

Step 3: 4-Chloro-6-methylpyridine-2-carboxylic Acid Hydrochloride

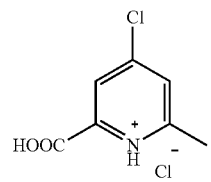

A solution of 4-chloro-6-methylpyridine-2-carbonitrile (420.0 mg, 2.75 mmol) in 6M HCl (20.0 mL, 120 mmol) was stirred at 90° C. overnight. The solution was concentrated under reduced pressure to afford 4-chloro-6-methylpyridine-2-carboxylic acid hydrochloride (570 mg, quantitative yield) as a white solid. The crude product was used in the next step without further purification. LC-MS calc. for C$_7$H$_5$ClNO$_2$ [M−H]$^−$: m/z=170.0/172.0. Found 170.0/171.9.

Step 4: 6-Methyl-4-methylsulfonylpyridine-2-carboxylic acid

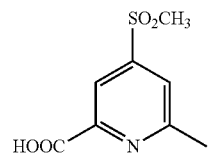

To a solution of 4-chloro-6-methylpyridine-2-carboxylic acid hydrochloride (100.0 mg, 0.58 mmol) in DMSO (2 mL) was added potassium carbonate (241.65 mg, 1.75 mmol), methylsulfinyloxysodium (208.25 mg, 2.04 mmol), L-proline (53.68 mg, 0.47 mmol) and copper(I) iodide (55.5 mg, 0.29 mmol). The resulting mixture was stirred at 90° C. for 2 h. The reaction was quenched by adding 20 mL of water followed by 20 mL of DCM. The pH of the aqueous layer was adjusted to 3-4. The mixture was extracted with DCM (20 mL×3). The combined organic layer was dried over sodium sulfate, filtered, and concentrated under reduced pressure. The resulting residue was purified by prep-HPLC on C18 column (30×250 mm, 10 μm) with MeCN/H$_2$O (20% to 100% w/0.1% TFA) to afford 6-methyl-4-methylsulfonylpyridine-2-carboxylic acid (38 mg, 30% yield) as a white solid. LC-MS calc. for C$_8$H$_8$NO$_4$S [M−H]$^−$: m/z=214.0. Found 214.0.

Intermediate 38

3-Nitro-4-(tetrahydropyran-4-ylmethylamino)benzoic acid

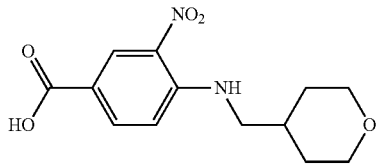 [SMILES: O=C(O)c1ccc(NCC2CCOCC2)c([N+](=O)[O-])c1]

This compound was prepared using procedures analogous to those described for preparing Intermediate 13 using 4-fluoro-3-nitro-benzoic acid to replace 2-chloro-4-fluoro-3-methyl-5-nitro-benzoic acid.

Intermediate 39

2-Chloro-3-methyl-5-nitro-4-methoxybenzoic acid

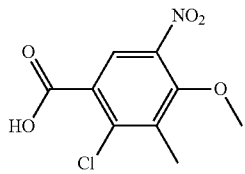 [SMILES: COc1c([N+](=O)[O-])cc(C(=O)O)c(Cl)c1C]

This compound was prepared using procedures analogous to those described for preparing Intermediate 28 using sodium methoxide solution to replace 4-hydroxymethyltetrahydropyran.

Intermediate 40

2-Chloro-3-methyl-5-nitro-4-ethoxybenzoic acid

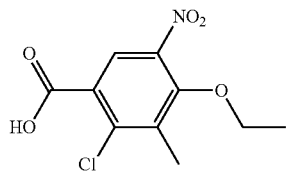 [SMILES: CCOc1c([N+](=O)[O-])cc(C(=O)O)c(Cl)c1C]

This compound was prepared using procedures analogous to those described for preparing Intermediate 28 using sodium ethoxide solution to replace 4-hydroxymethyltetrahydropyran.

Intermediate 41

2-Chloro-3-methyl-5-nitro-4-(oxetan-3-ylmethoxy)benzoic acid

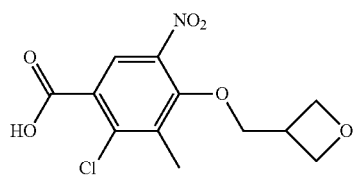 [SMILES: Cc1c(Cl)c(C(=O)O)cc([N+](=O)[O-])c1OCC1COC1]

This compound was prepared using procedures analogous to those described for preparing Intermediate 28 using oxetan-3-ylmethanol to replace 4-hydroxymethyltetrahydropyran.

Intermediate 42

2-Chloro-4-(1,4-dioxan-2-ylmethylamino)-3-methyl-5-nitrobenzoic acid

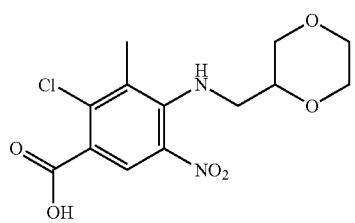 [SMILES: Cc1c(Cl)c(C(=O)O)cc([N+](=O)[O-])c1NCC1COCCO1]

This compound was prepared using procedures analogous to those described for Intermediate 13 using 1,4-dioxan-2-ylmethanamine (0.05 mL, 0.09 mmol) to replace tetrahydropyran-4-ylmethanamine. LC-MS calc. for $C_{13}H_{14}ClN_2O_6[M-H]^-$: m/z=329.1/331.1. Found 329.0/331.1.

Intermediate 43

2-Chloro-4-(1,4-dioxan-2-ylmethoxy)-3-methyl-5-nitrobenzoic acid

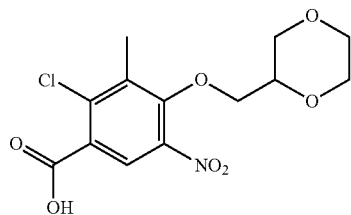 [SMILES: Cc1c(Cl)c(C(=O)O)cc([N+](=O)[O-])c1OCC1COCCO1]

This compound was prepared using procedures analogous to those described for Intermediate 28 using 1,4-dioxan-2-ylmethanol to replace 4-hydroxymethyltetrahydropyran. LC-MS calc. $C_{13}H_{13}ClNO_7$ $[M-H]^-$: m/z=330.0/332.0. Found 329.9/332.0.

Intermediate 44

2-Chloro-3-methyl-5-nitro-4-(oxolan-3-ylmethoxy)benzoic acid

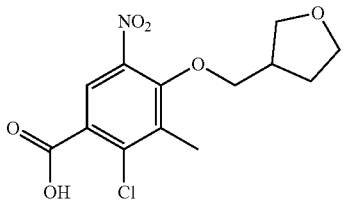 [SMILES: Cc1c(Cl)c(C(=O)O)cc([N+](=O)[O-])c1OCC1CCOC1]

This compound was prepared using procedures analogous to those described for Intermediate 28 using oxolan-3-ylmethanol to replace 4-hydroxymethyltetrahydropyran. LC-MS calc. $C_{13}H_{13}ClNO_6$ [M−H]⁻: m/z=314.04/316.04. Found: 313.8/315.8.

Intermediate 45

Step 1: 2-Chloro-3-methyl-5-nitro-4-(oxolan-2-ylmethoxy)benzoic acid

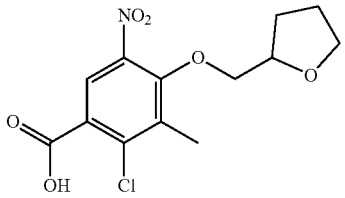 [SMILES: Cc1c(Cl)c(C(=O)O)cc([N+](=O)[O-])c1OCC1CCCO1]

This compound was prepared using procedures analogous to those described for Intermediate 28 using oxolan-2-ylmethanol to replace 4-hydroxymethyltetrahydropyran. LC-MS calc. $C_{13}H_{13}ClNO_6$ [M−H]⁻: m/z=314.04/316.04. Found: 313.8/315.7.

Compounds provided for herein include, for example, the compounds identified in Tables 2-4 as shown at below.

EXAMPLE COMPOUNDS

Example 1

6-Chloro-N-[4-[4-[[2-(4-chlorophenyl)-4,4-dimethylcyclohexen-1-yl]methyl]piperazin-1-yl]phenyl]sulfonyl-5-fluoropyridine-2-carboxamide

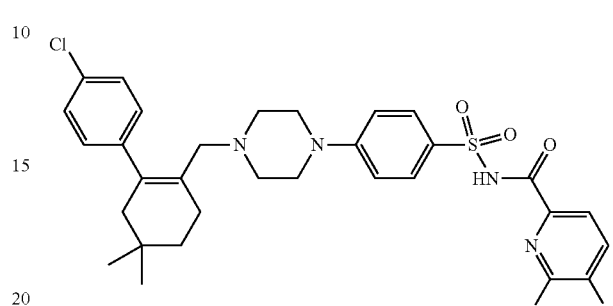

4-[4-[[2-(4-chlorophenyl)-4,4-dimethylcyclohexen-1-yl]methyl]piperazin-1-yl]benzenesulfonamide (20.0 mg, 0.04 mmol, Intermediate 1) and 6-chloro-5-fluoropyridine-2-carboxylic acid (22.2 mg, 0.13 mmol) were dissolved in DCM (1 mL). 4-dimethylaminopyridine (DMAP) (30.9 mg, 0.25 mmol) and N-ethyl-N'-(3-dimethylaminopropyl)carbodiimide hydrochloride (EDCI) (32.3 mg, 0.17 mmol) were added sequentially. The mixture was stirred at r.t. overnight. The mixture was quenched with HCl(aq) (0.5 M, 2 mL) and extracted with DCM (2 mL×3). The organic layer was concentrated under reduced pressure and the resulting residue was purified by prep-HPLC on a C18 column eluting with MeCN:H₂O (15% to 100%) to afford 6-chloro-N-[4-[4-[[2-(4-chlorophenyl)-4,4-dimethylcyclohexen-1-yl]methyl]piperazin-1-yl]phenyl]sulfonyl-5-fluoropyridine-2-carboxamide (14 mg, 53% yield). LC-MS calc. for $C_{31}H_{34}Cl_2FN_4O_3S$ [M+H]⁺: m/z=631.17/633.17. Found: 630.9/632.9. ¹H NMR (300 MHz, Chloroform-d) δ 9.99 (s, 1H), 8.05 (ddd, J=21.9, 8.7, 2.5 Hz, 3H), 7.70-7.58 (m, 1H), 7.36 (d, J=8.3 Hz, 2H), 7.03-6.93 (m, 2H), 6.92-6.83 (m, 2H), 3.64 (s, 2H), 3.58 (m, 4H), 2.61 (d, J=28.5 Hz, 2H), 2.32 (d, J=6.5 Hz, 2H), 2.10 (s, 2H), 2.02 (d, J=1.8 Hz, 1H), 1.36-1.23 (m, 3H), 1.00 (d, J=1.8 Hz, 6H).

The compounds listed in Table 2 below were prepared by using Intermediate 1 and an appropriate acid as the methods substantially analogous to those disclosed for preparing Example 1.

TABLE 2

Preparation of Examples ("Ex")

| Ex # | Structure | Name | [M + H]⁺ Calc./Found |
|---|---|---|---|
| 2 | (structure shown) | 6-chloro-N-[4-[4-[[2-(4-chlorophenyl)-4,4-dimethylcyclohexen-1-yl]methyl]piperazin-1-yl]phenyl]sulfonyl-5-nitropyridine-2-carboxamide | 658.2/ 657.9 |

TABLE 2-continued

Preparation of Examples ("Ex")

| Ex # | Structure | Name | [M + H]+ Calc./ Found |
|---|---|---|---|
| 3 | 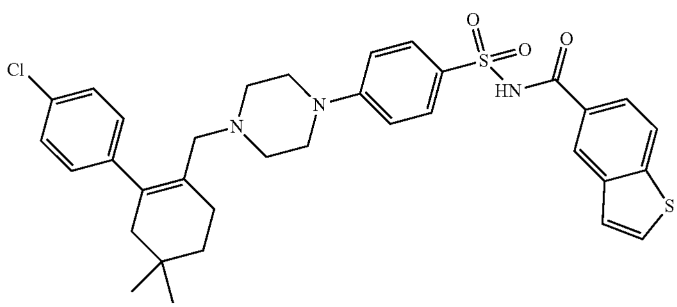 [SMILES: CC1(C)CCC(CN2CCN(c3ccc(S(=O)(=O)NC(=O)c4ccc5sccc5c4)cc3)CC2)=C(c2ccc(Cl)cc2)C1] | N-[4-[4-[[2-(4-chlorophenyl)-4,4-dimethylcyclohexen-1-yl]methyl]piperazin-1-yl]phenyl]sulfonylbenzo[b]thiophene-5-carboxamide | 634.2/ 633.9 |
| 4 | 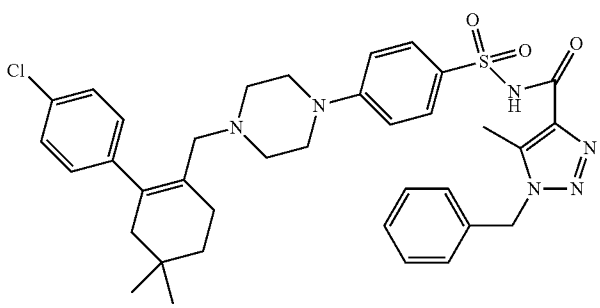 [SMILES: Cc1c(C(=O)NS(=O)(=O)c2ccc(N3CCN(CC4=C(c5ccc(Cl)cc5)CC(C)(C)CC4)CC3)cc2)nnn1Cc1ccccc1] | 1-benzyl-N-[4-[4-[[2-(4-chlorophenyl)-4,4-dimethylcyclohexen-1-yl]methyl]piperazin-1-yl]phenyl]sulfonyl-5-methyl-1H-1,2,3-triazole-4-carboxamide | 673.3/ 673.0 |
| 5 | 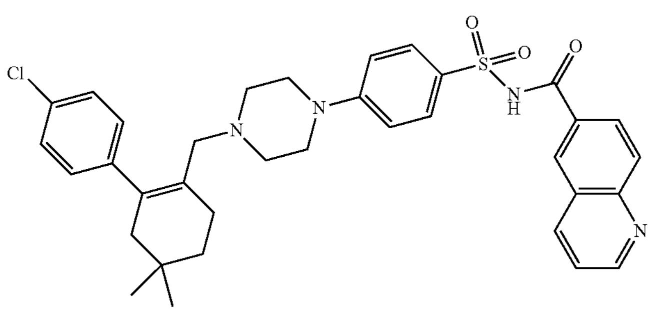 [SMILES: CC1(C)CCC(CN2CCN(c3ccc(S(=O)(=O)NC(=O)c4ccc5ncccc5c4)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)quinoline-6-carboxamide | 629.2/ 629.1 |
| 6 | 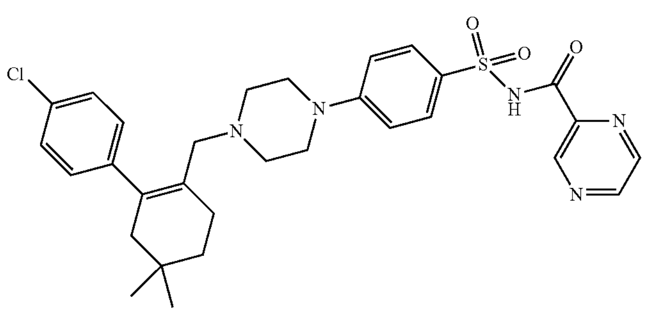 [SMILES: CC1(C)CCC(CN2CCN(c3ccc(S(=O)(=O)NC(=O)c4cnccn4)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)pyrazine-2-carboxamide | 580.2/ 582.0 |

TABLE 2-continued

Preparation of Examples ("Ex")

| Ex # | Structure | Name | [M + H]+ Calc./ Found |
|---|---|---|---|
| 7 | 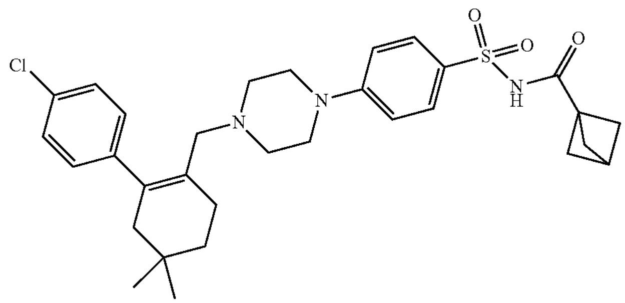 [SMILES: CC1(C)CCC(CN2CCN(c3ccc(S(=O)(=O)NC(=O)C45CC(C4)C5)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)bicyclo[1.1.1]pentane-1-carboxamide | 568.2/ 568.0 |
| 8 | 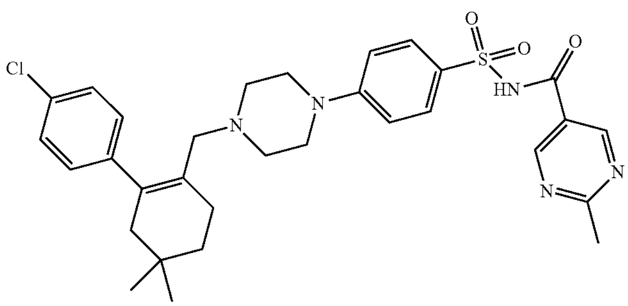 [SMILES: Cc1ncc(C(=O)NS(=O)(=O)c2ccc(N3CCN(CC4=C(c5ccc(Cl)cc5)CC(C)(C)CC4)CC3)cc2)cn1] | N-([4-[4-[[2-(4-chlorophenyl)-4,4-dimethylcyclohexen-1-yl]methyl]piperazin-1-yl]phenyl]sulfonyl)-2-methylpyrimidine-5-carboxamide | 594.2/ 594.0 |
| 9 | 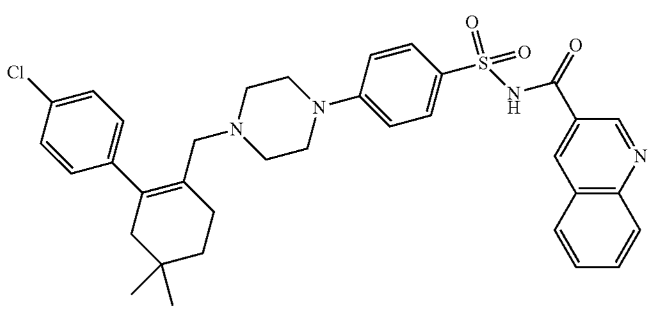 [SMILES: CC1(C)CCC(CN2CCN(c3ccc(S(=O)(=O)NC(=O)c4cnc5ccccc5c4)cc3)CC2)=C(c2ccc(Cl)cc2)C1] | N-((4-(4-((4'-chloro-5,5-dimethyl-3,4,5,6-tetrahydro-[1,1'-biphenyl]-2-yl)methyl)piperazin-1-yl)phenyl)sulfonyl)quinoline-3-carboxamide | 629.2/ 629.2 |
| 10 | 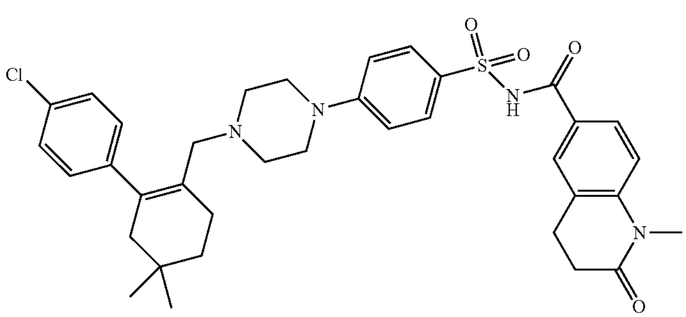 [SMILES: CN1C(=O)CCc2cc(C(=O)NS(=O)(=O)c3ccc(N4CCN(CC5=C(c6ccc(Cl)cc6)CC(C)(C)CC5)CC4)cc3)ccc21] | N-([4-[4-[[2-(4-chlorophenyl)-4,4-dimethylcyclohexen-1-yl]methyl]piperazin-1-yl]phenyl]sulfonyl)-1-methyl-2-oxo-1,2,3,4-tetrahydroquinoline-6-carboxamide | 661.3/ 661.3 |

TABLE 2-continued

Preparation of Examples ("Ex")

| Ex # | Structure | Name | [M + H]+ Calc./ Found |
|---|---|---|---|
| 11 | 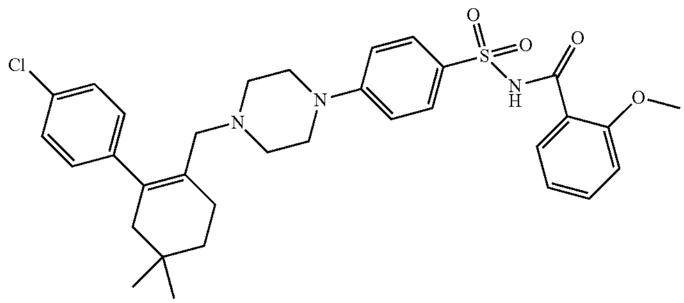 [SMILES: COc1ccccc1C(=O)NS(=O)(=O)c1ccc(N2CCN(CC3=C(c4ccc(Cl)cc4)CC(C)(C)CC3)CC2)cc1] | N-([4-[4-[[2-(4-chlorophenyl)-4,4-dimethylcyclohexen-1-yl]methyl]piperazin-1-yl]phenyl]sulfonyl)-2-methoxybenzamide | 608.2/ 607.9 |
| 12 | 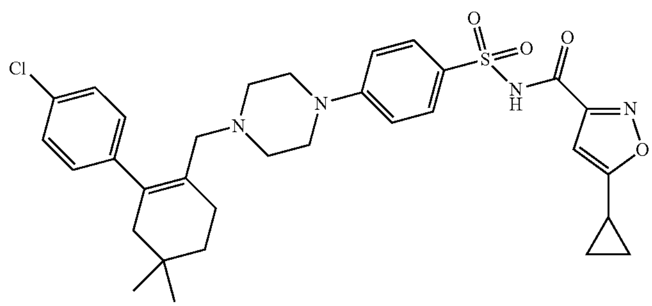 [SMILES: CC1(C)CCC(CN2CCN(c3ccc(S(=O)(=O)NC(=O)c4cc(C5CC5)on4)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)-5-cyclopropylisoxazole-3-carboxamide | 609.2/ 609.0 |
| 13 | 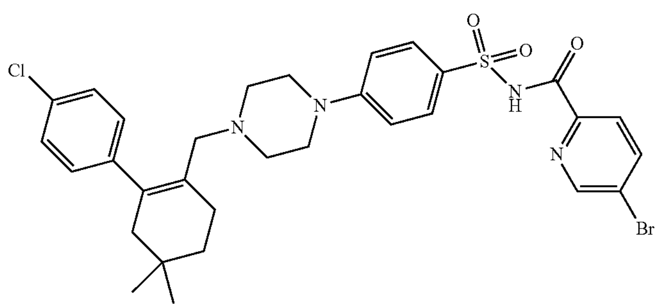 [SMILES: CC1(C)CCC(CN2CCN(c3ccc(S(=O)(=O)NC(=O)c4ccc(Br)cn4)cc3)CC2)=C(c2ccc(Cl)cc2)C1] | 5-bromo-N-([4-[4-[[2-(4-chlorophenyl)-4,4-dimethylcyclohexen-1-yl]methyl]piperazin-1-yl]phenyl]sulfonyl)pyridine-2-carboxamide | 657.1/ 657.0 |
| 14 | 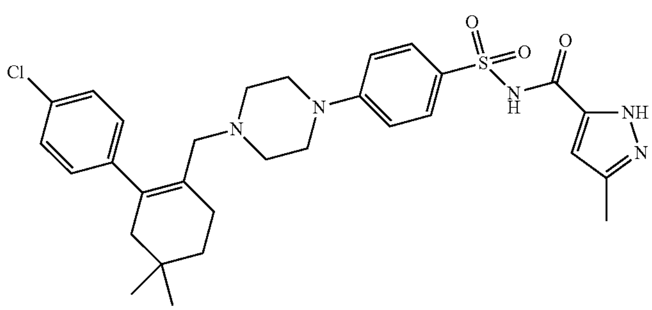 [SMILES: Cc1cc(C(=O)NS(=O)(=O)c2ccc(N3CCN(CC4=C(c5ccc(Cl)cc5)CC(C)(C)CC4)CC3)cc2)[nH]n1] | N-([4-[4-[[2-(4-chlorophenyl)-4,4-dimethylcyclohexen-1-yl]methyl]piperazin-1-yl]phenyl]sulfonyl)-3-methyl-1H-pyrazole-5-carboxamide | 582.2/ 581.9 |
| 15 | 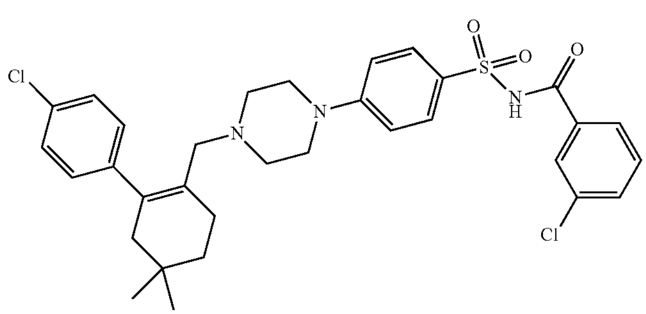 [SMILES: CC1(C)CCC(CN2CCN(c3ccc(S(=O)(=O)NC(=O)c4cccc(Cl)c4)cc3)CC2)=C(c2ccc(Cl)cc2)C1] | 3-chloro-N-([4-[4-[[2-(4-chlorophenyl)-4,4-dimethylcyclohexen-1-yl]methyl]piperazin-1-yl]phenyl]sulfonyl)benzamide | 612.2/ 612.0 |

TABLE 2-continued

Preparation of Examples ("Ex")

| Ex # | Structure | Name | [M + H]+ Calc./ Found |
|---|---|---|---|
| 16 | 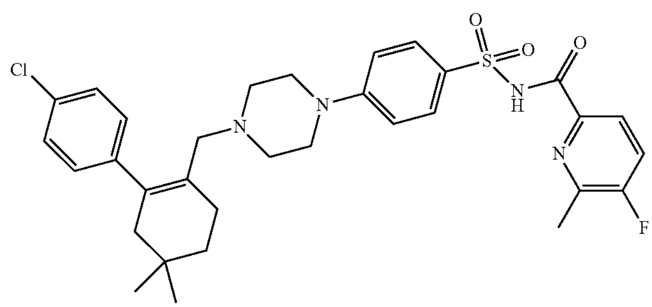 [SMILES: Cc1nc(C(=O)NS(=O)(=O)c2ccc(N3CCN(CC4=C(c5ccc(Cl)cc5)CC(C)(C)CC4)CC3)cc2)ccc1F] | N-([4-[4-[[2-(4-chlorophenyl)-4,4-dimethylcyclohexen-1-yl]methyl]piperazin-1-yl]phenyl]sulfonyl)-5-fluoro-6-methyl pyridine-2-carboxamide | 611.2/ 611.1 |
| 17 | 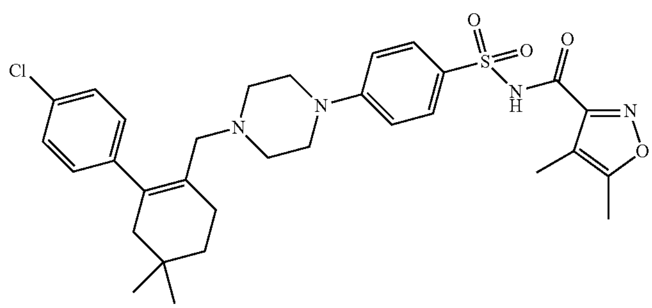 [SMILES: Cc1onc(C(=O)NS(=O)(=O)c2ccc(N3CCN(CC4=C(c5ccc(Cl)cc5)CC(C)(C)CC4)CC3)cc2)c1C] | N-([4-[4-[[2-(4-chlorophenyl)-4,4-dimethylcyclohexen-1-yl]methyl]piperazin-1-yl]phenyl]sulfonyl)-4,5-dimethylisoxazole-3-carboxamide | 597.2/ 597.0 |
| 18 | 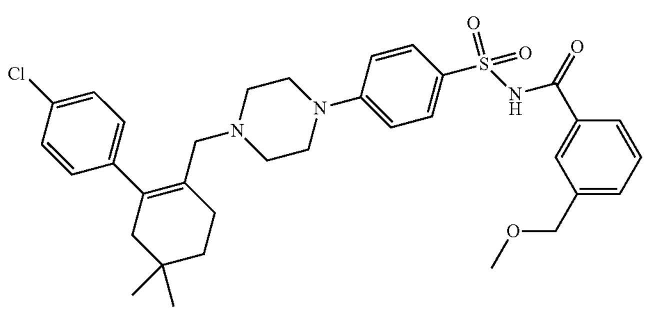 [SMILES: COCc1cccc(C(=O)NS(=O)(=O)c2ccc(N3CCN(CC4=C(c5ccc(Cl)cc5)CC(C)(C)CC4)CC3)cc2)c1] | N-([4-[4-[[2-(4-chlorophenyl)-4,4-dimethylcyclohexen-1-yl]methyl]piperazin-1-yl]phenyl]sulfonyl)-3-(methoxymethyl)benzamide | 622.2/ 622.0 |
| 19 | 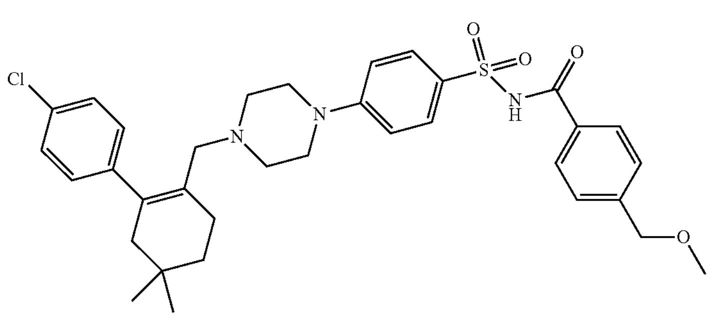 [SMILES: COCc1ccc(C(=O)NS(=O)(=O)c2ccc(N3CCN(CC4=C(c5ccc(Cl)cc5)CC(C)(C)CC4)CC3)cc2)cc1] | N-([4-[4-[[2-(4-chlorophenyl)-4,4-dimethylcyclohexen-1-yl]methyl]piperazin-1-yl]phenyl]sulfonyl)-4-(methoxymethyl)benzamide | 622.2/ 622.1 |

TABLE 2-continued

Preparation of Examples ("Ex")

| Ex # | Structure | Name | [M + H]+ Calc./ Found |
|---|---|---|---|
| 20 | 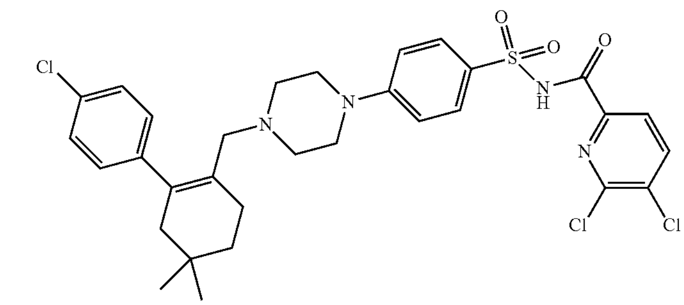 [SMILES: CC1(C)CCC(CN2CCN(c3ccc(S(=O)(=O)NC(=O)c4ccc(Cl)c(Cl)n4)cc3)CC2)=C(c2ccc(Cl)cc2)C1] | 5,6-dichloro-N-([4-[4-[[2-(4-chlorophenyl)-4,4-dimethylcyclohexen-1-yl]methyl]piperazin-1-yl]phenyl]sulfonyl)pyridine-2-carboxamide | 647.1/ 647.2 |
| 21 | 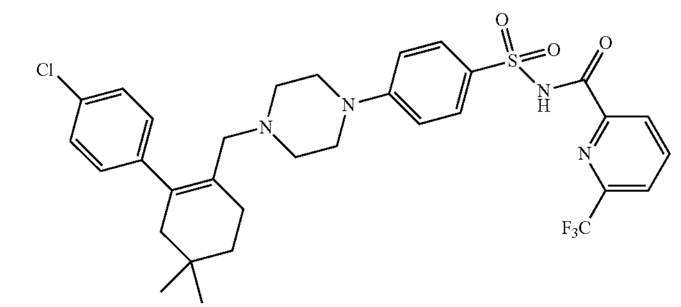 [SMILES: CC1(C)CCC(CN2CCN(c3ccc(S(=O)(=O)NC(=O)c4cccc(C(F)(F)F)n4)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)-6-(trifluoromethyl)pyridine-2-carboxamide | 647.2/ 647.0 |
| 22 | 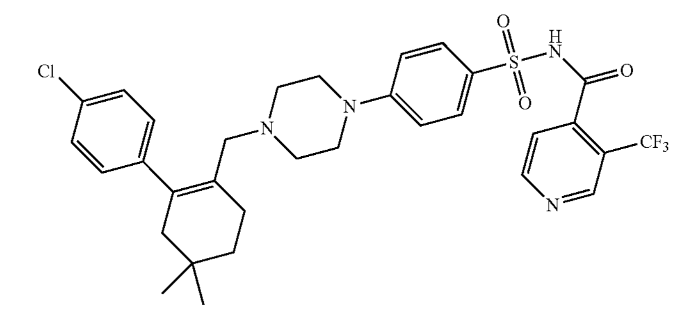 [SMILES: CC1(C)CCC(CN2CCN(c3ccc(S(=O)(=O)NC(=O)c4ccncc4C(F)(F)F)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)-3-(trifluoromethyl)pyridine-4-carboxamide | 647.2/ 646.9 |
| 23 | 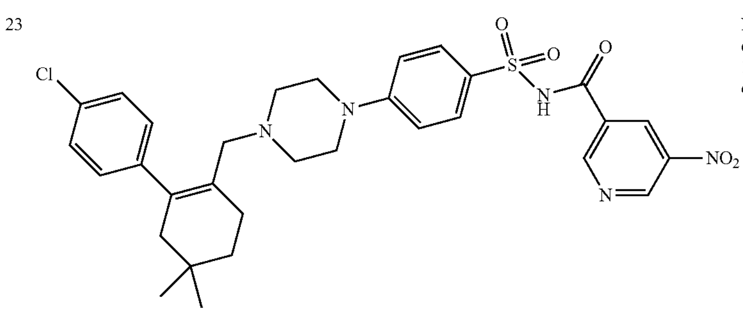 | N-([4-[4-[[2-(4-chlorophenyl)-4,4-dimethylcyclohexen-1-yl]methyl]piperazin-1-yl]phenyl]sulfonyl)-5-nitropyridine-3-carboxamide | 624.2/ 624.2 |
| 24 | 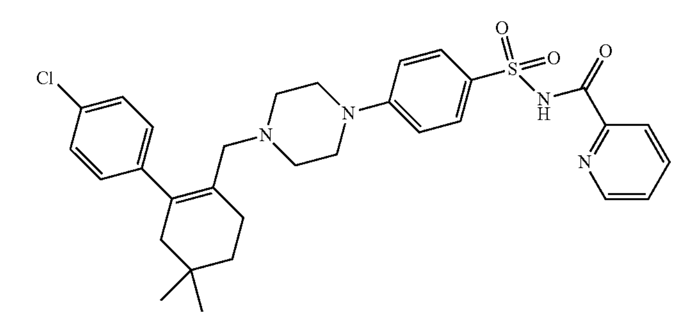 [SMILES: CC1(C)CCC(CN2CCN(c3ccc(S(=O)(=O)NC(=O)c4ccccn4)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)pyridine-2-carboxamide | 579.2/ 578.9 |

TABLE 2-continued

Preparation of Examples ("Ex")

| Ex # | Structure | Name | [M + H]+ Calc./ Found |
|---|---|---|---|
| 25 | 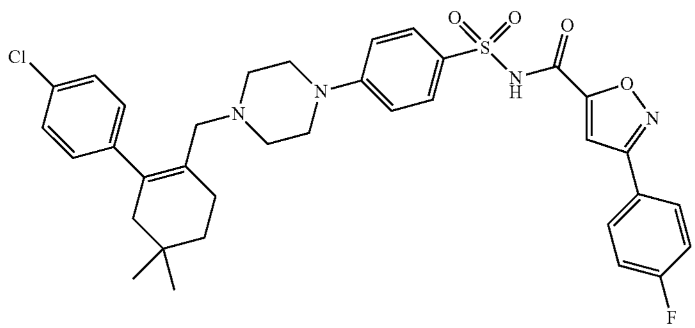 [SMILES: CC1(C)CCC(CN2CCN(c3ccc(S(=O)(=O)NC(=O)c4cc(-c5ccc(F)cc5)no4)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)-3-(4-fluorophenyl)isoxazole-5-carboxamide | 663.2/ 663.0 |
| 26 | 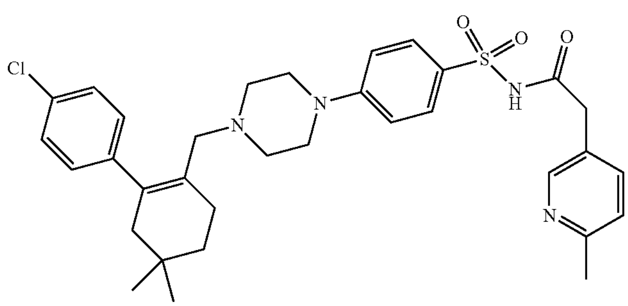 [SMILES: Cc1ccc(CC(=O)NS(=O)(=O)c2ccc(N3CCN(CC4=C(c5ccc(Cl)cc5)CC(C)(C)CC4)CC3)cc2)cn1] | N-([4-[4-[[2-(4-chlorophenyl)-4,4-dimethylcyclohexen-1-yl]methyl]piperazin-1-yl]phenyl]sulfonyl)-2-(6-methylpyridin-3-yl)acetamide | 607.2/ 607.0 |
| 27 | 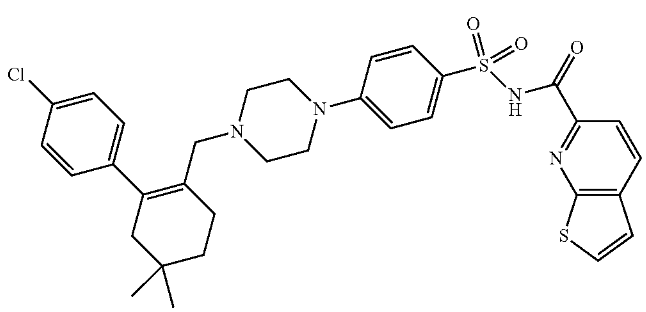 [SMILES: CC1(C)CCC(CN2CCN(c3ccc(S(=O)(=O)NC(=O)c4ccc5ccsc5n4)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)thieno[2,3-b]pyridine-6-carboxamide | 635.2/ 635.0 |
| 28 | 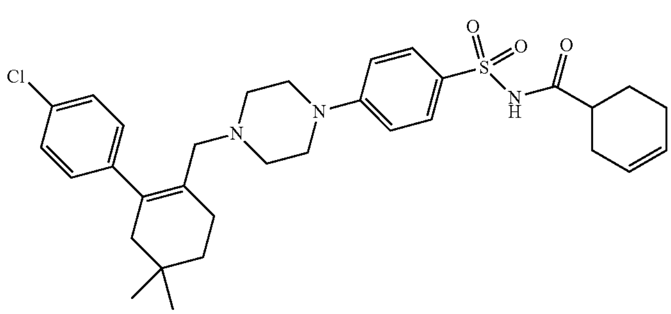 [SMILES: CC1(C)CCC(CN2CCN(c3ccc(S(=O)(=O)NC(=O)C4CC=CCC4)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)cyclohex-3-ene-1-carboxamide | 582.2/ 582.1 |

TABLE 2-continued

Preparation of Examples ("Ex")

| Ex # | Structure | Name | [M + H]+ Calc./Found |
|---|---|---|---|
| 29 | 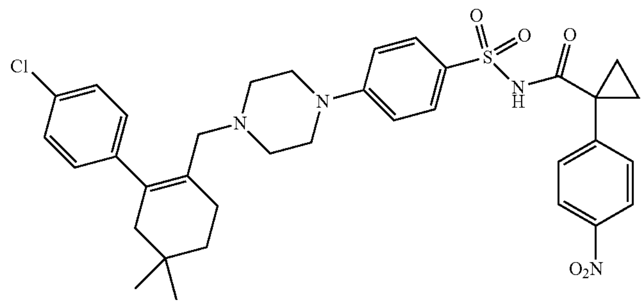 [SMILES: CC1(C)CCC(CN2CCN(c3ccc(S(=O)(=O)NC(=O)C4(c5ccc([N+](=O)[O-])cc5)CC4)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)-1-(4-nitrophenyl)cyclopropane-1-carboxamide | 663.2/663.2 |
| 30 | 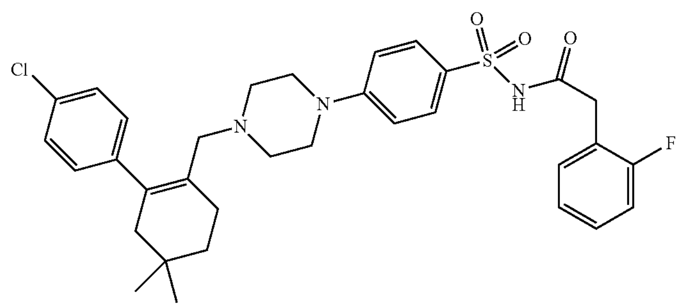 [SMILES: CC1(C)CCC(CN2CCN(c3ccc(S(=O)(=O)NC(=O)Cc4ccccc4F)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)-2-(2-fluorophenyl)acetamide | 610.2/610.1 |
| 31 | 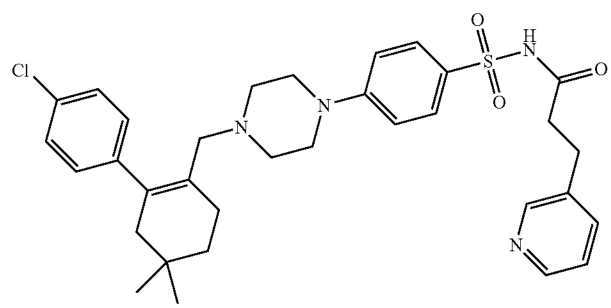 [SMILES: CC1(C)CCC(CN2CCN(c3ccc(S(=O)(=O)NC(=O)CCc4cccnc4)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)-3-(pyridin-3-yl)propanamide | 607.2/607.3 |
| 32 | 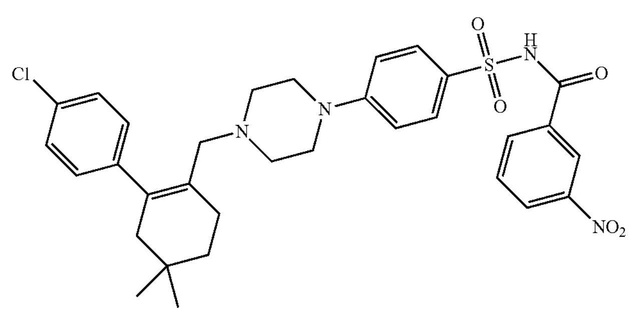 [SMILES: CC1(C)CCC(CN2CCN(c3ccc(S(=O)(=O)NC(=O)c4cccc([N+](=O)[O-])c4)cc3)CC2)=C(c2ccc(Cl)cc2)C1] | N-([4-[4-[[2-(4-chlorophenyl)-4,4-dimethylcyclohexen-1-yl]methyl]piperazin-1-yl]phenyl]sulfonyl)-3-nitrobenzamide | 623.2/623.1 |
| 33 | 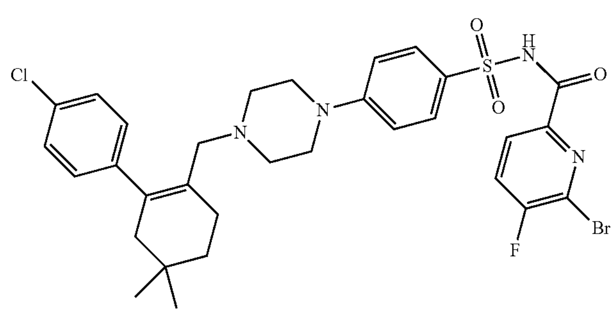 [SMILES: CC1(C)CCC(CN2CCN(c3ccc(S(=O)(=O)NC(=O)c4ccc(F)c(Br)n4)cc3)CC2)=C(c2ccc(Cl)cc2)C1] | 6-bromo-N-([4-[4-[[2-(4-chlorophenyl)-4,4-dimethylcyclohexen-1-yl]methyl]piperazin-1-yl]phenyl]sulfonyl)-5-fluoropyridine-2-carboxamide | 675.1/675.0 |

TABLE 2-continued

Preparation of Examples ("Ex")

| Ex # | Structure | Name | [M + H]+ Calc./ Found |
|---|---|---|---|
| 34 | 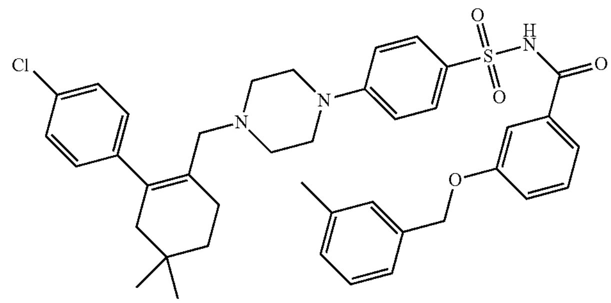 [SMILES: Cc1cccc(COc2cccc(C(=O)NS(=O)(=O)c3ccc(N4CCN(CC5=C(c6ccc(Cl)cc6)CC(C)(C)CC5)CC4)cc3)c2)c1] | N-([4-[4-[[2-(4-chlorophenyl)-4,4-dimethylcyclohexen-1-yl]methyl]piperazin-1-yl]phenyl]sulfonyl)-3-((3-methylbenzyl)oxy)benzamide | 698.3/ 698.2 |
| 35 | 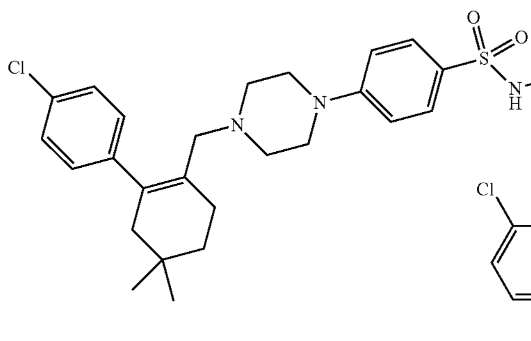 | N-([4-[4-[[2-(4-chlorophenyl)-4,4-dimethylcyclohexen-1-yl]methyl]piperazin-1-yl]phenyl]sulfonyl)-4-((2,5-dichlorophenoxy)methyl)benzamide | 752.2/ 751.9 |
| 36 | 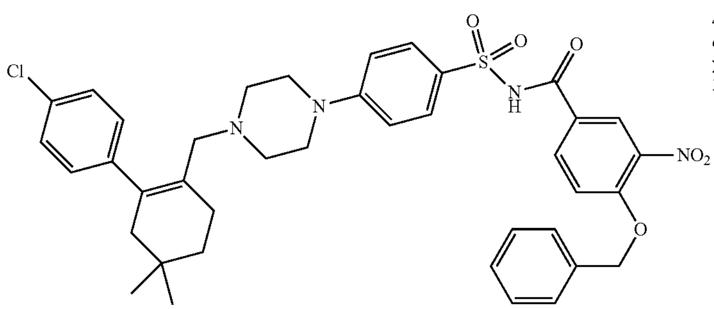 [SMILES: CC1(C)CCC(CN2CCN(c3ccc(S(=O)(=O)NC(=O)c4ccc(OCc5ccccc5)c([N+](=O)[O-])c4)cc3)CC2)=C(c2ccc(Cl)cc2)C1] | 4-(benzyloxy)-N-([4-[4-[[2-(4-chlorophenyl)-4,4-dimethylcyclohexen-1-yl]methyl] piperazin-1-yl]phenyl]sulfonyl)-3-nitrobenzamide | 729.2/ 729.0 |
| 37 | 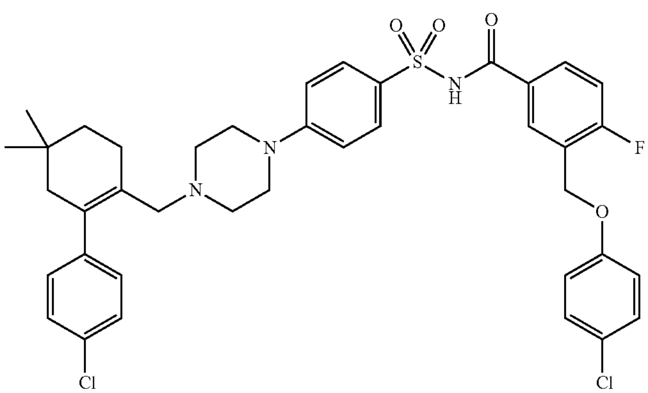 [SMILES: CC1(C)CCC(CN2CCN(c3ccc(S(=O)(=O)NC(=O)c4ccc(F)c(COc5ccc(Cl)cc5)c4)cc3)CC2)=C(c2ccc(Cl)cc2)C1] | N-([4-[4-[[2-(4-chlorophenyl)-4,4-dimethylcyclohexen-1-yl]methyl] piperazin-1-yl]phenyl]sulfonyl)-3-((4-chlorophenoxy)methyl)-4-fluorobenzamide | 736.2/ 736.0 |

TABLE 2-continued

Preparation of Examples ("Ex")

| Ex # | Structure | Name | [M + H]+ Calc./ Found |
|---|---|---|---|
| 38 | 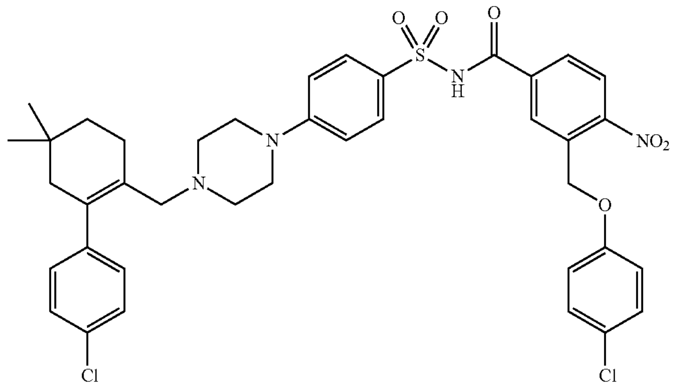 [SMILES: CC1(C)CCC(CN2CCN(c3ccc(S(=O)(=O)NC(=O)c4ccc([N+](=O)[O-])c(COc5ccc(Cl)cc5)c4)cc3)CC2)=C(c2ccc(Cl)cc2)C1] | N-([4-[4-[[2-(4-chlorophenyl)-4,4-dimethylcyclohexen-1-yl]methyl] piperazin-1-yl]phenyl]sulfonyl)-3-((4-chlorophenoxy)methyl)-4-nitrobenzamide | 763.2/ 763.1 |
| 39 | 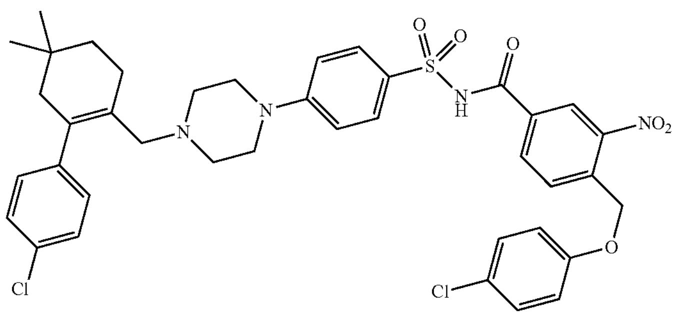 [SMILES: CC1(C)CCC(CN2CCN(c3ccc(S(=O)(=O)NC(=O)c4ccc(COc5ccc(Cl)cc5)c([N+](=O)[O-])c4)cc3)CC2)=C(c2ccc(Cl)cc2)C1] | N-([4-[4-[[2-(4-chlorophenyl)-4,4-dimethylcyclohexen-1-yl]methyl] piperazin-1-yl]phenyl]sulfonyl)-4-((4-chlorophenoxy)methyl)-3-nitrobenzamide | 763.2/ 763.0 |
| 40 | 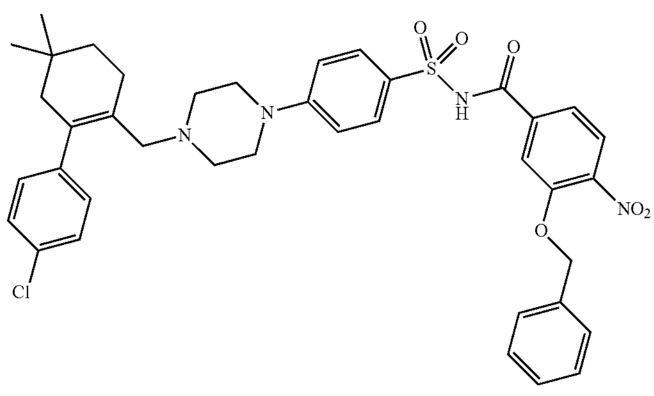 [SMILES: CC1(C)CCC(CN2CCN(c3ccc(S(=O)(=O)NC(=O)c4ccc([N+](=O)[O-])c(OCc5ccccc5)c4)cc3)CC2)=C(c2ccc(Cl)cc2)C1] | 3-(benzyloxy)-N-([4-[4-[[2-(4-chlorophenyl)-4,4-dimethylcyclohexen-1-yl]methyl] piperazin-1-yl]phenyl]sulfonyl)-4-nitrobenzamide | 729.2/ 729.0 |
| 41 | 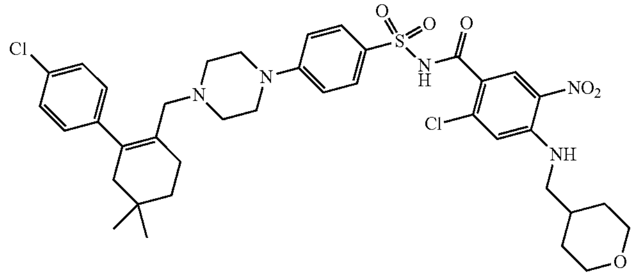 [SMILES: CC1(C)CCC(CN2CCN(c3ccc(S(=O)(=O)NC(=O)c4cc([N+](=O)[O-])c(NCC5CCOCC5)cc4Cl)cc3)CC2)=C(c2ccc(Cl)cc2)C1] | 2-Chloro-N-[4-[4-[[2-(4-chlorophenyl)-4,4-dimethylcyclohexen-1-yl]methyl] piperazin-1-yl]phenyl]sulfonyl-5-nitro-4-(tetrahydropyran-4-ylmethylamino)benzamide | 770.2/ 770.2 |

TABLE 2-continued

Preparation of Examples ("Ex")

| Ex # | Structure | Name | [M + H]+ Calc./ Found |
|---|---|---|---|
| 42 | 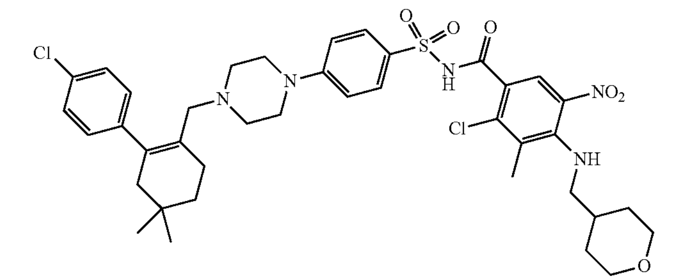 [SMILES: Cc1c(Cl)c(C(=O)NS(=O)(=O)c2ccc(N3CCN(CC4=C(c5ccc(Cl)cc5)CC(C)(C)CC4)CC3)cc2)cc([N+](=O)[O-])c1NCC1CCOCC1] | 2-Chloro-N-([4-[4-[[2-(4-chlorophenyl)-4,4-dimethylcyclohexen-1-yl]methyl]piperazin-1-yl]phenyl]sulfonyl)-3-methyl-5-nitro-4-(tetrahydropyran-4-ylmethylamino)benzamide | 784.3/ 784.4 |
| 43 | 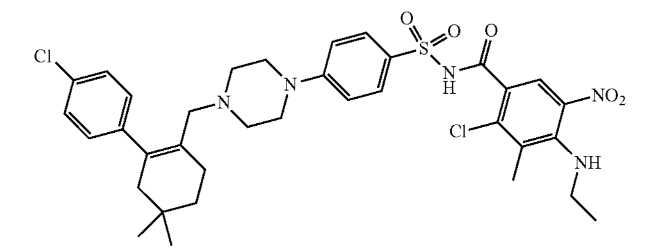 [SMILES: CCNc1c([N+](=O)[O-])cc(C(=O)NS(=O)(=O)c2ccc(N3CCN(CC4=C(c5ccc(Cl)cc5)CC(C)(C)CC4)CC3)cc2)c(Cl)c1C] | 2-chloro-N-[4-[4-[[2-(4-chlorophenyl)-4,4-dimethylcyclohexen-1-yl]methyl]piperazin-1-yl]phenyl]sulfonyl-4-(ethylamino)-3-methyl-5-nitrobenzamide | 714.2/ 714.0 |
| 44 | 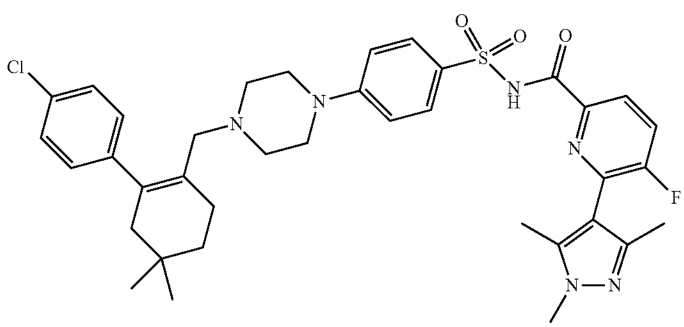 [SMILES: Cc1nn(C)c(C)c1-c1nc(C(=O)NS(=O)(=O)c2ccc(N3CCN(CC4=C(c5ccc(Cl)cc5)CC(C)(C)CC4)CC3)cc2)ccc1F] | N-[4-[4-[[2-(4-chlorophenyl)-4,4-dimethylcyclohexen-1-yl]methyl]piperazin-1-yl]phenyl]sulfonyl-5-fluoro-6-(1,3,5-trimethylpyrazol-4-yl)pyridine-2-carboxamide | 705.3/ 705.0 |
| 45 | 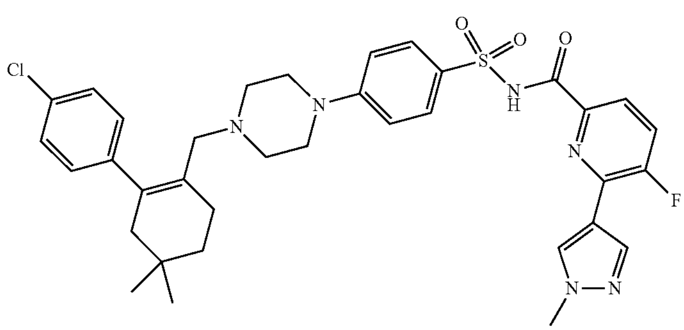 [SMILES: Cn1cc(-c2nc(C(=O)NS(=O)(=O)c3ccc(N4CCN(CC5=C(c6ccc(Cl)cc6)CC(C)(C)CC5)CC4)cc3)ccc2F)cn1] | N-[4-[4-[[2-(4-chlorophenyl)-4,4-dimethylcyclohexen-1-yl]methyl]piperazin-1-yl]phenyl]sulfonyl-5-fluoro-6-(1-methyl-1H-pyrazol-4-yl)pyridine-2-carboxamide | 677.2/ 677.0 |
| 46 | 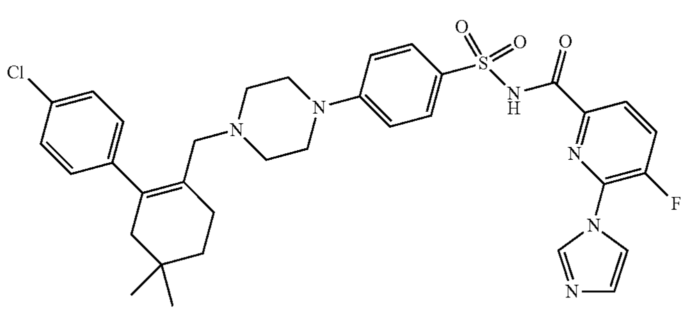 [SMILES: CC1(C)CCC(CN2CCN(c3ccc(S(=O)(=O)NC(=O)c4ccc(F)c(-n5ccnc5)n4)cc3)CC2)=C(c2ccc(Cl)cc2)C1] | N-[4-[4-[[2-(4-chlorophenyl)-4,4-dimethylcyclohexen-1-yl]methyl]piperazin-1-yl]phenyl]sulfonyl-5-fluoro-6-(1H-imidazol-1-yl)pyridine-2-carboxamide | 663.2/ 663.0 |

TABLE 2-continued

Preparation of Examples ("Ex")

| Ex # | Structure | Name | [M + H]+ Calc./ Found |
|---|---|---|---|
| 47 | 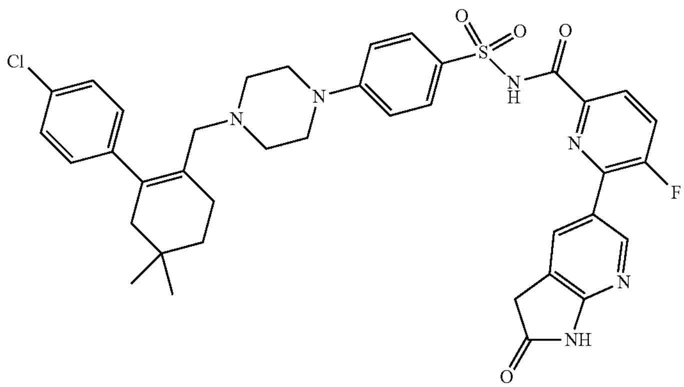 [SMILES: CC1(C)CCC(CN2CCN(c3ccc(S(=O)(=O)NC(=O)c4ccc(F)c(-c5cnc6c(c5)CC(=O)N6)n4)cc3)CC2)=C(c2ccc(Cl)cc2)C1] | N-[4-[4-[[2-(4-chlorophenyl)-4,4-dimethylcyclohexen-1-yl]methyl]piperazin-1-yl]phenyl]sulfonyl-5-fluoro-6-(2-oxo-2,3-dihydro-1H-pyrrolo[2,3-b]pyridin-5-yl)pyridine-2-carboxamide | 729.2/ 729.1 |
| 48 | 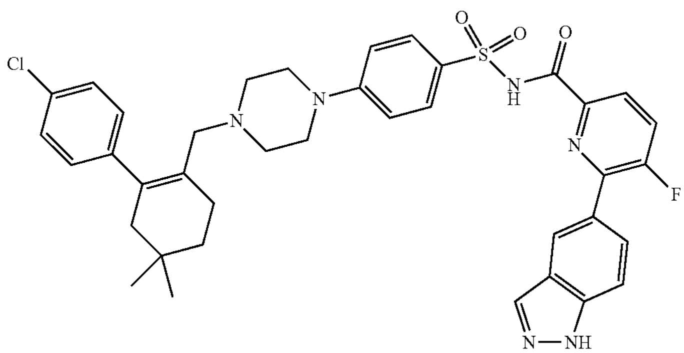 [SMILES: CC1(C)CCC(CN2CCN(c3ccc(S(=O)(=O)NC(=O)c4ccc(F)c(-c5ccc6[nH]ncc6c5)n4)cc3)CC2)=C(c2ccc(Cl)cc2)C1] | N-[4-[4-[[2-(4-chlorophenyl)-4,4-dimethylcyclohexen-1-yl]methyl]piperazin-1-yl]phenyl]sulfonyl-5-fluoro-6-(1H-indazol-5-yl)pyridine-2-carboxamide | 713.2/ 713.0 |
| 49 | 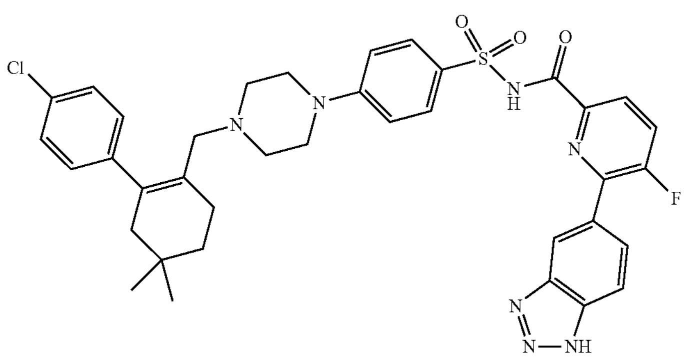 [SMILES: CC1(C)CCC(CN2CCN(c3ccc(S(=O)(=O)NC(=O)c4ccc(F)c(-c5ccc6[nH]nnc6c5)n4)cc3)CC2)=C(c2ccc(Cl)cc2)C1] | 6-(1H-benzo[d][1,2,3]triazol-5-yl)-N-[4-[4-[[2-(4-chlorophenyl)-4,4-dimethylcyclohexen-1-yl]methyl]piperazin-1-yl]phenyl]sulfonyl-5-fluoro pyridine-2-carboxamide | 714.2/ 714.0 |
| 50 | 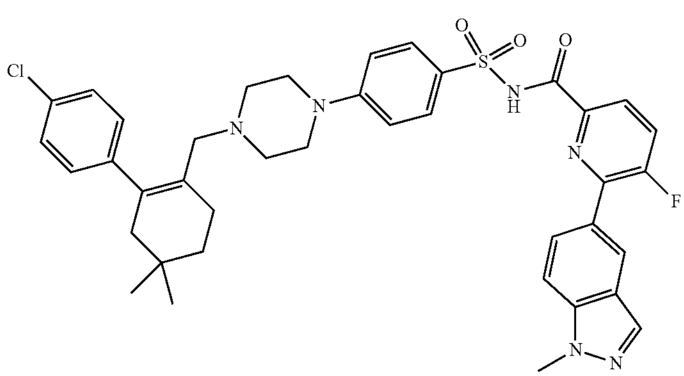 [SMILES: Cn1ncc2cc(-c3nc(C(=O)NS(=O)(=O)c4ccc(N5CCN(CC6=C(c7ccc(Cl)cc7)CC(C)(C)CC6)CC5)cc4)ccc3F)ccc21] | N-[4-[4-[[2-(4-chlorophenyl)-4,4-dimethylcyclohexen-1-yl]methyl]piperazin-1-yl]phenyl]sulfonyl-5-fluoro-6-(1-methyl-1H-indazol-5-yl)pyridine-2-carboxamide | 727.3/ 727.0 |

TABLE 2-continued

Preparation of Examples ("Ex")

| Ex # | Structure | Name | [M + H]+ Calc./ Found |
|---|---|---|---|
| 51 | 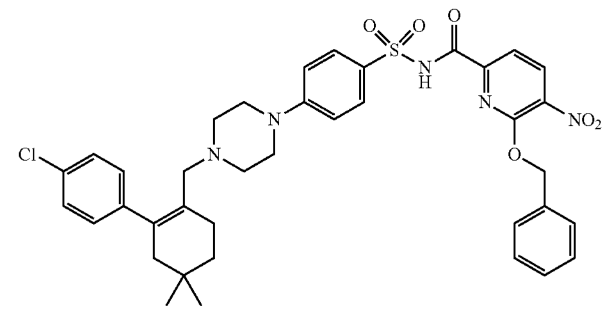 [SMILES: CC1(C)CCC(CN2CCN(c3ccc(S(=O)(=O)NC(=O)c4ccc([N+](=O)[O-])c(OCc5ccccc5)n4)cc3)CC2)=C(c2ccc(Cl)cc2)C1] | 6-(benzyloxy)-N-[4-[4-[[2-(4-chlorophenyl)-4,4-dimethylcyclohexen-1-yl]methyl]piperazin-1-yl]phenyl]sulfonyl-5-nitropyridine-2-carboxamide | 730.2/ 730.1 |
| 52 | 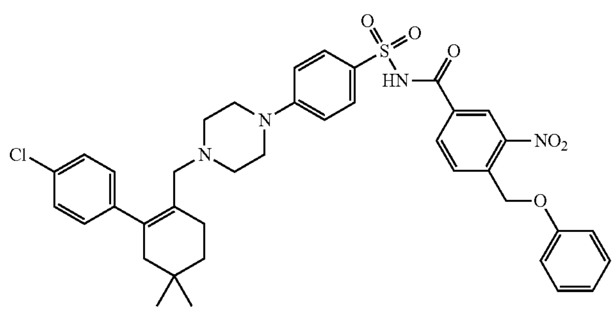 [SMILES: CC1(C)CCC(CN2CCN(c3ccc(S(=O)(=O)NC(=O)c4ccc(COc5ccccc5)c([N+](=O)[O-])c4)cc3)CC2)=C(c2ccc(Cl)cc2)C1] | N-[4-[4-[[2-(4-chlorophenyl)-4,4-dimethylcyclohexen-1-yl]methyl]piperazin-1-yl]phenyl]sulfonyl-3-nitro-4-(phenoxymethyl)benzamide | 729.2/ 729.1 |
| 53 | 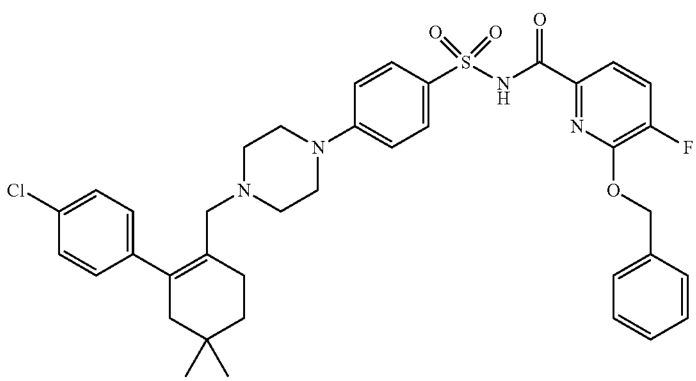 [SMILES: CC1(C)CCC(CN2CCN(c3ccc(S(=O)(=O)NC(=O)c4ccc(F)c(OCc5ccccc5)n4)cc3)CC2)=C(c2ccc(Cl)cc2)C1] | 3-(benzyloxy)-N-[4-[4-[[2-(4-chlorophenyl)-4,4-dimethylcyclohexen-1-yl]methyl]piperazin-1-yl]phenyl]sulfonyl-4-fluorobenzamide | 702.3/ 702.1 |
| 54 | 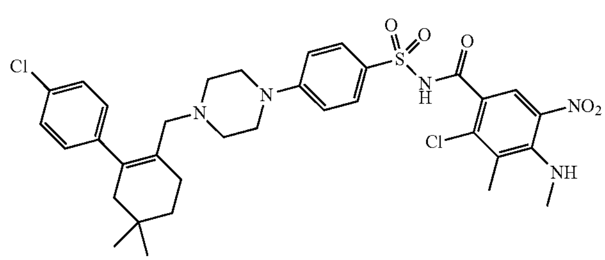 [SMILES: CNc1c([N+](=O)[O-])cc(C(=O)NS(=O)(=O)c2ccc(N3CCN(CC4=C(c5ccc(Cl)cc5)CC(C)(C)CC4)CC3)cc2)c(Cl)c1C] | 2-chloro-N-[4-[4-[[2-(4-chlorophenyl)-4,4-dimethylcyclohexen-1-yl]methyl]piperazin-1-yl]phenyl]sulfonyl-4-(methylamino)-3-methyl-5-nitrobenzamide | 700.2/ 700.0 |

Example 55

N-[4-[4-[[2-(4-Chlorophenyl)-4,4-dimethylcyclohexen-1-yl]methyl]piperazin-1-yl]phenyl]sulfonyl-5-fluoro-6-(2-methoxypyridin-4-yl)pyridine-2-carboxamide

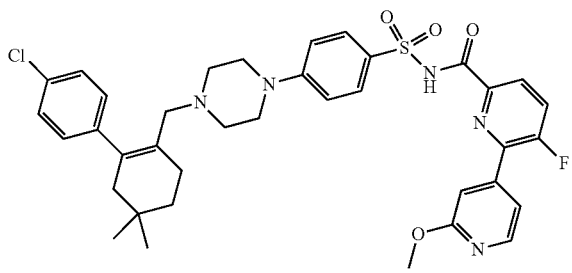 [SMILES: COc1cc(-c2nc(C(=O)NS(=O)(=O)c3ccc(N4CCN(CC5=C(c6ccc(Cl)cc6)CC(C)(C)CC5)CC4)cc3)ccc2F)ccn1]

A mixture of 6-bromo-N-[4-[4-[[2-(4-chlorophenyl)-4,4-dimethyl-cyclohexen-1-yl]methyl]piperazin-1-yl]phenyl]sulfonyl-5-fluoro-pyridine-2-carboxamide (25.0 mg, 0.04 mmol, Example 33), potassium phosphate (23.52 mg, 0.11 mmol), Pd(dppf)Cl$_2$ (4.82 mg, 0.01 mmol) and 2-methoxy-4-(4,4,5,5-tetramethyl-1,3,2-dioxaborolan-2-yl)pyridine (13.04 mg, 0.06 mmol) in water (1 mL) and 1,4-Dioxane (3 mL) was de-gassed and re-charged with N$_2$ for three cycles, and then stirred at 80° C. under N$_2$ overnight. The mixture was quenched with water (2 mL) and extracted with ethyl acetate (3 mL×3). The organic layer was concentrated under reduced pressure. The resulting residue was purified by prep-HPLC on a C18 column eluting with MeCN/H$_2$O (15% to 100%) to afford N-[4-[4-[[2-(4-chlorophenyl)-4,4-dimethylcyclohexen-1-yl]methyl]piperazin-1-yl]phenyl]sulfonyl-5-fluoro-6-(2-methoxypyridin-4-yl)pyridine-2-carboxamide (8 mg, 31% yield). LC-MS calc. for C$_{37}$H$_{40}$ClFN$_5$O$_4$S [M+H]$^+$: m/z=704.2/706.2. Found: 704.1/706.4. $^1$H NMR (300 MHz, CDCl$_3$) δ 8.23 (d, J=5.5 Hz, 1H), 8.09-7.71 (m, 4H), 7.56 (d, J=5.5 Hz, 1H), 7.43 (s, 1H), 7.31 (s, 2H), 7.09-6.94 (m, 4H), 3.93 (s, 2H), 3.66 (s, 3H), 3.32-3.26 (m, 1H), 3.17 (s, 4H), 2.24 (s, 2H), 2.08 (s, 2H), 1.53 (t, J=6.3 Hz, 2H), 1.24 (d, J=11.6 Hz, 4H), 0.97 (s, 6H).

The compounds listed in Table 3 below were prepared by using Example 33 and an appropriate boronic ester or acid using the methods substantially analogous to those disclosed for preparing Example 55.

TABLE 3

Preparation of Examples ("Ex")

| Ex # | Structure | Name | [M + H]$^+$ Calc./ Found |
| --- | --- | --- | --- |
| 56 | 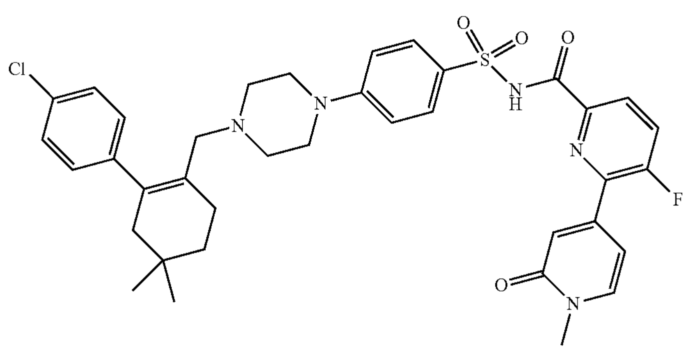 [SMILES: Cn1ccc(-c2nc(C(=O)NS(=O)(=O)c3ccc(N4CCN(CC5=C(c6ccc(Cl)cc6)CC(C)(C)CC5)CC4)cc3)ccc2F)cc1=O] | N-[4-[4-[[2-(4-Chlorophenyl)-4,4-dimethylcyclohexen-1-yl]methyl]piperazin-1-yl]phenyl]sulfonyl-3-fluoro-1'-methyl-2'-oxo-1',2'-dihydro-[2,4'-bipyridine]-6-carboxamide | 704.2/ 703.8 |
| 57 | 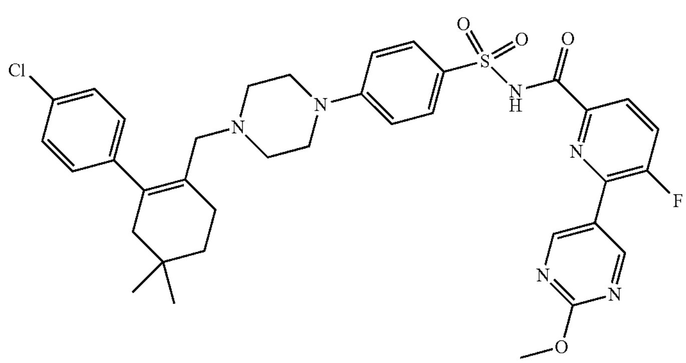 [SMILES: COc1ncc(-c2nc(C(=O)NS(=O)(=O)c3ccc(N4CCN(CC5=C(c6ccc(Cl)cc6)CC(C)(C)CC5)CC4)cc3)ccc2F)cn1] | N-[4-[4-[[2-(4-Chlorophenyl)-4,4-dimethylcyclohexen-1-yl]methyl]piperazin-1-yl]phenyl]sulfonyl-5-fluoro-6-(2-methoxypyrimidin-5-yl)pyridine-2-carboxamide | 705.2/ 705.0 |

TABLE 3-continued

Preparation of Examples ("Ex")

| Ex # | Structure | Name | [M + H]+ Calc./ Found |
|---|---|---|---|
| 58 | 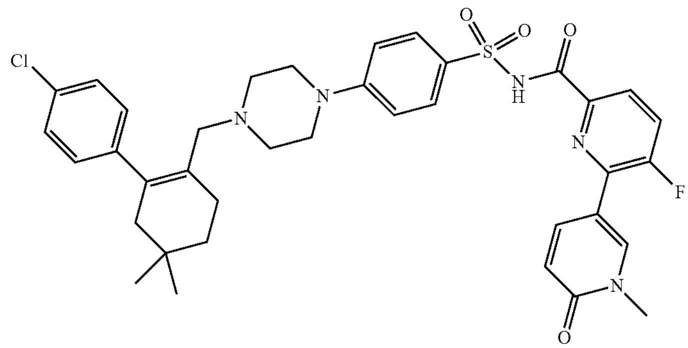 [SMILES: Cn1cc(-c2nc(C(=O)NS(=O)(=O)c3ccc(N4CCN(CC5=C(c6ccc(Cl)cc6)CC(C)(C)CC5)CC4)cc3)ccc2F)ccc1=O] | N-[4-[4-[[2-(4-Chlorophenyl)-4,4-dimethylcyclohexen-1-yl]methyl]piperazin-1-yl]phenyl]sulfonyl-3-fluoro-1'-methyl-6'-oxo-1',6'-dihydro-[2,3'-bipyridine]-6-carboxamide | 704.2/ 703.8 |
| 59 | 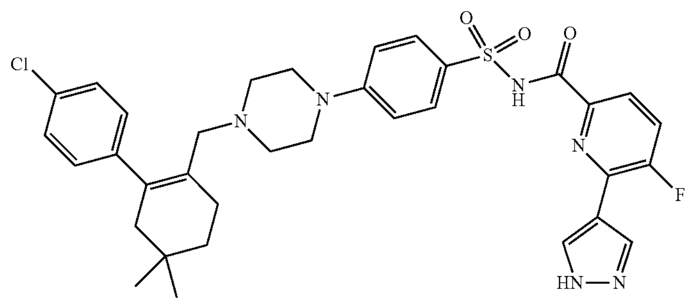 [SMILES: CC1(C)CCC(CN2CCN(c3ccc(S(=O)(=O)NC(=O)c4ccc(F)c(-c5cn[nH]c5)n4)cc3)CC2)=C(c2ccc(Cl)cc2)C1] | N-[4-[4-[[2-(4-Chlorophenyl)-4,4-dimethylcyclohexen-1-yl]methyl]piperazin-1-yl]phenyl]sulfonyl-5-fluoro-6-(1H-pyrazol-4-yl)pyridine-2-carboxamide | 663.2/ 663.2 |
| 60 | 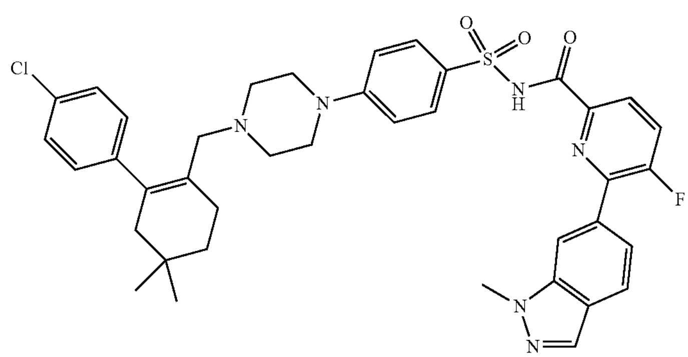 [SMILES: Cn1ncc2ccc(-c3nc(C(=O)NS(=O)(=O)c4ccc(N5CCN(CC6=C(c7ccc(Cl)cc7)CC(C)(C)CC6)CC5)cc4)ccc3F)cc21] | N-[4-[4-[[2-(4-Chlorophenyl)-4,4-dimethylcyclohexen-1-yl]methyl]piperazin-1-yl]phenyl]sulfonyl-5-fluoro-6-(1-methyl-1H-indazol-6-yl)pyridine-2-carboxamide | 727.3/ 727.1 |
| 61 | 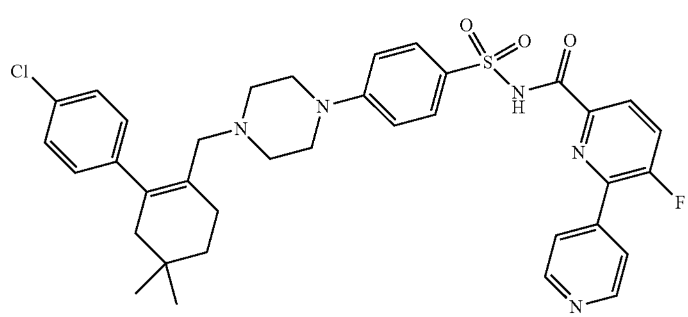 [SMILES: CC1(C)CCC(CN2CCN(c3ccc(S(=O)(=O)NC(=O)c4ccc(F)c(-c5ccncc5)n4)cc3)CC2)=C(c2ccc(Cl)cc2)C1] | N-[4-[4-[[2-(4-chlorophenyl)-4,4-dimethyl-cyclohexen-1-yl]methyl]piperazin-1-yl]phenyl]sulfonyl-5-fluoro-6-(4-pyridyl)pyridine-2-carboxamide | 674.2/ 674.0 |

Example 62

N-[4-[4-[[2-(4-Chlorophenyl)-4,4-dimethylcyclohexen-1-yl]methyl]piperazin-1-yl]-2-(1H-pyrrolo[2,3-b]pyridin-5-yloxy)phenyl]sulfonyl-5-fluoro-6-(2-methoxypyridin-4-yl)pyridine-2-carboxamide

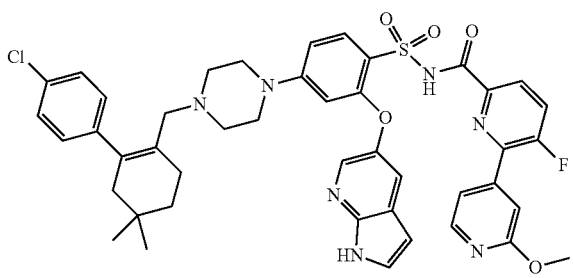 [SMILES: COc1cc(-c2nc(C(=O)NS(=O)(=O)c3ccc(N4CCN(CC5=C(c6ccc(Cl)cc6)CC(C)(C)CC5)CC4)cc3Oc3cnc4[nH]ccc4c3)ccc2F)ccn1]

This compound was prepared using procedures analogous to those described for preparing Example 55 using 6-bromo-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-fluoropyridine-2-carboxamide (Example 59) and 2-methoxy-5-(4,4,5,5-tetramethyl-1,3,2-dioxaborolan-2-yl)pyridine. LC-MS calc. for $C_{44}H_{44}ClFN_7O_5S$ [M+H]$^+$: m/z=836.28/838.28. Found: 836.2/837.7. $^1$H NMR (300 MHz, Chloroform-d) δ 8.55 (s, 1H), 8.22-7.86 (m, 3H), 7.86-7.66 (m, 2H), 7.47-7.25 (m, 4H), 7.07 (d, J=8.3 Hz, 2H), 6.85 (dd, J=9.1, 2.3 Hz, 1H), 6.66 (d, J=8.8 Hz, 1H), 6.36 (d, J=2.3 Hz, 1H), 6.18 (d, J=3.5 Hz, 1H), 3.93 (s, 3H), 3.67 (s, 2H), 2.36-1.91 (m, 5H), 1.56 (t, J=6.3 Hz, 2H), 1.32 (d, J=11.3 Hz, 7H), 1.00 (s, 6H).

Example 63

N-[4-[4-[[2-(4-Chlorophenyl)-4,4-dimethylcyclohexen-1-yl]methyl]piperazin-1-yl]-2-(1H-pyrrolo[2,3-b]pyridin-5-yloxy)phenyl]sulfonyl-5-fluoro-6-(1-methylpyrazol-4-yl)pyridine-2-carboxamide

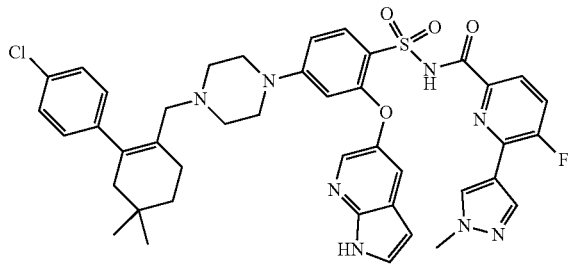 [SMILES: Cn1cc(-c2nc(C(=O)NS(=O)(=O)c3ccc(N4CCN(CC5=C(c6ccc(Cl)cc6)CC(C)(C)CC5)CC4)cc3Oc3cnc4[nH]ccc4c3)ccc2F)cn1]

This compound was prepared using procedures analogous to those described for preparing Example 55 using 6-bromo-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-fluoropyridine-2-carboxamide (Example 59) and 1-methyl-4-(4,4,5,5-tetramethyl-1,3,2-dioxaborolan-2-yl)pyrazole. LC-MS calc. for $C_{42}H_{43}ClFN_8O_4S$ [M+H]$^+$: m/z=809.28/811. Found: 809.2/810.7. $^1$H NMR (300 MHz, Chloroform-d) δ 12.39 (s, 1H), 10.27 (s, 1H), 8.14 (dd, J=9.0, 1.8 Hz, 1H), 7.94-7.82 (m, 4H), 7.78 (s, 1H), 7.58-7.41 (m, 2H), 7.38-7.30 (m, 2H), 6.94 (dd, J=8.3, 1.9 Hz, 2H), 6.74 (d, J=9.0 Hz, 1H), 6.49-6.41 (m, 1H), 6.23 (d, J=2.3 Hz, 1H), 3.93 (d, J=1.8 Hz, 3H), 3.61 (s, 2H), 2.27 (s, 3H), 2.07 (s, 2H), 1.65 (s, 1H), 1.49 (s, 2H), 1.36-1.24 (m, 5H), 0.96 (d, J=1.9 Hz, 6H).

Example 64

N-[4-[1-[[2-(4-Chlorophenyl)-4,4-dimethylcyclohexen-1-yl]methyl]-3,6-dihydro-2H-pyridin-4-yl]-2-(1H-pyrrolo[2,3-b]pyridin-5-yloxy)phenyl]sulfonyl-6-methyl-4-nitropyridine-2-carboxamide

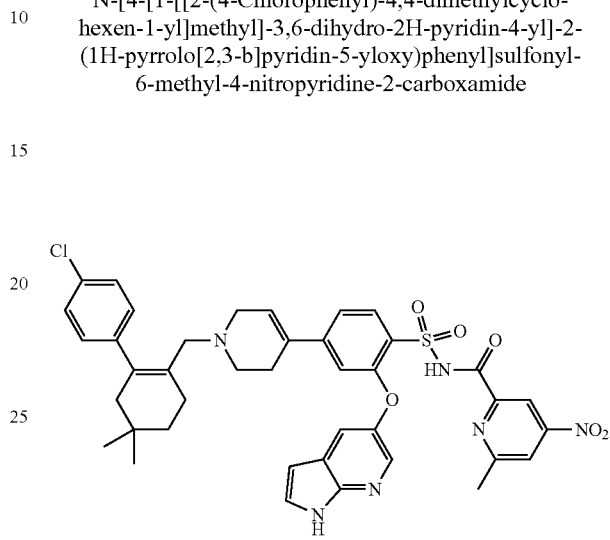

Step 1: 4-bromo-2-fluoro-N,N-bis[(4-methoxyphenyl)methyl]benzenesulfonamide

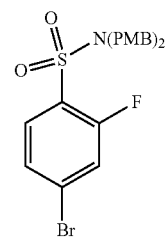

A mixture of 4-bromo-2-fluorobenzenesulfonyl chloride (5.0 g, 18.28 mmol), bis-(4-methoxybenzyl)amine (4.7 g, 18.28 mmol), triethylamine (20 mL), and 4-dimethylaminopyridine ("DMAP") (236.0 mg, 1.83 mmol) in DCM (100 mL) was stirred at r.t. for overnight. LC-MS showed that the starting material was consumed. The reaction was added HCl (1N, 100 mL) and extracted with ethyl acetate (100 mL×3). The combined organic layers were dried over Na$_2$SO$_4$, filtered, and concentrated under reduced pressure to afford the desired product 4-bromo-2-fluoro-N,N-bis[(4-methoxyphenyl)methyl]benzenesulfonamide (8.55 g, 96% yield). TLC: R$_f$=0.72 (ethyl acetate/heptanes 1:3).

Step 2: 4-bromo-N,N-bis[(4-methoxyphenyl)methyl]-2-(1H-pyrrolo[2,3-b]pyridin-5-yloxy)benzenesulfonamide

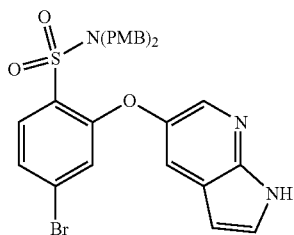

A mixture of 4-bromo-2-fluoro-N,N-bis[(4-methoxyphenyl)methyl]benzenesulfonamide (600.0 mg, 1.21 mmol), 1H-pyrrolo[2,3-b]pyridin-5-ol (162.8 mg, 1.21 mmol) and sodium tert-butoxide (174.96 mg, 1.82 mmol) in DMF (4 mL) was stirred at r.t. for overnight. LC-MS showed that the starting material was consumed. The reaction was neutralized with HCl aqueous solution (1N, 8 mL) and extracted with ethyl acetate (8 mL×3). The combined organic layers were dried over $Na_2SO_4$, filtered, and concentrated under reduced pressure. The resulting residue was purified by flash chromatography on a silica gel column with EtOAc/Heptanes (5-80%) to afford the desired product 4-bromo-N,N-bis[(4-methoxyphenyl)methyl]-2-(1H-pyrrolo[2,3-b]pyridin-5-yloxy)benzenesulfonamide (690 mg, 92% yield). LC-MS calc. for $C_{29}H_{27}BrN_3O_5S$ $[M+H]^+$: m/z=608.1/610.1. Found 607.8/609.7. Thin layer chromatography: $R_f$=0.35 (ethyl acetate/heptanes 1:1).

Step 3: 4-[4-[bis[(4-methoxyphenyl)methyl]sulfamoyl]-3-(1H-pyrrolo[2,3-b]pyridin-5-yloxy)phenyl]-3,6-dihydro-2H-pyridine-1-carboxylate

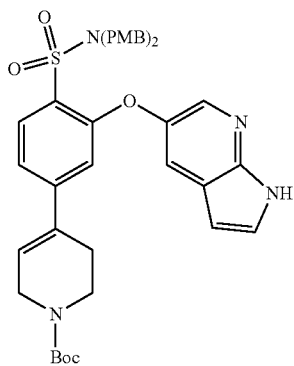

A mixture of 4-bromo-N,N-bis[(4-methoxyphenyl)methyl]-2-(1H-pyrrolo[2,3-b]pyridin-5-yloxy)benzenesulfonamide (800.0 mg, 1.31 mmol), N-Boc-1,2,3,6-tetrahydropyridine-4-boronic acid pinacol ester (406.5 mg, 1.31 mmol) and Pd(dppf)Cl$_2$ (85.7 mg, 0.13 mmol) in water (3 mL) and 1,4-dioxane (12 mL) was de-gassed and re-charged with nitrogen for three cycles, and stirred at 100° C. for 3 h. LC-MS showed that the starting material was consumed. The reaction was cooled to r.t., and neutralized with HCl aq. (1N, 10 mL). The mixture was extracted with ethyl acetate (10 mL×3). The combined organic layers were dried over $Na_2SO_4$, filtered, and concentrated under reduced pressure. The resulting residue was purified by flash chromatography on a silica gel column with EtOAc/Heptanes (5-90%) to afford the desired product tert-butyl 4-[4-[bis[(4-methoxyphenyl)methyl]sulfamoyl]-3-(1H-pyrrolo[2,3-b]pyridin-5-yloxy)phenyl]-3,6-dihydro-2H-pyridine-1-carboxylate (680 mg, 73% yield). LC-MS calc. for $C_{39}H_{43}N_4O_7S$ $[M+H]^+$: m/z=711.3. Found 711.5.

Step 4: N,N-bis[(4-methoxyphenyl)methyl]-2-(1H-pyrrolo[2,3-b]pyridin-5-yloxy)-4-(1,2,3,6-tetrahydropyridin-4-yl)benzenesulfonamide

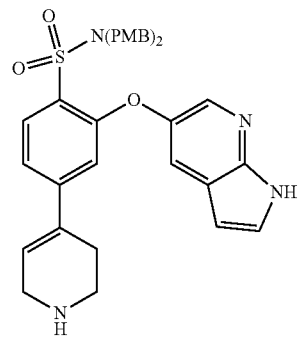

A mixture of tert-butyl 4-[4-[bis[(4-methoxyphenyl)methyl]sulfamoyl]-3-(1H-pyrrolo[2,3-b]pyridin-5-yloxy)phenyl]-3,6-dihydro-2H-pyridine-1-carboxylate (250.0 mg, 0.35 mmol) and HCl in isopropanol (IPA) (5N-6N) in IPA (2 mL) was stirred at r.t. overnight. The solvent was removed under reduced pressure to afford N,N-bis[(4-methoxyphenyl)methyl]-2-(1H-pyrrolo[2,3-b]pyridin-5-yloxy)-4-(1,2,3,6-tetrahydropyridin-4-yl)benzenesulfonamide (200 mg, 93% yield) as a pale yellow solid. LC-MS calc. for $C_{34}H_{35}N_4O_5S$ $[M+H]^+$: m/z=611.2. Found 611.6.

Step 5: 4-[1-[[2-(4-chlorophenyl)-4,4-dimethylcyclohexen-1-yl]methyl]-3,6-dihydro-2H-pyridin-4-yl]-N,N-bis[(4-methoxyphenyl)methyl]-2-(1H-pyrrolo[2,3-b]pyridin-5-yloxy)benzenesulfonamide

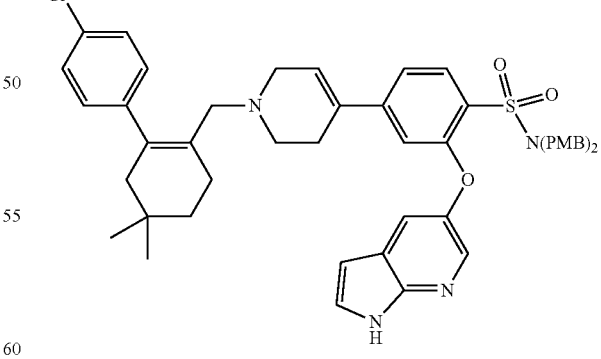

A mixture of N,N-bis[(4-methoxyphenyl)methyl]-2-(1H-pyrrolo[2,3-b]pyridin-5-yloxy)-4-(1,2,3,6-tetrahydropyridin-4-yl)benzenesulfonamide (150.0 mg, 0.25 mmol), 1-[2-(bromomethyl)-5,5-dimethylcyclohexen-1-yl]-4-chlorobenzene (77.0 mg, 0.25 mmol, Step 4 of Intermediate 1) and $K_2CO_3$ (127 mg, 0.98 mmol) in DMSO (4 mL) was stirred at r.t. for 3 h. The reaction was quenched with HCl aq. (1N, 8 mL) and extracted with ethyl acetate (8 mL×3). The combined organic layers were dried over $Na_2SO_4$, filtered, and concentrated under reduced pressure to provide 4-[1-[[2-(4-chlorophenyl)-4,4-dimethylcyclohexen-1-yl]methyl]-3,6-dihydro-2H-pyridin-4-yl]-N,N-bis[(4-methoxyphenyl)methyl]-2-(1H-pyrrolo[2,3-b]pyridin-5-yloxy)benzenesulfonamide (150 mg, 72% yield), which is directly used in the next step without further purification. LC-MS calc. for $C_{49}H_{52}ClN_4O_5S$ $[M+H]^+$: m/z=843.3/845.3. Found 843.4/845.7.

Step 6: 4-[1-[[2-(4-chlorophenyl)-4,4-dimethylcyclohexen-1-yl]methyl]-3,6-dihydro-2H-pyridin-4-yl]-2-(1H-pyrrolo[2,3-b]pyridin-5-yloxy)benzenesulfonamide

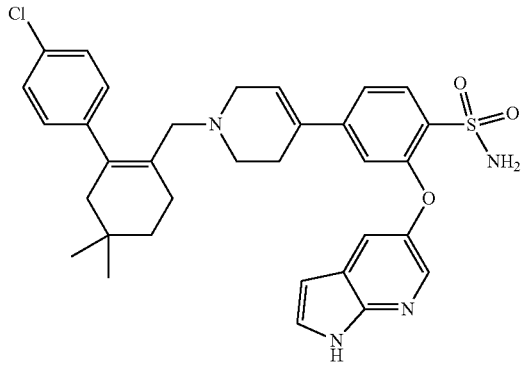 [SMILES: CC1(C)CCC(CN2CC=C(c3ccc(S(N)(=O)=O)c(Oc4cnc5[nH]ccc5c4)c3)CC2)=C(c2ccc(Cl)cc2)C1]

A mixture of 4-[1-[[2-(4-chlorophenyl)-4,4-dimethylcyclohexen-1-yl]methyl]-3,6-dihydro-2H-pyridin-4-yl]-N,N-bis[(4-methoxyphenyl)methyl]-2-(1H-pyrrolo[2,3-b]pyridin-5-yloxy)benzenesulfonamide (150.0 mg, 0.18 mmol) and TFA (2.0 mL, 26.14 mmol) in DCM (4 mL) was stirred at 40° C. for 5 h. The solvent was removed under reduced pressure. The resulting residue was purified by prep-HPLC on C18 column (30×250 mm, 10 μm) with MeCN/$H_2O$ (20 to 100%) to afford 4-[1-[[2-(4-chlorophenyl)-4,4-dimethylcyclohexen-1-yl]methyl]-3,6-dihydro-2H-pyridin-4-yl]-2-(1H-pyrrolo[2,3-b]pyridin-5-yloxy)benzenesulfonamide (89.2 mg, 83% yield). LC-MS calc. for $C_{33}H_{36}ClN_4O_3S$ $[M+H]^+$: m/z=603.2/605.2. Found 603.2/604.9.

Step 7: N-[4-[1-[[2-(4-chlorophenyl)-4,4-dimethylcyclohexen-1-yl]methyl]-3,6-dihydro-2H-pyridin-4-yl]-2-(1H-pyrrolo[2,3-b]pyridin-5-yloxy)phenyl]sulfonyl-6-methyl-4-nitropyridine-2-carboxamide A mixture of 4-[1-[[2-(4-chlorophenyl)-4,4-dimethylcyclohexen-1-yl]methyl]-3,6-dihydro-2H-pyridin-4-yl]-2-(1H-pyrrolo[2,3-b]pyridin-5-yloxy)benzenesulfonamide (20.0 mg, 0.03 mmol), EDC (10.1 mg, 0.10 mmol), DMAP (12.9 mg, 0.10 mmol), and 6-methyl-4-nitropyridine-2-carboxylic acid (6.0 mg, 0.03 mmol) in DMF (3 mL) was stirred at 40° C. for 5 h. The reaction was quenched with HCl (1N, 3 mL) and extracted with DCM (3 mL×3). The combined organic layers were dried over $Na_2SO_4$, filtered, and concentrated under reduced pressure. The resulting residue was purified by prep-HPLC on C18 column (30×250 mm, 10 μm) using mobile phase 20 to 100% MeCN/$H_2O$ (tR=15 min) to afford N-[4-[1-[[2-(4-chlorophenyl)-4,4-dimethylcyclohexen-1-yl]methyl]-3,6-dihydro-2H-pyridin-4-yl]-2-(1H-pyrrolo[2,3-b]pyridin-5-yloxy)phenyl]sulfonyl-6-methyl-4-nitropyridine-2-carboxamide (6.8 mg, 27% yield) as a white solid. LC-MS calc. for $C_{40}H_{40}ClN_6O_6S$ $[M+H]^+$: m/z=767.2/769.2. Found 767.2/769.5; HPLC: C18 column (4.6×150 mm, 5 μm); flow rate=1 mL/min; mobile phase: 5% MeCN/$H_2O$ (with 0.1% TFA) to 95% 10 min, 95% 5 min; λ=220 nm. tR=6.54 min; $^1$H NMR (300 MHz, $CDCl_3$) δ 11.83 (s, NH), 8.37 (d, J=8.3 Hz, 1H), 8.29 (d, J=8.3 Hz, 1H), 8.12 (d, J=8.4 Hz, 1H), 7.97 (s, 1H), 7.85 (s, 1H), 7.52 (d, J=2.9 Hz, 1H), 7.41-7.33 (m, 1H), 7.31 (s, 1H), 7.20 (d, J=8.3 Hz, 1H), 6.95 (d, J=8.3 Hz, 2H), 6.78 (s, 1H), 6.57 (s, 1H), 5.83 (s, 1H), 4.14-3.09 (m, 8H), 2.73 (s, 3H), 2.30 (d, J=7.2 Hz, 2H), 2.06 (d, J=15.6 Hz, 2H), 1.50 (t, J=6.2 Hz, 2H), 0.94 (m, 6H).

Example 65

N-[4-[1-[[2-(4-Chlorophenyl)-4,4-dimethylcyclohexen-1-yl]methyl]-3,6-dihydro-2H-pyridin-4-yl]-2-fluorophenyl]sulfonyl-6-methyl-4-nitropyridine-2-carboxamide

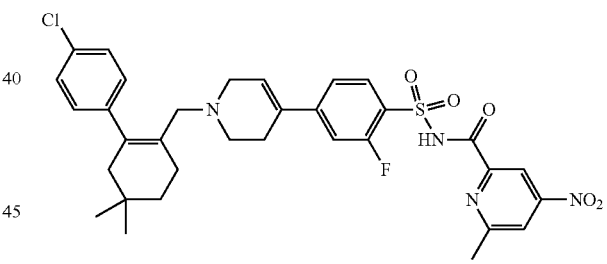

This compound was prepared using procedures analogous to those described for Steps 3-7 of Example 64 using a mixture of 4-bromo-2-fluoro-N,N-bis[(4-methoxyphenyl)methyl]benzenesulfonamide to replace 4-bromo-N,N-bis[(4-methoxyphenyl)methyl]-2-(1H-pyrrolo[2,3-b]pyridin-5-yloxy)benzenesulfonamide in Step 3. LC-MS calc. for $C_{33}H_{35}ClN_4O_5S$ $[M+H]^+$: m/z=653.2/655.3. Found 652.5/654.9; HPLC: C18 column (4.6×150 mm, 5 μm); flow rate=1 mL/min; mobile phase: 5% MeCN/$H_2O$ (with 0.1% TFA) to 95% 10 min, 95% 5 min; λ=220 nm. tR=6.67 min; $^1$H NMR (300 MHz, $CDCl_3$) δ 8.42 (d, J=8.3 Hz, 1H), 8.15 (dd, J=15.1, 8.0 Hz, 2H), 7.31 (s, 1H), 7.28 (d, J=0.9 Hz, 1H), 7.19 (d, J=8.6 Hz, 1H), 7.05-6.92 (m, 3H), 5.95 (s, 1H), 4.70-3.06 (m, 8H), 2.94 (s, 3H), 2.34 (s, 2H), 2.12 (s, 2H), 1.54 (s, 2H), 0.99 (m, 6H).

Example 66

N-[4-[4-[[2-(4-Chlorophenyl)-4,4-dimethylcyclohexen-1-yl]methyl]piperazin-1-yl]-2-(1H-pyrrolo[2,3-b]pyridin-5-yloxy)phenyl]sulfonyl-6-methyl-4-nitropyridine-2-carboxamide

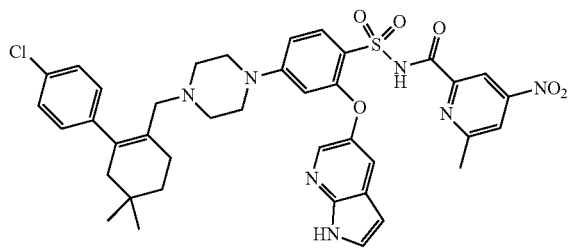 [SMILES: Cc1cc([N+](=O)[O-])cc(C(=O)NS(=O)(=O)c2ccc(N3CCN(CC4=C(c5ccc(Cl)cc5)CC(C)(C)CC4)CC3)cc2Oc2cnc3[nH]ccc3c2)n1]

A mixture of 4-[4-[[2-(4-chlorophenyl)-4,4-dimethylcyclohexen-1-yl]methyl]piperazin-1-yl]-2-(1H-pyrrolo[2,3-b]pyridin-5-yloxy)benzenesulfonamide (28.0 mg, 0.05 mmol, Intermediate 2), 6-methyl-4-nitropyridine-2-carboxylic acid (7.57 mg, 0.04 mmol), DMAP (22.57 mg, 0.18 mmol), and 1-ethyl-3-(3-dimethylaminopropyl)carbodiimide ("EDCI") (26.56 mg, 0.14 mmol) in DCM (1 mL) was stirred at r.t. overnight. The mixture was quenched with 0.5 M HCl(aq) (2 mL) and extracted with DCM (2 mL×3). The organic layer was concentrated under reduced pressure. The resulting residue was purified by prep-HPLC on a C18 column eluting with MeCN:H$_2$O (15% to 100%) to afford N-[4-[4-[[2-(4-chlorophenyl)-4,4-dimethylcyclohexen-1-yl]methyl]piperazin-1-yl]-2-(1H-pyrrolo[2,3-b]pyridin-5-yloxy) phenyl]sulfonyl-6-methyl-4-nitropyridine-2-carboxamide (9 mg, 25% yield). LC-MS calc. for $C_{39}H_{41}ClN_7O_6S$ [M+H]$^+$: m/z=770.25/772.25; Found: 770.1/772.3. $^1$H NMR (300 MHz, Chloroform-d) δ 8.35 (dd, J=8.4, 2.9 Hz, 1H), 8.06-7.86 (m, 3H), 7.43-7.25 (m, 4H), 7.09 (dd, J=8.4, 2.8 Hz, 2H), 6.89 (dt, J=9.1, 2.7 Hz, 1H), 6.51 (d, J=2.5 Hz, 1H), 6.22 (t, J=3.2 Hz, 1H), 3.70 (d, J=2.8 Hz, 3H), 2.54 (d, J=2.8 Hz, 3H), 2.31-2.17 (m, 3H), 2.12 (s, 2H), 1.58 (d, J=6.0 Hz, 3H), 1.39-1.28 (m, 6H), 1.02 (d, J=2.8 Hz, 6H).

The compounds listed in Table 4 below were prepared by using Intermediate 2 and an appropriate acid using the methods substantially analogous to those disclosed for preparing Example 66.

TABLE 4

Preparation osf Examples ("Ex")

| Ex # | Structure | Name | [M + H]$^+$ Calc./ Found |
|---|---|---|---|
| 67 | 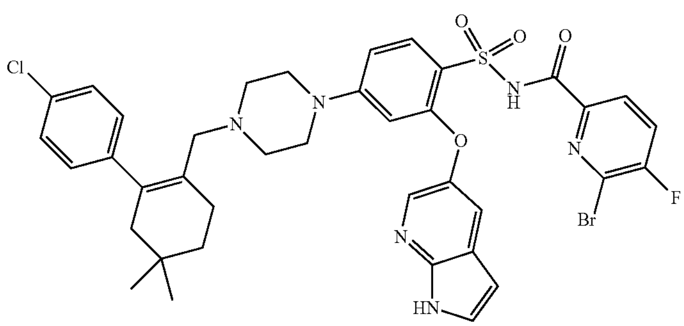 [SMILES: CC1(C)CCC(CN2CCN(c3ccc(S(=O)(=O)NC(=O)c4ccc(F)c(Br)n4)c(Oc4cnc5[nH]ccc5c4)c3)CC2)=C(c2ccc(Cl)cc2)C1] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-6-bromo-5-fluoropyridine-2-carboxamide | 807.2/ 806.9 |
| 68 | 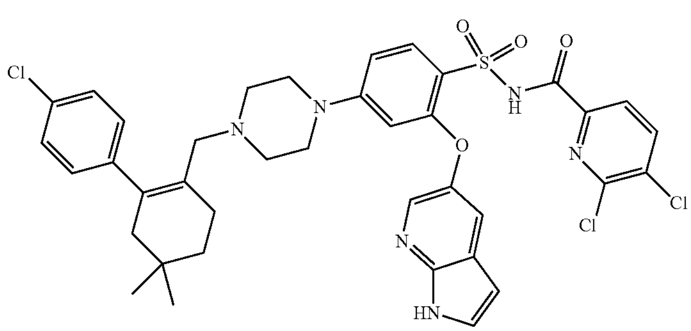 [SMILES: CC1(C)CCC(CN2CCN(c3ccc(S(=O)(=O)NC(=O)c4ccc(Cl)c(Cl)n4)c(Oc4cnc5[nH]ccc5c4)c3)CC2)=C(c2ccc(Cl)cc2)C1] | 5,6-Dichloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonylpyridine-2-carboxamide | 779.2/ 779.0 |

TABLE 4-continued

Preparation osf Examples ("Ex")

| Ex # | Structure | Name | [M + H]+ Calc./ Found |
|---|---|---|---|
| 69 | 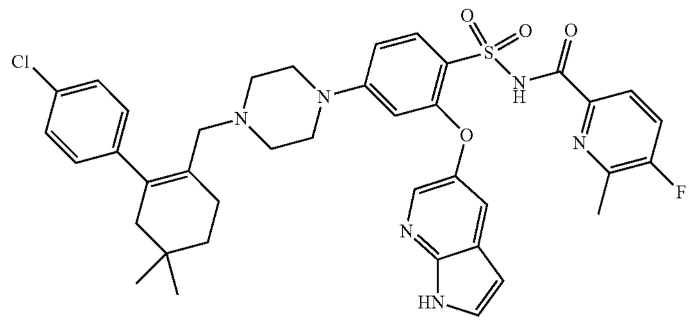 [SMILES: Cc1nc(C(=O)NS(=O)(=O)c2ccc(N3CCN(CC4=C(c5ccc(Cl)cc5)CC(C)(C)CC4)CC3)cc2Oc2cnc3[nH]ccc3c2)ccc1F] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-fluoro-6-methylpyridine-2-carboxamide | 743.3/ 743.1 |
| 70 | 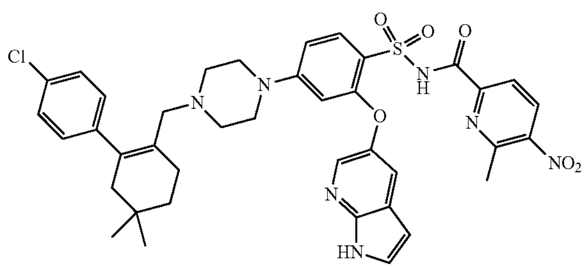 [SMILES: Cc1nc(C(=O)NS(=O)(=O)c2ccc(N3CCN(CC4=C(c5ccc(Cl)cc5)CC(C)(C)CC4)CC3)cc2Oc2cnc3[nH]ccc3c2)ccc1[N+](=O)[O-]] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-6-methyl-5-nitropyridine-2-carboxamide | 770.2/ 770.0 |
| 71 | 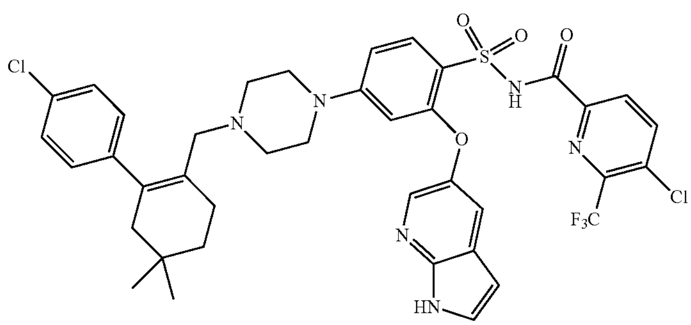 | 5-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-6-(trifluoromethyl)pyridine-2-carboxamide | 813.2/ 813.0 |
| 72 | 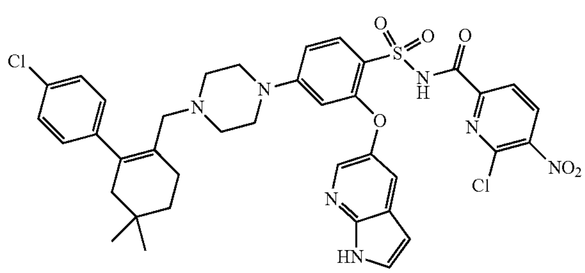 [SMILES: CC1(C)CCC(CN2CCN(c3ccc(S(=O)(=O)NC(=O)c4ccc([N+](=O)[O-])c(Cl)n4)c(Oc4cnc5[nH]ccc5c4)c3)CC2)=C(c2ccc(Cl)cc2)C1] | 6-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-nitropyridine-2-carboxamide | 790.2/ 790.1 |
| 73 | 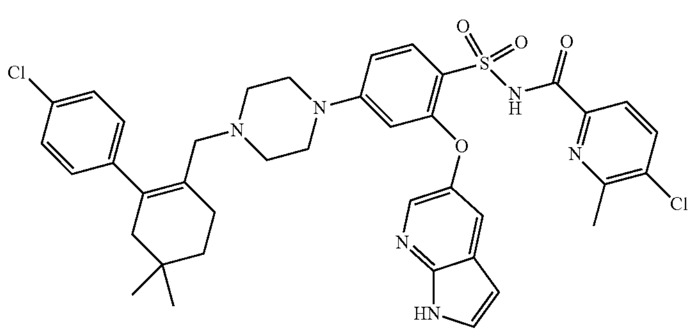 [SMILES: Cc1nc(C(=O)NS(=O)(=O)c2ccc(N3CCN(CC4=C(c5ccc(Cl)cc5)CC(C)(C)CC4)CC3)cc2Oc2cnc3[nH]ccc3c2)ccc1Cl] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-chloro-6-methylpyridine-2-carboxamide | 759.2/ 759.0 |

TABLE 4-continued

Preparation osf Examples ("Ex")

| Ex # | Structure | Name | [M + H]+ Calc./ Found |
|---|---|---|---|
| 74 | 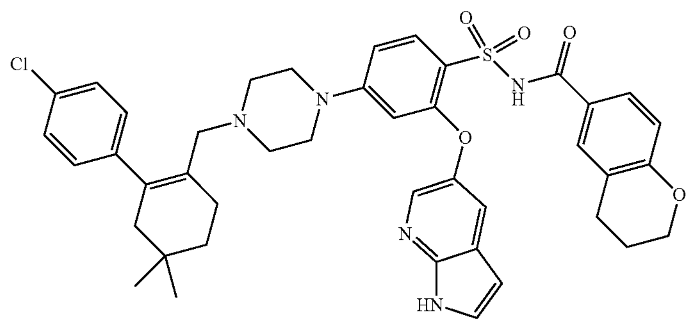 [SMILES: CC1(C)CCC(CN2CCN(c3ccc(S(=O)(=O)NC(=O)c4ccc5c(c4)CCCO5)c(Oc4cnc5[nH]ccc5c4)c3)CC2)=C(c2ccc(Cl)cc2)C1] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3,4-dihydro-2H-chromene-6-carboxamide | 766.3/ 766.2 |
| 75 | 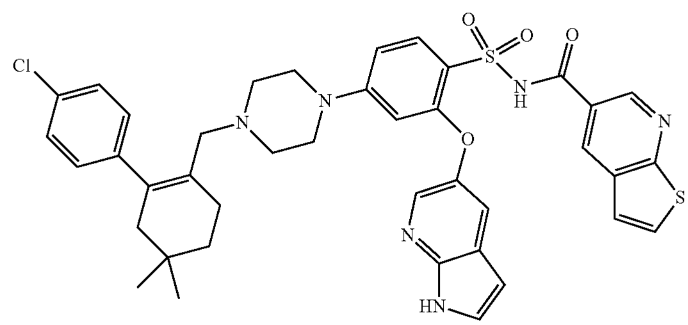 [SMILES: CC1(C)CCC(CN2CCN(c3ccc(S(=O)(=O)NC(=O)c4cnc5sccc5c4)c(Oc4cnc5[nH]ccc5c4)c3)CC2)=C(c2ccc(Cl)cc2)C1] | N-((2-(((1H-pyrrolo[2,3-b]pyridin-5-yl)oxy)-4-(4-[[2-(4-Chlorophenyl)-4,4-dimethylcyclohexen-1-yl]methyl]piperazin-1-yl]phenyl)sulfonyl)thieno[2,3-b]pyridine-5-carboxamide | 767.2/ 767.1 |
| 76 | 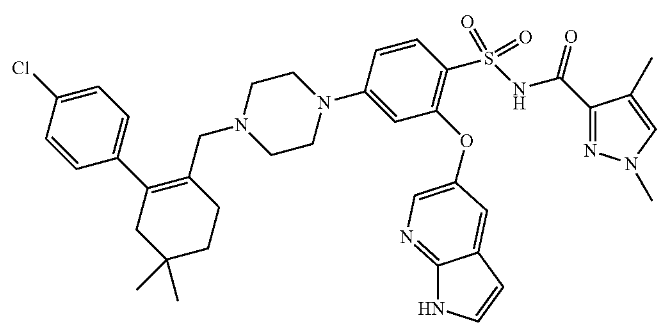 [SMILES: Cc1cn(C)nc1C(=O)NS(=O)(=O)c1ccc(N2CCN(CC3=C(c4ccc(Cl)cc4)CC(C)(C)CC3)CC2)cc1Oc1cnc2[nH]ccc2c1] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-1,4-dimethylpyrazole-3-carboxamide | 728.3/ 728.0 |
| 77 | 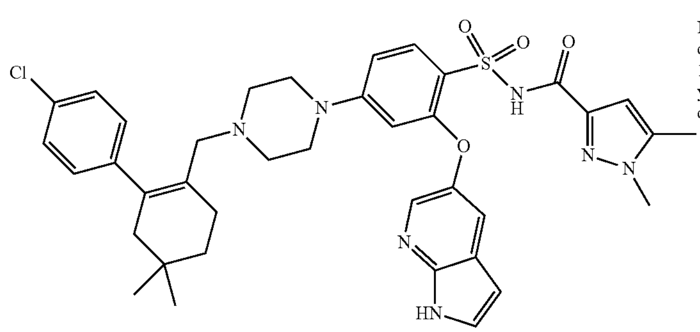 [SMILES: Cc1cc(C(=O)NS(=O)(=O)c2ccc(N3CCN(CC4=C(c5ccc(Cl)cc5)CC(C)(C)CC4)CC3)cc2Oc2cnc3[nH]ccc3c2)nn1C] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-1,5-dimethylpyrazole-3-carboxamide | 728.3/ 728.2 |

TABLE 4-continued

Preparation osf Examples ("Ex")

| Ex # | Structure | Name | [M + H]+ Calc./ Found |
|---|---|---|---|
| 78 | 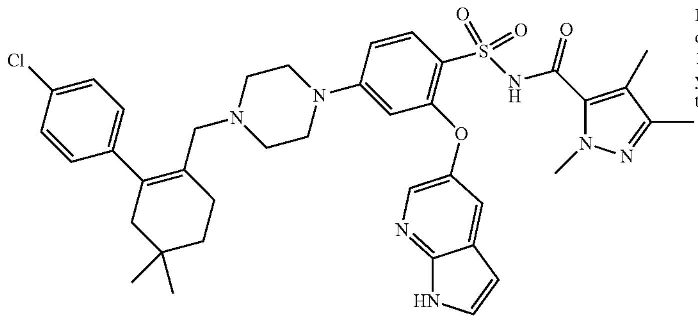 [SMILES: Cc1nn(C)c(C(=O)NS(=O)(=O)c2ccc(N3CCN(CC4=C(c5ccc(Cl)cc5)CC(C)(C)CC4)CC3)cc2Oc2cnc3[nH]ccc3c2)c1C] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-2,4,5-trimethylpyrazole-3-carboxamide | 742.3/ 742.1 |
| 79 | 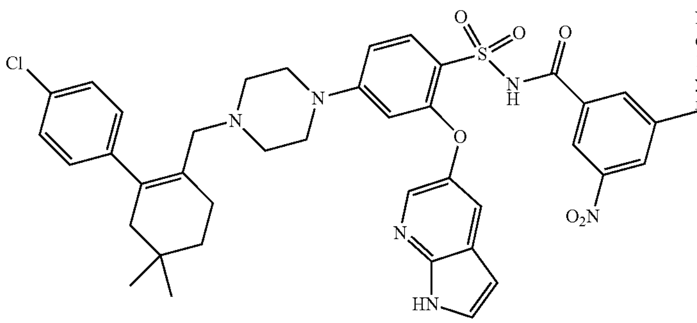 [SMILES: Cc1cc(C(=O)NS(=O)(=O)c2ccc(N3CCN(CC4=C(c5ccc(Cl)cc5)CC(C)(C)CC4)CC3)cc2Oc2cnc3[nH]ccc3c2)cc([N+](=O)[O-])c1] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitrobenzamide | 769.2/ 769.1 |
| 80 | 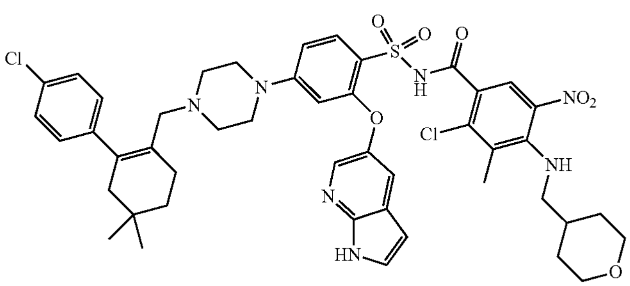 [SMILES: Cc1c(Cl)c(C(=O)NS(=O)(=O)c2ccc(N3CCN(CC4=C(c5ccc(Cl)cc5)CC(C)(C)CC4)CC3)cc2Oc2cnc3[nH]ccc3c2)cc([N+](=O)[O-])c1NCC1CCOCC1] | 2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxan-4-ylmethylamino)benzamide | 916.3/ 916.6 |
| 81 | 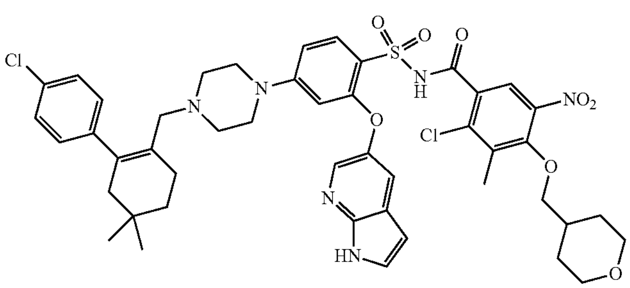 [SMILES: Cc1c(Cl)c(C(=O)NS(=O)(=O)c2ccc(N3CCN(CC4=C(c5ccc(Cl)cc5)CC(C)(C)CC4)CC3)cc2Oc2cnc3[nH]ccc3c2)cc([N+](=O)[O-])c1OCC1CCOCC1] | 2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxan-4-ylmethoxy)benzamide | 917.3/ 917.1 |
| 82 | 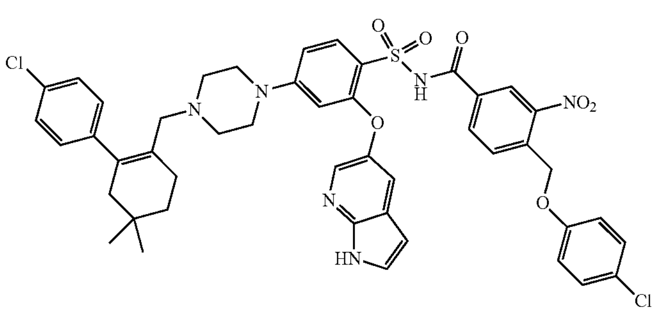 [SMILES: CC1(C)CCC(CN2CCN(c3ccc(S(=O)(=O)NC(=O)c4ccc(COc5ccc(Cl)cc5)c([N+](=O)[O-])c4)c(Oc4cnc5[nH]ccc5c4)c3)CC2)=C(c2ccc(Cl)cc2)C1] | N-((2-((1H-pyrrolo[2,3-b]pyridin-5-yl)methyl)-4-(4-[[2-(4-Chlorophenyl)-4,4-dimethylcyclohexen-1-yl]methyl]piperazin-1-yl]phenyl)sulfonyl)-4-((4-chlorophenoxy)methyl)-3-nitrobenzamide | 895.2/ 895.1 |

TABLE 4-continued

Preparation osf Examples ("Ex")

| Ex # | Structure | Name | [M + H]+ Calc./ Found |
|---|---|---|---|
| 83 | 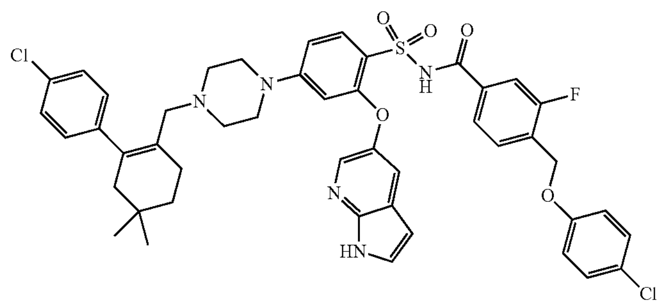 [SMILES: CC1(C)CCC(CN2CCN(c3ccc(S(=O)(=O)NC(=O)c4ccc(COc5ccc(Cl)cc5)c(F)c4)c(Oc4cnc5[nH]ccc5c4)c3)CC2)=C(c2ccc(Cl)cc2)C1] | 4-[(4-Chlorophenoxy)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-fluorobenzamide | 868.2/ 868.2 |
| 84 | 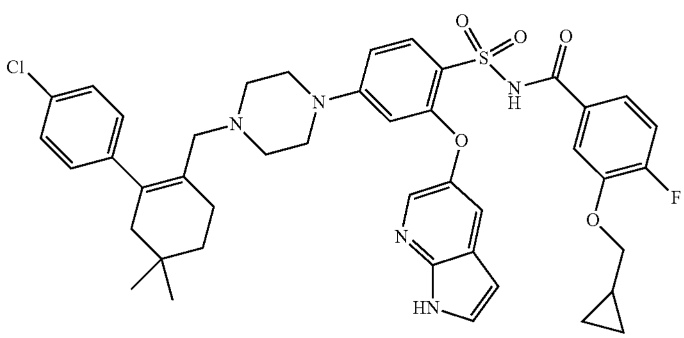 [SMILES: CC1(C)CCC(CN2CCN(c3ccc(S(=O)(=O)NC(=O)c4ccc(F)c(OCC5CC5)c4)c(Oc4cnc5[nH]ccc5c4)c3)CC2)=C(c2ccc(Cl)cc2)C1] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-(cyclopropyloxymethyl)-4-fluorobenzamide | 798.3/ 798.3 |
| 85 | 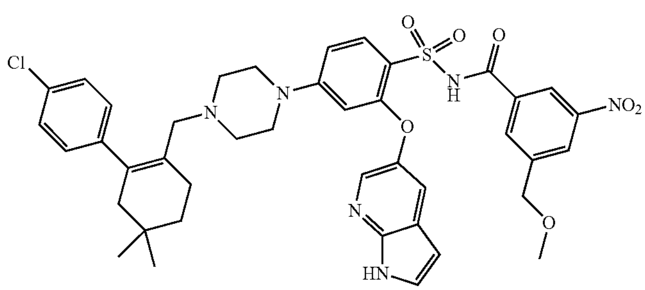 [SMILES: COCc1cc(C(=O)NS(=O)(=O)c2ccc(N3CCN(CC4=C(c5ccc(Cl)cc5)CC(C)(C)CC4)CC3)cc2Oc2cnc3[nH]ccc3c2)cc([N+](=O)[O-])c1] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-(methoxymethyl)-5-nitrobenzamide | 799.3/ 799.2 |
| 86 | 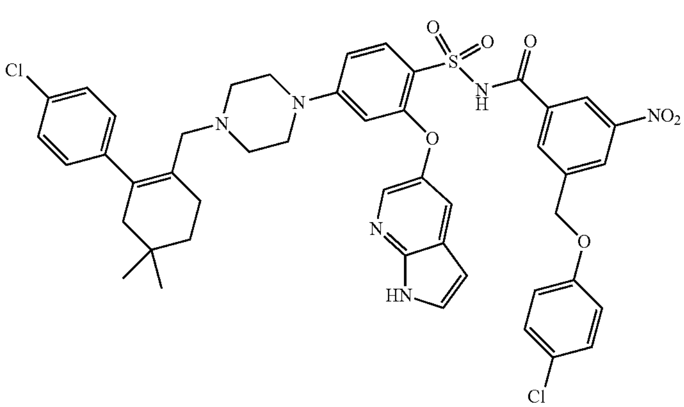 [SMILES: CC1(C)CCC(CN2CCN(c3ccc(S(=O)(=O)NC(=O)c4cc(COc5ccc(Cl)cc5)cc([N+](=O)[O-])c4)c(Oc4cnc5[nH]ccc5c4)c3)CC2)=C(c2ccc(Cl)cc2)C1] | 3-[(4-Chlorophenoxy)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-nitrobenzamide | 895.2/ 895.2 |

TABLE 4-continued

Preparation osf Examples ("Ex")

| Ex # | Structure | Name | [M + H]+ Calc./ Found |
|---|---|---|---|
| 87 | 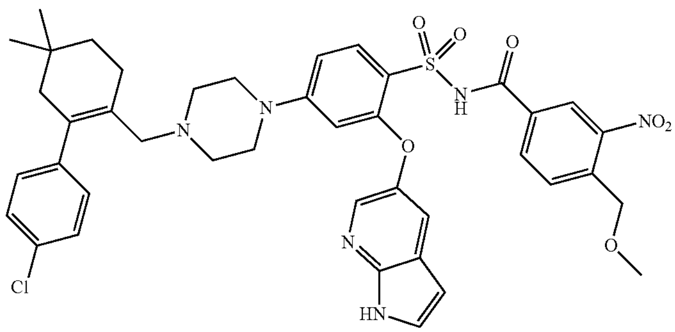 [SMILES: COCc1ccc(C(=O)NS(=O)(=O)c2ccc(N3CCN(CC4=C(c5ccc(Cl)cc5)CC(C)(C)CC4)CC3)cc2Oc2cnc3[nH]ccc3c2)cc1[N+](=O)[O-]] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(methoxymethyl)-3-nitrobenzamide | 799.3/ 799.2 |
| 88 | 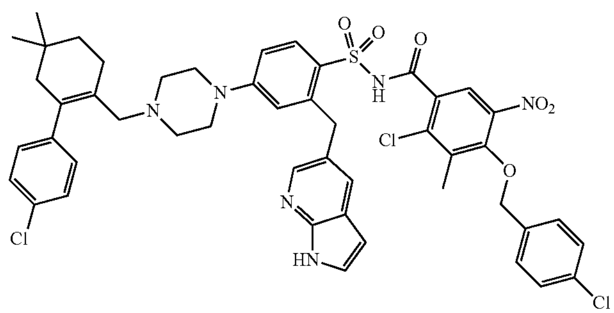 [SMILES: Cc1c(Cl)c(C(=O)NS(=O)(=O)c2ccc(N3CCN(CC4=C(c5ccc(Cl)cc5)CC(C)(C)CC4)CC3)cc2Cc2cnc3[nH]ccc3c2)cc([N+](=O)[O-])c1OCc1ccc(Cl)cc1] | 2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-[(4-chlorophenyl)methoxy]-3-methyl-5-nitrobenzamide | 943.2/ 943.1 |
| 89 | 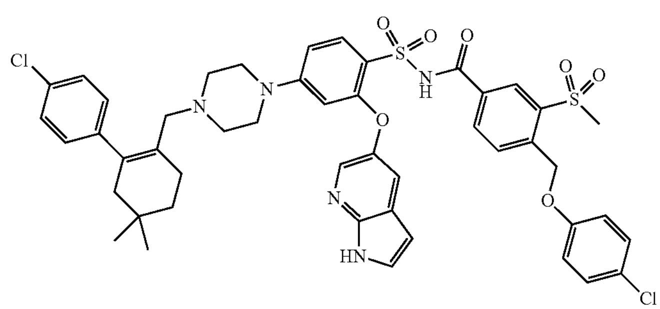 [SMILES: CC1(C)CCC(CN2CCN(c3ccc(S(=O)(=O)NC(=O)c4ccc(COc5ccc(Cl)cc5)c(S(C)(=O)=O)c4)c(Oc4cnc5[nH]ccc5c4)c3)CC2)=C(c2ccc(Cl)cc2)C1] | 4-[(4-chlorophenoxy)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methylsulfonylbenzamide | 928.2/ 928.0 |
| 90 | 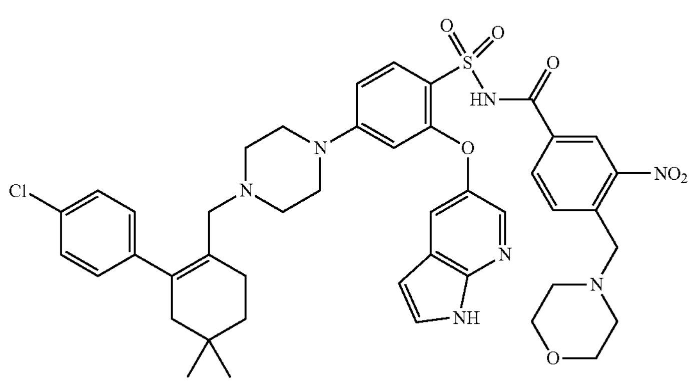 [SMILES: CC1(C)CCC(CN2CCN(c3ccc(S(=O)(=O)NC(=O)c4ccc(CN5CCOCC5)c([N+](=O)[O-])c4)c(Oc4cnc5[nH]ccc5c4)c3)CC2)=C(c2ccc(Cl)cc2)C1] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(morpholin-4-ylmethyl)-3-nitrobenzamide | 854.3/ 854.3 |

TABLE 4-continued

Preparation osf Examples ("Ex")

| Ex # | Structure | Name | [M + H]+ Calc./ Found |
|---|---|---|---|
| 91 | 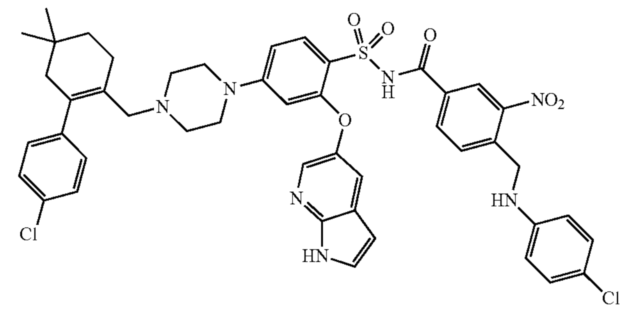 [SMILES: CC1(C)CCC(CN2CCN(c3ccc(S(=O)(=O)NC(=O)c4ccc(CNc5ccc(Cl)cc5)c([N+](=O)[O-])c4)c(Oc4cnc5[nH]ccc5c4)c3)CC2)=C(c2ccc(Cl)cc2)C1] | 4-[(4-chloroanilino)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-nitrobenzamide | 894.3/ 894.4 |
| 92 | 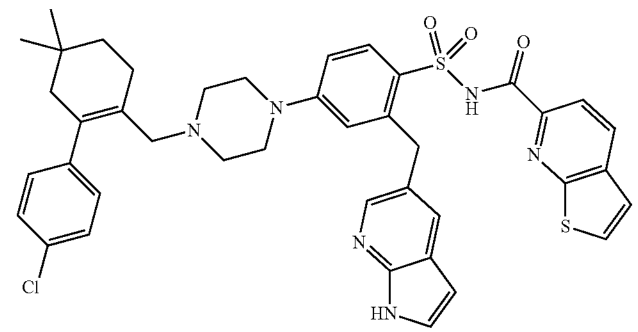 [SMILES: CC1(C)CCC(CN2CCN(c3ccc(S(=O)(=O)NC(=O)c4ccc5ccsc5n4)c(Cc4cnc5[nH]ccc5c4)c3)CC2)=C(c2ccc(Cl)cc2)C1] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonylthieno[2,3-b]pyridine-6-carboxamide | 767.2/ 767.0 |
| 93 | 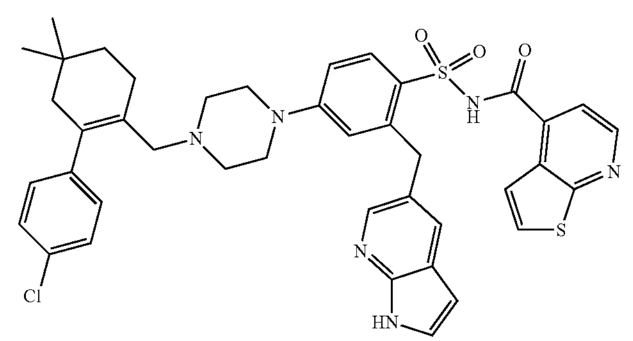 [SMILES: CC1(C)CCC(CN2CCN(c3ccc(S(=O)(=O)NC(=O)c4ccnc5sccc45)c(Cc4cnc5[nH]ccc5c4)c3)CC2)=C(c2ccc(Cl)cc2)C1] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonylthieno[2,3-b]pyridine-4-carboxamide | 767.2/ 767.0 |
| 94 | 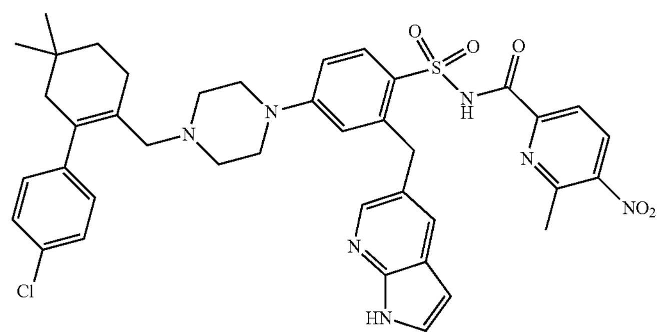 [SMILES: Cc1nc(C(=O)NS(=O)(=O)c2ccc(N3CCN(CC4=C(c5ccc(Cl)cc5)CC(C)(C)CC4)CC3)cc2Cc2cnc3[nH]ccc3c2)ccc1[N+](=O)[O-]] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-6-methyl-5-nitropyridine-2-carboxamide | 770.2/ 770.0 |

TABLE 4-continued

Preparation osf Examples ("Ex")

| Ex # | Structure | Name | [M + H]+ Calc./ Found |
|---|---|---|---|
| 95 | 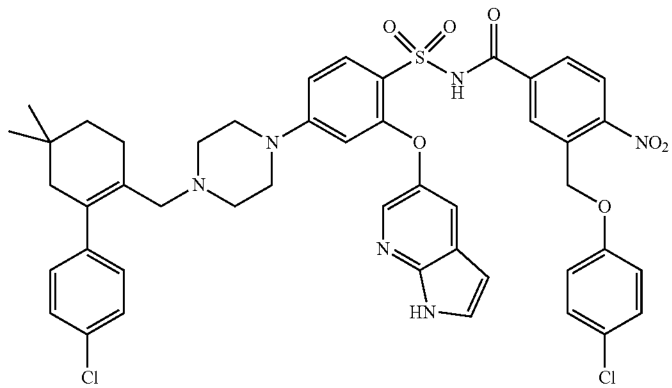 [SMILES: CC1(C)CCC(CN2CCN(c3ccc(S(=O)(=O)NC(=O)c4ccc([N+](=O)[O-])c(COc5ccc(Cl)cc5)c4)c(Oc4cnc5[nH]ccc5c4)c3)CC2)=C(c2ccc(Cl)cc2)C1] | 3-[(4-Chlorophenoxy)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-nitrobenzamide | 895.2/ 895.1 |
| 96 | 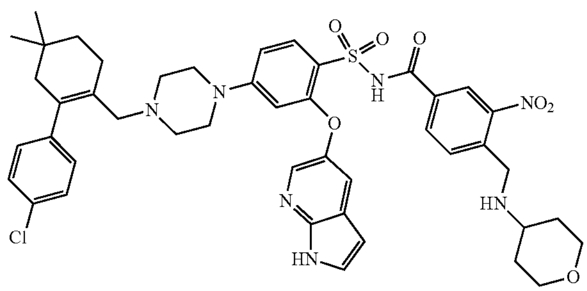 [SMILES: CC1(C)CCC(CN2CCN(c3ccc(S(=O)(=O)NC(=O)c4ccc(CNC5CCOCC5)c([N+](=O)[O-])c4)c(Oc4cnc5[nH]ccc5c4)c3)CC2)=C(c2ccc(Cl)cc2)C1] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-nitro-4-[(oxan-4-ylamino)methyl]benzamide | 868.3/ 868.2 |
| 97 | 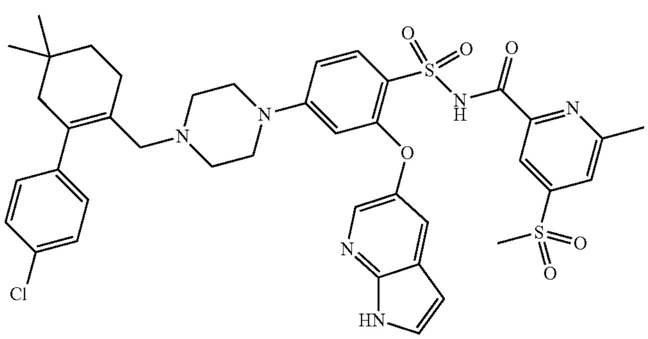 [SMILES: Cc1cc(S(C)(=O)=O)cc(C(=O)NS(=O)(=O)c2ccc(N3CCN(CC4=C(c5ccc(Cl)cc5)CC(C)(C)CC4)CC3)cc2Oc2cnc3[nH]ccc3c2)n1] | N-[4-[4-[[2-(4-Chlorophenyl)-4,4-dimethylcyclohexen-1-yl]methyl]piperazin-1-yl]-2-(1H-pyrrolo[2,3-b]pyridin-5-yloxy)phenyl]sulfonyl-6-methyl-4-methylsulfonylpyridine-2-carboxamide | 803.3/ 803.1 |
| 98 | 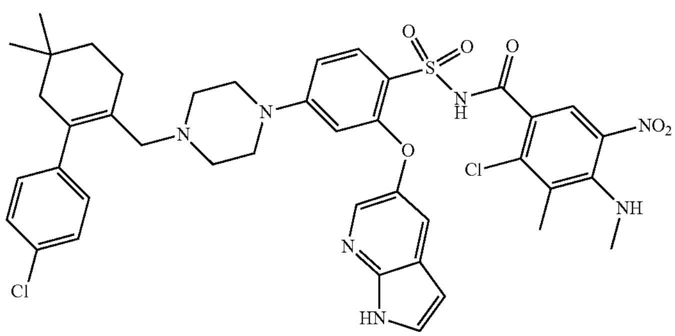 [SMILES: CNc1c([N+](=O)[O-])cc(C(=O)NS(=O)(=O)c2ccc(N3CCN(CC4=C(c5ccc(Cl)cc5)CC(C)(C)CC4)CC3)cc2Oc2cnc3[nH]ccc3c2)c(Cl)c1C] | 2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-4-(methylamino)-5-nitrobenzamide | 832.2/ 832.3 |

TABLE 4-continued

Preparation osf Examples ("Ex")

| Ex # | Structure | Name | [M + H]+ Calc./ Found |
|---|---|---|---|
| 99 | 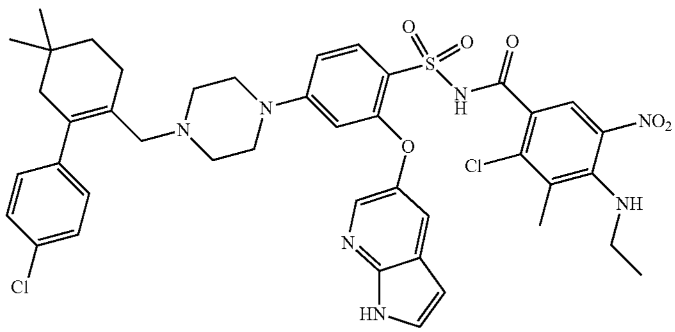 [SMILES: CCNc1c([N+](=O)[O-])cc(C(=O)NS(=O)(=O)c2ccc(N3CCN(CC4=C(c5ccc(Cl)cc5)CC(C)(C)CC4)CC3)cc2Oc2cnc3[nH]ccc3c2)c(Cl)c1C] | 2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(ethylamino)-3-methyl-5-nitrobenzamide | 846.3/ 846.1 |
| 100 | 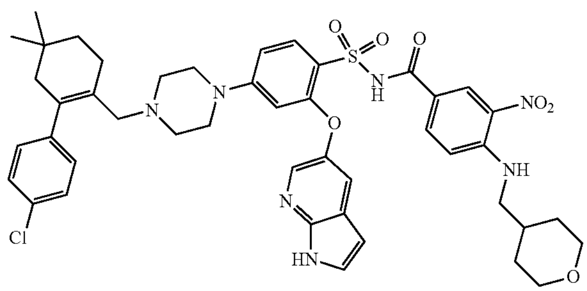 [SMILES: CC1(C)CCC(CN2CCN(c3ccc(S(=O)(=O)NC(=O)c4ccc(NCC5CCOCC5)c([N+](=O)[O-])c4)c(Oc4cnc5[nH]ccc5c4)c3)CC2)=C(c2ccc(Cl)cc2)C1] | N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-nitro-4-(oxan-4-ylmethylamino)benzamide | 868.3/ 868.2 |
| 101 | 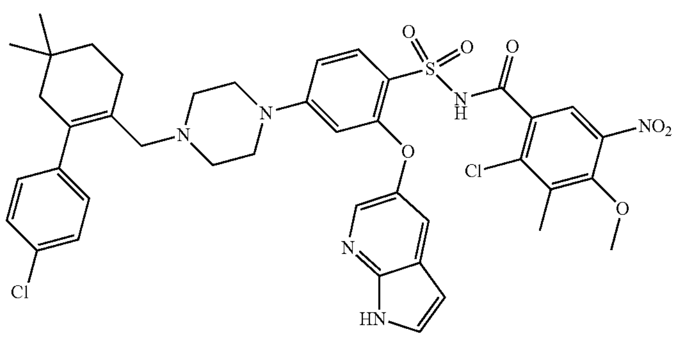 [SMILES: COc1c([N+](=O)[O-])cc(C(=O)NS(=O)(=O)c2ccc(N3CCN(CC4=C(c5ccc(Cl)cc5)CC(C)(C)CC4)CC3)cc2Oc2cnc3[nH]ccc3c2)c(Cl)c1C] | 2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-methoxy-3-methyl-5-nitrobenzamide | 833.2/ 833.3 |
| 102 | 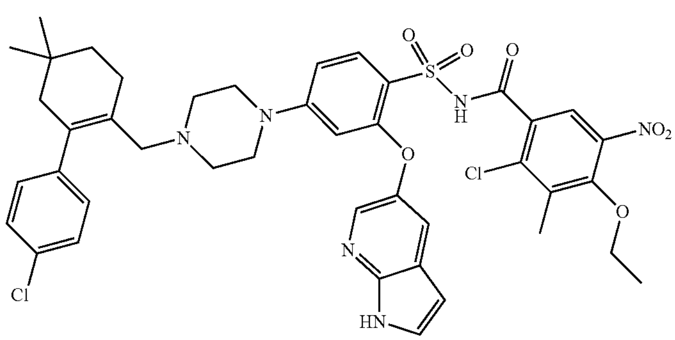 [SMILES: CCOc1c([N+](=O)[O-])cc(C(=O)NS(=O)(=O)c2ccc(N3CCN(CC4=C(c5ccc(Cl)cc5)CC(C)(C)CC4)CC3)cc2Oc2cnc3[nH]ccc3c2)c(Cl)c1C] | 2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-ethoxy-3-methyl-5-nitrobenzamide | 847.2/ 847.1 |

TABLE 4-continued

Preparation osf Examples ("Ex")

| Ex # | Structure | Name | [M + H]+ Calc./ Found |
|---|---|---|---|
| 103 | 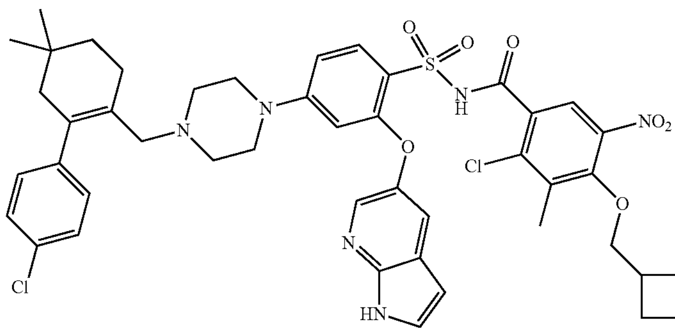 | 2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxetan-3-ylmethoxy)benzamide | 889.3/ 889.1 |
| 104 | 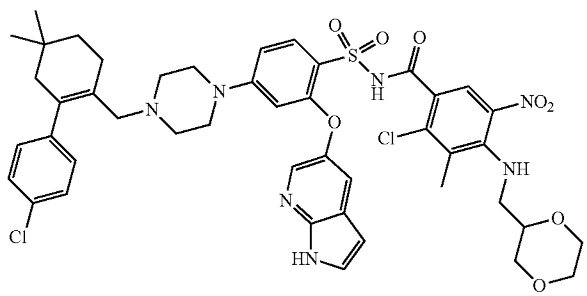 [SMILES: Cc1c(Cl)c(C(=O)NS(=O)(=O)c2ccc(N3CCN(CC4=C(c5ccc(Cl)cc5)CC(C)(C)CC4)CC3)cc2Oc2cnc3[nH]ccc3c2)cc([N+](=O)[O-])c1NCC1COCCO1] | 2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(1,4-dioxan-2-ylmethylamino)-3-methyl-5-nitrobenzamide | 918.3/ 918.1 |
| 105 | 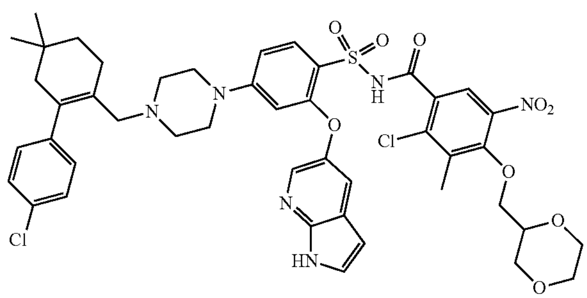 [SMILES: Cc1c(Cl)c(C(=O)NS(=O)(=O)c2ccc(N3CCN(CC4=C(c5ccc(Cl)cc5)CC(C)(C)CC4)CC3)cc2Oc2cnc3[nH]ccc3c2)cc([N+](=O)[O-])c1OCC1COCCO1] | 2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(1,4-dioxan-2-ylmethoxy)-3-methyl-5-nitrobenzamide | 919.3/ 919.1 |
| 106 | 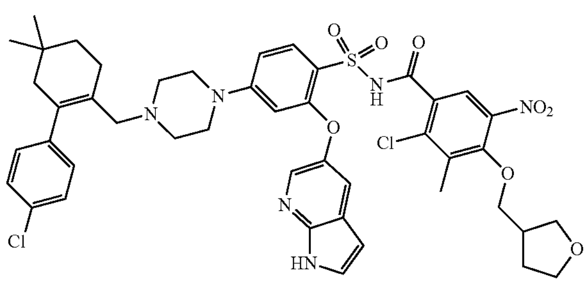 [SMILES: Cc1c(Cl)c(C(=O)NS(=O)(=O)c2ccc(N3CCN(CC4=C(c5ccc(Cl)cc5)CC(C)(C)CC4)CC3)cc2Oc2cnc3[nH]ccc3c2)cc([N+](=O)[O-])c1OCC1CCOC1] | 2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxolan-3-ylmethoxy)benzamide | 903.3/ 903.3 |
| 107 | 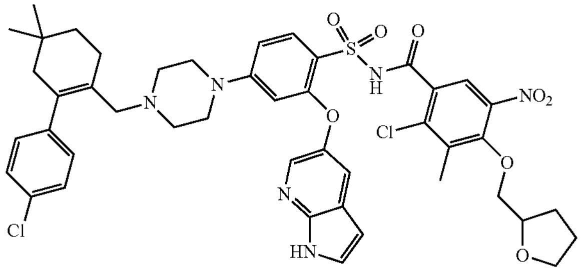 [SMILES: Cc1c(Cl)c(C(=O)NS(=O)(=O)c2ccc(N3CCN(CC4=C(c5ccc(Cl)cc5)CC(C)(C)CC4)CC3)cc2Oc2cnc3[nH]ccc3c2)cc([N+](=O)[O-])c1OCC1CCCO1] | 2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxolan-2-ylmethoxy)benzamide | 903.3/ 903.3 |

TABLE 5

| Ex# | $^1$HNMR (MHz, Solvent) δ |
|---|---|
| 2 | $^1$H NMR (300 MHz, CDCl$_3$) δ 8.55 (d, J = 8.2 Hz, 1H), 8.17 (d, J = 8.0 Hz, 1H), 7.99 (d, J = 8.3 Hz, 2H), 7.41 (d, J = 7.8 Hz, 2H), 7.11 (dd, J = 15.4, 8.4 Hz, 4H), 4.04-3.63 (m, 2H), 2.16 (s, 2H), 1.38-1.27 (m, 12H), 1.04 (d, J = 6.9 Hz, 6H). |
| 7 | $^1$H NMR (300 MHz, CDCl$_3$) δ 11.81 (s, 1H), 10.41 (s, 1H), 7.77-7.60 (m, 2H), 7.49-7.31 (m, 2H), 7.17 (dd, J = 20.2, 8.2 Hz, 2H), 7.03 (d, J = 8.8 Hz, 2H), 3.91 (d, J = 12.8 Hz, 2H), 3.57 (dd, J = 10.9, 9.7 Hz, 2H), 3.35 (s, 4H), 2.80 (d, J = 9.1 Hz, 2H), 2.36 (d, J = 1.1 Hz, 2H), 2.12-2.01 (m, 2H), 1.99-1.91 (m, 6H), 1.48 (s, 2H), 1.10-0.86 (m, 6H). |
| 17 | $^1$H NMR (300 MHz, CDCl$_3$) δ 7.97-7.89 (m, 2H), 7.43-7.37 (m, 2H), 7.16-7.11 (m, 2H), 7.09-7.03 (m, 2H), 3.75 (s, 2H), 3.32 (p, J = 1.6 Hz, 8H), 2.45-2.23 (m, 5H), 2.15 (s, 1H), 2.01 (s, 3H), 1.60 (t, J = 6.3 Hz, 2H), 1.38-1.27 (m, 1H), 1.05 (s, 6H). |
| 20 | $^1$H NMR (300 MHz, CD$_3$OD) δ 8.16 (d, J = 8.2 Hz, 1H), 7.97 (dd, J = 8.5, 4.9 Hz, 3H), 7.40 (d, J = 8.3 Hz, 2H), 7.13 (d, J = 8.3 Hz, 2H), 7.07 (d, J = 9.1 Hz, 2H), 5.50 (s, 1H), 3.74 (s, 2H), 3.32 (t, J = 1.6 Hz, 8H), 2.31 (d, J = 6.2 Hz, 2H), 2.16 (s, 2H), 1.61 (t, J = 6.2 Hz, 2H), 1.05 (s, 6H). |
| 21 | $^1$H NMR (300 MHz, CD$_3$OD) δ 8.29-8.20 (m, 2H), 8.07 (dd, J = 5.9, 3.0 Hz, 1H), 8.03-7.95 (m, 2H), 7.43-7.35 (m, 2H), 7.17-7.02 (m, 4H), 3.74 (s, 2H), 3.50-2.86 (m, 8H), 2.32 (s, 2H), 2.15 (s, 2H), 1.60 (t, J = 6.2 Hz, 2H), 1.04 (s, 6H) |
| 22 | $^1$H NMR (300 MHz, CD$_3$OD) δ 8.90 (d, J = 5.1 Hz, 1H), 8.72 (s, 1H), 7.92 (d, J = 8.9 Hz, 2H), 7.76 (d, J = 5.2 Hz, 1H), 7.41 (d, J = 8.3 Hz, 2H), 7.11 (dd, J = 13.9, 8.7 Hz, 4H), 3.75 (s, 2H), 3.65-3.04 (m, 8H), 2.33 (s, 2H), 2.15 (s, 2H), 1.60 (t, J = 6.2 Hz, 2H), 1.04 (s, 6H) |
| 23 | $^1$H NMR (300 MHz, CDCl$_3$) δ 9.55 (dd, J = 24.5, 11.4 Hz, 2H), 9.09 (d, J = 21.5 Hz, 1H), 7.73 (d, J = 8.6 Hz, 2H), 7.36 (d, J = 8.4 Hz, 2H), 6.97 (d, J = 8.3 Hz, 2H), 6.64 (d, J = 8.7 Hz, 2H), 3.61 (s, 2H), 3.09 (s, 3H), 2.37-2.18 (m, 3H), 2.06 (s, 3H), 1.43-1.20 (m, 5H), 1.01-0.65 (m, 6H) |
| 24 | $^1$H NMR (300 MHz, CDCl$_3$) δ 10.45 (s, 1H), 8.58 (d, J = 4.7 Hz, 1H), 8.14-8.00 (m, 3H), 7.88 (t, J = 7.7 Hz, 1H), 7.53 (dd, J = 7.6, 4.8 Hz, 1H), 7.38 (t, J = 10.1 Hz, 2H), 7.01 (dd, J = 20.5, 8.2 Hz, 2H), 6.87 (t, J = 9.8 Hz, 2H), 3.74-3.47 (m, 7H), 2.89 (s, 1H), 2.55 (s, 2H), 2.32 (s, 2H), 2.10 (s, 2H), 1.52 (t, J = 6.0 Hz, 2H), 1.09-0.90 (m, 6H). |
| 25 | $^1$H NMR (300 MHz, CDCl$_3$) δ 9.17 (s, 1H), 8.04 (d, J = 9.0 Hz, 2H), 7.77 (dd, J = 8.8, 5.1 Hz, 2H), 7.37 (d, J = 8.4 Hz, 2H), 7.20 (t, J = 8.6 Hz, 2H), 6.98 (d, J = 8.4 Hz, 2H), 6.90 (d, J = 9.0 Hz, 2H), 6.84 (s, 1H), 3.70 (d, J = 19.3 Hz, 5H), 2.89 (s, 2H), 2.55 (s, 2H), 2.32 (s, 2H), 2.10 (s, 2H), 1.53 (t, J = 6.1 Hz, 2H), 1.30 (d, J = 16.8 Hz, 1H), 1.08-0.92 (m, 6H) |
| 26 | $^1$H NMR (300 MHz, CD$_3$OD) δ 8.56 (s, 1H), 8.28 (d, J = 8.3 Hz, 1H), 7.84 (t, J = 8.8 Hz, 3H), 7.42 (dd, J = 8.4, 1.9 Hz, 2H), 7.15 (dd, J = 8.4, 1.9 Hz, 2H), 7.04 (d, J = 9.0 Hz, 2H), 3.84 (s, 2H), 3.75 (s, 2H), 3.57-2.93 (m, 8H), 2.76 (s, 3H), 2.34 (s, 2H), 2.16 (s, 2H), 1.61 (t, J = 5.9 Hz, 2H), 1.05 (s, 6H). |
| 27 | $^1$H NMR (300 MHz, CD$_3$OD) δ 8.35 (d, J = 8.3 Hz, 1H), 8.01 (ddd, J = 9.7, 6.4, 1.5 Hz, 4H), 7.47 (d, J = 6.0 Hz, 1H), 7.38 (d, J = 8.1 Hz, 2H), 7.09 (dd, J = 11.9, 8.6 Hz, 4H), 3.72 (s, 2H), 3.30 (d, J = 1.6 Hz, 8H), 2.29 (d, J = 6.6 Hz, 2H), 2.14 (s, 2H), 1.60 (t, J = 6.4 Hz, 2H), 1.03 (s, 6H) |
| 29 | $^1$H NMR (300 MHz, CD$_3$OD) δ 8.19-8.14 (m, 2H), 7.83 (d, J = 8.9 Hz, 2H), 7.45-7.39 (m, 4H), 7.18-7.12 (m, 2H), 7.06 (d, J = 9.1 Hz, 2H), 3.77 (s, 2H), 3.43-3.36 (m, 2H), 2.33 (s, 3H), 2.19 (d, J = 8.3 Hz, 3H), 1.63 (t, J = 6.2 Hz, 4H), 1.50 (q, J = 4.6 Hz, 3H), 1.28-1.23 (m, 3H), 1.06 (s, 6H) |
| 30 | $^1$H NMR (300 MHz, CDCl$_3$) δ 7.85 (d, J = 8.9 Hz, 2H), 7.46-7.39 (m, 2H), 7.28 (q, J = 6.0, 5.5 Hz, 1H), 7.18-6.99 (m, 7H), 3.74 (s, 2H), 3.58 (d, J = 1.3 Hz, 2H), 3.08 (s, 4H), 2.17 (s, 2H), 1.62 (t, J = 6.2 Hz, 3H), 1.32 (d, J = 12.5 Hz, 5H), 1.06 (s, 6H) |
| 31 | $^1$H NMR (300 MHz, CDCl$_3$) δ 8.44 (s, 1H), 7.74 (d, J = 8.5 Hz, 2H), 7.60 (d, J = 4.8 Hz, 2H), 7.41-7.34 (m, 3H), 7.21 (s, 1H), 7.01 (d, J = 8.1 Hz, 2H), 6.81 (d, J = 8.5 Hz, 2H), 3.68 (s, 2H), 3.13 (s, 2H), 2.85 (s, 2H), 2.35-2.25 (m, 4H), 2.13 (s, 2H), 2.02 (s, 2H), 1.66 (s, 2H), 1.55 (d, J = 5.8 Hz, 2H), 1.33 (s, 2H), 1.02 (s, 6H) |
| 32 | $^1$H NMR (300 MHz, CD$_3$OD) δ 8.62 (s, 1H), 8.45 (d, J = 8.2 Hz, 1H), 8.17 (d, J = 7.8 Hz, 1H), 7.96 (d, J = 9.0 Hz, 2H), 7.74 (t, J = 8.0 Hz, 1H), 7.41 (t, J = 10.1 Hz, 2H), 7.10 (dd, J = 18.5, 8.7 Hz, 4H), 4.09-3.45 (m, 6H), 3.09 (s, 4H), 2.33 (s, 2H), 2.16 (s, 2H), 1.61 (t, J = 6.2 Hz, 2H), 1.02 (d, J = 18.8 Hz, 6H) |
| 33 | $^1$H NMR (300 MHz, CDCl$_3$) δ 10.01 (s, 1H), 8.10 (dd, J = 8.4, 3.6 Hz, 1H), 8.01 (t, J = 10.0 Hz, 2H), 7.57 (dd, J = 8.3, 7.0 Hz, 1H), 7.36 (d, J = 8.4 Hz, 2H), 6.96 (t, J = 9.7 Hz, 2H), 6.90 (t, J = 8.1 Hz, 2H), 3.60 (d, J = 18.9 Hz, 5H), 2.34 (s, 3H), 2.09 (s, 2H), 2.02 (s, 2H), 1.54 (dd, J = 16.0, 9.9 Hz, 3H), 1.30 (d, J = 17.7 Hz, 1H), 1.00 (s, 6H) |
| 35 | $^1$H NMR (300 MHz, CDCl$_3$) δ 8.09-7.86 (m, 3H), 7.77 (d, J = 7.8 Hz, 1H), 7.67 (d, J = 7.7 Hz, 1H), 7.52-7.37 (m, 1H), 7.42-7.25 (m, 3H), 7.12 (d, J = 8.8, 2.5 Hz, 2H), 6.98 (dd, J = 8.5, 2.3 Hz, 2H), 6.83 (td, J = 6.1, 2.9 Hz, 3H), 5.21-5.00 (m, 2H), 3.67 (s, 2H), 3.45 (s, 3H), 2.57 (s, 2H), 2.31 (s, 2H), 2.09 (s, 2H), 2.03 (s, 1H), 1.52 (d, J = 6.2 Hz, 2H), 1.35-1.23 (m, 2H), 0.99 (d, J = 2.2 Hz, 6H) |
| 37 | $^1$H NMR (300 MHz, CDCl$_3$) δ 8.03 (dd, J = 6.6, 2.0 Hz, 1H), 7.96 (d, J = 8.5 Hz, 2H), 7.88-7.80 (m, 1H), 7.36 (d, J = 8.1 Hz, 2H), 7.23 (d, J = 8.5 Hz, 2H), 7.14 (t, J = 8.9 Hz, 1H), 6.98 (d, J = 8.2 Hz, 2H), 6.85 (dd, J = 16.7, 8.6 Hz, 4H), 5.06 (s, 2H), 3.93-3.20 (m, 10H), 2.54 (s, 2H), 2.32 (s, 2H), 2.10 (s, 2H), 1.52 (t, J = 6.0 Hz, 2H), 1.03-0.93 (m, 6H) |
| 38 | $^1$H NMR (300 MHz, CD$_3$OD) δ 8.25-8.17 (m, 2H), 8.00-7.91 (m, 3H), 7.40 (d, J = 8.2 Hz, 2H), 7.29 (t, J = 6.0 Hz, 2H), 7.15-7.00 (m, 6H), 5.45 (s, 2H), 3.75 (s, 2H), 2.99 (d, J = 56.1 Hz, 8H), 2.32 (s, 2H), 2.17 (s, 2H), 1.62 (t, J = 6.3 Hz, 2H), 1.03 (d, J = 11.8 Hz, 6H) |
| 39 | $^1$H NMR (300 MHz, CDCl$_3$) δ 8.54 (d, J = 1.8 Hz, 1H), 8.12 (dd, J = 8.2, 1.9 Hz, 1H), 7.95 (q, J = 3.6, 2.5 Hz, 2H), 7.56-7.34 (m, 4H), 7.34-7.21 (m, 2H), 7.18-6.93 (m, 6H), |

TABLE 5-continued

<sup>1</sup>H NMR data of Examples ("Ex")

| Ex# | <sup>1</sup>HNMR (MHz, Solvent) δ |
|---|---|
|  | 5.51 (s, 2H), 3.74 (s, 2H), 3.10 (d, J = 80.0 Hz, 3H), 2.31 (s, 2H), 2.15 (s, 3H), 1.60 (t, J = 6.2 Hz, 2H), 1.30 (d, J = 11.9 Hz, 3H), 1.04 (d, J = 2.1 Hz, 6H) |
| 41 | <sup>1</sup>H NMR (300 MHz, CDCl$_3$) δ 8.14 (d, J = 2.8 Hz, 1H), 7.84 (dd, J = 9.1, 2.9 Hz, 2H), 7.31 (dt, J = 8.6, 2.0 Hz, 2H), 7.07-6.97 (m, 5H), 3.94-3.81 (m, 3H), 3.67 (s, 3H), 3.40-3.24 (m, 6H), 2.23 (d, J = 6.7 Hz, 2H), 2.07 (s, 3H), 1.87 (qd, J = 7.5, 6.9, 3.8 Hz, 2H), 1.70-1.47 (m, 5H), 1.30 (dtd, J = 20.5, 12.5, 6.5 Hz, 5H), 0.96 (d, J = 3.0 Hz, 6H) |
| 42 | <sup>1</sup>H NMR (300 MHz, CDCl$_3$) δ 7.98-7.82 (m, 3H), 7.46-7.34 (m, 2H), 7.19-7.01 (m, 4H), 4.04-3.85 (m, 3H), 3.76 (s, 2H), 3.40 (d, J = 2.1 Hz, 1H), 3.36 (d, J = 2.1 Hz, 1H), 3.32 (h, J = 1.8 Hz, 6H), 3.15 (dd, J = 6.8, 2.0 Hz, 3H), 2.42 (d, J = 2.0 Hz, 3H), 2.34 (d, J = 6.8 Hz, 2H), 2.16 (s, 2H), 1.78 (dtq, J = 14.6, 6.8, 3.4 Hz, 1H), 1.66-1.51 (m, 4H), 1.28 (td, J = 13.6, 12.6, 6.0 Hz, 4H), 1.05 (d, J = 2.0 Hz, 6H) |
| 43 | <sup>1</sup>H NMR (300 MHz, CDCl$_3$) δ 7.95-7.89 (m, 2H), 7.86 (s, 1H), 7.44-7.38 (m, 2H), 7.17-7.05 (m, 4H), 3.76 (s, 3H), 3.32-3.22 (m, 10H), 2.44-2.28 (m, 5H), 2.16 (s, 2H), 1.62 (t, J = 6.3 Hz, 2H), 1.32 (d, J = 12.1 Hz, 1H), 1.21 (t, J = 7.1 Hz, 3H), 1.06 (s, 6H) |
| 46 | <sup>1</sup>H NMR (300 MHz, CDCl$_3$) δ 9.88 (s, 1H), 8.22-8.05 (m, 2H), 7.87 (dd, J = 25.2, 7.5 Hz, 3H), 7.57 (s, 1H), 7.30 (dd, J = 11.5, 4.4 Hz, 3H), 6.99 (d, J = 7.9 Hz, 2H), 6.80 (d, J = 7.2 Hz, 2H), 3.84-3.36 (m, 8H), 2.67 (d, J = 30.8 Hz, 2H), 2.32 (s, 2H), 2.08 (s, 3H), 1.51 (s, 2H), 1.07-0.92 (m, 6H) |
| 47 | <sup>1</sup>H NMR (300 MHz, CDCl$_3$) δ 10.13 (s, NH), 8.70 (s, 1H), 8.17 (dd, J = 10.5, 5.4 Hz, 2H), 8.06 (d, J = 8.9 Hz, 2H), 7.75-7.66 (m, 1H), 7.41-7.33 (m, 2H), 6.99 (dd, J = 8.4, 2.1 Hz, 2H), 6.90 (d, J = 9.0 Hz, 2H), 3.76 (s, 2H), 3.67 (s, 2H), 3.61-3.37 (m, 8H), 2.32 (s, 2H), 2.11 (s, 2H), 1.53 (s, 2H), 0.96 (d, J = 23.2 Hz, 6H) |
| 50 | <sup>1</sup>H NMR (300 MHz, CDCl$_3$) δ 10.30 (s, 1H), 8.35 (s, 1H), 8.16 (s, 1H), 8.11-7.98 (m, 4H), 7.70-7.54 (m, 2H), 7.41-7.31 (m, 2H), 7.04-6.93 (m, 2H), 6.87 (d, J = 8.9 Hz, 2H), 4.15 (t, J = 10.8 Hz, 3H), 3.82-3.33 (m, 8H), 2.59 (s, 2H), 2.29 (s, 2H), 2.09 (s, 2H), 1.51 (s, 2H), 1.03-0.88 (m, 6H) |
| 51 | <sup>1</sup>H NMR (300 MHz, CDCl$_3$) δ 8.45 (dd, J = 8.1, 1.6 Hz, 1H), 8.03-7.92 (m, 2H), 7.73 (dd, J = 8.1, 1.6 Hz, 1H), 7.54 (dd, J = 8.3, 1.5 Hz, 1H), 7.48-7.29 (m, 5H), 7.19-7.03 (m, 4H), 5.73 (s, 2H), 3.75 (s, 2H), 2.98 (s, 1H), 2.32 (s, 2H), 2.16 (s, 3H), 1.62 (t, J = 6.3 Hz, 3H), 1.32 (d, J = 11.9 Hz, 4H), 1.05 (d, J = 1.7 Hz, 7H) |
| 52 | <sup>1</sup>H NMR (300 MHz, CDCl$_3$.55 (d, J = 1.8 Hz, 1H), 8.13 (dd, J = 8.2, 1.9 Hz, 1H), 8.05-7.92 (m, 3H), 7.46-7.35 (m, 2H), 7.37-7.24 (m, 2H), 7.19-6.83 (m, 7H), 5.53 (s, 2H), 3.75 (s, 2H), 2.33 (s, 2H), 2.16 (s, 2H), 1.62 (d, J = 12.7 Hz, 1H), 1.38-1.26 (m, 4H), 1.05 (s, 11H) |
| 53 | <sup>1</sup>H NMR (300 MHz, CDCl$_3$) δ 8.00-7.87 (m, 2H), 7.61 (dd, J = 7.9, 2.2 Hz, 1H), 7.48-7.32 (m, 8H), 7.25-7.17 (m, 1H), 7.10 (ddd, J = 19.5, 9.0, 2.3 Hz, 4H), 5.18 (s, 2H), 3.75 (s, 2H), 3.31 (d, J = 1.6 Hz, 8H), 2.33 (d, J = 7.4 Hz, 2H), 2.16 (s, 2H), 1.60 (d, J = 6.3 Hz, 2H), 1.32 (d, J = 11.8 Hz, 1H), 1.05 (s, 6H) |
| 54 | <sup>1</sup>H NMR (300 MHz, CDCl$_3$) δ 7.99-7.87 (m, 2H), 7.77 (d, J = 2.2 Hz, 1H), 7.47-7.36 (m, 2H), 7.20-7.03 (m, 4H), 3.76 (s, 2H), 3.32 (h, J = 2.0 Hz, 8H), 2.89 (d, J = 2.0 Hz, 3H), 2.38 (d, J = 2.2 Hz, 3H), 2.34 (d, J = 8.3 Hz, 4H), 2.17 (s, 2H), 1.62 (t, J = 6.4 Hz, 2H), 1.32 (d, J = 12.4 Hz, 1H), 1.06 (s, 6H) |
| 55 | <sup>1</sup>H NMR (300 MHz, CDCl$_3$) δ 8.23 (d, J = 5.5 Hz, 1H), 8.09-7.71 (m, 4H), 7.56 (d, J = 5.5 Hz, 1H), 7.43 (s, 1H), 7.31 (s, 2H), 7.09-6.94 (m, 4H), 3.93 (s, 2H), 3.66 (s, 3H), 3.32-3.26 (m, 1H), 3.17 (s, 4H), 2.24 (s, 2H), 2.08 (s, 2H), 1.53 (t, J = 6.3 Hz, 2H), 1.24 (d, J = 11.6 Hz, 4H), 0.97 (s, 6H) |
| 56 | <sup>1</sup>H NMR (300 MHz, DMSO-d$_6$) δ 12.26 (s, 1H), 9.39 (s, 1H), 8.11-8.00 (m, 2H), 7.90-7.80 (m, 2H), 7.46-7.37 (m, 2H), 7.31 (s, 1H), 7.22-7.02 (m, 4H), 7.02-6.93 (m, 1H), 3.97 (s, 2H), 3.64 (s, 2H), 3.51 (d, J = 1.3 Hz, 3H), 3.40-3.15 (m, 4H), 2.85 (s, 2H), 2.26 (d, J = 6.9 Hz, 2H), 2.06 (s, 2H), 1.48 (d, J = 6.8 Hz, 2H), 0.98 (s, 6H) |
| 57 | <sup>1</sup>H NMR (300 MHz, CD$_3$OD) δ 9.32 (d, J = 1.2 Hz, 2H), 8.15-7.82 (m, 4H), 7.50-7.29 (m, 2H), 7.19-7.04 (m, 4H), 5.35 (t, J = 4.9 Hz, 0H), 4.13 (s, 3H), 3.75 (s, 2H), 2.32 (s, 2H), 2.16 (s, 2H), 1.62 (t, J = 6.3 Hz, 3H), 1.34 (s, 6H), 1.05 (s, 6H), 1.02-0.86 (m, 1H) |
| 58 | <sup>1</sup>H NMR (300 MHz, DMSO-d$_6$) δ 12.12 (s, 1H), 9.51 (s, 1H), 8.60 (d, J = 2.6 Hz, 1H), 8.39 (dd, J = 9.0, 2.4 Hz, 1H), 8.00-7.79 (m, 4H), 7.41 (d, J = 8.3 Hz, 2H), 7.15-7.04 (m, 3H), 6.59 (d, J = 9.6 Hz, 1H), 3.96 (s, 2H), 3.65 (s, 2H), 3.59 (s, 3H), 3.28 (d, J = 39.0 Hz, 4H), 2.85 (s, 2H), 2.25 (s, 2H), 2.05 (s, 2H), 1.49 (t, J = 6.2 Hz, 2H), 0.97 (s, 6H) |
| 59 | <sup>1</sup>H NMR (300 MHz, CD$_3$OD) δ 8.47 (s, 2H), 8.01 (d, J = 8.9 Hz, 2H), 7.91 (dd, J = 8.5, 3.7 Hz, 1H), 7.76 (d, J = 10.5, 8.5 Hz, 1H), 7.44-7.33 (m, 2H), 7.17-7.00 (m, 4H), 3.74 (s, 2H), 3.56-2.84 (m, 8H), 2.32 (s, 2H), 2.16 (s, 2H), 1.61 (s, 2H), 1.05 (s, 6H) |
| 60 | <sup>1</sup>H NMR (300 MHz, CD$_3$OD) δ 8.30 (d, J = 1.6 Hz, 1H), 8.20-7.88 (m, 5H), 7.94-7.79 (m, 2H), 7.40 (dd, J = 8.4, 1.6 Hz, 2H), 7.11 (ddd, J = 13.3, 8.6, 1.6 Hz, 4H), 4.19 (d, J = 1.6 Hz, 3H), 3.75 (s, 2H), 2.95 (s, 6H), 2.32 (s, 2H), 2.16 (s, 2H), 1.62 (t, J = 6.2 Hz, 2H), 1.32 (d, J = 12.0 Hz, 2H), 1.06 (s, 1H), 1.05 (s, 5H) |
| 69 | <sup>1</sup>H NMR (300 MHz, CDCl$_3$) δ 12.46 (s, 1H), 8.12 (d, J = 9.0 Hz, 1H), 7.54 (dd, J = 3.5, 2.0 Hz, 1H), 7.44 (t, J = 8.4 Hz, 1H), 7.37-7.30 (m, 2H), 6.98-6.90 (m, 2H), 6.73 (dd, J = 9.1, 2.3 Hz, 1H), 6.58 (dd, J = 3.6, 1.7 Hz, 1H), 6.23 (d, J = 2.3 Hz, 1H), 3.56 (d, J = 28.5 Hz, 10H), 2.60 (s, 2H), 2.39 (d, J = 2.8 Hz, 3H), 2.27 (s, 2H), 2.07 (s, 2H), 1.49 (t, J = 6.2 Hz, 2H), 1.30 (d, J = 17.3 Hz, 1H), 0.96 (s, 6H) |
| 70 | <sup>1</sup>H NMR (300 MHz, CD$_3$OD) δ 8.35 (d, J = 8.4 Hz, 1H), 8.02 (d, J = 9.1 Hz, 1H), 7.96-7.88 (m, 2H), 7.42-7.35 (m, 2H), 7.32 (d, J = 3.5 Hz, 1H), 7.27 (d, J = 2.6 Hz, 1H), 7.08 (d, J = 8.3 Hz, 2H), 6.89 (dd, J = 9.1, 2.3 Hz, 1H), 6.50 (d, J = 2.3 Hz, 1H), 6.21 (d, J = 3.5 Hz, 1H), 3.69 (s, 2H), 3.31 (d, J = 1.7 Hz, 8H), 2.54 (s, 3H), 2.26 (d, J = 6.4 Hz, 2H), 2.12 (s, 2H), 1.57 (t, J = 6.2 Hz, 2H), 1.01 (s, 6H) |
| 71 | <sup>1</sup>H NMR (300 MHz, CDCl$_3$) δ 12.25 (s, NH), 8.22 (d, J = 8.3 Hz, 1H), 8.14-8.04 (m, 2H), 7.90 (d, J = 11.7 Hz, 2H), 7.54 (d, J = 3.1 Hz, 1H), 7.33 (d, J = 8.2 Hz, 2H), 6.94 (d, J = |

TABLE 5-continued

¹H NMR data of Examples ("Ex")

| Ex# | ¹HNMR (MHz, Solvent) δ |
|---|---|
| | 8.3 Hz, 2H), 6.72 (d, J = 9.1 Hz, 1H), 6.60 (s, 1H), 6.22 (d, J = 2.0 Hz, 1H), 3.60 (s, 2H), 3.38 (d, J = 88.2 Hz, 8H), 2.29 (d, J = 5.3 Hz, 2H), 2.07 (s, 2H), 1.49 (t, J = 6.1 Hz, 2H), 1.01-0.91 (m, 6H) |
| 72 | ¹H NMR (300 MHz, CDCl₃) δ 8.41 (dd, J = 8.2, 1.9 Hz, 1H), 8.02 (ddd, J = 9.4, 7.1, 2.0 Hz, 3H), 7.38 (ddd, J = 6.7, 3.7, 2.0 Hz, 4H), 7.09 (dt, J = 9.0, 2.3 Hz, 2H), 6.88 (dt, J = 9.1, 2.2 Hz, 1H), 6.50 (d, J = 2.2 Hz, 1H), 6.28 (dd, J = 3.5, 1.9 Hz, 1H), 3.69 (s, 2H), 2.24 (dt, J = 25.1, 7.1 Hz, 3H), 2.12 (s, 2H), 2.04 (d, J = 6.3 Hz, 1H), 1.58 (d, J = 6.6 Hz, 2H), 1.32 (dd, J = 9.7, 4.6 Hz, 6H), 1.02 (d, J = 1.9 Hz, 6H) |
| 74 | ¹H NMR (300 MHz, CDCl₃) δ 12.58 (s, 1H), 8.09-7.73 (m, 4H), 7.50 (s, 1H), 7.47-7.31 (m, 4H), 6.95 (s, 2H), 6.66 (d, J = 8.3 Hz, 1H), 6.55 (s, 1H), 6.22 (s, 1H), 4.20 (d, J = 5.4 Hz, 2H), 2.68 (s, 2H), 2.53 (s, 2H), 2.28 (d, J = 8.0 Hz, 3H), 2.07 (s, 2H), 1.98 (s, 4H), 1.64 (d, J = 7.9 Hz, 1H), 1.36-1.23 (m, 6H), 0.96 (s, 6H) |
| 76 | ¹H NMR (300 MHz, CDCl₃) δ 12.76 (s, 1H), 8.11-7.98 (m, 2H), 7.92 (d, J = 2.1 Hz, 1H), 7.55 (dt, J = 3.6, 1.7 Hz, 1H), 7.39-7.28 (m, 2H), 7.10 (t, J = 1.3 Hz, 1H), 6.95 (dd, J = 8.4, 1.8 Hz, 2H), 6.71 (dt, J = 9.1, 2.0 Hz, 1H), 6.62 (dd, J = 3.5, 1.7 Hz, 1H), 6.25 (d, J = 2.1 Hz, 1H), 3.70 (d, J = 1.7 Hz, 3H), 3.61 (s, 2H), 3.51 (s, 7H), 2.26 (s, 2H), 2.15 (d, J = 1.6 Hz, 3H), 1.54-1.43 (m, 2H), 1.35-1.23 (m, 3H), 0.97 (s, 1H), 0.96 (s, 5H) |
| 77 | ¹H NMR (300 MHz, CDCl₃) δ 12.77 (s, 1H), 9.32 (s, 1H), 8.13-7.97 (m, 2H), 7.85 (s, 1H), 7.56 (s, 1H), 7.34 (d, J = 7.2 Hz, 2H), 6.95 (d, J = 7.7 Hz, 2H), 6.75-6.60 (m, 2H), 6.45 (s, 1H), 6.19 (s, 1H), 3.65 (s, 3H), 3.58 (s, 9H), 2.26 (s, 3H), 2.07 (s, 2H), 1.36-1.23 (m, 5H), 0.97 (s, 6H) |
| 78 | ¹H NMR (300 MHz, CDCl₃) δ 12.29 (s, 1H), 8.13 (d, J = 9.0 Hz, 1H), 7.94 (s, 2H), 7.56 (s, 1H), 7.34 (d, J = 8.2 Hz, 2H), 6.94 (d, J = 8.3 Hz, 2H), 6.74 (d, J = 9.7 Hz, 1H), 6.62 (s, 1H), 6.19 (s, 1H), 3.97 (s, 3H), 3.56 (d, J = 31.6 Hz, 8H), 2.27 (s, 2H), 2.21 (s, 3H), 2.18 (s, 3H), 2.07 (s, 2H), 1.50 (d, J = 12.4 Hz, 2H), 1.28 (s, 2H), 0.97 (s, 6H) |
| 79 | ¹H NMR (300 MHz, CDCl₃) δ 11.95 (s, 1H), 8.43 (s, 1H), 8.12 (s, 1H), 8.06-7.93 (m, 2H), 7.75 (s, 1H), 7.64 (s, 1H), 7.46 (s, 1H), 7.31 (d, J = 7.6 Hz, 2H), 6.95 (d, J = 7.9 Hz, 2H), 6.68 (d, J = 9.0 Hz, 1H), 6.43 (s, 1H), 6.18 (s, 1H), 3.63 (s, 3H), 2.47 (s, 3H), 2.26 (d, J = 6.5 Hz, 3H), 2.04 (d, J = 15.7 Hz, 3H), 1.47 (s, 2H), 1.35-1.23 (m, 5H), 0.99-0.84 (m, 6H). |
| 80 | ¹H NMR (300 MHz, CDCl₃) δ 8.11 (d, J = 2.6 Hz, 1H), 8.03 (s, 1H), 7.95 (d, J = 9.1 Hz, 1H), 7.77 (d, J = 2.5 Hz, 1H), 7.49 (d, J = 3.5 Hz, 1H), 7.42-7.34 (m, 2H), 7.11-7.02 (m, 2H), 6.80 (dd, J = 9.1, 2.3 Hz, 1H), 6.50 (dd, J = 3.7, 1.4 Hz, 1H), 6.33 (d, J = 2.2 Hz, 1H), 3.91 (dd, J = 11.5, 4.3 Hz, 2H), 3.68 (s, 3H), 3.38 (d, J = 11.7, 2.0 Hz, 3H), 3.17 (d, J = 6.7 Hz, 4H), 2.46 (s, 3H), 2.29-2.15 (m, 3H), 2.08 (d, J = 21.9 Hz, 3H), 1.57 (s, 4H), 1.38-1.23 (m, 6H), 1.01 (d, J = 1.5 Hz, 6H) |
| 81 | ¹H NMR (300 MHz, CDCl₃) δ 12.76 (s, 1H), 8.11-7.98 (m, 2H), 7.92 (d, J = 2.1 Hz, 1H), 7.55 (dt, J = 3.6, 1.7 Hz, 1H), 7.39-7.28 (m, 2H), 7.10 (t, J = 1.3 Hz, 1H), 6.95 (dd, J = 8.4, 1.8 Hz, 2H), 6.71 (dt, J = 9.1, 2.0 Hz, 1H), 6.62 (dd, J = 3.5, 1.7 Hz, 1H), 6.25 (d, J = 2.1 Hz, 1H), 3.70 (d, J = 1.7 Hz, 3H), 3.61 (s, 2H), 3.51 (s, 7H), 2.26 (s, 2H), 2.15 (d, J = 1.6 Hz, 3H), 1.54-1.43 (m, 2H), 1.35-1.23 (m, 3H), 0.97 (s, 1H), 0.96 (s, 5H) |
| 83 | ¹H NMR (300 MHz, CDCl₃) δ 12.19 (s, 1H), 8.03 (d, J = 8.6 Hz, 1H), 7.83 (s, 1H), 7.74 (s, 1H), 7.52 (td, J = 20.4, 17.5, 11.1 Hz, 4H), 7.34-7.19 (m, 5H), 6.99-6.84 (m, 3H), 6.69 (s, 1H), 6.48 (s, 1H), 6.22 (s, 1H), 5.09 (s, 2H), 3.60 (s, 2H), 2.27 (d, J = 8.4 Hz, 3H), 2.05 (d, J = 11.7 Hz, 3H), 1.63 (s, 1H), 1.48 (s, 2H), 1.35-1.16 (m, 5H), 0.96 (s, 6H) |
| 84 | ¹H NMR (300 MHz, CDCl₃) δ 12.31 (s, NH), 8.05 (d, J = 8.5 Hz, 1H), 7.86 (d, J = 6.6 Hz, 3H), 7.76 (s, 1H), 7.48 (s, 1H), 7.34 (d, J = 7.7 Hz, 2H), 7.04 (t, J = 8.9 Hz, 1H), 6.95 (d, J = 7.7 Hz, 2H), 6.70 (d, J = 8.3 Hz, 1H), 6.51 (s, 1H), 6.20 (s, 1H), 4.66-4.45 (m, 2H), 3.81-3.18 (m, 10H), 3.36 (dd, J = 7.4, 4.1 Hz, 1H), 2.36 (s, 2H), 2.07 (s, 2H), 1.50 (s, 2H), 1.04-0.89 (m, 6H), 0.57 (dt, J = 10.4, 5.3 Hz, 2H), 0.53-0.41 (m, 2H) |
| 85 | ¹H NMR (300 MHz, CDCl₃) δ 11.42 (s, NH), 8.64 (s, 1H), 8.28 (s, 1H), 8.17 (s, 1H), 8.05 (d, J = 9.1 Hz, 1H), 7.46 (d, J = 12.8 Hz, 3H), 7.31 (d, J = 8.3 Hz, 2H), 6.94 (d, J = 8.3 Hz, 2H), 6.64 (d, J = 9.2 Hz, 1H), 6.37 (s, 1H), 6.06 (s, 1H), 4.55 (s, 3H), 3.54 (m, 10H), 2.30-2.22 (m, 2H), 2.06 (s, 2H), 1.47 (dd, J = 10.7, 4.4 Hz, 2H), 1.02-0.89 (m, 6H) |
| 86 | ¹H NMR (300 MHz, CDCl₃) δ 8.60 (s, 1H), 8.35 (d, J = 8.5 Hz, 1H), 8.23 (d, J = 6.5 Hz, 1H), 7.98 (d, J = 9.0 Hz, 1H), 7.65 (d, J = 9.4 Hz, 1H), 7.57 (s, 1H), 7.39 (d, J = 13.9 Hz, 1H), 7.30 (d, J = 8.3 Hz, 2H), 7.23 (d, J = 8.9 Hz, 2H), 6.99-6.91 (m, 2H), 6.88 (t, J = 8.2 Hz, 2H), 6.64 (d, J = 8.7 Hz, 1H), 6.37 (d, J = 12.3 Hz, 1H), 6.13 (d, J = 9.4 Hz, 1H), 5.09 (s, 2H), 3.59 (m, 10H), 2.24 (s, 2H), 2.06 (s, 2H), 1.44 (d, J = 15.1 Hz, 2H), 0.95 (s, 6H) |
| 87 | ¹H NMR (300 MHz, CDCl₃) δ 11.86 (s, NH), 8.52 (s, 1H), 8.08 (d, J = 8.0 Hz, 1H), 8.00 (d, J = 9.0 Hz, 1H), 7.86 (d, J = 8.2 Hz, 1H), 7.68 (d, J = 7.6 Hz, 2H), 7.44 (s, 1H), 7.30 (t, J = 5.8 Hz, 2H), 6.94 (d, J = 8.2 Hz, 2H), 6.66 (d, J = 8.9 Hz, 1H), 6.43 (s, 1H), 6.19 (s, 1H), 4.85 (d, J = 32.0 Hz, 2H), 3.77-3.26 (m, 10H), 3.49 (s, 3H), 2.25 (s, 2H), 2.06 (s, 2H), 1.47 (s, 2H), 1.06-0.79 (m, 6H) |
| 89 | 1H NMR (300 MHz, CDCl₃) δ 11.86 (s, 1H), 8.00-7.92 (m, 2H), 7.75 (s, 1H), 7.60 (s, 1H), 7.47 (s, 1H), 7.41 (s, 4H), 7.36-7.31 (m, 2H), 6.95 (d, J = 8.2 Hz, 2H), 6.60 (d, J = 9.0 Hz, 1H), 6.45 (s, 1H), 6.13 (s, 1H), 4.95 (s, 2H), 3.54 (d, J = 41.3 Hz, 8H), 2.41 (s, 3H), 2.25 (s, 2H), 2.07 (s, 2H), 1.30 (d, J = 14.3 Hz, 4H), 0.96 (s, 6H) |
| 89 | ¹H NMR (300 MHz, CDCl₃) δ 12.11 (s, 1H), 8.48 (s, 1H), 8.10 (d, J = 7.6 Hz, 1H), 8.02-7.71 (m, 4H), 7.37 (dt, J = 25.5 Hz, 3H), 6.93 (t, J = 8.7 Hz, 4H), 6.64 (s, 1H), 6.47 (s, 1H), 6.21 (s, 1H), 5.40 (s, 2H), 3.60 (s, 8H), 3.12 (s, 3H), 2.15 (d, J = 55.5 Hz, 6H), 1.47 (s, 2H), 1.29 (d, J = 11.9 Hz, 2H), 0.95 (s, 6H) |
| 92 | ¹H NMR (300 MHz, MeOH-d4) δ 8.55 (d, J = 4.9 Hz, 1H), 8.05 (d, J = 9.0 Hz, 1H), 7.99 (s, 1H), 7.90 (d, J = 6.0 Hz, 1H), 7.68 (d, J = 6.0 Hz, 1H), 7.58 (d, J = 2.3 Hz, 1H), 7.51 (d, J = 4.9 Hz, 1H), 7.43 (d, J = 3.5 Hz, 1H), 7.38 (d, J = 8.2 Hz, 2H), 7.08 (d, J = 8.2 Hz, 2H), |

TABLE 5-continued

¹H NMR data of Examples ("Ex")

| Ex# | ¹HNMR (MHz, Solvent) δ |
|---|---|
|  | 6.87 (dd, J = 9.3, 2.3 Hz, 1H), 6.39-6.29 (m, 2H), 3.68 (s, 2H), 3.25 (t, J = 1.7 Hz, 8H), 2.29 (s, 2H), 2.12 (s, 2H), 1.57 (t, J = 6.3 Hz, 2H), 1.01 (s, 6H). |
| 93 | ¹H NMR (300 MHz, MeOH-d4) δ 8.30 (d, J = 8.2 Hz, 1H), 8.01 (dd, J = 10.4, 8.6 Hz, 2H), 7.93 (d, J = 6.0 Hz, 1H), 7.89 (s, 1H), 7.47-7.32 (m, 4H), 7.29 (d, J = 3.4 Hz, 1H), 7.07 (d, J = 8.1 Hz, 2H), 6.85 (dd, J = 9.1, 2.3 Hz, 1H), 6.36 (d, J = 2.1 Hz, 1H), 6.20 (d, J = 3.5 Hz, 1H), 3.67 (s, 2H), 3.31 (s, 8H), 2.28 (s, 2H), 2.11 (s, 2H), 1.56 (t, J = 6.3 Hz, 2H), 1.00 (s, 6H). |
| 94 | ¹H NMR (300 MHz, MeOH-d4) δ 8.35 (d, J = 8.4 Hz, 1H), 8.02 (d, J = 9.1 Hz, 1H), 7.96-7.88 (m, 2H), 7.42-7.35 (m, 2H), 7.32 (d, J = 3.5 Hz, 1H), 7.27 (d, J = 2.6 Hz, 1H), 7.08 (d, J = 8.3 Hz, 2H), 6.89 (dd, J = 9.1, 2.3 Hz, 1H), 6.50 (d, J = 2.3 Hz, 1H), 6.21 (d, J = 3.5 Hz, 1H), 3.69 (s, 2H), 3.31 (d, J = 1.7 Hz, 8H), 2.54 (s, 3H), 2.26 (d, J = 6.4 Hz, 2H), 2.12 (s, 2H), 1.57 (t, J = 6.2 Hz, 2H), 1.01 (s, 6H) |
| 95 | ¹H NMR (300 MHz, CDCl₃) δ 11.87 (s, NH), 8.32 (s, 1H), 8.06 (dd, J = 20.4, 8.7 Hz, 2H), 7.92 (d, J = 8.5 Hz, 1H), 7.76 (s, 1H), 7.68 (s, 1H), 7.41 (s, 1H), 7.33 (d, J = 8.3 Hz, 2H), 7.18 (t, J = 9.4 Hz, 2H), 6.94 (d, J = 8.3 Hz, 2H), 6.81 (d, J = 8.9 Hz, 2H), 6.69 (d, J = 9.1 Hz, 1H), 6.41 (s, 1H), 6.19 (s, 1H), 5.34 (s, 2H), 3.96-2.91 (m, 10H), 2.25 (s, 2H), 2.07 (s, 2H), 1.47 (t, J = 5.9 Hz, 2H), 1.01-0.84 (m, 6H) |
| 96 | ¹H NMR (300 MHz, CDCl₃) δ 12.35 (s, 1H), 8.44 (s, 1H), 8.00 (d, J = 17.7 Hz, 2H), 7.91 (s, 1H), 7.70 (s, 1H), 7.62 (s, 1H), 7.46 (s, 1H), 7.34 (s, 2H), 6.99-6.91 (m, 2H), 6.77 (s, 1H), 6.59 (s, 1H), 6.34 (s, 1H), 5.36 (s, 1H), 4.45 (s, 2H), 4.03 (s, 6H), 3.66 (d, J = 17.4 Hz, 3H), 3.44 (d, J = 12.2 Hz, 2H), 2.81 (d, J = 13.8 Hz, 1H), 2.58 (s, 2H), 2.28 (s, 2H), 2.28 (d, J = 15.2 Hz, 1H), 2.08 (s, 4H), 1.86 (s, 2H), 1.65 (d, J = 7.5 Hz, 1H), 0.99 (d, J = 9.7 Hz, 6H). |
| 97 | ¹H NMR (300 MHz, CDCl₃) δ 12.46 (s, 1H), 10.42 (br, 1H), 8.30 (s, 1H), 8.12 (d, J = 9.0 Hz, 1H), 7.97 (s, 1H), 7.92 (d, J = 1.9 Hz, 1H), 7.85 (d, J = 1.0 Hz, 1H), 7.54 (s, 1H), 7.34 (d, J = 8.3 Hz, 2H), 6.95 (d, J = 8.3 Hz, 2H), 6.73 (dd, J = 9.1, 2.0 Hz, 1H), 6.59 (d, J = 1.9 Hz, 1H), 6.20 (d, J = 1.9 Hz, 1H), 3.66-3.20 (m, 8H), 3.09 (s, 3H), 2.60 (s, 3H), 2.26 (d, J = 5.5 Hz, 2H), 2.05 (d, J = 14.5 Hz, 2H), 1.49 (t, J = 6.0 Hz, 2H), 1.30 (d, J = 17.6 Hz, 2H), 1.00-0.87 (m, 6H) |
| 100 | 1H NMR (300 MHz, CDCl₃) δ 11.90 (s, 1H), 8.61 (s, 1H), 8.43 (s, 1H), 8.02 (d, J = 8.8 Hz, 1H), 7.85 (d, J = 8.7 Hz, 1H), 7.66 (d, J = 23.3 Hz, 1H), 7.43 (s, 1H), 7.30 (d, J = 8.2 Hz, 2H), 6.88 (dd, J = 34.3, 8.4 Hz, 3H), 6.66 (d, J = 8.9 Hz, 1H), 6.45 (s, 1H), 6.19 (s, 1H), 4.04 (dd, J = 11.9, 4.1 Hz, 2H), 3.86-3.35 (m, 8H), 3.26 (m, 3H), 2.54 (m, 2H), 2.26 (m, 2H), 2.17-1.85 (m, 3H), 1.73 (d, J = 13.0 Hz, 2H), 1.61-1.16 (m, 5H), 0.96 (s, 6H). |
| 103 | ¹H NMR (300 MHz, CDCl₃) δ 7.92 (d, J = 9.0 Hz, 1H), 7.84 (s, 1H), 7.51 (s, 1H), 7.43 (s, 2H), 7.33 (d, J = 8.0 Hz, 2H), 6.94 (d, J = 8.1 Hz, 2H), 6.63 (d, J = 9.0 Hz, 1H), 6.40 (s, 1H), 6.05 (s, 1H), 4.88 (t, J = 7.1 Hz, 2H), 4.58 (t, J = 6.1 Hz, 2H), 4.17 (d, J = 6.5 Hz, 2H), 3.60 (s, 2H), 3.48 (s, 8H), 2.41 (s, 3H), 2.35 (d, J = 4.2 Hz, 1H), 2.26 (d, J = 7.5 Hz, 2H), 2.06 (s, 2H), 1.47 (d, J = 6.4 Hz, 2H), 0.96 (s, 6H). |
| 104 | 1H NMR (300 MHz, CDCl₃) δ 8.20 (s, 1H), 7.98 (d, J = 9.0 Hz, 1H), 7.82 (d, J = 2.1 Hz, 1H), 7.65 (s, 1H), 7.46 (d, J = 2.7 Hz, 1H), 7.32 (d, J = 8.3 Hz, 2H), 6.94 (d, J = 8.3 Hz, 2H), 6.72-6.63 (m, 1H), 6.47 (d, J = 3.3 Hz, 1H), 6.17 (s, 1H), 3.81-3.21 (m, 18H), 2.40 (s, 3H), 2.25 (s, 3H), 2.06 (s, 2H), 1.48 (s, 2H), 1.30 (d, J = 12.9 Hz, 1H), 0.96 (s, 6H). |
| 105 | 1H NMR (300 MHz, CDCl₃) δ 7.96 (d, J = 11.0 Hz, 1H), 7.87 (s, 1H), 7.80 (s, 1H), 7.68 (s, 1H), 7.47 (s, 1H), 7.33 (dd, J = 8.0, 4.0 Hz, 2H), 6.95 (d, J = 7.9 Hz, 2H), 6.71 (dd, J = 20.1, 8.9 Hz, 1H), 6.48 (d, J = 13.4 Hz, 1H), 6.24 (d, J = 22.5 Hz, 1H), 3.97 (dd, J = 6.3, 3.6 Hz, 4H), 3.91-3.72 (m, 6H), 3.68-3.48 (m, 8H), 2.43 (s, 3H), 2.22 (s, 3H), 2.07 (s, 2H), 1.48 (s, 2H), 1.29 (d, J = 12.0 Hz, 1H), 0.95 (s, 6H). |
| 106 | ¹H NMR (300 MHz, CDCl₃) δ 11.71 (s, 1H), 8.07 (dd, J = 43.2, 8.8 Hz, 1H), 7.92-7.61 (m, 2H), 7.49 (s, 1H), 7.35 (d, J = 9.1 Hz, 2H), 6.96 (d, J = 7.8 Hz, 2H), 6.70 (dd, J = 21.6, 8.9 Hz, 1H), 6.51 (d, J = 17.6 Hz, 1H), 6.15 (d, J = 16.0 Hz, 1H), 5.37 (s, 1H), 3.92 (s, 5H), 3.77 (q, J = 9.0 Hz, 2H), 3.62 (s, 2H), 2.33-2.21 (m, 4H), 2.06 (d, J = 12.9 Hz, 4H), 1.66 (s, 3H), 1.29 (s, 6H), 0.95 (d, J = 18.9 Hz, 8H). |
| 107 | ¹H NMR (300 MHz, CDCl₃) δ 11.57 (s, 1H), 7.96 (d, J = 9.1 Hz, 1H), 7.87 (s, 1H), 7.62 (d, J = 5.0 Hz, 1H), 7.56 (s, 1H), 7.45 (s, 1H), 7.31 (d, J = 8.2 Hz, 2H), 6.98-6.88 (m, 2H), 6.63 (d, J = 9.2 Hz, 1H), 6.44 (s, 1H), 6.05 (s, 1H), 5.34 (s, 1H), 4.29-4.19 (m, 1H), 3.94 (d, J = 4.2 Hz, 1H), 3.95-3.74 (m, 2H), 3.59 (s, 3H), 2.42 (s, 3H), 2.23 (t, J = 7.6 Hz, 2H), 2.13-1.92 (m, 7H), 1.25 (s, 5H), 0.95 (s, 6H). |

Biological Assays:

Cell Free Bcl-2:Bak Affinity Assay (Bcl-2 Bak)

The assay is based on the competition of fluorescently labeled peptide binding to BCL-2 and the binding is monitored by HTRF signals between anti-GST-Tb and FAM-peptide using GST-Tag BCL proteins. Testing compounds were dissolved in DMSO at 10 mM and tested in 10-concentration IC$_{50}$ mode. The compounds of interest in DMSO were added in 3-fold serial dilution to each well containing 4 nM of BCL-2 recombinant protein, 20 mM K Phosphate, pH 7.5, 50 mM NaCl, 1 mM EDTA, 0.005% Triton X-100, by using acoustic technology (Labcyte echo 550), After 10 minutes incubation at room temperature, 100 nM of FAM-Bak was added and incubated for another 10 minutes before addition of Anti-GST-Tb. The plate was then sealed and further incubated at room temperature for 60 minutes in the dark before reading. Percentage of inhibition was calculated by % inhibition=100×($F_{DMSO}$−F)/($F_{DMSO}$−$F_{PC}$), in which $F_{DMSO}$ is DMSO control and $F_{PC}$ is a positive control. IC$_{50}$ values were determined from dose-response curve by fitting the percent inhibition against compound concentration using GraphPad Prism software.

MV-411 Cell Viability Assay Experimental

MV-411 cells (ATCC, CRL-9591) are cultured in non-TC treated T-75 flasks using RPMI-1640 growth media (Corning, #10-040-CV) with 10% FBS (Gibco, #26140079). Compounds are added to 384-well microplate plate (Nunc, #164610) using Tecan D300e digital dispenser prior to cell addition in 9-point concentration-responses. Columns 3-11 and 14-22 receive compound, columns 1, 12, 13, 24 receive DMSO. 10 ul of resuspended MV-411 cells are diluted 1:1 with Trypan Blue (Bio-Rad, #1450013) and counted using cell counter (Bio-Rad, TC20) to assess viable cell density. MV-411 cells are transferred to 50 ml conical (Corning, #430290) and spun down at 300RCF for 5 min (Beckman, Spinchron15). Supernatant is discarded and cell pellet is resuspended in growth media to a concentration of $2.5e^5$ cells per ml. Cell suspension is lightly vortexed and added to microplates containing compound at 20µ per well (columns 2-23) using Multidrop Combi (Thermo Scientific, #5840310) and a small tube combi cassette (Thermo Scientific, #24073295). Media is added to columns 1 & 24). Cells were immediately incubated in a humidified $CO_2$ incubator (Thermo Scientific, Forma) at 37° C. for 48 hours. ATP-lite reagent (Perkin Elmer, #6016731) is reconstituted per manufacturer's instructions and added to assay plates at 20 ul per well using the Multidrop Combi, small tube cassette. Plates are then incubated at room temperature for 10 min and read on a plate reader (Perkin Elmer, Envision 2105) using Ultra-Sensitive luminescence mode. Raw data are normalized to vehicle-treated cells (columns 12, 13) and background (columns 1, 24). Absolute IC50 curve fitting is done using GraphPad Prism (Version 8.3.1). The IC50s of the compounds as described herein are shown in Table 6.

TABLE 6

Cell free Bcl-2:Bak affinity assay (Bcl-2 Bak)

| Ex# | potency |
|---|---|
| 1 | ++ |
| 2 | ++ |
| 3 | ++ |
| 4 | ++ |
| 5 | ++ |
| 6 | ++ |
| 7 | ++ |
| 8 | ++ |
| 9 | ++ |
| 10 | ++ |
| 11 | ++ |
| 12 | + |
| 13 | ++ |
| 14 | ++ |
| 15 | ++ |
| 16 | ++ |
| 17 | ++ |
| 18 | ++ |
| 19 | ++ |
| 20 | ++ |
| 21 | ++ |
| 22 | ++ |
| 23 | ++ |
| 24 | ++ |
| 25 | ++ |
| 26 | + |
| 27 | ++ |
| 28 | + |
| 29 | + |
| 30 | ++ |
| 31 | + |
| 32 | # |
| 33 | ### |
| 34 | ++ |
| 35 | +++ |
| 36 | ++ |
| 37 | ### |
| 38 | ### |

TABLE 6-continued

Cell free Bcl-2:Bak affinity assay (Bcl-2 Bak)

| Ex# | potency |
|---|---|
| 39 | ### |
| 40 | ++ |
| 41 | ++ |
| 42 | +++ |
| 43 | ## |
| 44 | ++ |
| 45 | ++ |
| 46 | ++ |
| 47 | ++ |
| 48 | ++ |
| 49 | +++ |
| 50 | ++ |
| 51 | ++ |
| 52 | ++ |
| 53 | ++ |
| 54 | ++ |
| 55 | ++ |
| 56 | ++ |
| 57 | ++ |
| 58 | ++ |
| 59 | ++ |
| 60 | ++ |
| 61 | + |
| 62 | ## |
| 63 | ### |
| 64 | # |
| 65 | #### |
| 66 | ### |
| 67 | ### |
| 68 | ### |
| 69 | ### |
| 70 | ### |
| 71 | ## |
| 72 | ### |
| 73 | ### |
| 74 | ## |
| 75 | ## |
| 76 | ### |
| 77 | ## |
| 78 | ## |
| 79 | ### |
| 80 | #### |
| 81 | #### |
| 82 | #### |
| 83 | ### |
| 84 | ## |
| 85 | ### |
| 86 | ### |
| 87 | ### |
| 88 | #### |
| 89 | ## |
| 90 | ## |
| 91 | ### |
| 92 | ## |
| 93 | ### |
| 94 | ### |
| 95 | ## |
| 96 | ### |
| 97 | # |
| 98 | ### |
| 99 | ### |
| 100 | #### |
| 101 | ### |
| 102 | ## |
| 103 | ### |
| 104 |  |
| 105 |  |
| 106 | #### |
| 107 | #### |

The potency is presented as "% inhibition at 1 µM" or "IC50": "+" means that "% Inhibition at 1 µM" is less than 50%"; "++" means that "% Inhibition at 1 µM" is between 50% and 90%, inclusive"; "+++" means that "% Inhibition at 1 µM" is more than 90%"; " ####" means that "IC50" is less than 10 nM"; "###" means that "IC50" is between 10 nM and 100 nM, inclusive"; "##" means that "IC50" is in an range of more than 100 nM and equal to or less than 1000 nM"; "#" means that "IC50" is more than 1000 nM.

What is claimed:

1. A compound having the formula of Formula (I), or a pharmaceutically acceptable salt or solvate thereof:

Formula (I)

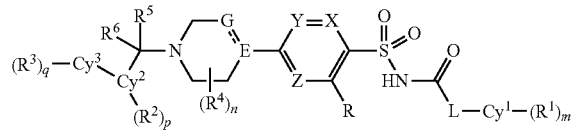

wherein:

L is absent, $(CR^{29}R^{30})_k$, O, $NR^{15}$, optionally substituted cycloalkyl, optionally substituted heterocycloalkyl, optionally substituted aryl, or optionally substituted heteroaryl;

E is C, N, or $CR^{11}$, wherein when E is C, ═══ is a double bond; when E is $CR^{11}$, ═══ is a single bond; and when E is N, ═══ is a single bond;

G is $CR^{16}$ or $CR^{16}R^{17}$, wherein when ═══ is a double bond, G is $CR^{16}$;

X, Y, and Z are each, independently, N or $CR^{20}$;

$Cy^1$ and $Cy^2$ are each, independently, optionally substituted aryl, optionally substituted cycloalkyl, optionally substituted cycloalkenyl, optionally substituted heteroaryl, or optionally substituted heterocycloalkyl;

$Cy^3$ is optionally substituted aryl, optionally substituted cycloalkyl, or optionally substituted heteroaryl;

R is H, D, halo, optionally substituted $C_{1-6}$ alkyl, $OR^8$, $SR^8$, or $NR^9R^{10}$,

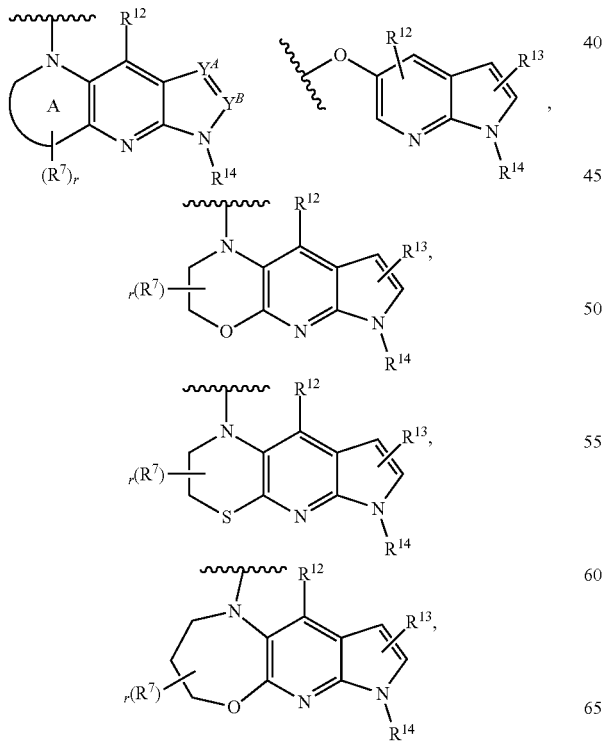

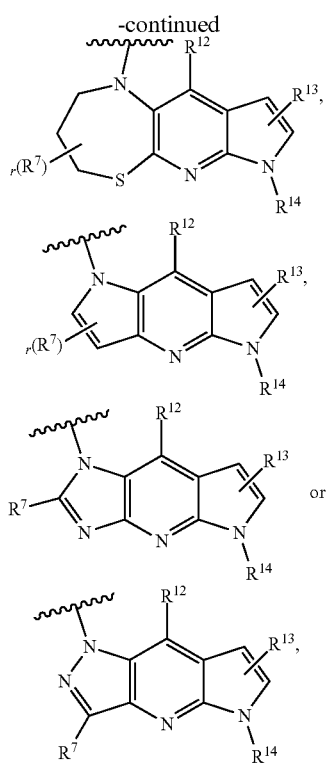

wherein ring A is a 4- to 14-membered heterocycle or heteroaryl containing at least one nitrogen;

$Y^A$ and $Y^B$ are each, independently, N, O, S, or $CR^{21}$;

$R^1$ is H, D, halo, oxo, $C_{1-6}$ alkyl, $C_{2-6}$ alkenyl, $C_{2-6}$ alkynyl, $C_{1-6}$ haloalkyl, CN, $NO_2$, $N_3$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^D$, $NR^CC(O)NR^CR^D$, $C(=NR^C)R^B$, $C(=NR^C)NR^CR^D$, $NR^CS(O)R^B$, $NR^CS(O)_2NR^CR^D$, $NR^CC(=NR^C)NR^CR^D$, $NR^CC(=NOR^A)NR^CR^D$, $NR^CC(=NCN)NR^CR^D$, $S(O)(=NR^C)R^B$, $S(O)(=NR^C)NR^CR^D$, $NR^CC(O)OR^A$, $P(O)R^ER^F$, $P(O)OR^EOR^F$, $OP(O)OR^EOR^F$, $SF_5$, $S(O)R^B$, $S(O)NR^CR^D$, $S(O)_2R^B$, $NR^CS(O)_2R^B$, $S(O)_2NR^CR^D$, $B(OR^A)_2$, $Cy^4$, $C_{1-6}$ alkyl-$Cy^4$, O—$C_{1-6}$ alkyl-$Cy^4$, or O—$C_{1-6}$ alkyl-$Cy^4$-$C_{0-6}$ alkyl-$Cy^5$, wherein said $C_{1-6}$ alkyl, $C_{2-6}$ alkenyl, $C_{2-6}$ alkynyl, $C_{1-6}$ haloalkyl, O—$C_{1-6}$ alkyl, $Cy^4$, and $Cy^5$ are each optionally substituted;

wherein two adjacent $R^1$, together with the atom or atoms to which they are attached, optionally form a fused 3- to 10-membered cycloalkyl ring or a fused 4- to 10-membered heterocycloalkyl ring, each of which is optionally substituted by 1, 2, 3, 4, 5, or 6 substituents, wherein each said substituent is independently D, halo, $C_{1-6}$ alkyl, $C_{2-6}$ alkenyl, $C_{2-6}$ alkynyl, $C_{1-6}$ haloalkyl, CN, $NO_2$, oxo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $C(=NR^c)R^b$, $C(=NR^c)NR^cR^d$, $NR^cS(O)R^b$, $NR^cS(O)_2NR^cR^d$, $NR^cC(=NR^c)NR^cR^d$, $NR^cC(=NOR^a)NR^cR^d$, $NR^c(=NCN)NR^cR^d$, $S(O)(=NR^c)R^b$, $S(O)(=NR^c)NR^cR^d$, $NR^cC(O)OR^a$, $P(O)R^eR^f$, $P(O)OR^eOR^f$, $OP(O)OR^eOR^f$, $S(O)R^b$, $S(O)NR^cR^d$, $S(O)_2R^b$, $NR^cS(O)_2R^b$, or $S(O)_2NR^cR^d$, $B(OR^a)_2$, aryl, cycloalkyl, heteroaryl, or heterocycloalkyl, wherein said $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl are each optionally substituted;

each $R^2$ is H, D, halo, oxo, $C_{1-6}$ alkyl, $C_{2-6}$ alkenyl, $C_{2-6}$ alkynyl, $C_{1-6}$ haloalkyl, $C_{1-6}$ haloalkoxy, cycloalkyl, heterocycloalkyl, CN, NO$_2$, OR$^A$, SR$^A$, C(O)R$^B$ C(O)NR$^C$R$^D$, C(O)OR$^A$, OC(O)R$^B$, OC(O)NR$^C$R$^D$, NR$^C$R$^D$, NR$^C$C(O)R$^D$, NR$^C$C(O)NR$^C$R$^D$, C(=NR$^C$)R$^B$, C(=NR$^C$)NR$^C$R$^D$, NR$^C$S(O)R$^B$, NR$^C$S(O)$_2$NR$^C$R$^D$, NR$^C$C(=NR$^C$)NR$^C$R$^D$, NR$^C$C(=NOR$^A$)NR$^C$R$^D$, NR$^C$C(=NCN)NR$^C$R$^D$, S(O)(=NR$^C$)R$^B$, S(O)(=NR$^C$)NR$^C$R$^D$, NR$^C$C(O)OR$^A$, P(O)R$^E$R$^F$, P(O)OR$^E$OR$^F$, OP(O)OR$^E$OR$^F$, SF$_5$, S(O)R$^B$, S(O)NR$^C$R$^D$, S(O)$_2$R$^B$, NR$^C$S(O)$_2$R$^B$, S(O)$_2$NR$^C$R$^D$ or B(OR$^A$)$_2$;

wherein two $R^2$, together with the atom or atoms to which they are attached form a 3- to 7-membered cycloalkyl group or 4- to 7-membered heterocycloalkyl group, each of which is optionally substituted by 1, 2, or 3 substituents, wherein each said substituent is independently H, D, halo, $C_{1-6}$ alkyl, $C_{2-6}$ alkenyl, $C_{2-6}$ alkynyl, $C_{1-6}$ haloalkyl, $C_{1-6}$ alkyl NR$^C$R$^d$, CN, NO$_2$, oxo, OR$^a$, SR$^a$, C(O)R$^b$, C(O)NR$^C$R$^d$, C(O)OR$^a$, OC(O)R$^b$, OC(O)NR$^C$R$^d$, NR$^C$R$^d$, NR$^C$C(O)R$^b$, NR$^C$C(O)NR$^C$R$^d$, C(=(NR$^C$)R$^b$, C(=NR)NR$^C$R$^d$, NR$^C$S(O)R$^b$, NR$^C$S(O)$_2$NR$^C$R$^d$, NR$^C$C(=NR)NR$^C$R$^d$, NR$^C$C(=NOR$^a$)NR$^C$R$^d$, NR$^c$(=NCN)NR$^C$R$^d$, S(O)(=NR$^c$)R$^b$, S(O)(=NR)NR$^C$R$^d$, NR$^C$C(O)OR$^a$, P(O)R$^e$R$^f$, P(O)OR$^e$OR$^f$, S(O)R$^b$, S(O)NR$^C$R$^d$, S(O)$_2$R$^b$, NR$^C$S(O)$_2$R$^b$, or S(O)$_2$NR$^C$R$^d$;

each $R^3$ is H, D, halo, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, Cy$^4$, $C_{1-6}$ alkyl-Cy$^4$, CN, NO$_2$, OR$^A$, SR$^A$, C(O)R$^B$, C(O)NR$^C$R$^D$, C(O)OR$^A$, OC(O)R$^B$, OC(O)NR$^C$R$^D$, NR$^C$R$^D$, NR$^C$C(O)R$^D$, NR$^C$C(O)NR$^C$R$^D$, C(=(NR$^C$)R$^B$, C(=NR$^C$)NR$^C$R$^D$, NR$^C$S(O)R$^B$, NR$^C$S(O)$_2$NR$^C$R$^D$, NR$^C$C(=NR$^C$)NR$^C$R$^D$, NR$^C$C(=NOR$^A$)NR$^C$R$^D$, NR$^C$C(=NCN)NR$^C$R$^D$, S(O)(=NR$^C$)R$^B$, S(O)(=NR$^C$)NR$^C$R$^D$, NR$^C$C(O)OR$^A$, P(O)R$^E$R$^F$, P(O)OR$^E$OR$^F$, OP(O)OR$^E$OR$^F$, SF$_5$, S(O)R$^B$, S(O)NR$^C$R$^D$, S(O)$_2$R$^B$, NR$^C$S(O)$_2$R$^B$, S(O)$_2$NR$^C$R$^D$, B(OR$^A$)$_2$;

wherein two $R^3$, together with the atom or atoms to which they are attached form a 3- to 7-membered cycloalkyl group or 4- to 7-membered heterocycloalkyl group, each of which is optionally substituted by 1, 2, or 3 substituents, wherein each said substituent is independently H, D, halo, $C_{1-6}$ alkyl, $C_{2-6}$ alkenyl, $C_{2-6}$ alkynyl, $C_{1-6}$ haloalkyl, $C_{1-6}$ alkyl NR$^C$R$^d$, CN, NO$_2$, oxo, OR$^a$, SR$^a$, C(O)R$^b$, C(O)NR$^C$R$^d$, C(O)OR$^a$, OC(O)R$^b$, OC(O)NR$^C$R$^d$, NR$^C$R$^d$, NR$^C$C(O)R$^b$, NR$^C$C(O)NR$^C$R$^d$, C(=(NR$^c$)R$^b$, C(=NR)NR$^C$R$^d$, NR$^C$S(O)R$^b$, NR$^C$S(O)$_2$NR$^C$R$^d$, NR$^C$C(=NR$^c$)NR$^C$R$^d$, NR$^C$C(=NOR$^a$)NR$^C$R$^d$, NR$^C$C(=NCN)NR$^C$R$^d$, S(O)(=NR$^c$)R$^b$, S(O)(=NR)NR$^C$R$^d$, NR$^C$C(O)OR$^a$, P(O)R$^e$R$^f$, P(O)OR$^e$OR$^f$, S(O)R$^b$, S(O)NR$^C$R$^d$, S(O)$_2$R$^b$, NR$^C$S(O)$_2$R$^b$, or S(O)$_2$NR$^C$R$^d$;

each $R^4$ is H, D, halo, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, Cy$^4$, $C_{1-6}$ alkyl-Cy$^4$, CN, NO$_2$, OR$^A$, SR$^A$, C(O)R$^B$, C(O)NR$^C$R$^D$, C(O)OR$^A$, OC(O)R$^B$, OC(O)NR$^C$R$^D$, NR$^C$R$^D$, NR$^C$C(O)R$^D$, NR$^C$C(O)NR$^C$R$^D$, C(=(NR$^C$)R$^B$, C(=NR$^C$)NR$^C$R$^D$, NR$^C$S(O)R$^B$, NR$^C$S(O)$_2$NR$^C$R$^D$, NR$^C$C(=NR$^C$)NR$^C$R$^D$, NR$^C$C(=NOR$^A$)NR$^C$R$^D$, NR$^C$C(=NCN)NR$^C$R$^D$, S(O)(=NR$^C$)R$^B$, S(O)(=NR$^C$)NR$^C$R$^D$, NR$^C$C(O)OR$^A$, P(O)R$^E$R$^F$, P(O)OR$^E$OR$^F$, OP(O)OR$^E$OR$^F$, SF$_5$, S(O)R$^B$, S(O)NR$^C$R$^D$, S(O)$_2$R$^B$, NR$^C$S(O)$_2$R$^B$, S(O)$_2$NR$^C$R$^D$, B(OR$^A$)$_2$;

wherein two $R^4$, together with the atom or atoms to which they are attached form a 3- to 7-membered cycloalkyl group or 4- to 7-membered heterocycloalkyl group, each of which is optionally substituted by 1, 2, or 3 substituents, wherein each said substituent is independently H, D, halo, $C_{1-6}$ alkyl, $C_{2-6}$ alkenyl, $C_{2-6}$ alkynyl, $C_{1-6}$ haloalkyl, $C_{1-6}$ alkyl, NR$^C$R$^d$, CN, NO$_2$, oxo, OR$^a$, SR$^a$, C(O)R$^b$, C(O)NR$^C$R$^d$, C(O)OR$^a$, OC(O)R$^b$, OC(O)NR$^C$R$^d$, NR$^C$R$^d$, NR$^C$C(O)R$^b$, NR$^C$C(O)NR$^C$R$^d$, C(=(NR$^c$)R$^b$, C(=NR)NR$^C$R$^d$, NR$^C$S(O)R$^b$, NR$^C$S(O)$_2$NR$^C$R$^d$, NR$^C$C(=NR)NR$^C$R$^d$, NR$^C$C(=NOR$^a$)NR$^C$R$^d$, NR$^C$(=NCN)NR$^C$R$^d$, S(O)(=NR$^c$)R$^b$, S(O)(=NR$^C$)NR$^C$R$^d$, NR$^C$C(O)OR$^a$, P(O)R$^e$R$^f$, P(O)OR$^e$OR$^f$, S(O)R$^b$, S(O)NR$^C$R$^d$, S(O)$_2$R$^b$, NR$^C$S(O)$_2$R$^b$, or S(O)$_2$NR$^C$R$^d$;

$R^5$, $R^6$, $R^7$, $R^{11}$, $R^{12}$, $R^{13}$, $R^{14}$, $R^{15}$, $R^{16}$, $R^{17}$, $R^{29}$, and $R^{30}$ are each, independently, absent, H, D, halo, oxo, $C_{1-6}$ alkyl, $C_{2-6}$ alkenyl, $C_{2-6}$ alkynyl, $C_{1-6}$ haloalkyl, $C_{3-6}$ cycloalkyl, CN, NO$_2$, C(O)NR$^C$R$^D$, C(O)OR$^A$ or B(OR$^A$)$_2$;

wherein $R^5$ and $R^6$, together with the atom or atoms to which they are attached form a 3- to 7-membered cycloalkyl group or 4- to 7-membered heterocycloalkyl group, each of which is optionally substituted by 1, 2, or 3 substituents, wherein each said substituent is independently H, D, halo, $C_{1-6}$ alkyl, $C_{2-6}$ alkenyl, $C_{2-6}$ alkynyl, $C_{1-6}$ haloalkyl, $C_{1-6}$ alkyl NR$^C$R$^d$, CN, NO$_2$, oxo, OR$^a$, SR$^a$, C(O)R$^b$, C(O)NR$^C$R$^d$, C(O)OR$^a$, OC(O)R$^b$, OC(O)NR$^C$R$^d$, NR$^C$R$^d$, NR$^C$C(O)R$^b$, NR$^C$C(O)NR$^C$R$^d$, C(=(NR$^c$)R$^b$, C(=NR)NR$^C$R$^d$, NR$^C$S(O)R$^b$, NR$^C$S(O)$_2$NR$^C$R$^d$, NR$^C$C(=NR)NR$^C$R$^d$, NR$^C$C(=NOR$^a$)NR$^C$R$^d$, NR$^C$C(=NCN)NR$^C$R$^d$, S(O)(=NR$^c$)R$^b$, S(O)(=NR)NR$^C$R$^d$, NR$^C$C(O)OR$^a$, P(O)R$^e$R$^f$, P(O)OR$^e$OR$^f$, S(O)R$^b$, S(O)NR$^C$R$^d$, S(O)$_2$R$^b$, NR$^C$S(O)$_2$R$^b$, or S(O)$_2$NR$^C$R$^d$;

$R^8$, $R^9$, and $R^{10}$ are each, independently, H, D, $C_{1-6}$ alkyl, $C_{2-6}$ alkenyl, $C_{2-6}$ alkynyl, $C_{1-6}$ haloalkyl, Cy$^4$, Cy$^4$-$C_{1-4}$ alkyl, wherein said $C_{1-4}$ alkyl, $C_{1-6}$ alkyl, $C_{2-6}$ alkenyl, $C_{2-6}$ alkynyl, $C_{1-6}$ haloalkyl, and Cy$^4$ are each optionally substituted;

wherein $R^9$ and $R^{10}$ together with the N atom to which they are attached, optionally form a fused 4- to 14-membered heterocycloalkyl ring or 4- to 14-membered heteroaryl ring, each of which is optionally substituted by 1, 2, or 3 substituents, wherein each said substituent is independently H, D, halo, $C_{1-6}$ alkyl, $C_{2-6}$ alkenyl, $C_{2-6}$ alkynyl, $C_{1-6}$ haloalkyl, CN, NO$_2$, oxo, OR$^a$, SR$^a$, C(O)R$^b$, C(O)NR$^C$R$^d$, C(O)OR$^a$, OC(O)R$^b$, OC(O)NR$^C$R$^d$, NR$^C$R$^d$, NR$^C$C(O)R$^b$, NR$^C$C(O)NR$^C$R$^d$, C(=(NR$^c$)R$^b$, C(=NR)NR$^C$R$^d$, NR$^C$S(O)R$^b$, NR$^C$S(O)$_2$NR$^C$R$^d$, NR$^C$C(=NR)NR$^C$R$^d$, NR$^C$C(=NOR$^a$)NR$^C$R$^d$, NR$^C$C(=NCN)NR$^C$R$^d$, S(O)(=NR$^c$)R$^b$, S(O)(=NR)NR$^C$R$^d$, NR$^C$C(O)OR$^a$, OP(O)OR$^e$OR$^f$, P(O)OR$^e$OR$^f$, S(O)R$^b$, S(O)NR$^C$R$^d$, S(O)$_2$R$^b$, NR$^C$S(O)$_2$R$^b$, or S(O)$_2$NR$^C$R$^d$;

$R^{20}$ and $R^{21}$ are each, independently, H, D, halo, $C_{1-6}$ alkyl, $C_{2-6}$ alkenyl, $C_{2-6}$ alkynyl, $C_{1-6}$ haloalkyl, $C_{3-6}$ cycloalkyl, CN, NO$_2$, OR$^A$, SR$^A$, C(O)R$^B$, C(O)NR$^C$R$^D$, C(O)OR$^A$, OC(O)R$^B$, OC(O)NR$^C$R$^D$, NR$^C$R$^D$, NR$^C$C(O)R$^D$, NR$^C$C(O)NR$^C$R$^D$, C(=(NR$^C$)R$^B$, C(=NR$^C$)NR$^C$R$^D$, NR$^C$S(O)R$^B$, NR$^C$S(O)$_2$NR$^C$R$^D$, NR$^C$C(=NR$^C$)NR$^C$R$^D$, NR$^C$C(=NOR$^A$)NR$^C$R$^D$, NR$^C$C(=NCN)NR$^C$R$^D$, S(O)(=NR$^C$)R$^B$, S(O)(=NR$^C$)NR$^C$R$^D$, NR$^C$C(O)OR$^A$, SF$_5$, S(O)R$^B$, S(O)NR$^C$R$^D$, S(O)$_2$R$^B$, NR$^C$S(O)$_2$R$^B$, S(O)$_2$NR$^C$R$^D$, NR$^C$S(O)$_2$NR$^C$R$^D$, B(OR$^A$)$_2$;

Cy$^4$ and Cy$^5$ are each, independently, aryl, cycloalkyl, heteroaryl, or heterocycloalkyl;

each $R^A$ is independently H, $C_{1-6}$ alkyl, $C_{2-4}$ alkenyl, $C_{2-4}$ alkynyl, Cy$^4$ or $C_{1-6}$ alkyl-Cy$^4$, wherein said $C_{1-6}$ alkyl, $C_{2-4}$ alkenyl, $C_{2-4}$ alkynyl, $C_{1-6}$ alkyl-Cy$^4$, and Cy$^4$ are optionally substituted with 1, 2, or 3 substituents, wherein each said substituent is independently OH, CN, halo, $C_{1-4}$ alkyl; $NO_2$, oxo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $C(=NR^c)R^b$, $C(=NR)NR^cR^d$, $NR^cS(O)R^b$, $NR^cS(O)_2NR^cR^d$, $NR^cC(=NR)NR^cR^d$, $NR^cC(=NOR^a)NR^cR^d$, $NR^cC(=NCN)NR^cR^d$, $S(O)(=NR^c)R^b$, $S(O)(=NR)NR^cR^d$, $NR^cC(O)OR^a$, $OP(O)OR^eR^f$, $P(O)OR^eOR^f$, $S(O)R^b$, $S(O)NR^cR^d$, $S(O)_2R^b$, $NR^cS(O)_2R^b$, or $S(O)_2NR^cR^d$;

each $R^B$ is independently H, $C_1$-$C_6$ alkyl, $C_{2-4}$ alkenyl, $C_{2-4}$ alkynyl, or $Cy^4$, wherein said $C_1$-$C_6$ alkyl, $C_{2-4}$ alkenyl, $C_{2-4}$ alkynyl, and $Cy^4$ are optionally substituted with 1, 2, or 3 substituents, wherein each said substituent is independently OH, CN, amino, alkylamino, dialkylamino, halo, or $C_1$-$C_4$ alkyl;

each $R^C$ and each $R^D$ are independently H, $C_{1-6}$ alkyl, $C_{2-4}$ alkenyl, or $C_{2-4}$ alkynyl, wherein said $C_{1-6}$ alkyl, $C_{2-4}$ alkenyl, and $C_{2-4}$ alkynyl are optionally substituted with 1, 2, or 3 substituents, wherein each said substituent is independently OH, CN, amino, alkylamino, dialkylamino, halo, or $C_{1-4}$ alkyl;

or $R^C$ and $R^D$ together with the N atom to which they are attached form a 4-, 5-, 6- or 7-membered heterocycloalkyl group or heteroaryl group, each of which is optionally substituted with 1, 2, or 3 substituents, wherein each said substituent is independently OH, CN, amino, alkylamino, dialkylamino, halo, or $C_{1-4}$ alkyl;

each $R^E$ and each $R^e$ are independently H, $C_{1-4}$ alkyl, $C_{1-4}$ haloalkyl, $C_{2-4}$ alkenyl, ($C_{1-4}$ alkoxy)-$C_{1-4}$ alkyl, $C_{2-4}$ alkynyl, aryl, cycloalkyl, heteroaryl, heterocycloalkyl, arylalkyl, cycloalkylalkyl, heteroarylalkyl, or heterocycloalkylalkyl;

each $R^F$ and each $R^f$ are independently H, $C_{1-4}$ alkyl, $C_{2-4}$ alkenyl, $C_{2-4}$ alkynyl, aryl, cycloalkyl, heteroaryl, or heterocycloalkyl;

each $R^a$ and each $R^b$ are independently H, D, $C_{1-4}$ alkyl, $C_{1-4}$ haloalkyl, $C_{2-4}$ alkenyl, $C_{2-4}$ alkynyl, aryl, cycloalkyl, heteroaryl, heterocycloalkyl, arylalkyl, heteroarylalkyl, cycloalkylalkyl, or heterocycloalkylalkyl, wherein said $C_{1-4}$ alkyl, $C_{1-4}$ haloalkyl, $C_{2-4}$ alkenyl, $C_{2-4}$ alkynyl, aryl, cycloalkyl, heteroaryl, heterocycloalkyl, arylalkyl, heteroarylalkyl, cycloalkylalkyl, and heterocycloalkylalkyl are optionally substituted with 1, 2, or 3 substituents, wherein each said substituent is independently OH, CN, amino, alkylamino, dialkylamino, halo, $C_{1-4}$ alkyl, $C_{1-4}$ alkoxy, $C_{1-4}$ haloalkyl, or $C_{1-4}$ haloalkoxy;

each $R^c$ and each $R^d$ are independently H, $C_{1-4}$ alkyl, $C_{1-4}$ haloalkyl, $C_{2-4}$ alkenyl, $C_{2-4}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, or biheteroaryl, wherein said $C_{1-4}$ alkyl, $C_{1-4}$ haloalkyl, $C_{2-4}$ alkenyl, $C_{2-4}$alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl are optionally substituted with 1, 2, or 3 substituents, wherein each said substituent is independently OH, CN, amino, alkylamino, dialkylamino, halo, $C_{1-4}$ alkyl, $C_{1-4}$ alkoxy, $C_{1-4}$ haloalkyl, $C_{1-4}$ haloalkoxy, $C_{1-4}$ hydroxyalkyl, $C_{1-4}$ cyanoalkyl, aryl, heteroaryl, $C(O)OR^{a2}$, $C(O)R^{b2}S(O)_2R^{b2}$, alkoxyalkyl, or alkoxyalkoxy;

or $R^c$ and $R^d$ together with the N atom to which they are attached form a 4-, 5-, 6- or 7-membered heterocycloalkyl group or heteroaryl group, each of which is optionally substituted with 1, 2, or 3 substituents, wherein each said substituent is independently OH, CN, amino, alkylamino, dialkylamino, halo, $C_{1-4}$ alkyl, $C_{1-4}$ alkoxy, $C_{1-4}$ haloalkyl, $C_{1-4}$ haloalkoxy, hydroxyalkyl, cyanoalkyl, aryl, heteroaryl, $C(O)OR^{a2}$, $C(O)R^{b2}$, $S(O)_2R^{b2}$, alkoxyalkyl, or alkoxyalkoxy;

each $R^{a2}$ and each $R^{b2}$ are independently H, D, $C_{1-4}$ alkyl, $C_{1-4}$ haloalkyl, $C_{2-4}$ alkenyl, $C_{2-4}$ alkynyl, aryl, cycloalkyl, heteroaryl, heterocycloalkyl, arylalkyl, heteroarylalkyl, cycloalkylalkyl, or heterocycloalkylalkyl, wherein said $C_{1-4}$ alkyl, $C_{1-4}$ haloalkyl, $C_{2-4}$ alkenyl, $C_{2-4}$ alkynyl, aryl, cycloalkyl, heteroaryl, heterocycloalkyl, arylalkyl, heteroarylalkyl, cycloalkylalkyl, and heterocycloalkylalkyl are optionally substituted with 1, 2, or 3 substituents, wherein each said substituent is independently OH, CN, amino, alkylamino, dialkylamino, halo, $C_{1-4}$ alkyl, $C_{1-4}$ alkoxy, $C_{1-4}$ haloalkyl, or $C_{1-4}$ haloalkoxy;

m is 0-5;

n is 0-8;

p, q, and r are each, independently, 0-6; and k is 0-3, wherein when k is 2 or 3, each $R^{29}$ is independent from any other $R^{29}$ and each $R^{30}$ is independent from any other $R^{30}$.

2. The compound of claim 1, or a pharmaceutically acceptable salt or solvate thereof, wherein $Cy^2$ is optionally substituted cycloalkenyl or optionally substituted cycloalkyl.

3. The compound of claim 1, or a pharmaceutically acceptable salt or solvate thereof, wherein $Cy^3$ is optionally substituted aryl or optionally substituted heteroaryl.

4. The compound of claim 1, or a pharmaceutically acceptable salt or solvate thereof, wherein $Cy^1$ is optionally substituted

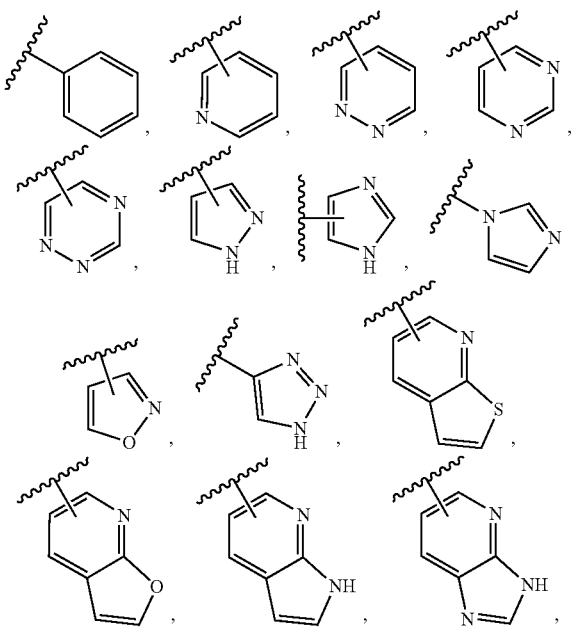

-continued

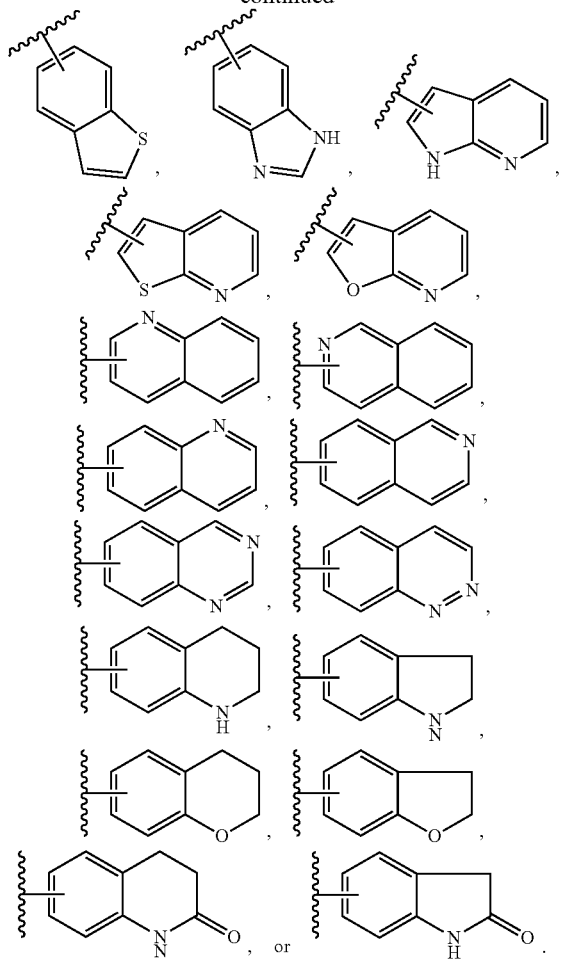

or

5. The compound of claim 1, or a pharmaceutically acceptable salt or solvate thereof, wherein $R^1$ is U—$V^A$—$W^A$, where U is absent, $CR^{29}R^{30}O$, $OCR^{29}R^{30}$, $(CR^{29}R^{30})_{nn}$, or $N(CR^{29}R^{30})_{nn}$, wherein $R^{29}$ and $R^{30}$ are as defined in claim 1 and nn is 0-10; $V^A$ is absent, heterocycle, cycloalkyl, heterocycloalkyl, aryl, or heteroaryl; $W^A$ is H, D, F, Br, Cl, I, $NO_2$, optionally substituted $C_{1-6}$ alkyl, optionally substituted $C_{1-6}$ alkoxy -continued

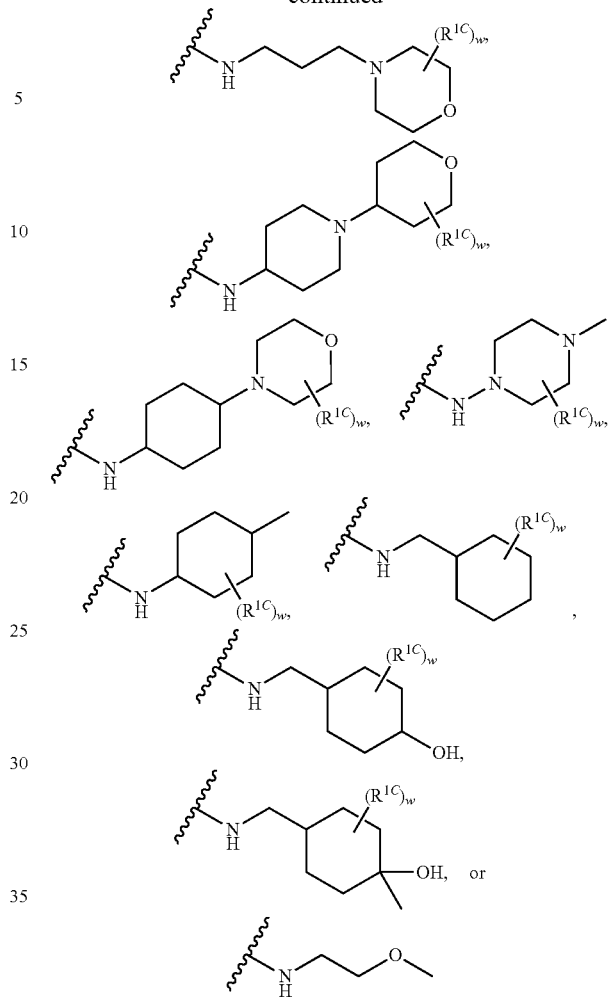

wherein $R^{1C}$ is H, D, halo, CN, $NO_2$, $OR^{a3}$, $SR^{a3}$, $NHOR^{a3}$, $C(O)R^{a3}$, $C(O)NR^{a3}R^{b3}$, $C(O)OR^{a3}$, $OC(O)R^{a3}$, $OC(O)NR^{a3}R^{b3}$, $NHR^{a3}$, $NR^{a3}R^{b3}$, $NR^{a3}C(O)R^{a3}$, $NR^{a3}C(O)OR^{a3}$, $NR^{a3}C(O)NR^{a3}R^{b3}$, $C(=NR^{a3})R^{a3}$, $C(=NR^{a3})NR^{a3}R^{b3}$, $NR^{a3}C(=NR^{a3})NR^{a3}R^{b3}$, $NR^{a3}C(=NOH)NR^{a3}R^{b3}$, $NR^{a3}C(=NCN)NR^{a3}R^{b3}$, $NR^{a3}S(O)R^{a3}$, $NR^{a3}S(O)_2R^{a3}$, $NR^{a3}S(O)_2NR^{a3}R^{b3}$, $S(O)R^{a3}$, $S(O)NR^{a3}R^{b3}S(O)_2R^{a3}$, $SF_5$, $P(O)R^{a3}R^{b3}$, $P(O)(OR^{a3})(OR^{b3})$, $B(OR^{a3})_2$, or $S(O)_2NR^{a3}R^{b3}$, or optionally substituted $C_{1-6}$ alkyl, $C_{1-6}$ alkoxy, $C_{2-6}$ alkenyl, $C_{2-6}$ alkynyl, $C_{1-6}$ haloalkyl, $C_{1-6}$haloalkoxy, $C_{6-10}$ aryl, $C_{3-10}$ cycloalkyl, 5- to 10-membered heteroaryl, 4- to 14-membered heterocycloalkyl, $C_{6-10}$ aryl-$C_{1-4}$ alkyl, $C_{3-10}$ cycloalkyl$C_{1-4}$alkyl, (5- to 14-membered heteroaryl)-$C_{1-4}$ alkyl, or (4- to 14-membered heterocycloalkyl)-$C_{1-4}$ alkyl, wherein each $R^{a3}$ and each $R^{b3}$ are independently H, D, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl are optionally substituted with 1, 2, or 3 substituents, wherein each said substituent is independently OH, CN, amino, halo, $C_{1-6}$ alkyl, $C_{1-6}$ alkoxy, $C_{1-6}$ haloalkyl, and $C_{1-6}$ haloalkoxy, $C_{3-10}$ cycloalkyl, $C_{1-6}$ heteroalkyl, 3- to 12-membered heterocyclyl, $C_{6-10}$ aryl, 5- to 10-membered heteroaryl, C(O)H, C(O)NH$_2$, C(O)NH(C$_{1-6}$ alkyl), C(O)N(C$_{1-6}$ alkyl)$_2$, COOH, C(O)C$_{1-6}$ alkyl, or C(O)OC$_{1-6}$ alkyl and W is 0 to 6.

6. The compound of claim 1, or a pharmaceutically acceptable salt or solvate thereof, wherein the compound has the formula of Formula (III)

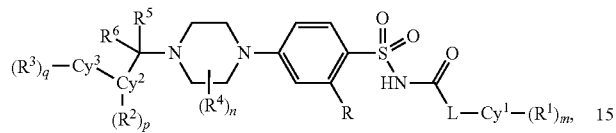

Formula (V)

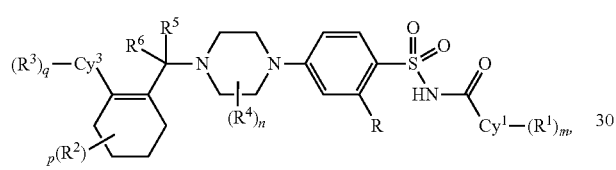

Formula (VII)

Formula (VIII)

or

Formula (IX)

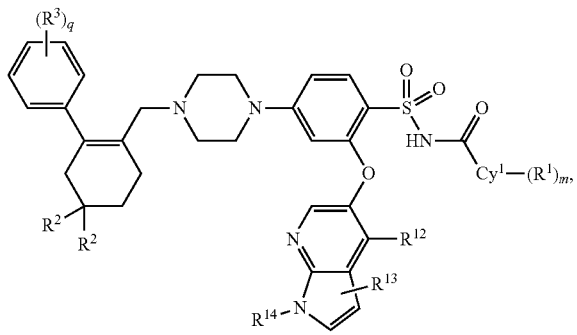

wherein the variables are as defined in claim 1.

7. The compound of claim 1, or a pharmaceutically acceptable salt or solvate thereof, wherein the compound has the formula of Formula (XII)

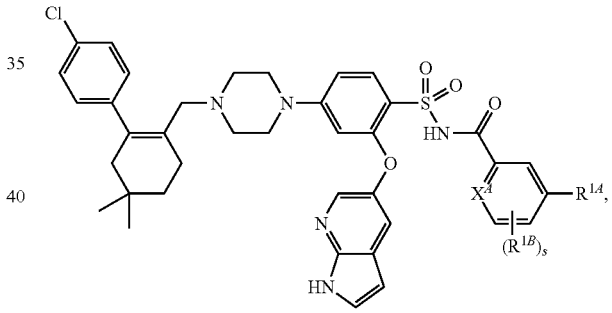

Formula (XX)

173

-continued or

Formula (XX-I)

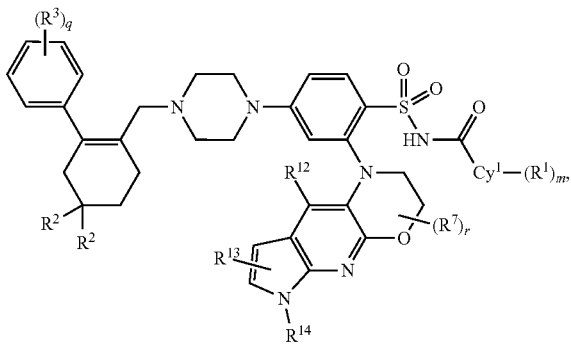

wherein:
X$^A$ is CR$^{1D}$ or N;
R$^{1A}$ is H, D, Me, CF$_3$, F, Cl, Br, OMe, NO$_2$, SO$_2$Me, or SO$_2$CF$_3$;
each R$^{1B}$ and R$^{1D}$ are each, independently, H, D, halo, oxo, C$_{1-6}$ alkyl, C$_{2-6}$ alkenyl, C$_{2-6}$ alkynyl, C$_{1-6}$haloalkyl, CN, NO$_2$, N$_3$, OR$^A$, SR$^A$, C(O)R$^B$, C(O)NR$^C$R$^D$, C(O)OR$^A$, OC(O)R$^B$, OC(O)NR$^C$R$^D$, NR$^C$R$^D$, NR$^C$C(O)R$^D$, NR$^C$C(O)NR$^C$R$^D$, C(=NR$^C$)R$^B$, C(=NR$^C$)NR$^C$R$^D$, NR$^C$S(O)R$^B$, NR$^C$S(O)$_2$NR$^C$R$^D$, NR$^C$C(=NR$^C$)NR$^C$R$^D$, NR$^C$C(=NOR$^A$)NR$^C$R$^D$, NR$^C$C(=NCN)NR$^C$R$^D$, S(O)(=NR$^C$)R$^B$, S(O)(=NR$^C$)NR$^C$R$^D$, NR$^C$C(O)OR$^A$, P(O)R$^E$R$^F$, P(O)OR$^E$OR$^F$, OP(O)OR$^E$OR$^F$, SF$_5$, S(O)R$^B$, S(O)NR$^C$R$^D$, S(O)$_2$R$^B$, NR$^C$S(O)$_2$R$^B$, S(O)$_2$NR$^C$R$^D$, B(OR$^A$)$_2$, Cy$^4$, C$_{1-6}$ alkyl-Cy$^4$, O—C$_{1-6}$ alkyl-Cy 4, or O—C$_{1-6}$ alkyl-Cy$^4$-C$_{0-6}$ alkyl-Cy$^5$, wherein said Cy$^4$, C$_{1-6}$ alkyl-Cy$^4$, O—C$_{1-6}$ alkyl-Cy$^4$, O—C$_{1-6}$ alkyl-Cy$^4$-C$_{0-6}$ alkyl-Cy$^5$, and Cy$^5$ are optionally substituted;
wherein two R$^{1B}$, one R$^{1B}$ and R$^{1A}$, or one R$^{1B}$ and one R$^{1D}$, together with the atom or atoms to which they are attached, optionally form a fused 4- to 10-membered cycloalkyl ring or a fused 4- to 10-membered heterocycloalkyl ring, each of which is optionally substituted by 1, 2, or 3 substituents, wherein each said substituent is independently halo, C$_{1-6}$ alkyl, C$_{2-6}$ alkenyl, C$_{2-6}$ alkynyl, C$_{1-6}$haloalkyl, CN, NO$_2$, oxo, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)NR$^c$R$^d$, C(=NR$^c$)R$^b$, C(=NR$^c$)NR$^c$R$^d$, NR$^c$S(O)R$^b$, NRS(O)$_2$NR$^c$R$^d$, NC(=NR)NR$^c$R$^d$, NR$^c$(=NOR$^a$)NR$^c$R$^d$, NR$^c$(=NCN)NR$^c$R$^d$, S(O)(=NR$^c$)R$^b$, S(O)(=NR)NR$^c$R$^d$, NR$^c$C(O)OR$^a$, P(O)R$^e$R$^f$, P(O)OR$^e$OR$^f$, OP(O)OR$^e$OR$^f$, S(O)R$^b$, S(O)NR$^c$R$^d$, S(O)$_2$R$^b$, NR$^c$S(O)$_2$R$^b$, or S(O)$_2$NR$^c$R$^d$, B(OR$^a$)$_2$, aryl, cycloalkyl, heteroaryl, or heterocycloalkyl and s is 0-3.

8. The compound of claim 7, or a pharmaceutically acceptable salt or solvate thereof, wherein R$^{1B}$ is H, D, F, Br, Cl, I, NO$_2$, C$_{1-6}$ alkyl, C$_{1-6}$ alkoxy, or O—C$_{1-6}$ alkyl-Cy$^4$, wherein said C$_{1-6}$ alkyl, C$_{1-6}$ alkoxy, or O—C$_{1-6}$ alkyl-Cy$^4$ is optionally substituted by 1, 2, or 3 substituents, wherein each said substituent is independently is H, D, halo, CN, NO$_2$, OR$^a$, SR$^a$, NHOR$^a$, C(O)R$^b$, C(O)NR$^c$R$^d$, C(O)OR$^a$, OC(O)R$^a$, OC(O)NR$^c$R$^d$, NHR$^c$, NR$^c$R$^d$, NR$^c$C(O)R$^b$, NR$^c$C(O)OR$^a$, NR$^c$C(O)NR$^c$R$^d$, C(=NR$^c$)R$^b$, C(=NR$^c$)NR$^c$R$^d$, NR$^c$S(O)R$^b$, NR$^c$S(O)$_2$NR$^c$R$^d$, NR$^c$C(=NR$^c$)NR$^c$R$^d$, NR$^c$C(=NOR$^a$)NR$^c$R$^d$, NR$^c$(=NCN)NR$^c$R$^d$, S(O)(=NR$^c$)R$^b$, S(O)(=NR$^c$)NR$^c$R$^d$, C(=NR$^c$)R$^d$, C(=NR$^c$)NR$^c$R$^d$, NR$^c$C

174

(=NR$^d$)NR$^c$R$^d$, NR$^c$C(=NOH)NR$^c$R$^d$, NR$^d$C(=NCN)NR$^c$R$^d$, NR$^c$S(O)R$^b$, NR$^c$S(O)$_2$R$^a$, NR$^c$S(O)$_2$NR$^c$R$^d$, S(O)R$^b$, S(O)NR$^c$R$^d$, S(O)$_2$R$^b$, SF$_5$, P(O)R$^e$R$^f$, P(O)(OR$^e$)(OR$^f$), B(OR$^a$)$_2$ and S(O)$_2$NR$^c$R$^d$ or optionally substituted C$_{1-6}$ alkyl, C$_{1-6}$ alkoxy, C$_{2-6}$ alkenyl, C$_{2-6}$ alkynyl, C$_{1-6}$ haloalkyl, C$_{1-6}$ haloalkoxy, C$_{6-10}$ aryl, C$_{3-10}$ cycloalkyl, 5- to 10-membered heteroaryl, 4- to 14-membered heterocycloalkyl, C$_{6-10}$ aryl-C$_{1-4}$ alkyl, C$_{3-10}$ cycloalkylC$_{1-4}$alkyl, (5- to 14-membered heteroaryl)-C$_{1-4}$ alkyl, or (4- to 14-membered heterocycloalkyl)-C$_{1-4}$ alkyl.

9. The compound of claim 1, or a pharmaceutically acceptable salt or solvate thereof, wherein the compound has the formula of Formula (XX)

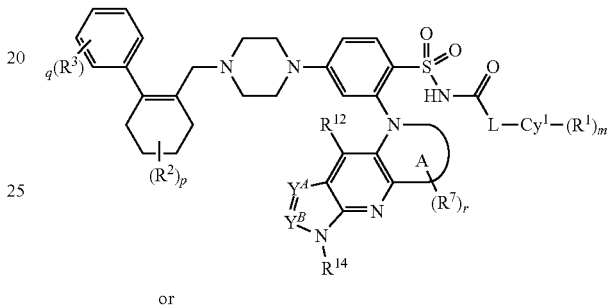

or

Formula (XX-I)

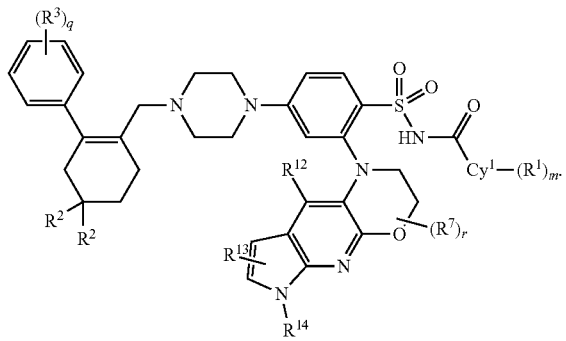

10. The compound of claim 1, or a pharmaceutically acceptable salt or solvate thereof, wherein the compound has the formula of Formula (XXI)

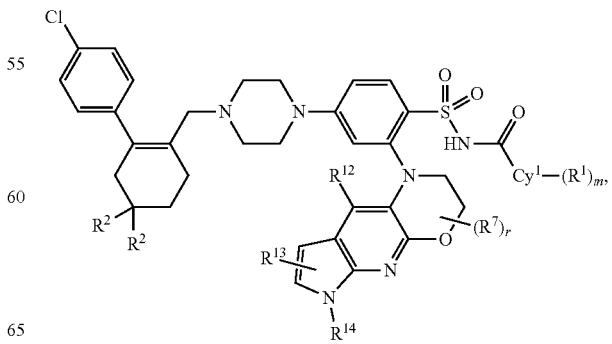

Formula (XXII)

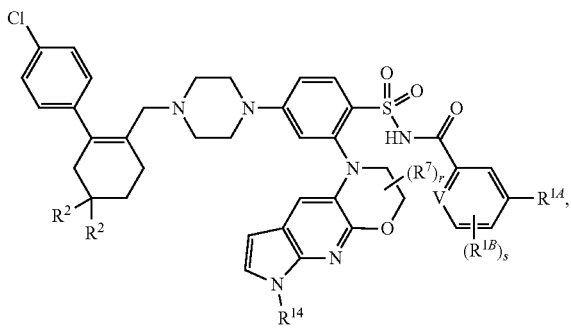

Formula (XXV)

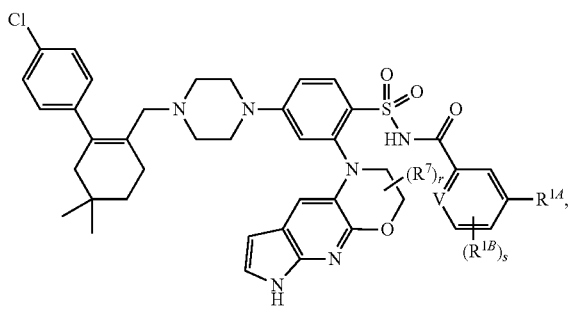

wherein:
V is $CR^{1D}$ or N;
$R^{1A}$ is H, D, Me, $CF_3$, F, Cl, Br, OMe, $NO_2$, $SO_2Me$, or $SO_2CF_3$;
$R^{1B}$ and $R^{1D}$ are each, independently, H, D, halo, oxo, $C_{1-6}$ alkyl, $C_{2-6}$ alkenyl, $C_{2-6}$ alkynyl, $C_{1-6}$haloalkyl, CN, $NO_2$, $N_3$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^D$, $NR^CC(O)NR^CR^D$, $C(=NR^C)R^B$, $C(=NR^C)NR^CR^D$, $NR^CS(O)R^B$ $NR^CS(O)_2NR^CR^D$, $NR^CC(=NR^C)NR^CR^D$, $NR^CC(=NOR^A)R^CR^D$, $NR^CC(=NCN)NR^CR^D$, $S(O)(=NR^C)R^B$, $S(O)(=NR^C)NR^CR^D$, $NR^CC(O)OR^A$, $P(O)R^ER^F$, $P(O)OR^EOR^F$, $OP(O)OR^EOR^F$, $SF_5$, $S(O)R^B$, $S(O)NR^CR^D$, $S(O)_2R^B$, $NR^CS(O)_2R^B$, $S(O)_2NR^CR^D$, $B(OR^A)_2$, $Cy^4$, $C_{1-6}$ alkyl-$Cy^4$, O—$C_{1-6}$ alkyl-$Cy^4$, or O—$C_{1-6}$ alkyl-$Cy^4$-$C_{0-6}$ alkyl-$Cy^5$, wherein said $Cy^4$, $C_{1-6}$ alkyl-$Cy^4$, O—$C_{1-6}$ alkyl-$Cy^4$, O—$C_{1-6}$ alkyl-$Cy^4$-$C_{0-6}$ alkyl-$Cy^5$, and $Cy^5$ are optionally substituted;
wherein two $R^{1B}$, one $R^{1B}$ and $R^{1A}$, or one $R^{1B}$ and $R^{1D}$, together with the atom or atoms to which they are attached, optionally form a fused 4-10 membered cycloalkyl ring or a fused 4-10 membered heterocycloalkyl ring, each optionally substituted by 1, 2, or 3 substituents, wherein each said substituent is independently halo, $C_{1-6}$ alkyl, $C_{2-6}$ alkenyl, $C_{2-6}$ alkynyl, $C_{1-6}$ haloalkyl, CN, $NO_2$, oxo, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^c(O)R^b$, $NR^cC(O)NR^cR^d$, $C(=NR^c)R^b$, $C(=NR^c)NR^cR^d$, $NR^cS(O)R^b$, $NRS(O)_2NR^cR^d$, $NR^cC(=NR^c)N^cR^d$, $NR^c(=NOR^a)NR^cR^d$, $NR^c(=NCN)NR^cR^d$, $S(O)(=NR^c)R^b$, $S(O)(=NR)NR^cR^d$, $NR^cC(O)OR^a$, $P(O)R^eR^f$, $P(O)OR^eR^f$, $OP(O)OR^eOR^f$, $S(O)R^b$, $S(O)$ $NR^cR^d$, $S(O)_2R^b$, $NR^cS(O)_2R^b$, or $S(O)_2NR^cR^d$, $B(OR^a)_2$, aryl, cycloalkyl, heteroaryl, and heterocycloalkyl; and s is 0-3.

11. The compound of claim 10, or a pharmaceutically acceptable salt or solvate thereof, wherein $R^{1A}$ is 11, D, $NO_2$, $SO_2Me$, or $SO_2CF_3$.

12. The compound of claim 11, or a pharmaceutically acceptable salt or solvate thereof, wherein r is 1.

13. The compound of claim 12, or a pharmaceutically acceptable salt or solvate thereof, wherein $R^7$ is absent.

14. The compound of claim 1, or a pharmaceutically acceptable salt or solvate thereof, wherein the compound is selected from the group consisting of
6-chloro-N-[4-[4-[[2-(4-chlorophenyl)-4,4-dimethylcyclohexen-1-yl]methyl] piperazin-1-yl]phenyl]sulfonyl-5-nitropyridine-2-carboxamide;
N-[4-[4-[[2-(4-chlorophenyl)-4,4-dimethylcyclohexen-1-yl]methyl]piperazin-1-yl]phenyl]sulfonylbenzo[b]thiophene-5-carboxamide;
1-benzyl-N-[4-[4-[[2-(4-chlorophenyl)-4,4-dimethylcyclohexen-1-yl]methyl]piperazin-1-yl]phenyl]sulfonyl-5-methyl-1H-1,2,3-triazole-4-carboxamide;
N-([4-[4-[[2-(4-chlorophenyl)-4,4-dimethylcyclohexen-1-yl]methyl]piperazin-1-yl]phenyl]sulfonyl)quinoline-6-carboxamide;
N-([4-[4-[[2-(4-chlorophenyl)-4,4-dimethylcyclohexen-1-yl]methyl]piperazin-1-yl]phenyl]sulfonyl)pyrazine-2-carboxamide;
N-([4-[4-[[2-(4-chlorophenyl)-4,4-dimethylcyclohexen-1-yl]methyl]piperazin-1-yl]phenyl]sulfonyl)bicyclo[1.1.1]pentane-1-carboxamide;
N-([4-[4-[[2-(4-chlorophenyl)-4,4-dimethylcyclohexen-1-yl]methyl]piperazin-1-yl]phenyl]sulfonyl)-2-methylpyrimidine-5-carboxamide;
N-((4-(4-((4'-chloro-5,5-dimethyl-3,4,5,6-tetrahydro-[1,1'-biphenyl]-2-yl)methyl)piperazin-1-yl)phenyl)sulfonyl)quinoline-3-carboxamide;
N-([4-[4-[[2-(4-chlorophenyl)-4,4-dimethylcyclohexen-1-yl]methyl]piperazin-1-yl]phenyl]sulfonyl)-1-methyl-2-oxo-1,2,3,4-tetrahydroquinoline-6-carboxamide;
N-([4-[4-[[2-(4-chlorophenyl)-4,4-dimethylcyclohexen-1-yl]methyl]piperazin-1-yl]phenyl]sulfonyl)-2-methoxybenzamide;
N-([4-[4-[[2-(4-chlorophenyl)-4,4-dimethylcyclohexen-1-yl]methyl]piperazin-1-yl]phenyl]sulfonyl)-5-cyclopropylisoxazole-3-carboxamide;
5-bromo-N-([4-[4-[[2-(4-chlorophenyl)-4,4-dimethylcyclohexen-1-yl]methyl]piperazin-1-yl]phenyl]sulfonyl)pyridine-2-carboxamide;
N-([4-[4-[[2-(4-chlorophenyl)-4,4-dimethylcyclohexen-1-yl]methyl]piperazin-1-yl]phenyl]sulfonyl)-3-methyl-1H-pyrazole-5-carboxamide;
3-chloro-N-([4-[4-[[2-(4-chlorophenyl)-4,4-dimethylcyclohexen-1-yl]methyl]piperazin-1-yl]phenyl]sulfonyl)benzamide;
N-([4-[4-[[2-(4-chlorophenyl)-4,4-dimethylcyclohexen-1-yl]methyl]piperazin-1-yl]phenyl]sulfonyl)-5-fluoro-6-methyl pyridine-2-carboxamide;
N-([4-[4-[[2-(4-chlorophenyl)-4,4-dimethylcyclohexen-1-yl]methyl]piperazin-1-yl]phenyl]sulfonyl)-4,5-dimethylisoxazole-3-carboxamide;
N-([4-[4-[[2-(4-chlorophenyl)-4,4-dimethylcyclohexen-1-yl]methyl]piperazin-1-yl]phenyl]sulfonyl)-3-(methoxymethyl)benzamide;
N-([4-[4-[[2-(4-chlorophenyl)-4,4-dimethylcyclohexen-1-yl]methyl]piperazin-1-yl]phenyl]sulfonyl)-4-(methoxymethyl)benzamide;

5,6-dichloro-N-([4-[4-[[2-(4-chlorophenyl)-4,4-dimethylcyclohexen-1-yl]methyl]piperazin-1-yl]phenyl]sulfonyl)pyridine-2-carboxamide;

N-([4-[4-[[2-(4-chlorophenyl)-4,4-dimethylcyclohexen-1-yl]methyl]piperazin-1-yl]phenyl]sulfonyl)-6-(trifluoromethyl)pyridine-2-carboxamide;

N-([4-[4-[[2-(4-chlorophenyl)-4,4-dimethylcyclohexen-1-yl]methyl]piperazin-1-yl]phenyl]sulfonyl)-3-(trifluoromethyl)pyridine-4-carboxamide;

N-([4-[4-[[2-(4-chlorophenyl)-4,4-dimethylcyclohexen-1-yl]methyl]piperazin-1-yl]phenyl]sulfonyl)-5-nitropyridine-3-carboxamide;

N-([4-[4-[[2-(4-chlorophenyl)-4,4-dimethylcyclohexen-1-yl]methyl]piperazin-1-yl]phenyl]sulfonyl)pyridine-2-carboxamide;

N-([4-[4-[[2-(4-chlorophenyl)-4,4-dimethylcyclohexen-1-yl]methyl]piperazin-1-yl]phenyl]sulfonyl)-3-(4-fluorophenyl)isoxazole-5-carboxamide;

N-([4-[4-[[2-(4-chlorophenyl)-4,4-dimethylcyclohexen-1-yl]methyl]piperazin-1-yl]phenyl]sulfonyl)-2-(6-methylpyridin-3-yl)acetamide;

N-([4-[4-[[2-(4-chlorophenyl)-4,4-dimethylcyclohexen-1-yl]methyl]piperazin-1-yl]phenyl]sulfonyl)thieno[2,3-b]pyridine-6-carboxamide;

N-([4-[4-[[2-(4-chlorophenyl)-4,4-dimethylcyclohexen-1-yl]methyl]piperazin-1-yl]phenyl]sulfonyl)cyclohex-3-ene-1-carboxamide;

N-([4-[4-[[2-(4-chlorophenyl)-4,4-dimethylcyclohexen-1-yl]methyl]piperazin-1-yl]phenyl]sulfonyl)-1-(4-nitrophenyl)cyclopropane-1-carboxamide;

N-([4-[4-[[2-(4-chlorophenyl)-4,4-dimethylcyclohexen-1-yl]methyl]piperazin-1-yl]phenyl]sulfonyl)-2-(2-fluorophenyl)acetamide;

N-([4-[4-[[2-(4-chlorophenyl)-4,4-dimethylcyclohexen-1-yl]methyl]piperazin-1-yl]phenyl]sulfonyl)-3-(pyridin-3-yl)propanamide;

N-([4-[4-[[2-(4-chlorophenyl)-4,4-dimethylcyclohexen-1-yl]methyl]piperazin-1-yl]phenyl]sulfonyl)-3-nitrobenzamide;

6-bromo-N-([4-[4-[[2-(4-chlorophenyl)-4,4-dimethylcyclohexen-1-yl]methyl]piperazin-1-yl]phenyl]sulfonyl)-5-fluoropyridine-2-carboxamide;

N-([4-[4-[[2-(4-chlorophenyl)-4,4-dimethylcyclohexen-1-yl]methyl]piperazin-1-yl]phenyl]sulfonyl)-3-((3-methylbenzyl)oxy)benzamide;

N-([4-[4-[[2-(4-chlorophenyl)-4,4-dimethylcyclohexen-1-yl]methyl]piperazin-1-yl]phenyl]sulfonyl)-4-((2,5-dichlorophenoxy)methyl)benzamide;

4-(benzyloxy)-N-([4-[4-[[2-(4-chlorophenyl)-4,4-dimethylcyclohexen-1-yl]methyl] piperazin-1-yl]phenyl] sulfonyl)-3-nitrobenzamide;

N-([4-[4-[[2-(4-chlorophenyl)-4,4-dimethylcyclohexen-1-yl]methyl] piperazin-1-yl]phenyl]sulfonyl)-3((4-chlorophenoxy)methyl)-4-fluorobenzamide;

N-([4-[4-[[2-(4-chlorophenyl)-4,4-dimethylcyclohexen-1-yl]methyl] piperazin-1-yl]phenyl]sulfonyl)-3-((4-chlorophenoxy)methyl)-4-nitrobenzamide;

N-([4-[4-[[2-(4-chlorophenyl)-4,4-dimethylcyclohexen-1-yl]methyl] piperazin-1-yl]phenyl]sulfonyl)-4-((4-chlorophenoxy)methyl)-3-nitrobenzamide;

3-(benzyloxy)-N-([4-[4-[[2-(4-chlorophenyl)-4,4-dimethylcyclohexen-1-yl]methyl] piperazin-1-yl]phenyl]sulfonyl)-4-nitrobenzamide;

2-Chloro-N-[4-[4-[[2-(4-chlorophenyl)-4,4-dimethylcyclohexen-1-yl]methyl] piperazin-1-yl]phenyl]sulfonyl-5-nitro-4-(tetrahydropyran-4-ylmethylamino)benzamide;

2-Chloro-N-([4-[4-[[2-(4-chlorophenyl)-4,4-dimethylcyclohexen-1-yl]methyl piperazin-1-yl]phenyl]sulfonyl)-3-methyl-5-nitro-4-(tetrahydropyran-4-ylmethylamino)benzamide;

2-chloro-N-[4-[4-[[2-(4-chlorophenyl)-4,4-dimethylcyclohexen-1-yl]methyl] piperazin-1-yl]phenyl]sulfonyl-4-(ethylamino)-3-methyl-5-nitrobenzamide;

N-[4-[4-[[2-(4-chlorophenyl)-4,4-dimethylcyclohexen-1-yl]methyl] piperazin-1-yl]phenyl]sulfonyl-5-fluoro-6-(1,3,5-trimethylpyrazol-4-yl)pyridine-2-carboxamide;

N-[4-[4-[[2-(4-chlorophenyl)-4,4-dimethylcyclohexen-1-yl]methyl] piperazin-1-yl]phenyl]sulfonyl-5-fluoro-6-(1-methyl-1H-pyrazol-4-yl)pyridine-2-carboxamide;

N-[4-[4-[[2-(4-chlorophenyl)-4,4-dimethylcyclohexen-1-yl]methyl]piperazin-1-yl]phenyl]sulfonyl-5-fluoro-6-(1H-imidazol-1-yl)pyridine-2-carboxamide;

N-[4-[4-[[2-(4-chlorophenyl)-4,4-dimethylcyclohexen-1-yl]methyl]piperazin-1-yl]phenyl]sulfonyl-5-fluoro-6-(2-oxo-2,3-dihydro-1H-pyrrolo[2,3-b]pyridin-5-yl)pyridine-2-carboxamide;

N-[4-[4-[[2-(4-chlorophenyl)-4,4-dimethylcyclohexen-1-yl]methyl]piperazin-1-yl]phenyl]sulfonyl-5-fluoro-6-(1H-indazol-5-yl)pyridine-2-carboxamide;

6-(1H-benzo[d][1,2,3]triazol-5-yl)-N-[4-[4-[[2-(4-chlorophenyl)-4,4-dimethylcyclohexen-1-yl]methyl] piperazin-1-yl]phenyl]sulfonyl-5-fluoro pyridine-2-carboxamide;

N-[4-[4-[[2-(4-chlorophenyl)-4,4-dimethylcyclohexen-1-yl]methyl]piperazin-1-yl]phenyl]sulfonyl-5-fluoro-6-(1-methyl-1H-indazol-5-yl) pyridine-2-carboxamide;

6-(benzyloxy)-N-[4-[4-[[2-(4-chlorophenyl)-4,4-dimethylcyclohexen-1-yl]methyl] piperazin-1-yl]phenyl]sulfonyl-5-nitropyridine-2-carboxamide;

N-[4-[4-[[2-(4-chlorophenyl)-4,4-dimethylcyclohexen-1-yl]methyl]piperazin-1-yl]phenyl]sulfonyl-3-nitro-4-(phenoxymethyl)benzamide;

3-(benzyloxy)-N-[4-[4-[[2-(4-chlorophenyl)-4,4-dimethylcyclohexen-1-yl]methyl]piperazin-1-yl]phenyl]sulfonyl-4-fluorobenzamide;

2-chloro-N-[4-[4-[[2-(4-chlorophenyl)-4,4-dimethylcyclohexen-1-yl]methyl]piperazin-1-yl]phenyl]sulfonyl-4-(methylamino)-3-methyl-5-nitrobenzamide;

N-[4-[4-[[2-(4-Chlorophenyl)-4,4-dimethylcyclohexen-1-yl]methyl]piperazin-1-yl]phenyl]sulfonyl-3-fluoro-1'-methyl-2'-oxo-1',2'-dihydro-[2,4'-bipyridine]-6-carboxamide;

N-[4-[4-[[2-(4-Chlorophenyl)-4,4-dimethylcyclohexen-1-yl]methyl]piperazin-1-yl]phenyl]sulfonyl-5-fluoro-6-(2-methoxypyrimidin-5-yl)pyridine-2-carboxamide;

N-[4-[4-[[2-(4-Chlorophenyl)-4,4-dimethylcyclohexen-1-yl]methyl]piperazin-1-yl]phenyl]sulfonyl-3-fluoro-1'-methyl-6'-oxo-1',6'-dihydro-[2,3'-bipyridine]-6-carboxamide;

N-[4-[4-[[2-(4-Chlorophenyl)-4,4-dimethylcyclohexen-1-yl]methyl]piperazin-1-yl]phenyl]sulfonyl-5-fluoro-6-(1H-pyrazol-4-yl)pyridine-2-carboxamide;

N-[4-[4-[[2-(4-Chlorophenyl)-4,4-dimethylcyclohexen-1-yl]methyl]piperazin-1-yl]phenyl]sulfonyl-5-fluoro-6-(1-methyl-1H-indazol-6-yl)pyridine-2-carboxamide;

N-[4-[4-[[2-(4-chlorophenyl)-4,4-dimethyl-cyclohexen-1-yl]methyl]piperazin-1-yl]phenyl]sulfonyl-5-fluoro-6-(4-pyridyl)pyridine-2-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-6-bromo-5-fluoropyridine-2-carboxamide;

5,6-Dichloro-N-[4-[4-[[2-(4-chlorophenyl)-4,4-dimethyl-cyclohexen-1-yl]methyl]piperazin-1-yl]-2-(1H-pyrrolo[2,3-b]pyridin-5-yloxy)phenyl]sulfonylpyridine-2-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-fluoro-6-methylpyridine-2-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-6-methyl-5-nitropyridine-2-carboxamide;

5-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-6-(trifluoromethyl)pyridine-2-carboxamide;

6-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-nitropyridine-2-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-chloro-6-methylpyridine-2-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3,4-dihydro-2H-chromene-6-carboxamide;

N-((2-((1H-pyrrolo[2,3-b]pyridin-5-yl)oxy)-4-(4-[[2-(4-Chlorophenyl)-4,4-dimethylcyclohexen-1-yl]methyl]piperazin-1-yl]phenyl)sulfonyl)thieno[2,3-b]pyridine-5-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-1,4-dimethylpyrazole-3-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-1,5-dimethylpyrazole-3-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-2,4,5-trimethylpyrazole-3-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitrobenzamide;

2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxan-4-ylmethylamino)benzamide;

2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxan-4-ylmethoxy)benzamide;

N-((2-((1H-pyrrolo[2,3-b]pyridin-5-yl)methyl)-4-(4-[[2-(4-Chlorophenyl)-4,4-dimethylcyclohexen-1-yl]methyl]piperazin-1-yl]phenyl)sulfonyl)-4-((4-chlorophenoxy)methyl)-3-nitrobenzamide;

4-[(4-Chlorophenoxy)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-fluorobenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-(cyclopropyloxymethyl)-4-fluorobenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-(methoxymethyl)-5-nitrobenzamide;

3-[(4-Chlorophenoxy)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-5-nitrobenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(methoxymethyl)-3-nitrobenzamide;

2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-[(4-chlorophenyl)methoxy]-3-methyl-5-nitrobenzamide;

4-[(4-chlorophenoxy)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methylsulfonylbenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(morpholin-4-ylmethyl)-3-nitrobenzamide;

4-[(4-chloroanilino)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-nitrobenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonylthieno[2,3-b]pyridine-6-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonylthieno[2,3-b]pyridine-4-carboxamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-6-methyl-5-nitropyridine-2-carboxamide;

3-[(4-Chlorophenoxy)methyl]-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-nitrobenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-nitro-4-[(oxan-4-ylamino)methyl]benzamide;

N-[4-[4-[[2-(4-Chlorophenyl)-4,4-dimethylcyclohexen-1-yl]methyl]piperazin-1-yl]-2-(1H-pyrrolo[2,3-b]pyridin-5-yloxy)phenyl]sulfonyl-6-methyl-4-methylsulfonylpyridine-2-carboxamide;

2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-4-(methylamino)-5-nitrobenzamide;

2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(ethylamino)-3-methyl-5-nitrobenzamide;

N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-nitro-4-(oxan-4-ylmethylamino)benzamide;

2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-methoxy-3-methyl-5-nitrobenzamide;

2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-ethoxy-3-methyl-5-nitrobenzamide;

2-chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxetan-3-ylmethoxy)benzamide;

2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(1,4-dioxan-2-ylmethylamino)-3-methyl-5-nitrobenzamide;

2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-4-(1,4-dioxan-2-ylmethoxy)-3-methyl-5-nitrobenzamide;

2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxolan-3-ylmethoxy)benzamide; and 2-Chloro-N-[4-[4-[[2-(4-chlorophenyl)-4,4-dimethylcyclohexen-1-yl]methyl]piperazin-1-yl]-2-(1H-pyrrolo[2,3-b]pyridin-5-yloxy)phenyl]sulfonyl-3-methyl-5-nitro-4-(oxolan-2-ylmethoxy)benzamide.

15. A pharmaceutical composition comprising a compound of claim 1, or a pharmaceutically acceptable salt or solvate thereof.

16. The pharmaceutical composition of claim 15, wherein the composition further comprises a pharmaceutically acceptable excipient, at least one chemotherapeutic agent, at least one epigenetic regulator, at least one kinase inhibitor, least one more BCL-2 inhibitor, at least one hormone therapy agent, at least one monoclonal antibody, at least one immunomodulatory agent, or pharmaceutically acceptable carrier.

17. The pharmaceutical composition of claim 15, wherein the pharmaceutical composition comprises an enantiomeric excess of at least 90%, 95%, 98%, or 99% of one enantiomer of the compound, or a pharmaceutically acceptable salt or solvate thereof.

18. A method, the method of comprising:
inhibiting the activity of BCL-2 protein comprising contacting the BCL protein with a compound of claim 1, or a pharmaceutically acceptable salt, a solvate, a prodrug, or a pharmaceutical composition thereof; or
treating, or ameliorating a disease or disorder condition responsive to inhibition of BCL-2 in a subject in need thereof comprising administering to the subject, a compound of claim 1, or a pharmaceutically acceptable salt, a solvate, a prodrug, or a pharmaceutical composition thereof.

19. The method of claim 18, wherein the disease or disorder condition is a cancer, a hyperproliferative disease, an autoimmune disease, a psychiatric disorder, a senescence-associated disease or disorder, a neoplastic disease, or a neurodegenerative disease.

20. The method of claim 18, wherein the compound, or a pharmaceutically acceptable salt, a solvate, or a prodrug, or a pharmaceutical composition thereof is administered in a therapeutically effective amount.

* * * * *